(12) United States Patent
Brown et al.

(10) Patent No.: US 11,312,722 B2
(45) Date of Patent: Apr. 26, 2022

(54) HSP90 INHIBITORS AND USES THEREOF

(71) Applicants: TRUSTEES OF BOSTON UNIVERSITY, Boston, MA (US); The Governing Council of the University of Toronto, Toronto (CA)

(72) Inventors: Lauren Elaine Brown, Waltham, MA (US); David S Huang, Cambridge, MA (US); Leah E. Cowen, Toronto (CA); Luke Whitesell, Toronto (CA); Paul Marcyk, Boston, MA (US)

(73) Assignees: TRUSTEES OF BOSTON UNIVERSITY, Boston, MA (US); The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 16/868,008

(22) Filed: May 6, 2020

(65) Prior Publication Data

US 2020/0354373 A1    Nov. 12, 2020

Related U.S. Application Data

(60) Provisional application No. 62/844,884, filed on May 8, 2019.

(51) Int. Cl.
| | | |
|---|---|---|
| *C07D 403/04* | (2006.01) | |
| *C07D 487/22* | (2006.01) | |
| *C07D 231/38* | (2006.01) | |
| *C07D 471/04* | (2006.01) | |
| *C07D 487/04* | (2006.01) | |
| *C07D 403/14* | (2006.01) | |
| *C07D 405/14* | (2006.01) | |
| *C07D 401/04* | (2006.01) | |
| *C07D 403/12* | (2006.01) | |
| *C07D 401/14* | (2006.01) | |
| *A61P 31/10* | (2006.01) | |

(52) U.S. Cl.
CPC ............ *C07D 487/22* (2013.01); *A61P 31/10* (2018.01); *C07D 231/38* (2013.01); *C07D 401/04* (2013.01); *C07D 401/14* (2013.01); *C07D 403/04* (2013.01); *C07D 403/12* (2013.01); *C07D 403/14* (2013.01); *C07D 405/14* (2013.01); *C07D 471/04* (2013.01); *C07D 487/04* (2013.01)

(58) Field of Classification Search
CPC .. C07D 487/22; C07D 231/38; C07D 401/04; C07D 401/14; C07D 403/04; C07D 403/12; C07D 403/14; C07D 405/14; C07D 471/04; C07D 487/04
See application file for complete search history.

(56) References Cited

U.S. PATENT DOCUMENTS

| | | | |
|---|---|---|---|
| 7,265,144 B2 * | 9/2007 | Rudolph | .............. C07D 401/04 514/406 |
| 8,212,012 B2 | 7/2012 | Blagg | |
| 8,329,736 B2 | 12/2012 | Chimmanamada | |
| 2008/0095531 A1 | 1/2008 | Cantin et al. | |
| 2008/0064734 A1 | 3/2008 | Rudolph | |
| 2013/0072536 A1 | 3/2013 | Ying et al. | |

OTHER PUBLICATIONS

Crenshaw et al., Journal of Medicinal Chemistry, 1976, vol. 19, No. 2, pp. 262-275.*
Huang et al., "Design and Synthesis of Fungal-Selective Resorcylate Aminopyrazole Hsp90 Inhibitors", Journal of Medicinal Chemistry, 63, 2139-2180, (2020).
Weininger, "Smiles, a Chemical Language and Information System. 1. An Introduction to Methodology and Encoding Rules," J. Chem. Inf. Comput. Sci., 28, 31-36, (1988).
Huang et al., "Design and Synthesis of Fungal-Selective Resorcylate Aminopyrazole Hsp90 Inhibitors, Supporting Information", Journal of Medicinal Chemistry, 63, S1-S6, (2020).
International Search Report, PCT/US2020/31615, dated Sep. 17, 2020.

* cited by examiner

*Primary Examiner* — Rebecca L Anderson
(74) *Attorney, Agent, or Firm* — Nixon Peabody LLP; Ronald I Eisentein; Ravinderjit Braich

(57) ABSTRACT

Herein is described the design and synthesis of resorcylate aminopyrazole compounds. These compounds show broad, potent and fungal-selective Hsp90 inhibitory activity. These compounds also find use in treating Hsp90 related diseases.

31 Claims, 8 Drawing Sheets
(5 of 8 Drawing Sheet(s) Filed in Color)

1 radicicol (X = Cl)
2 monocillin I (X = H)

3 CMLD013075

4 Onalespib

5 Luminespib

6 Ganetespib

7 KW-2478

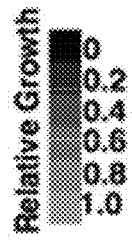
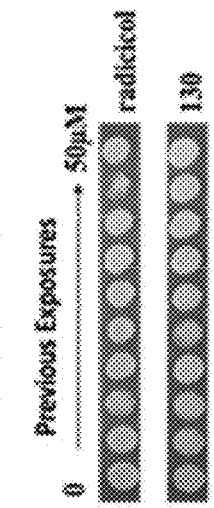
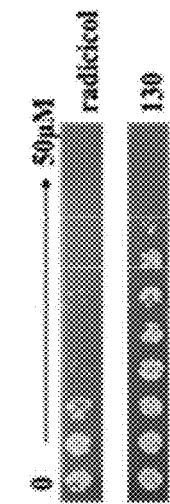
FIG. 4A
Dose-response assays in liquid medium:
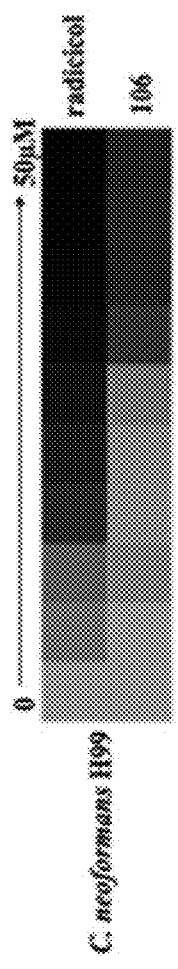
C. neoformans H99
FIG. 4B
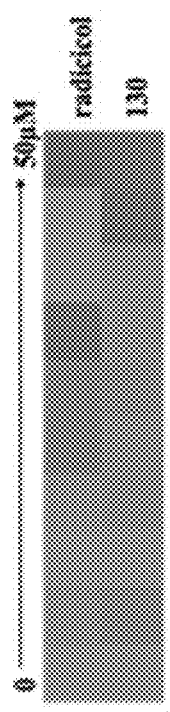
C. albicans CaCl2
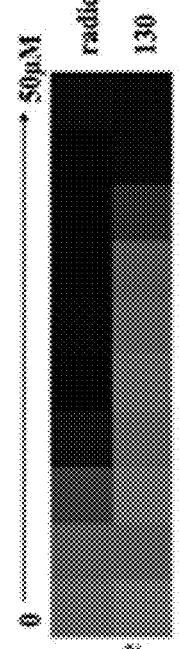
C. albicans CaCl2 +
8 µg/mL fluconazole 112
$T_{1/2}$ = 3.15 min
0% remaining at $T_{60}$ 113
$T_{1/2}$ = 3.44 min
0% remaining at $T_{60}$ 114
$T_{1/2}$ = 17.2 min
7% remaining at $T_{60}$ 83
$T_{1/2}$ = 3.1 min
1.8% remaining at $T_{60}$ 131
$T_{1/2}$ = 14.1 min
3.9% remaining at $T_{60}$ 132
$T_{1/2}$ = 31.0 min
20.6% remaining at $T_{60}$ 105
$T_{1/2}$ = 2.74 min
0.06% remaining at $T_{60}$ 129
$T_{1/2}$ = 6.44 min
0.5% remaining at $T_{60}$ 111
$T_{1/2}$ = 9.38 min
1.8% remaining at $T_{60}$ Dose-response assays in liquid medium:

Survival post exposure (no compound present):

HSP90 INHIBITORS AND USES THEREOF

RELATED APPLICATIONS

This application claims benefit under 35 U.S.C. § 119(e) of the U.S. Provisional Application No. 62/844,884 filed May 8, 2019, the content of which is incorporated herein by reference in its entirety.

GOVERNMENT SUPPORT

This invention was made with Government Support under Contract Nos. No. AI120958 awarded by the National Institutes of Health. The Government has certain rights in the invention.

FIELD OF THE INVENTION

This invention relates to heat shock protein 90 (Hsp90) inhibitors and their uses. More particularly, the invention is directed to Resorcylate Aminopyrazole type Hsp90 inhibitors, their preparation and uses in treating fungal infections and Hsp90 related diseases.

BACKGROUND

Heat shock proteins (HSP) are chaperone proteins which regulate the conformational stability and maturation of many cellular proteins. Numerous HSP's are known and are classified according to their molecular weight. HSP90 is a 90 k Dalton protein chaperone that plays a central role in regulating, for example, protein homeostasis. HSP90 regulates the stability of certain proteins ("client proteins") and maintains them in the appropriate three-dimensional conformation so they can perform their cellular functions. In humans, there are two HSP90 isoforms in the cytosol, HSP90α and HSP90β. These proteins are closely related and, to date, no differences in their activities have been identified.

In addition to normal cellular function, certain HSP90 client proteins are associated with abnormal cellular function. For example, many of the proteins stabilized by HSP90 are oncoproteins and cell-signaling proteins important in cancer cell proliferation and cancer cell survival, including many kinases and transcription factors. Hsp90 also has been extensively validated as a regulator of virulence and antifungal drug resistance in fungus.

Thus, there is a continuing need for novel compositions and methods for Hsp90 inhibitors. This disclosure addresses that need.

SUMMARY

In a first aspect, the disclosure is of a compound have the structure of Formula (I) or (II):

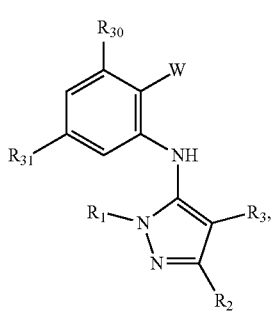

(I)

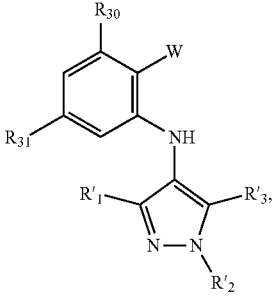

(II)

or stereoisomers, tautomers, or a pharmaceutically acceptable salt or ester thereof. $R_{30}$ and $R_{31}$ are independently selected from H, OH, halide, alkyl, alkenyl, alkynyl, alkoxy, acyl, cycloalkyl, heterocycle, aryl, protected hydroxyl, or benzyl. $R_1$, $R_2$, $R_3$, $R'_1$, $R'_2$ and $R'_3$ are independently selected from the H, OH, protected hydroxyl, $—CO_2H$, amide, alkyl, alkenyl, alkynyl, alkoxy, acyl, cycloalkyl, heterocycle, aryl, or benzyl. W is $—C(O)NR_4R_5$ or $—C(O)Z$ wherein Z is an aryl, heteroaryl, cycloalkyl or hererocyclyoxazol; and W and any one of $R_1$, $R_2$, $R_3$, $R'_1$, $R'_2$ or $R'_3$ can be connected. $R_4$ and $R_5$ are independently selected from H, alkyl, alkenyl, alkynyl, acyl, cycloalkyl, heterocycle, aryl, benzyl or $R_4$ and $R_5$ together with the nitrogen to which they are attached form a heterocyclic ring. Any alkyl, alkenyl, alkynyl, alkoxy, acyl, amide, cycloalkyl, and heterocycle is optionally substituted with one or more substituents independently selected from the group consisting of halogen, —OH, alkyl, O-alkyl, $—NR^AR^B$, —S-alkyl, —SO-alkyl, $—SO_2$-alkyl, alkenyl, alkynyl, aryl, heteroaryl, cycloalkyl or heterocycle; and the alkenyl, alkynyl, or acyl group optionally includes —O—, —S—, $—SO_2—$, $—N(R^E)—$ substituting one or more carbons in the carbon chain. Wherein any of the aryl, benzyl or heteroaryl, whether alone or as part of a substituent group, is optionally substituted with one or more substituents independently selected from the group consisting of halogen, OH, alkyl, O-alkyl, —COOH, $—C(O)—C_{1-4}$ alkyl, $—C(O)O—C_{1-4}$ alkyl, $—NR^CR^D$, —S-alkyl, —SO-alkyl and $—SO_2$-alkyl; wherein $R^A$, $R^B$, $R^C$, $R^D$, and $R^E$ are each independently selected from hydrogen and $C_{1-4}$ alkyl.

A second aspect of the disclosure is a pharmaceutical composition comprising a compound according to the first aspect and a pharmaceutically acceptable carrier, diluent or excipient.

A third aspect of the disclosure is the preparation of compounds having formula (I-H$_2$) and a fourth aspect of the disclosure is the preparation of compounds having formula (II-H$_2$). The method for preparing (I-H$_2$) comprises: providing a solution of a compound having formula (VI) and (VII) in the presence of a catalyst to provide protected product (I'), and de-protecting (I') to afford (I-H$_2$). The method for preparing compound (II-H$_2$) comprises: providing a solution of a compound having formula (VI) and (VII) in the presence of a noble metal catalyst to provide protected product (II'), and de-protecting (II') to afford (II-H$_2$). The structures are as follows:

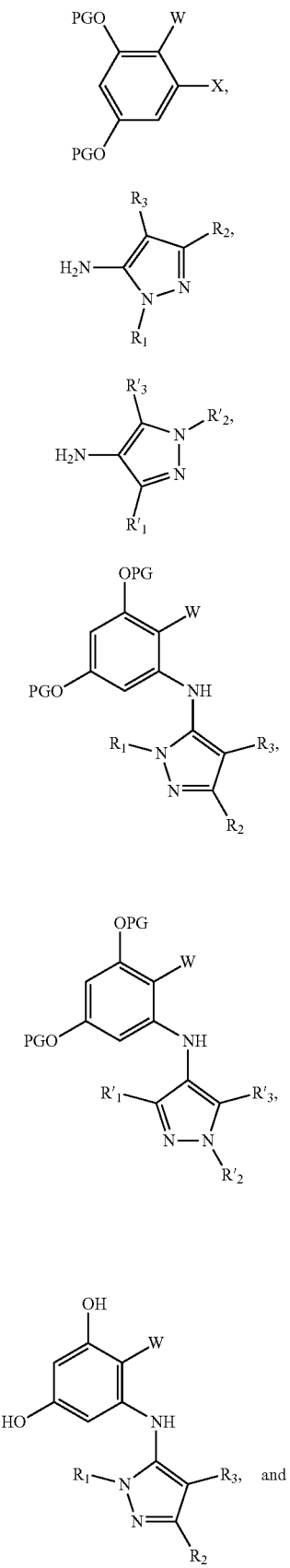

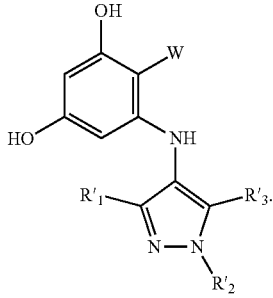

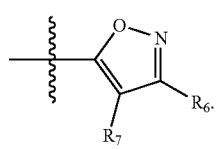

PG is a protecting group. X is a halide selected from chlorine, bromine or iodine. $R_1$, $R_2$, $R_3$, $R'_1$, $R'_2$ and $R'_3$ are independently selected from the group consisting of H, OH, protected hydroxyl, —$CO_2H$, amide, alkyl, alkenyl, alkynyl, alkoxy, acyl, cycloalkyl, heterocycle, aryl, or benzyl. W is —$C(O)NR_4R_5$ or oxazol (Ao), $R_4$ and $R_5$ are independently selected from H, alkyl, alkenyl, alkynyl, acyl, cycloalkyl, heterocycle, aryl, benzyl or $R_4$ and $R_5$ together with the nitrogen to which they are attached form a heterocyclic ring. $R_7$ and $R_8$ independently selected from H, OH, protected hydroxyl, —$CO_2H$, alkyl, alkenyl, alkynyl, alkoxy, acyl, amide, cycloalkyl, heterocycle, aryl, or benzyl. wherein any alkyl, alkenyl, alkynyl, alkoxy, acyl, cycloalkyl, is optionally substituted with one or more substituents independently selected from the group consisting of halogen, —OH, alkyl, O-alkyl, —$NR^AR^B$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —$N(R^E)$-substituting one or more carbons in the carbon chain. Wherein any aryl, benzyl or heteroaryl, whether alone or as part of a substituent group, is optionally substituted with one or more substituents independently selected from the group consisting of halogen, OH, alkyl, O-alkyl, —COOH, —C(O)—$C_{1-4}$ alkyl, —C(O)O—$C_{1-4}$ alkyl, —$NR^CR^D$, —S-alkyl, —SO-alkyl and —$SO_2$-alkyl; $R^A$, $R^B$, $R^C$, $R^D$, and $R^E$ are each independently selected from hydrogen and $C_{1-4}$ alkyl.

A fifth aspect of the disclosure is a method of inhibiting or treating fungal infection in a subject in need thereof. The method comprises administering to the subject a therapeutically effective amount of the compound according to the first aspect or the pharmaceutical composition according to the second aspect.

A sixth aspect of the disclosure is a method of inhibiting fungal growth or survival, the method comprising contacting a fungus with one or more of the compounds according to the first aspect.

A seventh aspect of the disclosure is a method of treating Hsp90 related disease or disorder in a subject in need thereof, the method comprising: administering to the subject a therapeutically effective amount of a compound according to the first aspect or the pharmaceutical composition according to the second aspect.

The compounds and preparation methods herein provide compounds having a wide variety of functionality and are shown to be efficiently synthesized. These compounds are effective for the treatment of various conditions such as fungal infections and Hsp90 related diseases.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 3C compares compound selectivity patterns between the two fungi.

FIGS. 4A and 4B show biological activity of some fungal-selective inhibitors.

DETAILED DESCRIPTION

Figure 1A:
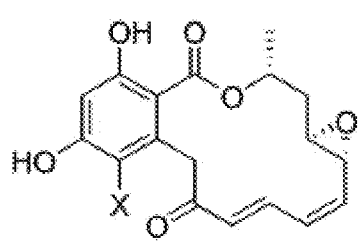
FIG. 1A shows structures of macrolactone Hsp90 inhibitors and a fungal-selective oxime derivative.
Figure 1A:
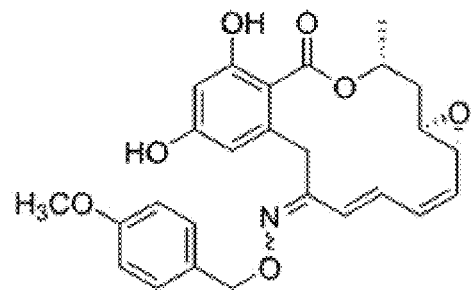

The present disclosure relates to resorcylate aminopyrazoles and methods for preparation of resorcylate aminopyrazoles. In addition, the use of these compounds for treatment of Hsp90 dependent conditions are described.

In one embodiment the aminopyrazoles are compounds having the structure of Formula (I) or (II):

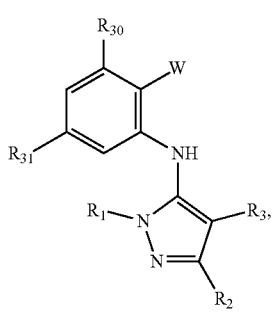

(I)

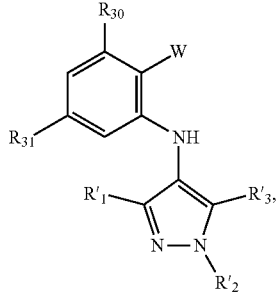

(II)

or stereoisomers, tautomers, or a pharmaceutically acceptable salt or ester thereof. $R_{30}$ and $R_{31}$ are independently selected from H, OH, halide, alkyl, alkenyl, alkynyl, alkoxy, acyl, cycloalkyl, heterocycle, aryl, protected hydroxyl, or benzyl. $R_1$, $R_2$, $R_3$, $R'_1$, $R'_2$ and $R'_3$ are independently selected from the H, OH, protected hydroxyl, —CO$_2$H, amide, alkyl, alkenyl, alkynyl, alkoxy, acyl, cycloalkyl, heterocycle, aryl, or benzyl. W is —C(O)NR$_4$R$_5$ or —C(O)Z wherein Z is an aryl, heteroaryl, cycloalkyl or hererocycly-oxazol; and W and any one of $R_1$, $R_2$, $R_3$, $R'_1$, $R'_2$ or $R'_3$ can be connected. $R_4$ and $R_5$ are independently selected from H, alkyl, alkenyl, alkynyl, acyl, cycloalkyl, heterocycle, aryl, benzyl or $R_4$ and $R_5$ together with the nitrogen to which they are attached form a heterocyclic ring. Any alkyl, alkenyl, alkynyl, alkoxy, acyl, amide, cycloalkyl, and heterocycle is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or acyl group optionally includes —O—, —S—, —SO$_2$—, —N(R$^E$)— substituting one or more carbons in the carbon chain. Wherein any of the aryl, benzyl or heteroaryl, whether alone or as part of a substituent group, is optionally substituted with one or more substituents independently selected from the group consisting of halogen, OH, alkyl, O-alkyl, —COOH, —C(O)—C$_{1-4}$ alkyl, —C(O)O—C$_{1-4}$ alkyl, —NR$^C$R$^D$, —S-alkyl, —SO-alkyl and —SO$_2$-alkyl; wherein R$^A$, R$^B$, R$^C$, R$^D$, and R$^E$ are each independently selected from hydrogen and C$_{1-4}$ alkyl.

As used herein, the term "alkyl", whether alone or as part of a substituent group, refers to a saturated C$_1$—C$_n$ carbon chain, wherein the carbon chain can be straight or branched; wherein the number of carbons in the chain can be 1, 2, 3, 4, 5, 6, 7, 8, 9 or 10. Suitable examples include, but are not limited to methyl, ethyl, propyl, isopropyl, butyl, isobutyl, sec-butyl, tert-butyl, n-pentyl and n-hexyl.

As used herein, the term "alkenyl", whether alone or as part of a substituent group, refers to a C$_2$—C$_n$ carbon chain, wherein the carbon chain can be straight or branched, wherein the carbon chain contains at least one carbon-carbon double bond, and wherein the number of carbons in that chain can be 2, 3, 4, 5, 6, 7, 8, 9, or 10.

As used herein, the term "alkynyl", whether alone or as part of a substituent group, refers to a C$_2$—C$_n$ wherein the carbon chain can be straight or branched, wherein the carbon chain contains at least one carbon-carbon triple bond, and wherein the number of carbons in the chain can be 2, 3, 4, 5, 6, 7, 8, 9, or 10.

As used herein, the term "aryl", whether alone or as part of a substituent group, refers to an unsubstituted carbocylic aromatic ring comprising between 6 to 14 carbon atoms. Suitable examples include, but are not limited to, phenyl, and naphthyl.

As used herein, the term "protected hydroxyl" refers to a hydroxyl group substituted with a suitably selected oxygen protecting group. More particularly, a "protected hydroxyl" refers to a substituent group of the Formula OPG wherein PG is a suitably selected oxygen protecting group. During any of the processes for preparation of the compounds of the present disclosure it can be necessary and/or desirable to protect sensitive or reactive groups on any of the molecules concerned. This can be achieved by means of conventional protecting groups, such as those described in "Protective Groups in Organic Chemistry", ed. J. F. W. McOmie, Plenum Press, 1973; and T. W. Greene & P. G. M. Wuts, Protective Groups in Organic Synthesis, John Wiley & Sons, 1991. The protecting groups can be removed at a convenient subsequent stage using methods known from the art.

As used herein, the term "oxygen protecting group" refers to a group which can be attached to an oxygen atom to protect said oxygen atom from participating in a reaction and which can be readily removed following the reaction. Suitable oxygen protecting groups include, but are not limited to, acetyl, benzoyl, t-butyl-dimethylsilyl, trimethylsilyl (TMS), MOM, and THP. Other suitable oxygen protecting groups can be found in texts such as "Protective Groups in Organic Synthesis," T. W. Greene & P. G. M. Wuts, John Wiley & Sons, 1991.

As used herein, the term "nitrogen protecting group" refers to a group which can be attached to a nitrogen atom to protect the said nitrogen atom from participating in a reaction and which can be readily removed following the reaction. Suitable nitrogen protecting groups include, but are not limited to, carbamate groups of the Formula —C(O)O—R wherein R can be methyl, ethyl, tert-butyl, benzyl, phenylethyl, $CH_2$=CH—$CH_2$, and the like; amides groups of the Formula C(O)—R' wherein R' can be methyl, phenyl, trifluoromethyl, and the like; N-sulfonyl derivatives groups of the Formula $SO_2$—R" wherein R" can be tolyl, phenyl, trifluoromethyl, 2,2,5,7,8-pentamethylchroman-6-yl-, 2,3,6-trimethyl-4-methoxybenzene, and the like. Other suitable nitrogen protecting groups can be found in texts such as T. W. Greene & P. G. M. Wuts, "Protective Groups in Organic Synthesis", John Wiley & Sons, 1991.

As used herein, the term "acyl" refers to a group of the formula CO—$C_n$ wherein $C_n$ represent a straight or branched alkyl chain wherein n can be 1, 2, 3, 4, 5, 6, 7, 8, 9, or 10.

As used herein, an "amide" or "amido" refers to a group containing a carbonyl group linked to a nitrogen atom. The amide group is represented by RC(O)NR'R". In some embodiments the amide has a formula —NHC(O)—$C_n$, or —C(O)NH—$C_n$, wherein $C_n$ represent a straight, branched and optionally substituted alkyl chain wherein n can be 1, 2, 3, 4, 5, 6, 7, 8, 9, or 10. In some options the hydrogen (H) atom is replaced by a second alkyl chain Cm which is a straight, branched and optionally substituted alkyl chain wherein n can be 1, 2, 3, 4, 5, 6, 7, 8, 9, or 10. In some embodiments the amide has a formula —C(O)NH—$C_n$. In some embodiments the alkyl chains represented by $C_n$ and Cm are linked, for example making a cyclic structure.

As used herein, the term "heteroaryl" refers to any five or six membered monocyclic aromatic ring structure containing at least one heteroatom selected from the group consisting of O, N and S, and optionally containing one to three additional heteroatoms independently selected from the group consisting of O, N and S; or a nine- or ten-membered bicyclic aromatic ring structure containing at least one heteroatom selected from the group consisting of O, N and S, and optionally containing one to four additional heteroatoms independently selected from the group consisting of O, N, and S. The heteroaryl group can be attached at any heteroatom or carbon atom of the ring such that the result is a stable structure. Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl and pteridinyl.

As used herein "cycloalkyl" refers to a stable non-aromatic monocyclic or polycyclic hydrocarbon radical consisting solely of carbon and hydrogen atoms. The cycloalkyl can be a monocyclic, bicyclic, tricyclic or tetracyclic ring system, which may include fused, spiro or bridged ring systems, having from three to fifteen carbon atoms, in some embodiments having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo [2.2.1]heptanyl, and the like.

As used herein "heterocyclyl", "heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused, spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

The groups of the present disclosure can be unsubstituted or substituted, as herein defined. In addition, the substituted groups can be substituted with one or more groups such as a $C_1$-$C_6$ alkyl, $C_{1-4}$ alkyl, —O—$C_{1-4}$ alkyl, hydroxyl, amino, ($C_{1-4}$ alkyl)amino, di($C_{1-4}$ alkyl)amino, —S—($C_{1-4}$ alkyl), —SO—($C_{1-4}$ alkyl), $SO_2$ ($C_{1-4}$alkyl), halogen, aryl, heteroaryl, and the like.

With reference to substituents, the term "independently" means that when more than one of such substituents is possible, such substituents can be the same or different from each other.

As used herein "Amino" refers to a —$NH_2$ substituent.

As used herein "Carboxyl" refers to the —$CO_2H$ substituent.

As used herein "Carbonyl" refers to a —C(O)—, —(CO)— or —C(=O)— group. All notations are used interchangeably within the specification.

As used herein "Cyano" refers to the —C≡N substituent.

As used herein "Hydroxy" or "hydroxyl" refers to the —OH substituent.

As used herein "Oxo" refers to a =O substituent.

As used herein a "halide" can be fluorine, chlorine, bromine or iodine.

As used herein "Thio" or "thiol" refer to an —SH substituent. Compound words have the meaning of the individual functional groups or fragments as would be understood in the art. For example, "hydroxyalkyl" refers to the -(alkyl)-OH substituent, "thioalkyl" refers to the -(alkyl)-SH substituent, "cyanoalkylene" refers to the -(alkylene)C≡N substituent; "hydroxyalkylene" refers to the -(alkylene)OH substituent; "arylmethoxy" refers to a methoxy substituted aryl group.

The compound in some embodiments can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, some embodiments encompass compounds and their uses as described herein in the form of their optical isomers, diastereoisomers and mixtures thereof, including a racemic mixture. Optical isomers of the compounds according to some embodiments can be obtained by known techniques such as asymmetric synthesis, chiral chromatography, or via chemical separation of stereoisomers through the employment of optically active resolving agents.

In some embodiments the compounds have structure (I) where $R_1$, $R_2$, and $R_3$ are independently selected from H, methyl, ethyl, butyl, phenyl, isopropyl, t-butyl, cyclopropyl, cyclopentyl, cyclohexyl, phenyl-2,3-disubstituted, phenyl-2,5-disubstituted, phenyl-2,4-disubstituted, phenyl-3,4-disubstituted, phenyl-2-methyl, phenyl-4-methyl, phenyl-4-methoxy, phenyl-3-methoxy, phenyl-2-methoxy, phenyl-2-$CF_3$, phenyl-3-methyl, phenyl-2-fluro, phenyl-3-chloro, phenyl-2-$OCF_3$, phenyl-4-fluoro, phenyl-2,6-disubstituted, phenyl-3-fluoro, phenyl-4-t-butyl, phenyl-3-$OCF_3$, phenyl-4-$CF_3$, 2-pyridine, 3-pyridine, 3-furan, phenyl-4-$OCF_3$, —$CH_2CO_2H$, —$CH_2$-cyclohexyl, benzyl, benzyl-2-chloro, benzyl-4-$CF_3$, benzyl-4-isopropyl, benzyl-4-methyl, benzyl-2-methyl, benzyl-4-isopropyl, —$CH_2$-2-furan, $CH_2$C(O)NHMe, or benzyl-4-methoxy. In some embodiments $R_1$ is selected from phenyl, methyl, —$CH_2CO_2H$, phenyl-4-methoxy, —$CH_2$-cyclohexyl, t-butyl, isopropyl, isobutyl, cyclohexyl, benzyl, benzyl-2-chloro, benzyl-4-$CF_3$, benzyl-4-isopropyl, benzyl-4-methyl, benzyl-2-methyl, benzyl-4-isopropyl, —$CH_2$-2-furan, $CH_2$C(O)NHMe, benzyl-4-methoxy, or cyclopentyl. In some embodiments $R_2$ is selected from H, methyl, ethyl, t-butyl, phenyl, isopropyl, cyclopropyl, cyclopentyl, cyclohexyl, phenyl-2,3-disubstituted, phenyl-2,5-disubstituted, phenyl-2-methyl, phenyl-3-methyl, phenyl-4-methyl, phenyl-2-methoxy, phenyl-3-methoxy, phenyl-2-$CF_3$, phenyl-4-$CF_3$, phenyl-2-fluro, phenyl-3-chloro, phenyl-2-$OCF_3$, phenyl-3-fluoro, phenyl-4-fluoro, phenyl-2,6-disubstituted, phenyl-4-t-butyl, phenyl-3-$OCF_3$, phenyl-4-$OCF_3$, 2-pyridine, 3-pyridine, or 3-furan. In some embodiments $R_3$ is selected form H, methyl, isopropyl, phenyl, benzyl.

In some embodiments the compound has structure (II) and $R'_1$, $R'_2$, and $R'_3$ are independently selected from H, methyl, ethyl, isopropyl, phenyl, phenyl-2,4-disubstituted, phenyl-2,3-disubstituted, phenyl-3,5-disubstituted, phenyl-3,4-disubstituted, phenyl-2-$CF_3$, phenyl-3-$CF_3$, phenyl-2-methoxy, phenyl-3-methyl, phenyl-2-methyl, and —$CH_2CH_2NMe_2$. In some embodiments $R'_1$ is selected from H, methyl, phenyl-3-$CF_3$, phenyl-2-methoxy, phenyl-2-$CF_3$, phenyl, i-propyl, phenyl-3-methyl, ethyl, phenyl-2-methyl, and —$CH_2CH_2NMe_2$. In some embodiments $R'_2$ is selected from H, methyl, i-propyl, ethyl phenyl-3-$CF_3$, phenyl-2-methoxy, phenyl-3-methyl, phenyl-2-methoxy, phenyl-2-$CF_3$, phenyl, phenyl-2-methyl, and —$CH_2CH_2NMe_2$. In some embodiments $R'_3$ is selected from methyl and H.

In some embodiments the compound has structure (I) or (II), and W is —C(O)$NR_4R_5$.

In some embodiments the compound has structure (I) or (II), and where W is —C(O)Z, and where Z is a heterocyclic ring of structure (III);

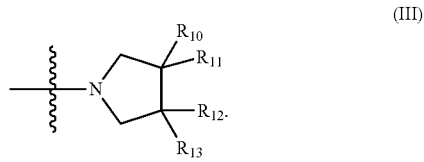

(III)

$R_{10}$, $R_{11}$, $R_{12}$, and $R_{13}$, are independently selected from the group consisting of H, OH, protected hydroxyl, —$CO_2H$, amide, halide, alkyl, alkenyl, alkynyl, alkoxy, acyl, cycloalkyl, heterocycle, aryl, or benzyl; any $R_{10}$, $R_{11}$, $R_{12}$, and $R_{13}$ and carbons to which they are attached can form a spiro or fused ring structure.

In some embodiments the compound has structure (I) or (II), and W is —C(O)Z, where Z is a heterocyclic ring of structure (IV);

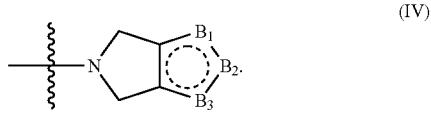

(IV)

$B_2$ and $B_3$ are independently $CR_{15}$, $CR_{16}$, $NR_{17}$ or N. $R_{15}$, $R_{16}$, $R_{17}$ are independently selected from the group consisting of H, OH, protected hydroxyl, —$CO_2H$, amide, halide, alkyl, alkenyl, alkynyl, alkoxy, acyl, cycloalkyl, heterocycle, aryl, or benzyl. In some embodiments two of $B_1$, $B_2$ and $B_3$ are $CR_{15}$ and $CR_{16}$, and the remaining $B_1$, $B_2$ or $B_3$ is $NR_{17}$.

In some embodiments one of $B_1$, $B_2$ and $B_3$ is $CR_{15}$, one of $B_1$, $B_2$ and $B_3$ is N, and one of $B_1$, $B_2$ and $B_3$ is $NR_{17}$.

In some embodiments the compound has structure (I) or (II), and W is —C(O)Z, where Z is a heterocyclic ring of structure (V);

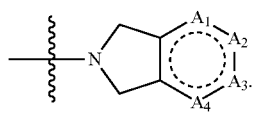

(V)

$A_1$ is N, C(O), $NR_{24}$ or $CR_{20}$; $A_2$ is N, C(O), $NR_{24}$ or $CR_{21}$; $A_3$ is N, C(O), NH or $CR_{22}$; $A_4$ is N, C(O), $NR_{24}$ or $CR_{23}$. $R_{20}$, $R_{21}$, $R_{22}$ and $R_{23}$ are independently selected from the group consisting of H, OH, protected hydroxyl, —$CO_2H$, amide, halide, alkyl, alkenyl, alkynyl, alkoxy, acyl, cycloalkyl, heterocycle, aryl, or benzyl. $R_{24}$ is H, OH, protected hydroxyl, —$CO_2H$, amide, halide, alkyl, alkenyl, alkynyl, alkoxy, acyl, cycloalkyl, heterocycle, aryl, or benzyl.

In some embodiments W is an oxazol amide having the structure of (Ao),

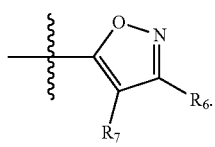

(Ao)

$R_7$ and $R_6$ are independently selected from H, OH, protected hydroxyl, —$CO_2H$, alkyl, alkenyl, alkynyl, alkoxy, acyl, amide, cycloalkyl, heterocycle, aryl, or benzyl. Any alkyl, alkenyl, alkynyl, alkoxy, acyl, amide, cycloalkyl, and heterocycle is optionally substituted with one or more substituents independently selected from the group consisting of halogen, —OH, alkyl, O-alkyl, —$NR^IR_J$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —N($R^K$)— substituting one or more carbons in the carbon chain; wherein $R^I$, $R^J$, and $R^K$ are each independently selected from hydrogen and $C_{1-4}$ alkyl.

In some embodiments the compound has structure (I) or (II) and W is oxazole amide ($A_{30}$) having structure,

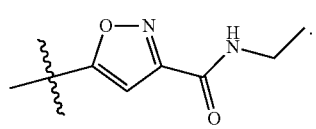

(A30)

In some other embodiments W is —C(O)$NR_4R_5$ wherein $R_4$ and $R_5$ are independently selected from H and ethyl; or methyl and —$CH_2$-3-pyridine; or H and benzyl; or methyl and benzyl; or methyl and $CH_2$-oxazole; or methyl and —$CH_2$-pyran; or methyl and —$CH_2$-4-pyridine; or methyl and —$CH_2$-cyclopropyl. In some embodiments W is —C(O)Z, where Z is a heterocyclic ring selected from:

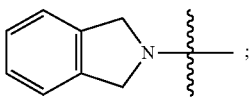
(A1)

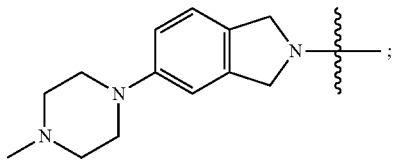
(A2)

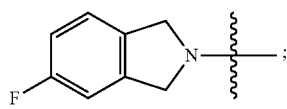
(A3)

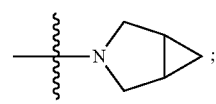
(A4)

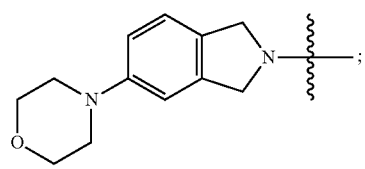
(A5)

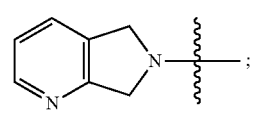
(A6)

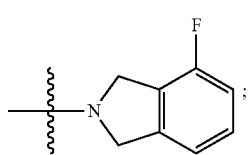
(A7)

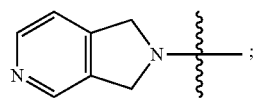
(A8)

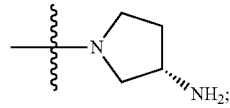
(A9)

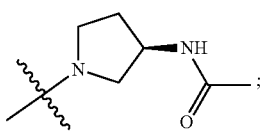
(A10)

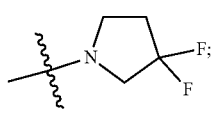
(A11)

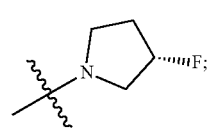
(A12)

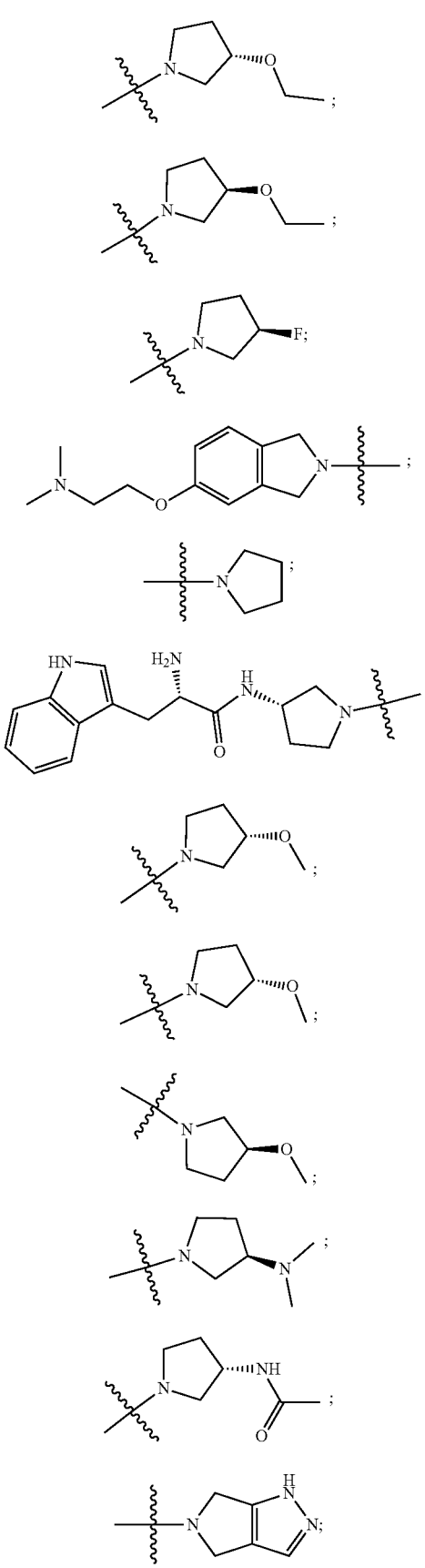
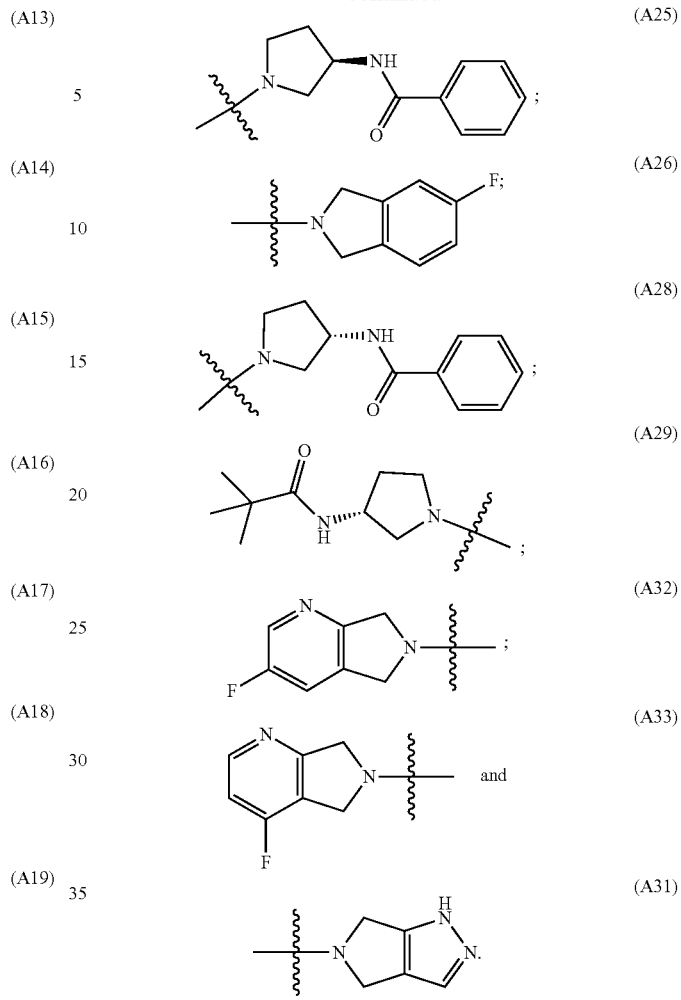

In some embodiments the compound has compound has structure (I), wherein W is oxazole amide (A30) or W is —C(O)NR$_4$R$_5$ wherein R$_4$ and R$_5$ are independently selected from H and ethyl; or methyl and —CH$_2$-3-pyridine; or H and benzyl; or methyl and CH$_2$Oxazole; or methyl and CH$_2$-pyran; or methyl and —CH$_2$-4-pyridine; or W is —C(O)Z, where Z is a heterocyclic ring selected from (A1); (A2); (A3); (A4); (A5); (A6); (A7); (A8); (A9); (A10); (A11); (A12); (A13); (A14); (A15); (A16); (A17); (A18); (A22); (A23); (A24); (A25); (A26); (A28); and (A29).

In some embodiments the compound has structure (II), and W is oxazole amide (A30), or W is —C(O)Z, where Z is a heterocyclic ring selected from; (A1); (A14); (A19); (A15); (A12); (A21); (A11); (A13) (A4); (A10); (A22); and (A23).

In some embodiments W is not an oxazole (Ao).

In some embodiments of compounds (I) and (II) R$_{30}$ and R$_{31}$ are independently OH and a halide. In some embodiments R$_{30}$ and R$_{31}$ are independently OH, F, C$_1$ or Br. In some embodiments R$_{30}$ and R$_{31}$ are OH. In some embodiments one of R$_{30}$ and R$_{31}$, or both of R$_{30}$ and R$_{31}$ are not iodine, alkyl, alkenyl, alkynyl, alkoxy, acyl, cycloalkyl, heterocycle, aryl, protected hydroxyl, or benzyl. Without being bound by a specific theory functional groups that are about larger than a hydroxyl group bind poorly or not at all to Hsp90 due to size constraints of the binding site.

In some embodiments the compound has structure (I) and is further defined as structure (X);

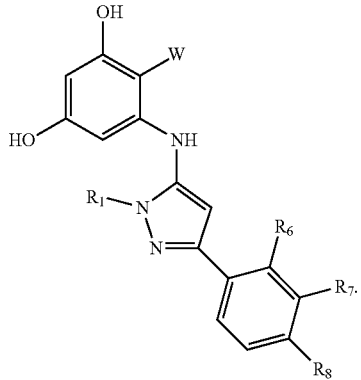

(X)

W is —C(O)Z, where Z is a heterocyclic ring selected from; (A1), (A6), (A24); (A32), or (A33). $R_1$, $R_6$, $R_7$, $R_8$ are independently selected from H, alkyl, and alkoxy. Any alkyl or alkoxy is optionally substituted with one or more substituents independently selected from the group consisting of halogen, —OH, alkyl, O-alkyl, —$NR^F R^G$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —N($R^H$) substituting one or more carbons in the carbon chain. $R^F$, $R^G$, and $R^H$ are each independently selected from hydrogen and $C_{1-4}$ alkyl. In some embodiments $R_1$, $R_6$, $R_7$, $R_8$ are independently selected from H, methyl, isopropyl, t-butyl, —$CF_3$, —$OCH_3$, or —$OCF_3$. In some embodiments $R_6$ and $R_7$ are H. In some embodiments $R_1$ is methyl and $R_8$ is selected from methyl, t-butyl, —$CF_3$, —$OCH_3$, or —$OCF_3$. In some embodiments $R_7$ and $R_8$ are H. In some embodiments $R_1$ is methyl, and $R_6$ is selected from methyl, t-butyl, —$CF_3$, —$OCH_3$, or —$OCF_3$. In some embodiments $R_6$ and $R_8$ are H. In some embodiments $R_1$ is methyl and $R_7$ is methyl, —$CF_3$, or —$OCH_3$.

In some embodiments the compound has structure (II) and is further defined as structure (XI);

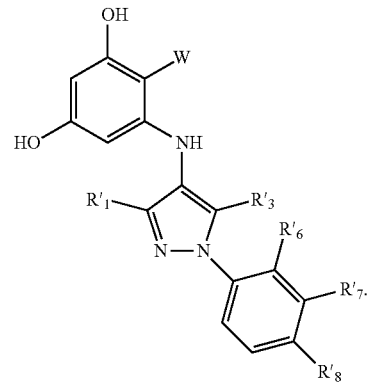

(XI)

W is —C(O)Z, where Z is (A1). $R'_1$, $R'_3$, $R'_6$, $R'_7$, $R'_8$ are independently selected from H, alkyl, and alkoxy. alkyl or alkoxy is optionally substituted with one or more substituents independently selected from the group consisting of halogen, —OH, alkyl, O-alkyl, —$NR^L R^M$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —N($R^N$)— substituting one or more carbons in the carbon chain. $R^L$, $R^M$, and $R^N$ are each independently selected from hydrogen and $C_{1-4}$ alkyl. In some embodiments $R'_1$ and $R'_3$ are independently H or alkyl; and $R'_6$, $R'_7$ and R's are independently H, alkyl, alkoxy or —$CF_3$. In some embodiments $R'_6$ is alkoxy or —$CF_3$.

In some embodiments the compound is any compound selected from Table 1. In Table 1 the compound designations are given and the structure is listed according to their Simplified Molecular Input Line Entry System (SMILES). SMILES allows rigorous structure specification by use a compact use of natural grammar as described in detail by D. Weiniger "SMILES, a Chemical Language and Information System. 1. Introduction to Methodology and Encoding Rules" *J. Chem. J Inf. Comput. Sci.*, Vol. 28, No. 1, 1988, pages 31-36; the entirety of which are incorporated herein by reference.

TABLE 1

Compounds

| Comp. | SMILES |
|---|---|
| ACSM01497 | CC1=CC(=CC=C1)C1=NN(C(NC2=CC(O)=CC(O)=C2C(=O)N2CC3=C(C2)C=CC=C3)=C1)C(C)(C)C |
| 21 | COC1=CC=C(CN2N=C(C=C2NC2=CC(O)=CC(O)=C2C(=O)N2CC3=C(C2)C=CC=C3)C2=CC=C(C2)C=C1 |
| ACSM01362 | CN1N=C(C=C1NC1=CC(O)=CC(O)=C1C(=O)N1CC2=C(C1)C=CC=C2)C1=CC=CC(C1)=C1 |
| ACSM01132 | COC1=CC=CC=C1C1=NN(C)C(NC2=CC(O)=CC(O)=C2C(=O)N2CC3=C(C2)C=CC=C3)=C1 |
| ACSM01273 | CN1N=C(C=C1NC1=CC(O)=CC(O)=C1C(=O)N1CC2=C(C1)C=CC=C2)C1=CC=CC(C)=C1F |
| ACSM01131 | CN1N=C(C=C1NC1=CC(O)=CC(O)=C1C(=O)N1CC2=C(C1)C=CC=C2)C1=CC=C(Cl)C=C1 |
| ACSM01265 | COC1=CC=CC=C1C1=NN(C(C)C)C(NC2=C(C(=O)N3CC4=C(C3)C=CC=C4)C(O)=CC(O)=C2)=C1 |
| ACSM01266 | COC1=CC=CC=C1C1=NN(C2CCCCC2)C(NC2=CC(O)=CC(O)=C2C(=O)N2CC3=C(C2)C=CC=C3)=C1 |
| ACSM01496 | COC1=CC(=CC=C1)C1=NN(C(NC2=CC(O)=CC(O)=C2C(=O)N2CC3=C(C2)C=CC=C3)=C1)C(C)(C)C |
| 29 | COC1=CC=C(CN2N=C(C=C2NC2=CC(O)=CC(O)=C2C(=O)N2CC3=C(C2)C=C(F)C=C3)C2=CC=CC=C2)C=C1 |
| 65 | OC1=CC(O)=C(C(=O)N2CC3=C(C2)C=CC=C3)C(NC2=CC=NN2CC2CCCCC2)=C1 |
| 27 | COC1=CC=C(CN2N=C(C=C2NC2=CC(O)=CC(O)=C2C(=O)N2CC3=C(C2)(F)C=C=C3)C2=CC=CC=C2)C=C1 |
| ACSM01268 | CN1N=C(C=C1NC1=CC(O)=CC(O)=C1C(=O)N1CC2=C(C1)C=CC=C2)C1=CC(C)=CC=C1F |
| ACSM01267 | COC1=CC=CC=C1C1=NN(C2CCCC2)C(NC2=CC(O)=CC(O)=C2C(=O)N2CC3=C(C2)C=CC=C3)=C1 |
| 49 | COC1=CC=C(CN2N=C(C=C2NC2=CC(O)=CC(O)=C2C(=O)N2CC3=C(C2)C=CC=C3)C(C)(C)C)C=C1 |
| ACSM01473 | CN1N=C(C=C1NC1=CC(O)=CC(O)=C1C(=O)N1CC2=C(C1)C=CC=C2)C1=CC(F)=CC=C1C |
| ACSM01275 | COC1=CC=CC=C1C1=NN(CC(C)C)C(NC2=C(C(=O)N3CC4=C(C3)C=CC=C4)C(O)=CC(O)=C2)=C1 |
| ACSM01498 | CC(C)(C)N1N=C(C=C1NC1=CC(O)=CC(O)=C1C(=O)N1CC2=C(C1)C=CC=C2)C1=CC=CC(=C1)C(F)(F)F |
| ACSM01305 | OC1=CC(O)=C(C(=O)N2CC3=C(C2)C=CC=C3)C(NC2=CC(=NN2C2=CC=CC=C2)C2=CC=CC=C2)=C1 |

TABLE 1-continued

Compounds

| Comp. | SMILES |
|---|---|
| ACSM01474 | CN1N=C(C=C1NC1=C(C(=O)N2CC3=C(C2)C=CC=C3)C(O)=CC(O)=C1)C1=CC=CC=C1C(F)(F)F |
| ACSM01269 | CN1N=C(C=C1NC1=CC(O)=CC(O)=C1C(=O)N1CC2=C(C1)C=CC=C2)C1=CC=CC(F)=C1F |
| ACSM01505 | CC(C)(C)N1N=C(C=C1NC1=CC(O)=CC(O)=C1C(=O)N1CC2=C(C1)C=CC=C2)C1=CC=CC(OC(F)(F)F)=C1 |
| 106 | CN1N=C(C=C1NC1=CC(O)=CC(O)=C1C(=O)N1CC2=C(C1)C=CC=C2)C1=CC=CC=C1C |
| ACSM01345 | CN1N=C(C=C1NC1=CC(O)=CC(O)=C1C(=O)N1CC2=C(C1)C=CC=C2)C1=CC=CC(F)=C1 |
| ACSM01135 | CN1N=C(C=C1NC1=CC(O)=CC(O)=C1C(=O)N1CC2=C(C1)C=C(F)C=C2)C1=CC=CC=C1C |
| ACSM01270 | CN1N=C(C=C1NC1=CC(O)=CC(O)=C1C(=O)N1CC2=C(C1)C=CC=C2)C1=CC(F)=CC=C1F |
| 88 | CC1=NN(C(C=C2=CC=C(C)C=C2)C(NC2=CC(O)=CC(O)=C2C(=O)N2CC3=C(C2)C=CC=C3)=C1 |
| ACSM01274 | COC1=CC=CC=C1C1=NN(C(NC2=CC(O)=CC(O)=C2C(=O)N2CC3=C(C2)C=CC=C3)=C1)C(C)(C)C |
| ACSM01344 | CN1N=C(C=C1NC1=CC(O)=CC(O)=C1C(=O)N1CC2=C(C1)C=CC=C2)C1=CC=CC=C1F |
| ACSM01307 | CC(C)(C)C1=NN(C(NC2=CC(O)=CC(O)=C2C(=O)N2CC3=C(C2)C=CC=C3)=C1)C1=CC=CC=C1 |
| ACSM01372 | CN1N=C(C=C1NC1=C(C(=O)N2CC3=C(C2)C=NN3)C(O)=CC(O)=C1)C1=CC=CC=C1OC(F)(F)F |
| ACSM01278 | CN1N=C(C=C1NC1=CC(O)=CC(O)=C1C(=O)N1CC2=C(C1)C=CC=C2)C1=C(F)C=CC=C1F |
| ACSM01361 | CN1N=C(C=C1NC1=CC(O)=CC(O)=C1C(=O)N1CC2=C(C1)C=CC=C2)C1=CC=CC=C1Cl |
| ACSM01360 | CN1N=C(C=C1NC1=CC(O)=CC(O)=C1C(=O)N1CC2=C(C1)C=CC=C2)C1=CC=C(F)C=C1 |
| ACSM01503 | CN1N=C(C=C1NC1=C(C(=O)N2CC3=C(C2)C=CC=C3)C(O)=CC(O)=C1)C1=CC=CC=C1OC(F)(F)F |
| ACSM01348 | COC1=CC=CC=C1C1=NN(C)C(NC2=CC(C(=O)N3CC[C@@H](C3)NC(C)=O)C(O)=CC(O)=C2)=C1 |
| ACSM01368 | CN1N=C(C=C1NC1=C(C(=O)N2CC[C@H](N)C2)C(O)=CC(O)=C1)C1=CC=CC(OC(F)(F)F)=C1 |
| CMLD012896 | CCNC(=O)C1=C(O)C=C(O)C=C1NC1=CC(=NN1CC1=CC=C(OC)C=C1)C1=CC=CC=C1 |
| CMLD012892 | COC1=CC=C(CN2N=C(C=C2NC2=CC(O)=CC(O)=C2C(=O)N(C)CC2=CN=CC=C2)C2=CC=CC=C2)C=C1 |
| ACSM01365 | CN1N=C(C=C1NC1=C(C(=O)N2CC[C@H](N)C2)C(O)=CC(O)=C1)C1=CC=CC(C)=C1 |
| ACSM01499 | COC1=CC(=CC=C1)C1=NN(C)C(NC2=C(C(=O)N3CC[C@H](C3)NC(C)=O)C(O)=CC(O)=C2)=C1 |
| ACSM01366 | CN1N=C(C=C1NC1=C(C(=O)N2CC[C@H](N)C2)C(O)=CC(O)=C1)C1=CC=CC=C1 |
| ACSM01364 | CN1N=C(C=C1NC1=CC(O)=CC(O)=C1C(=O)N1CC[C@H](N)C1)C1=CC=CC(F)=C1 |
| ACSM01367 | COC1=CC(=CC=C1)C1=NN(C)C(NC2=CC(O)=CC(O)=C2C(=O)N3CC[C@H](N)C3)C(O)=CC(O)=C2)=C1 |
| ACSM01375 | COC1=CC(=CC=C1)C1=NN(C)C(NC2=CC(O)=CC(O)=C2C(=O)N2CC3=C(C2)C=C(C=C3)N2CCN(CC2)=C1 |
| ACSM01280 | CN1N=C(C=C1NC1=CC(O)=CC(O)=C1C(=O)N1CC2=C(C1)C=C(C=C2)N1CCOCC1)C1=CC=CC(C)=C1 |
| ACSM01301 | CN1N=CC=C1NC1=C(C(=O)N2CC3CC2C(O)=CC(O)=C1 |
| ACSM01376 | COC1=CC(=CC=C1)C1=NN(C)C(NC2=CC(O)=CC(O)=C2C(=O)N2CC3=C(C2)C=C(C=C3)N2CCOCC2)=C1 |
| ACSM01304 | CN1N=CC=C1NC1=C(C(=O)N2CCC(F)(F)C2)C(O)=CC(O)=C1 |
| ACSM01311 | CN1N=CC=C1NC1=C(C(=O)N2CC[C@H](F)C2)C(O)=CC(O)=C1 |
| ACSM01302 | CN1N=C(C)C=C1NC1=CC(O)=CC(O)=C1C(=O)N1CC2CC2C1 |
| ACSM01308 | CN1N=C(C)C=C1NC1=CC(O)=CC(O)=C1C(=O)N1CCC(F)(F)C1 |
| ACSM01333 | CCO[C@H]1CCN(C1)C(=O)C1=C(NC2=CC=NN2C)C=C(O)C=C1O |
| ACSM01336 | CCO[C@H]1CCN(C1)C(=O)C1=C(O)C=C(O)C=C1NC1=CC(C)=NN1C |
| ACSM01337 | CCO[C@@H]1CCN(C1)C(=O)C1=C(NC2=CC=NN2C)C=C(O)C=C1O |
| ACSM01340 | CCO[C@@H]1CCN(C1)C(=O)C1=C(O)C=C(O)C=C1NC1=CC(C)=NN1C |
| BUCMD00420 | COC1=CC=C(CN2N=C(C=C2NC2=CC(O)=CC(O)=C2C(=O)N(C)CC2CC2)C=C1 |
| BUCMD00433 | COC1=CC=C(CN2N=C(C=C2NC2=CC(O)=CC(O)=C2C(=O)N2CC3=C(C2)C=NC=C3)C2=CC=CC=C2)C=C1 |
| 131 | CN1N=C(C=C1NC1=CC(O)=CC(O)=C1C(=O)N1CC2=C(C1)N=CC=C2)C1=CC=C(OC(F)(F)F)C=C1 |
| 132 | CN1N=C(C=C1NC1=CC(O)=CC(O)=C1CC2=C(C1)C=NN2)C1=CC=C(OC(F)(F)F)C=C1 |
| 130 | CN1N=C(C=C1NC1=CC(O)=CC(O)=C1C(=O)N1CC2=C(C1)C=NN2)C1=CC=C(OC(F)(F)F)C=C1 |
| ACSM01349 | COC1=CC=CC=C1C1=NN(C)C(NC2=CC(C(=O)N3CC[C@@H](C3)NC(C)=O)C(O)=CC(O)=C2)=C1 |
| ACSM01350 | CO[C@@H]1CCN(C1)C(=O)C1=C(NC2=CC=NN2C)C2=CC=CC=C2OC)C=C(O)C=C1O |
| 23 | COC1=CC=C(CN2N=C(C=C2NC2=CC(O)=CC(O)=C2C(=O)N2CC3=C(C2)N=CC=C3)C2=CC=CC=C2)C=C1 |
| 121 | COC1=CC=CC=C1C1=NN(C)C(NC2=CC(O)=CC(O)=C2C(=O)N2CC3=C(C2)C=CC=C3)=C1 |
| 129 | CN1N=C(C=C1NC1=CC(O)=CC(O)=C1C(=O)N1CC2=C(C1)C=NN2)C1=CC=C(C=C1)C(C)(C)C |
| 126 | CN1N=C(C=C1NC1=CC(O)=CC(O)=C1C(=O)N1CC2=C(C1)C=NN2)C1=CC=C(C=C1)C(F)(F)F |
| 125 | CN1N=C(C=C1NC1=CC(O)=CC(O)=C1C(=O)N1CC2=C(C1)N=CC=C2)C1=CC=C(C=C1)C(F)(F)F |
| 117 | CN1N=C(C=C1NC1=CC(O)=CC(O)=C1C(=O)N1CC2=C(C1)C=NN2)C1=CC=CC(=C1)C(F)(F)F |
| ACSM01351 | CO[C@H]1CCN(C1)C(=O)C1=C(NC2=CC=NN2C)C2=CC=CC=C2OC)C=C(O)C=C1O |
| 128 | CN1N=C(C=C1NC1=CC(O)=CC(O)=C1C(=O)N1CC2=C(C1)N=CC=C2)C1=CC=CC(=C1)C(C)(C)C |
| 116 | CN1N=C(C=C1NC1=CC(O)=CC(O)=C1C(=O)N1CC2=C(C1)N=CC=C2)C1=CC=CC(=C1)C(F)(F)F |
| 95 | CC(C)(C)N1N=C(C=C1NC1=CC(O)=CC(O)=C1C(=O)N1CC2=C(C1)C=NN2)C1=CC=CC=C1 |
| 119 | CN1N=C(C=C1NC1=CC(O)=CC(O)=C1C(=O)N1CC2=C(C1)N=CC=C2)C1=CC=CC=C1 |
| 25 | COC1=CC=C(CN2N=C(C=C2NC2=CC(O)=CC(O)=C2C(=O)N2CC3=C(C2)C=NN3)C2=CC=CC=C2)C=C1 |
| 94 | CC(C)(C)N1N=C(C=C1NC1=CC(O)=CC(O)=C1C(=O)N1CC2=C(C1)N=CC=C2)C1=CC=CC=C1 |
| ACSM01491 | CN1N=C(C=C1NC1=CC(O)=CC(O)=C1C(=O)N1CC2=C(C1)C=NC=C2)C1=CC=CC=C1C(F)(F)F |
| ACSM01279 | CN1N=C(C=C1NC1=CC(O)=CC(O)=C1C(=O)N1CC2=C(C1)C=C(C=C2)N1CCN(C)CC1)C1=CC=CC(C)=C1 |
| ACSM01371 | COC1=CC=CC=C1C1=NN(C)C(NC2=C(C(=O)N3CC[C@@H](C3)N3(=O)[C@@H](N)CC3=CC=CC=C3)C(O)=CC(O)=C2)=C1 |
| 123 | COC1=CC=C(C=C1)C1=NN(C)C(NC2=CC(O)=CC(O)=C2C(=O)N2CC3=C(C2)C=NN3)=C1 |
| 120 | CN1N=C(C=C1NC1=CC(O)=CC(O)=C1C(=O)N1CC2=C(C1)C=NN2)C1=CC=C(C)C=C1 |
| 124 | CN1N=C(C=C1NC1=CC(O)=CC(O)=C1C(=O)N1CC2=C(C1)C=NN2)C1=CC=CC(=C1)C(F)(F)F |
| 122 | COC1=CC=C(C=C1)C1=NN(C)C(NC2=CC(O)=CC(O)=C2C(=O)N2CC3=C(C2)N=CC=C3)=C1 |
| 109 | CN1N=C(C=C1NC1=CC(O)=CC(O)=C1C(=O)N1CC2=C(C1)C=CC=C2)C1=CC=CC(C)=C1 |
| ACSM01373 | CN1N=C(C=C1NC1=C(C(=O)N2CC3=C(C2)C=NN3)C(O)=CC(O)=C1)C1=CC=CC(OC(F)(F)F)=C1 |
| 118 | CN1N=C(C=C1NC1=CC(O)=CC(O)=C1C(=O)N1CC2=C(C1)C=CC=C2)C1=CC=C(C)C=C1 |
| 111 | CN1N=C(C=C1NC1=CC(O)=CC(O)=C1C(=O)N1CC2=C(C1)C=NN2)C1=CC=CC(C)=C1 |
| 110 | CN1N=C(C=C1NC1=CC(O)=CC(O)=C1C(=O)N1CC2=C(C1)N=CC=C2)C1=CC=CC(C)=C1 |
| ACSM01487 | CN1N=C(C=C1NC1=CC(O)=CC(O)=C1C(=O)N1CC2=C(C1)C=C(C=C2)N1CCN(C)CC1)C1=CC=CC(=C1)C(F)(F)F |
| ACSM01271 | COC1=CC=CC=C1C1=NN(C)C(NC2=CC(C(=O)N3CC[C@H](N)C3)C(O)=CC(O)=C2)=C1 |
| 43 | COC1=CC=C(CN2N=CC=C2NC2=CC(O)=CC(O)=C2C(=O)N2CC3=C(C2)C=CC=C3)C2=CC=CC=C2)C=C1 |
| 115 | CN1N=C(C=C1NC1=CC(O)=CC(O)=C1C(=O)N1CC2=C(C1)C=CC=C2)C1=CC=CC(=C1)C(F)(F)F |
| 112 | COC1=CC=C(C=C1)C1=NN(C)C(NC2=CC(O)=CC(O)=C2C(=O)N2CC3=C(C2)C=CC=C3)=C1 |

TABLE 1-continued

Compounds

| Comp. | SMILES |
|---|---|
| 33 | COC1=CC=C(CN2N=C(C=C2NC2=CC(O)=CC(O)=C2C(=O)N2CC3=C(C2)C=C(NC2CCN(C)CC2)C=C3)C2=CC=CC=C2)C=C1 |
| BUCMD00438 | CCNC(=O)C1=NOC(=C1)C1=C(O)C=C(O)C=C1NC1=CC=NN1C |
| ACSM01347 | COC1=CC=CC=C1C1=NN(C)C(NC2=C(C(=O)N3CC4=C(C3)C=NC=C4)C(O)=CC(O)=C2)=C1 |
| 35 | COC1=CC=C(CN2N=C(C=C2NC2=CC(O)=CC(O)=C2C(=O)N2CC3=C(C2)C=C(OCCN(C)C)C=C3)C2=CC=CC=C2)C=C1 |
| 96 | OC1=CC(O)=C(C(=O)N2CC3=C(C2)N=CC=C3)C(NC2=CC(=NN2C2CCCCC2)C2=CC=CC=C2)=C1 |
| ACSM01262 | COC1=CC=CC=C1C1=NN(C)C(NC2=C(C(=O)N3CC4=C(C3)C=C(=C4)N3CCOCC3)C(O)=CC(O)=C2)=C1 |
| 113 | COC1=CC(=CC=C1)C1=NN(C)C(NC2=CC(O)=CC(O)=C2C(=O)N2CC3=C(C2)N=CC=C3)=C1 |
| 98 | CC(C)CN1N=C(C=C1NC1=CC(O)=CC(O)=C1C(=O)N1CC2=C(C1)N=CC=C2)C1=CC=CC=C1 |
| 103 | CN1N=C(C=C1NC1=CC(O)=CC(O)=C1C(=O)N1CC2=C(C1)C=CC=C2)C1CCCCC1 |
| 97 | OC1=CC(O)=C(C(=O)N2CC3=C(C2)C=NN3)C(NC2=CC(=NN2C2CCCCC2)C2=CC=CC=C2)=C1 |
| 99 | CC(C)CN1N=C(C=C1NC1=CC(O)=CC(O)=C1C(=O)N1CC2=C(C1)C=NN2)C1=CC=CC=C1 |
| ACSM01476 | OC(=O)CN1N=C(C=C1NC1=CC(O)=CC(O)=C1C(=O)N1CC2=C(C1)C=CC=C2)C1=CC=CC=C1 |
| ACSM01504 | CN1N=C(C=C1NC1=C(C(=O)N2CC3=C(C2)C=CC=C3)C(O)=CC(O)=C1)C1=CC=CC(OC(F)(F)F)=C1 |
| ACSM01479 | CN1N=C(C=C1NC1=C(C(=O)N2CC3=C(C2)C=CC=C3)C(O)=CC(O)=C1)C1=NC=CC=C1 |
| 114 | COC1=CC=(CC=C1)C1=NN(C)C(NC2=CC(O)=CC(O)=C2C(=O)N2CC3=C(C2)C=NN3)=C1 |
| 38 | COC1=CC=C(CN2N=C(C=C2NC2=CC(O)=CC(O)=C2C(=O)N2CCCC2)C2=CC=CC=C2)C=C1 |
| 83 | CC(C)C1=CC=C(CN2N=C=C2NC2=CC(O)=CC(O)=C2C(=O)N2CC3=C(C2)C=CC=C3)C=C1 |
| 44 | COC1=CC=C(CN2N=CC(CC3=CC=CC=C3)=C2NC2=CC(O)=CC(O)=C2C(=O)N2CC3=C(C2)C=CC=C3)C=C1 |
| ACSM01272 | CN1N=C(C=C1NC1=CC(O)=CC(O)=C1C(=O)N1CC2=C(C1)C=CC=C2)C1=CC=C(C)=C1C |
| ACSM01492 | COC1=CC=(CC=C1)C1=NN(C)C(NC2=CC(O)=CC(O)=C2C(=O)N2CC3=C(C2)C=NC=C3)=C1 |
| 52 | COC1=CC=C(CN2N=C(C=C2NC2=CC(O)=CC(O)=C2C(=O)N2CC3=C(C2)N=CC=C3)C2CCCC2)C=C1 |
| 53 | COC1=CC=C(CN2N=C(C=C2NC2=CC(O)=CC(O)=C2C(=O)N2CC3=C(C2)C=NN3)C2CCCC2)C=C1 |
| 73 | OC1=CC(O)=C(C(=O)N2CC3=C(C2)C=NN3)C(NC2=CC=NN2C2CCCCC2)=C1 |
| 72 | OC1=CC(O)=C(C(=O)N2CC3=C(C2)N=CC=C3)C(NC2=CC=NN2C2CCCCC2)=C1 |
| 40 | COC1=CC=C(CN2N=CC=C2NC2=CC(O)=CC(O)=C2C(=O)N2CC3=C(C2)C=CC=C3)C=C1 |
| ACSM01134 | CN1N=C(C)C=C1NC1=CC(O)=CC(O)=C1C(=O)N1CC2=C(C1)C=CC=C2 |
| 20 | COC1=CC=C(CN2N=C(C)C=C2NC2=CC(O)=CC(O)=C2C(=O)N2CC3=C(C2)C=CC=C3)C=C1 |
| 84 | CC(C)C1=CC=C(CN2N=CC=C2NC2=CC(O)=CC(O)=C2C(=O)N2CC3=C(C2)N=CC=C3)C=C1 |
| 71 | OC1=CC(O)=C(C(=O)N2CC3=C(C2)C=CC=C3)C(NC2=CC=NN2C2CCCCC2)=C1 |
| 66 | OC1=CC(O)=C(C(=O)N2CC3=C(C2)C=CC=C3)C(NC2=CC=NN2CC2CCCCC2)=C1 |
| 87 | OC1=CC(O)=C(C(=O)N2CC3=C(C2)C=NN3)C(NC2=CC=NN2CC=C(C=C2)C(F)(F)F)=C1 |
| 54 | COC1=CC=C(CN2N=C(C=C2NC2=CC(O)=CC(O)=C2C(=O)N2CC3=C(C2)N=CC=C3)C2=COC=C2)C=C1 |
| 108 | CN1N=C(C=C1NC1=CC(O)=CC(O)=C1C(=O)N1CC2=C(C1)C=NN2)C1=CC=CC=C1C |
| ACSM01263 | CN1N=C(C=C1NC1=C(C(=O)N2CC3=C(C2)C=C(C=C3)N2CCOCC2)C(O)=CC(O)=C1)C1=CC=CC=C1C |
| ACSM01130 | COC1=CC(=CC=C1)C1=NN(C)C(NC2=CC(O)=CC(O)=C2C(=O)N2CC3=C(C2)C(F)=CC=C3)=C1 |
| 67 | OC1=CC(O)=C(C(=O)N2CC3=C(C2)N=NN3)C(NC2=CC=NN2CCCCC2)=C1 |
| 48 | COC1=CC=C(CN2N=C(C=C2NC2=CC(O)=CC(O)=C2C(=O)N2CC3=C(C2)C=NN3)C(C)C)C=C1 |
| 85 | CC(C)C1=CC=C(CN2N=C(C=C2NC2=CC(O)=CC(O)=C2C(=O)N2CC3=C(C2)C=NN3)C=C1 |
| 68 | OC1=CC(O)=C(C(=O)N2CC3=C(C2)C=CC=C3)C(NC2=CC=NN2C2=CC=CC=C2)=C1 |
| 76 | OC1=CC(O)=C(C(=O)N2CC3=C(C2)N=CC=C3)C(NC2=CC=NN2C2=CC=CC=C2)=C1 |
| 70 | OC1=CC(O)=C(C(=O)N2CC3=C(C2)C=NN3)C(NC2=CC=NN2C2=CC=CC=C2)=C1 |
| 74 | OC1=CC(O)=C(C(=O)N2CC3=C(C2)C=CC=C3)C(NC2=CC=NN2CC2=CC=CC=C2)=C1 |
| 75 | OC1=CC(O)=C(C(=O)N2CC3=C(C2)N=CC=C3)C(NC2=CC=NN2CC2=CC=CC=C2)=C1 |
| 86 | OC1=CC(O)=C(C(=O)N2CC3=C(C2)C=CC=C3)C(NC2=CC=NN2CC=C(C=C2)C(F)(F)F)=C1 |
| 82 | OC1=CC(O)=C(C(=O)N2CC3=C(C2)C=NN3)C(NC2=CC=NN2CC2=CC=CO2)=C1 |
| 92 | CN1N=C(C=C1NC1=CC(O)=CC(O)=C1C(=O)N1CC2=C(C1)N=CC=C2)C1=CC=CC=C1 |
| ACSM01480 | CN1N=C(C=C1NC1=C(C(=O)N2CC3=C(C2)C=CC=C3)C(O)=CC(O)=C1)C1=CC=CN=C1 |
| 107 | CN1N=C(C=C1NC1=CC(O)=CC(O)=C1C(=O)N1CC2=C(C1)N=CC=C2)C1=CC=CC=C1C |
| 47 | COC1=CC=C(CN2N=C(C=C2NC2=CC(O)=CC(O)=C2C(=O)N2CC3=C(C2)N=CC=C3)C(C)C)C=C1 |
| 55 | COC1=CC=C(CN2N=C(C=C2NC2=CC(O)=CC(O)=C2C(=O)N2CC3=C(C2)C=NN3)C2=COC=C2)C=C1 |
| 69 | OC1=CC(O)=C(C(=O)N2CC3=C(C2)N=CC=C3)C(NC2=CC=NN2CC2=CC=CC=C2)=C1 |
| 41 | COC1=CC=C(CN2N=C(C)C=C2NC2=CC(O)=CC(O)=C2C(=O)N2CC3=C(C2)C=CC=C3)C=C1 |
| 80 | OC1=CC(O)=C(C(=O)N2CC3=C(C2)C=CC=C3)C(NC2=CC=NN2CC2=CC=CO2)=C1 |
| 62 | CC(C)CN1N=CC=C1NC1=CC(O)=CC(O)=C1C(=O)N1CC2=C(C1)C=CC=C2 |
| 77 | OC1=CC(O)=C(C(=O)N2CC3=C(C2)C=CC=C3)C(NC2=CC=NN2CC=CN=C2)=C1 |
| 59 | CC(C)N1N=CC=C1NC1=CC(O)=CC(O)=C1C(=O)N1CC2=C(C1)C=CC=C2 |
| 34 | COC1=CC=C(CN2N=C(C)C=C2NC2=CC(O)=CC(O)=C2C(=O)N2CC3=C(C2)C=C(OCCN(C)C)C=C3)C=C1 |
| 78 | OC1=CC(O)=C(C(=O)N2CC3=C(C2)N=CC=C3)C(NC2=CC=NN2CC2=CC=CN=C2)=C1 |
| 61 | CC(C)N1N=CC=C1NC1=CC(O)=CC(O)=C1C(=O)N1CC2=C(C1)C=NN2 |
| 79 | OC1=CC(O)=C(C(=O)N2CC3=C(C2)C=NN3)C(NC2=CC=NN2CC2=CC=CN=C2)=C1 |
| 60 | CC(C)CN1N=CC=C1NC1=CC(O)=CC(O)=C1C(=O)N1CC2=C(C1)N=CC=C2 |
| 58 | CN1N=CC=C1NC1=CC(O)=CC(O)=C1C(=O)N1CC2=C(C1)C=NN2 |
| ACSM01477 | CNC(=O)CN1N=C(C=C1NC1=CC(O)=CC(O)=C1C(=O)N1CC2=C(C1)C=CC=C2)C1=CC=CC=C1 |
| 57 | CN1N=CC=C1NC1=CC(O)=CC(O)=C1C(=O)N1CC2=C(C1)N=CC=C2 |
| ACSM01264 | CN1N=C(C=C1NC1=C(C(=O)N2CC3=C(C2)C=C(C=C3)N2CCN(C)CC2)C(O)=CC(O)=C1)C1=CC=CC=C1C |
| 46 | CCC1=NN(CC2=CC=C(OC)C=C2)C(NC2=CC(O)=CC(O)=C2C(=O)N2CC3=C(C2)C=NN3)=C1 |
| 50 | COC1=CC=C(CN2N=C(C=C2NC2=CC(O)=CC(O)=C2C(=O)N2CC3=C(C2)N=CC=C3)C2CC2)C=C1 |
| 100 | CC(C)C1=NN(C)C(NC2=CC(O)=CC(O)=C2C(=O)N2CC3=C(C2)C=CC=C3)=C1 |
| 64 | CC(C)CN1N=CC=C1NC1=CC(O)=CC(O)=C1C(=O)N1CC2=C(C1)C=NN2 |
| 81 | OC1=CC(O)=C(C(=O)N2CC3=C(C2)N=CC=C3)C(NC2=CC=NN2CC2=CC=CO2)=C1 |
| 105 | CN1N=C(C=C1NC1=CC(O)=CC(O)=C1C(=O)N1CC2=C(C1)C=NN2)C1CCCCC1 |
| 63 | CC(C)CN1N=CC=C1NC1=CC(O)=CC(O)=C1C(=O)N1CC2=C(C1)N=CC=C2 |
| 36 | COC1=CC=C(CN2N=C(C)C=C2NC2=CC(O)=CC(O)=C2C(=O)N2CC3=C(C2)C=C(C=C3)N2CCN(C)CC2)C=C1 |
| 93 | CN1N=C(C=C1NC1=CC(O)=CC(O)=C1C(=O)N1CC2=C(C1)C=NN2)C1=CC=CC=C1 |

TABLE 1-continued

Compounds

| Comp. | SMILES |
|---|---|
| ACSM01133 | CN1N=C(C=C1NC1=CC(O)=CC(O)=C1C(=O)N1CC2=C(C1)C=CC=C2)C1CC1 |
| ACSM01260 | CN1N=C(C=C1NC1=CC(O)=CC(O)=C1C(=O)N1CC2=C(C1)C=NC=C2)C1=CC=CC=C1F |
| ACSM01489 | CN1N=C(C=C1NC1=CC(O)=CC(O)=C1C(=O)N1CC2=C(C1)C=NC=C2)C1=CC=CC=C1C |
| 45 | CCC1=NN(CC2=CC=C(OC)C=C2)C(NC2=CC(O)=CC(O)=C2C(=O)N2CC3=C(C2)N=CC=C3)=C1 |
| 51 | COC1=CC=C(CN2N=C(=C2NC2=CC(O)=CC(O)=C2C(=O)N2CC3=C(C2)C=NN3)C2CC2)C=C1 |
| 28 | COC1=CC=C(CN2N=C(C)C=C2NC2=CC(O)=CC(O)=C2C(=O)N2CC3=C(C2)C=C(F)C=C3)C=C1 |
| 102 | CC(C)C1=NN(C)C(NC2=CC(O)=CC(O)=C2C(=O)N2CC3=C(C2)C=NN3)=C1 |
| 42 | COC1=CC=C(CN2N=CC(C)C)=C2NC2=CC(O)=CC(O)=C2C(=O)N2CC3=C(C2)C=CC=C3)C=C1 |
| 24 | COC1=CC=C(CN2N=C(C)C=C2NC2=CC(O)=CC(O)=C2C(=O)N2CC3=C(C2)C=NN3)C=C1 |
| ACSM01374 | CN1N=C(C=C1NC1=CC(O)=CC(O)=C1C(=O)N1CC2=C(C1)C=NN2)C1=CC=CC=C1F |
| ACSM01261 | CN1N=C(C=C1NC1=CC(O)=CC(O)=C1C(=O)N1CC2=CC=CN=C2C1)C1=CC=CC=C1F |
| ACSM01346 | CN1N=C(C=C1NC1=CC(O)=CC(O)=C1C(=O)N1CC2=C(C1)C=NC=C2)C1=CC=CC=C1C |
| 56 | CN1N=CC=C1NC1=CC(O)=CC(O)=C1C(=O)N1CC2=C(C1)C=CC=C2 |
| 89 | CC1=NN(CC2=C(C1)C=CC=C2)C(NC2=CC(O)=CC(O)=C2C(=O)N2CC3=C(C2)C=CC=C3)=C1 |
| 26 | COC1=CC=C(CN2N=C(C)C=C2NC2=CC(O)=CC(O)=C2C(=O)N2CC3=C(C2)C(F)=CC=C3)C=C1 |
| 90 | CC1=NN(CC2=C(C)C=CC=C2)C(NC2=CC(O)=CC(O)=C2C(=O)N2CC3=C(C2)C=CC=C3)=C1 |
| 32 | COC1=CC=C(CN2N=C(C)C=C2NC2=CC(O)=CC(O)=C2C(=O)C=C(NC2CCN(C)CC2)C=C3)C=C1 |
| 22 | COC1=CC=C(CN2N=C(C)C=C2NC2=CC(O)=CC(O)=C2C(=O)N2CC3=C(C2)N=CC=C3)C=C1 |
| ACSM01490 | CN1N=C(C=C1NC1=CC(O)=CC(O)=C1C(=O)N1CC2=C(C1)C=NC=C2)C1=CC=CC=C1C(F)(F)F |
| 91 | CN1N=C(C=C1NC1=CC(O)=CC(O)=C1C(=O)N1CC2=C(C1)C=CC=C2)C1=CC=CC=C1 |
| 104 | CN1N=C(C=C1NC1=CC(O)=CC(O)=C1C(=O)N1CC2=C(C1)N=CC=C2)C1CCCCC1 |
| BUCMD00467 | CN1N=C(C=C1NC1=CC(O)=CC(O)=C1C(=O)N1CC2=C(C1)C=NC=C2)C1=CC=CC=C1 |
| ACSM01136 | CN1N=C(C=C1NC1=CC(O)=CC(O)=C1C(=O)N1CC2=C(C1)C=CC=C2)C(C)(C)C |
| 101 | CC(C)C1=NN(C)C(NC2=CC(O)=CC(O)=C2C(=O)N2CC3=C(C2)N=CC=C3)=C1 |
| ACSM01369 | COC1=CC=CC=C1C1=NN(C)C(NC2=C(C(=O)N3CC[C@@H](C3)NC(=O)[C@@H](N)CC3=CNC4=C3C=CC=C4)C(O)=CC(O)=C2)=C1 |
| ACSM01281 | CN1N=CC=C1NC1=C(C(=O)N2CC[C@@H](F)C2)C(O)=CC(O)=C1 |
| ACSM01313 | CN1N=C(C)C=C1NC1=CC(O)=CC(O)=C1C(=O)N1CC[C@H](F)C1 |
| 37 | COC1=CC=C(CN2N=C(C)C=C2NC2=CC(O)=CC(O)=C2C(=O)N(C)CC2=CC=CC=C2)C=C1 |
| ACSM01564 | CN1N=C(C=C1NC1=CC(O)=CC(O)=C1C(=O)N1CC2=C(C1)C(F)=CC=C2)C1=CC=CC(C)=C1F |
| ACSM01565 | CN1N=C(C=C1NC1=CC(O)=CC(O)=C1C(=O)N1CC2=C(C1)C(F)=CC=C2)C1=CC(F)=CC=C1C |
| ACSM01567 | CN1N=C(C=C1NC1=CC(O)=CC(O)=C1C(=O)N1CC2=C(C1)C(F)=CC=C2)C1=CC=CC(=C1)C(F)(F)FC(F)(F)F |
| ACSM01566 | CC(C)(C)N1N=C(C=C1NC1=CC(O)=CC(O)=C1C(=O)N1CC2=C(C1)C(F)=CC=C2)C1=CC=CC(F)=C1F |
| ACSM01668 | COC1=CC=CC=C1C1=NN(C2CCCCC2)C(NC2=CC(O)=CC(O)=C2C(=O)N2CC3=C(C2)C(F)=CC=C3)=C1 |
| ACSM01670 | CN1N=C(C=C1NC1=CC(O)=CC(O)=C1C(=O)N1CC2=C(C1)C=C(F)C=C2)C1=CC=CC=C1C |
| ACSM01671 | CN1N=C(C=C1NC1=CC(O)=CC(O)=C1C(=O)N1CC2=C(C1)C=C(F)C=C2)C1=CC=CC(C)=C1F |
| ACSM01669 | COC1=CC=CC=C1C1=NN(C2CCCCC2)C(NC2=CC(O)=CC(O)=C2C(=O)N2CC3=C(C2)C=C(F)C=C3)=C1 |
| ACSM01666 | CN1N=C(C=C1NC1=C(C(=O)N2CC3=C(C2)C=C=C3)C(O)=CC(O)=C1)C1=CC=CC(C1C)C(F)(F)F |
| ACSM01667 | CN1N=C(C=C1NC1=CC(O)=CC(O)=C1C(=O)N1CC2=C(C1)C=CC=C2)C1=CC(=CC=C1F)C(F)(F)F |
| ACSM01665 | CN1N=C(C=C1NC1=CC(O)=CC(O)=C1C(=O)N1CC2=C(C1)C=CC=C2)C1=CC(=CC=C1)C(F)(F)FC(F)(F)F |
| ACSM01562 | CC1=CC=CC=C1C1=NN(C(NC2=CC(O)=CC(O)=C2C(=O)N2CC3=C(C2)C=CC=C3)=C1)C(C)(C)C |
| ACSM01520 | CC(C)(C)N1N=C(C=C1NC1=CC(O)=CC(O)=C1C(=O)N1CC2=C(C1)C=CC=C2)C1=CC=CC(F)=C1 |
| ACSM01561 | CC(C)(C)N1N=C(C=C1NC1=CC(O)=CC(O)=C1C(=O)N1CC2=C(C1)C=CC=C2)C1=CC=CC(C1)=C1 |
| ACSM01664 | CC(C)(C)N1N=C(C=C1NC1=CC(O)=CC(O)=C1C(=O)N1CC2=C(C1)C=CC=C2)C1=CC=CC(F)=C1F |
| ACSM01672 | CC1=C(C)C(=CC=C1)C1=NN(C(NC2=CC(O)=CC(O)=C2C(=O)N2CC3=C(C2)C=CC=C3)=C1)C(C)(C)C |
| ACSM01527 | CC1=C(F)C(=CC=C1)C1=NN(C(NC2=CC(O)=CC(O)=C2C(=O)N2CC3=C(C2)C=CC=C3)=C1)C(C)(C)C |
| ACSM01673 | CC1=CC=C(F)C=C1C1=NN(C(NC2=CC(O)=CC(O)=C2C(=O)N2CC3=C(C2)C=CC=C3)=C1)C(C)(C)C |
| ACSM01563 | OC1=CC(O)=C(C(=O)N2CC3=C(C2)C=CC=C3)C(NC2=CC(=NN2C2CCCCC2)C2=CC=CC(Cl)=C2)=C1 |
| ACSM01528 | CC1=C(F)C(=CC=C1)C1=NN(C2CCCCC2)C(NC2=CC(O)=CC(O)=C2C(=O)N2CC3=C(C2)C=CC=C3)=C1 |
| ACSM01537 | CN1N=C(C=C1NC1=CC(O)=CC(O)=C1C(=O)N1CC2=C(C1)C=NN2)C1=CC=CC(C)=C1C |
| ACSM01536 | CN1N=C(C=C1NC1=CC(O)=CC(O)=C1C(=O)N1CC2=C(C1)C=NN2)C1=CC=CC(C)=C1F |
| ACSM01541 | COC1=CC=CC=C1C1=NN(C(C)C)C(NC2=C(C(=O)N3CC4=C(C3)C=NN4)C(O)=CC(O)=C2)=C1 |
| ACSM01542 | COC1=CC=CC=C1C1=NN(CC(C)C)C(NC2=C(C(=O)N3CC4=C(C3)C=NN4)C(O)=CC(O)=C2)=C1 |
| ACSM01540 | COC1=CC=CC=C1C1=NN(C(NC2=CC(O)=CC(O)=C2C(=O)N2CC3=C(C2)C=NN3)=C1)C(C)(C)C |
| ACSM01539 | COC1=CC=CC=C1C1=NN(C2CCCC2)C(NC2=CC(O)=CC(O)=C2C(=O)N2CC3=C(C2)C=NN3)=C1 |
| ACSM01538 | COC1=CC=CC=C1C1=NN(C2CCCCC2)C(NC2=CC(O)=CC(O)=C2C(=O)N2CC3=C(C2)C=NN3)=C1 |
| ACSM01529 | CC(C)(C)C1=NN(C(NC2=CC(O)=CC(O)=C2C(=O)N2CC3=C(C2)C=NN3)=C1)C1=CC=CC=C1 |
| ACSM01535 | OC1=CC(O)=C(C(=O)N2CC3=C(C2)C=NN3)C(NC2=CC(=NN2C2=CC=CC=C2)C2=CC=CC=C2)=C1 |
| ACSM01506 | COC1=CC=CC=C1C1=NN(C)C(NC2=C(C(=O)N3CC4CC4C3)C(O)=CC(O)=C2)=C1 |
| ACSM01509 | COC1=CC=CC=C1C1=NN(C)C(NC2=C(C(=O)N3CCC(F)(F)C3)C(O)=CC(O)=C2)=C1 |
| ACSM01512 | CN1N=C(C=C1NC1=C(C(=O)N2CC[C@H](C2)NC(C)=O)C(O)=CC(O)=C1)C1=CC=CC=C1C |
| ACSM01518 | CN1N=C(C=C1NC1=C(C(=O)N2CC[C@H](C2)NC(C)=O)C(O)=CC(O)=C1)C1=CC=CC(C)=C1 |
| ACSM01521 | CC(=O)N[C@@H]1CCN(C1)C(=O)C1=C(NC1NC1=CC(O)=CC(C)(C)C1)C1=CC=CC=C1C |
| ACSM01523 | COC1=CC=CC=C1C1=NN(NC2=CC(O)=CC(O)=C2C(=O)N2CC[C@H](C2)NC(C)=O)C1C(C)(C)C |
| ACSM01510 | CC(=O)N[C@@H]1CCN(C1)C(=O)C1=C(O)C=C(O)C=C1NC1=CC(=NN1C(C)(C)C)C1=CC=CC(C)=C1 |
| ACSM01530 | CN1N=C(C=C1NC1=C(C(=O)N2CC[C@H](C2)NC(=O)C2=CC=CC=C2)C(O)=CC(O)=C1)C1=CC=CC(C)=C1 |
| ACSM01559 | CN1N=C(C=C1NC1=C(C(=O)N2CC[C@H](C2)NC(=O)C2=CC=CC=C2)C(O)=CC(O)=C1)C1=CC(C1)=CC=C1 |
| ACSM01543 | CN1N=C(C=C1NC1=CC(O)=CC(O)=C1C(=O)N1CC[C@H](C1)NC(=O)C1=CC=CC=C1)C1=CC=CC(C)=C1F |
| ACSM01532 | CC1=CC(=CC=C1)C1=NN(C(NC2=CC(O)=CC(O)=C2C(=O)N2CC[C@H](C2)NC(=O)C2=CC=CC=C2)=C1)C(C)(C)C |
| ACSM01545 | CC1=C(F)C(=CC=C1)C1=NN(C(NC2=CC(O)=CC(O)=C2C(=O)N2CC[C@H](C2)NC(=O)C2=CC=CC=C2)=C1)C(C)(C)C |
| ACSM01547 | CN1N=C(C=C1NC1=CC(O)=CC(O)=C1C(=O)N1CC[C@H](C1)NC(=O)C(C)(C)C)C1=CC=CC(C)=C1F |
| ACSM01549 | CC1=C(F)C(=CC=C1)C1=NN(C(NC2=CC(O)=CC(O)=C2C(=O)N2CC[C@H](C2)NC(=O)C(C)(C)C)=C1)C(C)(C)C |
| ACSM01514 | CO[C@@H]1CCN(C1)C(=O)C1=C(NC2=CC(=NN2C)C2=CC=CC=C2C)C=C(O)C=C1O |
| ACSM01516 | CO[C@@H]1CCN(C1)C(=O)C1=C(NC2=CC(=NN2C)C2=CC=CC(C)=C2)C=C(O)C=C1O |

TABLE 1-continued

Compounds

| Comp. | SMILES |
|---|---|
| ACSM01525 | CO[C@@H]1CCN(C1)C(=O)C1=C(NC2=CC(=NN2C)C2=CC=CC(OC)=C2)C=C(O)C=C1O |
| ACSM01551 | CO[C@@H]1CCN(C1)C(=O)C1=C(NC2=CC(=NN2C(C)(C)C)C2=C(C)C=CC=C2)C=C(O)C=C1O |
| ACSM01553 | CO[C@@H]1CCN(C1)C(=O)C1=C(NC2=CC(=NN2C(C)(C)C)C2=C(OC)C=CC=C2)C=C(O)C=C1O |
| ACSM01555 | CO[C@@H]1CCN(C1)C(=O)C1=C(NC2=CC(=NN2C(C)(C)C)C2=CC(C)=CC=C2)C=C(O)C=C1O |
| ACSM01557 | CO[C@@H]1CCN(C1)C(=O)C1=C(NC2=CC(=NN2C(C)(C)C)C2=CC(OC)=CC=C2)C=C(O)C=C1O |
| ACSM01513 | CN1N=C(C=C1NC1=C(C(=O)N2CC[C@@H](C2)NC(C)=O)C(O)=CC(O)=C1)C1=CC=CC=C1C |
| ACSM01519 | CN1N=C(C=C1NC1=C(C(=O)N2CC[C@@H](C2)NC(C)=O)C(O)=CC(O)=C1)C1=CC=CC(C)=C1 |
| ACSM01522 | CC(=O)N[C@H]1CCN(C1)C(=O)C1=C(O)C=C(O)C=C1NC1=CC(=NN1C(C)(C)C)C1=CC=CC=C1C |
| ACSM01524 | COC1=CC=CC=C1C1=NN(C(NC2=CC(O)=CC(O)=C2C(=O)N2CC[C@@H](C2)NC(C)=O)=C1)C(C)(C)C |
| ACSM01511 | CC(=O)N[C@H]1CCN(C1)C(=O)C1=C(O)C=C(O)C=C1NC1=CC(=NN1C(C)(C)C)C1=CC=CC(C)=C1 |
| ACSM01531 | CN1N=C(C=C1NC1=C(C(=O)N2CC[C@@H](C2)NC(=O)C2=CC=CC=C2)C(O)=CC(O)=C1)C1=CC=CC(C)=C1 |
| ACSM01560 | CN1N=C(C=C1NC1=C(C(=O)N2CC[C@@H](C2)NC(=O)C2=CC=CC=C2)C(O)=CC(O)=C1)C1=CC(Cl)=CC=C1 |
| ACSM01544 | CN1N=C(C=C1NC1=CC(O)=C1C(=O)N1CC[C@@H](C1)NC(=O)C1=CC=CC=C1)C1=CC=CC(C)=C1F |
| ACSM01533 | CC1=CC(=CC=C1)C1=NN(C(NC2=CC(O)=CC(O)=C2C(=O)N2CC[C@@H](C2)NC(=O)C2=CC=CC=C2)=C1)C(C)(C)C |
| ACSM01546 | CC1=C(F)C(=CC=C1)C1=NN(C(NC2=CC(O)=CC(O)=C2C(=O)N2CC[C@@H](C2)NC(=O)C2=CC=CC=C2)=C1)C(C)(C)C |
| ACSM01548 | CN1N=C(C=C1NC1=CC(O)=CC(O)=C1C(=O)N1CC[C@@H](C1)NC(=O)C(C)(C)C)C1=CC=CC(C)=C1F |
| ACSM01550 | CC1=C(F)C(=CC=C1)C1=NN(C(NC2=CC(O)=CC(O)=C2C(=O)N2CC[C@@H](C2)NC(=O)C(C)(C)C)=C1)C(C)(C)C |
| ACSM01515 | CO[C@H]1CCN(C1)C(=O)C1=C(NC2=CC(=NN2C)C2=CC=CC=C2C)C=C(O)C=C1O |
| ACSM01517 | CO[C@H]1CCN(C1)C(=O)C1=C(NC2=CC(=NN2C)C2=CC=CC=C2)C=C(O)C=C1O |
| ACSM01526 | CO[C2H]1CCN(C1)C(=O)C1=C(NC2=CC(=NN2C)C2=CC=CC(OC)=C2)C=C(O)C=C1O |
| ACSM01552 | CO[C@H]1CCN(C1)C(=O)C1=C(NC2=CC(=NN2C(C)(C)C)C2=C(C)C=CC=C2)C=C(O)C=C1O |
| ACSM01554 | CO[C@H]1CCN(C1)C(=O)C1=C(NC2=CC(=NN2C(C)(C)C)C2=C(OC)C=CC=C2)C=C(O)C=C1O |
| ACSM01556 | CO[C@H]1CCN(C1)C(=O)C1=C(NC2=CC(=NN2C(C)(C)C)C2=CC(C)=CC=C2)C=C(O)C=C1O |
| ACSM01558 | CO[C@H]1CCN(C1)C(=O)C1=C(NC2=CC(=NN2C(C)(C)C)C2=CC(OC)=CC=C2)C=C(O)C=C1O |
| CMLD012897 | COC1=CC=C(CN2N=C(C=C2NC2=CC(O)=CC(O)=C2C(=O)NCC2=CC=CC=C2)C2=CC=CC=C2)C=C1 |
| CMLD012890 | COC1=CC=C(CN2N=C(C=C2NC2=CC(O)=CC(O)=C2C(=O)N(C)CC2=NOC=C2)C2=CC=CC=C2)C=C1 |
| 39 | CCN(CC)C(=O)C1=C(O)C=C(O)C=C1NC1=CC(=NN1C1=CC(=O)C(=O)C=C1)C1=CC=CC=C1 |
| CMLD012891 | COC1=CC=C(CN2N=C(C=C2NC2=CC(O)=CC(O)=C2C(=O)N(C)CC2CCOCC2)C2=CC=CC=C2)C=C1 |
| ACSM01285 | CN1N=C(C=C1NC1=CC(O)=C1C(=O)N1CC[C@@H](F)C1 |
| ACSM01310 | CN1N=CC=C1NC1=C(C(=O)N2CC[C@H](C2)NC(C)=O)=CC(O)=C1 |
| ACSM01501 | COC1=CC(=CC=C1)C1=NN(C(NC2=CC(O)=CC(O)=C2C(=O)N2CC[C@H](C2)NC(C)=O)=C1)C(C)(C)C |
| ACSM01296 | CN(C)[C@@H]1CCN(C1)C(=O)C1=C(NC2=CC=NN2C)C=C(O)C=C1O |
| ACSM01298 | CN(C)[C@@H]1CCN(C1)C(=O)C1=C(O)C=C(O)C=C1NC1=CC(C)=NN1C |
| ACSM01326 | CO[C@@H]1CCN(C1)C(=O)C1=C(NC2=CC=NN2C)C=C(O)C=C1O |
| ACSM01329 | CO[C@@H]1CCN(C1)C(=O)C1=C(O)C=C(O)C=C1NC1=CC(C)=NN1C |
| ACSM01320 | CN1N=CC=C1NC1=C(C(=O)N2CC[C@H](C2)NC(C)=O)C(O)=CC(O)=C1 |
| ACSM01500 | COC1=CC(=CC=C1)C1=NN(C(NC2=C(C(=O)N3CC[C@@H](C3)NC(C)=O)C(O)=CC(O)=C2)=C1 |
| ACSM01502 | COC1=CC(=CC=C1)C1=NN(C(NC2=CC(O)=CC(O)=C2C(=O)N2CC[C@@H](C2)NC(C)=O)=C1)C(C)(C)C |
| CMLD012893 | COC1=CC=C(CN2N=C(C=C2NC2=CC(O)=CC(O)=C2C(=O)N(C)CC2=CC=NC=C2)C2=CC=CC=C2)C=C1 |
| 31 | COC1=CC=C(CN2N=C(C=C2NC2=CC(O)=CC(O)=C2C(=O)NC)C2=CC=CC=C2)C=C1 |
| 127 | CN1N=C(C=C1NC1=CC(O)=CC(O)=C1C(=O)N1CC2=C(C1)C=C=C(=C1)C(C)(C)C |
| BUCMD00474 | COC1=CC=C(CN2N=C(C)C=C2NC2=CC(OC(C)=O)=CC(OC(C)=O)=C2C(=O)N2CC3=C(C2)C=CC=C3)C=C1 |
| ACSM01481 | COC1=CC=CC=C1N1C=C(NC2=C(C(=O)N3CC4=C(C3)C=CC=C4)C(O)=CC(O)=C2)C=N1 |
| ACSM01478 | OC1=CC(NC2=CN(N=C2)C2=CC=CC=C2)=C(C(=O)N2CC3=C(C2)C=CC=C3)C(O)=C1 |
| ACSM01482 | OC1=CC(NC2=CN(N=C2)C2=CC=CC=C2C(F)(F)F)=C(C(=O)N2CC3=C(C2)C=CC=C3)C(O)=C1 |
| ACSM01334 | CCO[C@@H]1CCN(C1)C(=O)C1=C(NC2=C(C)N(C)N=C2C)C=C(O)C=C1O |
| ACSM01327 | CO[C@@H]1CCN(C1)C(=O)C1=C(NC2=C(C)N(C)N=C2C)C=C(O)C=C1O |
| ACSM01321 | CO[C@H]1CCN(C1)C(=O)C1=C(NC2=CN(N=C2)C2=CC=CC=C2)C=C(O)C=C1O |
| CMLD012910 | CCNC(=O)C1=NOC(=C1)C1=C(O)C=C(O)C=C1NC1=NN(C)C=C1 |
| ACSM01494 | CC1=NN(C(C)=C1NC1=CC(O)=CC(O)=C1C(=O)N1CC2=C(C1)C=CC=C2)C1=CC=CC(=C1)C(F)(F)F |
| ACSM01287 | CC(C)N1C=C(NC2=C(C(=O)N3CC[C@@H](F)C3)C(O)=CC(O)=C2)C=N1 |
| ACSM01312 | CN1N=C(C)C=C1NC1=C(C(=O)N3CC[C@H](F)C3)C(O)=CC(O)=C2)=C1C |
| ACSM01493 | COC1=CC=CC=C1N1N=C(C)C(NC2=C(C(=O)N3CC4=C(C3)C=CC=C4)C(O)=CC(O)=C2)=C1C |
| ACSM01323 | CO[C@H]1CCN(C1)C(=O)C1=C(NC2=CN(N=C2)C(C)(C)C)C=C(O)C=C1O |
| ACSM01330 | CO[C@@H]1CCN(C1)C(=O)C1=C(NC2=CN(N=C2)C(C)(C)C)C=C(O)C=C1O |
| ACSM01292 | CN1N=C(C)C(NC2=C(C(=O)N3CCC(F)(F)C3)C(O)=CC(O)=C2)=C1C |
| ACSM01295 | CC(C)N1C=C(NC2=C(C(=O)N3CCC(F)(F)C3)C(O)=CC(O)=C2)C=N1 |
| ACSM01484 | OC1=CC(NC2=CN(N=C2)C2=CC=CC(=C2)C(F)(F)F)=C(C(=O)N2CC3=C(C2)C=CC=C3)C(O)=C1 |
| ACSM01338 | CCO[C@@H]1CCN(C1)C(=O)C1=C(NC2=C(C)N(C)N=C2C)C=C(O)C=C1O |
| ACSM01486 | CC1=NN(C(C)=C1NC1=CC(O)=CC(O)=C1C(=O)N1CC2=C(C1)C=CC=C2)C1=CC=CC(C)=C1 |
| ACSM01483 | CC1=CC=CC=C1)N1C=C(NC2=C(C(=O)N3CC4=C(C3)C=CC=C4)C(O)=CC(O)=C2)C=N1 |
| ACSM01276 | CN1N=C(C)C(NC2=C(C(=O)N3CC4=C(C3)C=CC=C4)C(O)=CC(O)=C2)=C1C |
| ACSM01306 | CCN1C=C(NC2=CC(O)=CC(O)=C2C(=O)N2CC3=C(C2)C=CC=C3)C=N1 |
| ACSM01485 | CC1=CC=CC=C1N1C=C(NC2=C(C(=O)N3CC4=C(C3)C=CC=C4)C(O)=CC(O)=C2)C=N1 |
| ACSM01277 | CC(C)N1C=C(NC2=C(C(=O)N3CC4=C(C3)C=CC=C4)C(O)=CC(O)=C2)C=N1 |
| ACSM01283 | CN1N=C(C)C(NC2=C(C(=O)N3CC[C@@H](F)C3)C(O)=CC(O)=C2)=C1C |
| ACSM01289 | CN1C=C(NC2=CC(O)=CC(O)=C2C(=O)N2CC3CC3C2)C(C)=N1 |
| ACSM01300 | CN1C=C(NC2=C(C(=O)N3CC4CC4C3)C(O)=CC(O)=C2)C=N1 |
| ACSM01288 | CN1N=C(C)C(NC2=C(C(=O)N3CCC(F)(F)C3)C(O)=CC(O)=C2)=C1C |
| ACSM01291 | CC(C)N1C=C(NC2=C(C(=O)N3CC4CC4C3)C(O)=CC(O)=C2)C=N1 |
| ACSM01290 | CN(C)CCN1C=C(NC2=CC(O)=CC(O)=C2C(=O)N2CC3CC3C2)C=N1 |
| ACSM01293 | CN1C=C(NC2=CC(O)=CC(O)=C2C(=O)N2CCC(F)(F)C2)C(C)=N1 |
| ACSM01303 | CN1C=C(NC2=C(C(=O)N3CCC(F)(F)C3)C(O)=CC(O)=C2)C=N1 |
| ACSM01294 | CN(C)CCN1C=C(NC2=CC(O)=CC(O)=C2C(=O)N2CCC(F)(F)C2)C=N1 |

TABLE 1-continued

Compounds

| Comp. | SMILES |
|---|---|
| ACSM01282 | CN1C=C(NC2=C(C(=O)N3CC[C@@H](F)C3)C(O)=CC(O)=C2)C=N1 |
| ACSM01284 | CN1C=C(NC2=CC(O)=CC(O)=C2C(=O)N2CC[C@@H](F)C2)C(C)=N1 |
| ACSM01286 | CN(C)CCN1C=C(NC2=CC(O)=CC(O)=C2C(=O)N2CC[C@@H](F)C2)C=N1 |
| ACSM01319 | CN1C=C(NC2=C(C(=O)N3CC[C@H](C3)NC(C)=O)C(O)=CC(O)=C2)C=N1 |
| ACSM01297 | CN(C)[C@@H]1CCN(C1)C(=O)C1=C(O)C=C(O)C=C1NC1=CN(C)N=C1C |
| ACSM01299 | CC(C)N1C=C(NC2=C(C(=O)N3CC[C@H](C3)N(C)C)C(O)=CC(O)=C2)C=N1 |
| ACSM01339 | CCO[C@@H]1CCN(C1)C(=O)C1=C(O)C=C(O)C=C1NC1=CN(C)N=C1C |
| ACSM01341 | CCO[C@@H]1CCN(C1)C(=O)C1=C(NC2=CN(C)N=C2)C=C(O)C=C1O |
| ACSM01328 | CO[C@@H]1CCN(C1)C(=O)C1=C(O)C=C(O)C=C1NC1=CN(C)N=C1C |
| ACSM01331 | CO[C@@H]1CCN(C1)C(=O)C1=C(O)C=C(O)C=C1NC1=CN(CCN(C)C)N=C1 |
| ACSM01316 | CN1C=C(NC2=C(C(=O)N3CC[C@H](F)C3)C(O)=CC(O)=C2)C=N1 |
| ACSM01315 | CC(C)N1C=C(NC2=C(C(=O)N3CC[C@H](F)C3)C(O)=CC(O)=C2)C=N1 |
| ACSM01314 | CN(C)CCN1C=C(NC2=CC(O)=CC(O)=C2C(=O)N2CC[C@H](F)C2)C=N1 |
| ACSM01309 | CN1C=C(NC2=C(C(=O)N3CC[C@@H](C3)NC(C)=O)C(O)=CC(O)=C2)C=N1 |
| ACSM01335 | CCO[C@H]1CCN(C1)C(=O)C1=C(O)C=C(O)C=C1NC1=CN(C)N=C1C |
| ACSM01342 | CCO[C@H]1CCN(C1)C(=O)C1=C(NC2=CN(C)N=C2)C=C(O)C=C1O |
| ACSM01322 | CO[C@H]1CCN(C1)C(=O)C1=C(O)C=C(O)C=C1NC1=CN(C)N=C1C |
| ACSM01324 | CO[C@H]1CCN(C1)C(=O)C1=C(O)C=C(O)C=C1NC1=CN(CCN(C)C)N=C1 |

In some embodiments the compound is selected from (ACSM01348); (ACSM01375); (ACSM01280); (ACSM01301); (BUCMD00420); (BUCMD00433); (ACSM01349); (ACSM01350); (117); (ACSM01351); (116); (95); (119) (94); (ACSM01491); (ACSM01279); (ACSM01371); (123); (120); (122); (109); (118); (111); (110); (ACSM01487) (ACSM01271); (115); (112); (113); (ACSM01476); (114); (83); (ACSM01272); (ACSM01492); (108); (ACSM01130); (BUCMD00429); (107); (58); (93); (91); (104); (BUCMD00467); (ACSM01494); (ACSM01493); or (ACSM01486). In some embodiments the compound is selected from (ACSM01362); (ACSM01273); (ACSM01268); (ACSM01473); (ACSM01305); (ACSM01269); (106); (ACSM01345); (ACSM01135); or (ACSM01270). In some embodiments the compound is (ACSM01348); (BUCMD00433); (131); (132); (130); (ACSM01349); (ACSM01350); (23); (121); or (121).

In some embodiments the compound (I) or (II) is a macrocyle wherein W and $R_1$ or $R'_1$. For example, in some embodiments compound (I) is further defined as the structures;

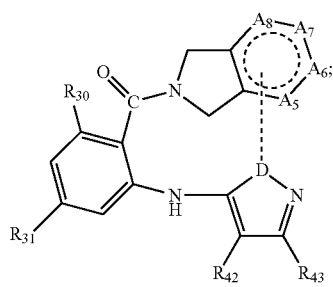
(XV)

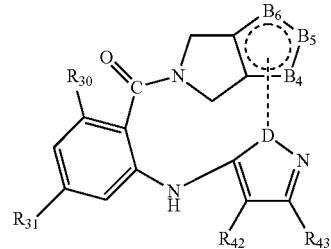
(XVI)

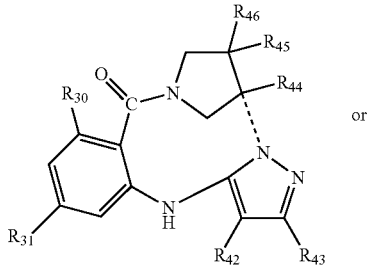
(XVII)

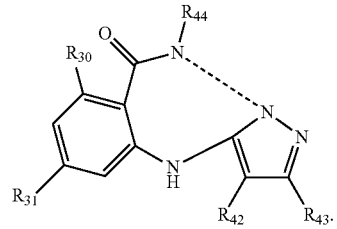
(XVIII)

structure (XV) D is N, and 3 of the $A_5$, $A_6$, $A_7$ and $A_8$ are independently $NR_{50}$, $CR_{51}$, and the remaining $A_5$, $A_6$, $A_7$ and $A_8$ is C and is bonded to D by a linker (-----). In structure (XVI) D is N, and 2 of the $B_4$, $B_5$, and $B_6$ are independently N, $NR_{50}$, or $CR_{51}$, and the remaining $B_4$, $B_5$, and $B_6$ is C or N and is bonded to D by a linker (-----). The linker (-----) is a linking group comprising a chain of 2 to 12 carbons wherein one or more carbons in the chain is substituted with —O—, —S—, —N($R^R$)—, —N($R^S$)C(O)—, —SO$_2$—, —C≡C—, —C=C—, and wherein any carbon is optionally substituted with one or more substituents. $R_{42}$, $R_{43}$, are independently H, —CO$_2$H, amide, halide, alkyl, alkenyl, alkynyl, alkoxy, acyl, cycloalkyl, heterocycle, aryl, or benzyl. $R_{44}$, $R_{45}$, and $R_{46}$ are independently H, —$CO_2H$, amide, halide, alkyl, alkenyl, alkynyl, alkoxy, acyl, cycloalkyl, heterocycle, aryl, or benzyl; any $R_{44}$, $R_{45}$, and $R_{46}$ and carbons to which they are attached can form a spiro or fused ring structure. any alkyl or alkoxy is optionally substituted with one or more substituents independently selected from the group consisting of halogen, —OH, alkyl, O-alkyl, —$NR^OR^P$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —$N(R^Q)$— substituting one or more carbons in the carbon chain. $R^O$, $R^P$, and $R^Q$ are each independently selected from hydrogen and $C_{1-4}$ alkyl. In some embodiments the linker includes

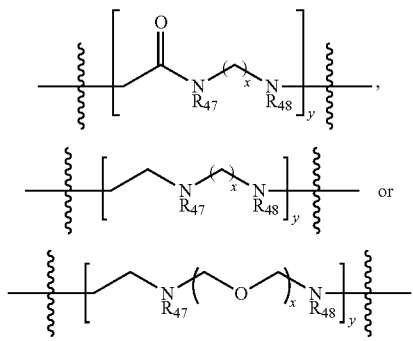

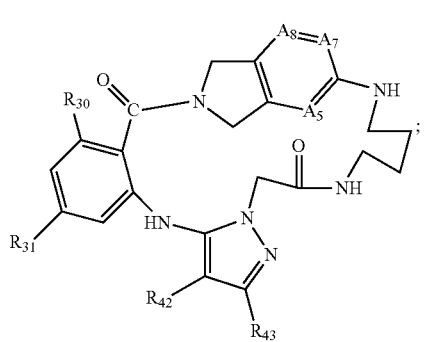

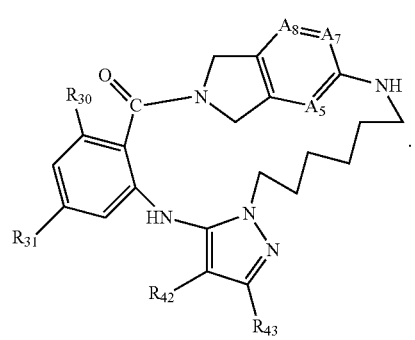

wherein $R_{47}$ and $R_{48}$ are independently H or alkyl, x is 1 to 10, and y is 1 to 5. In some embodiments the macrocycle has the structure (XX) or (XXI):

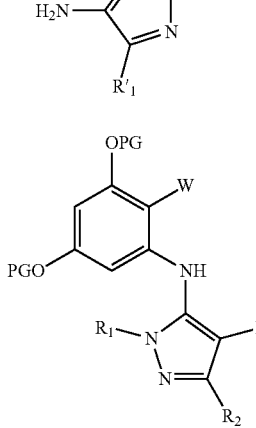

In some embodiments the compounds are prepared by cross coupling reactions. For example, compounds having formula (I-$H_2$) and compounds having formula (II-$H_2$) can be prepared by cross coupling appropriated stating aryl and amine compounds. In some embodiments preparing (I-$H_2$) comprises: providing a solution of a compound having formula (VI) and (VII) in the presence of a catalyst to provide protected product (I'), and de-protecting (I') to afford (I-$H_2$). In some embodiments preparing compound (II-$H_2$) comprises: providing a solution of a compound having formula (VI) and (VII) in the presence of a noble metal catalyst to provide protected product (II'), and de-protecting (II') to afford (II-$H_2$). The structures are as follows:

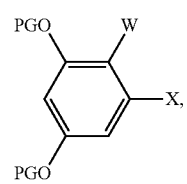

(VI)

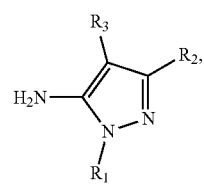

(VII)

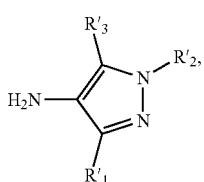

(VIII)

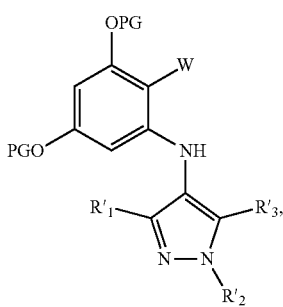

(I')

(II')

-continued

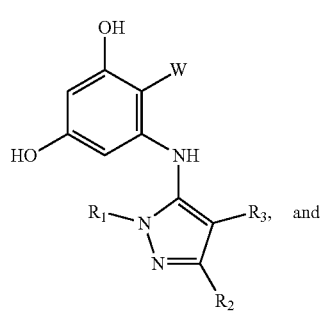
(I-H₂)

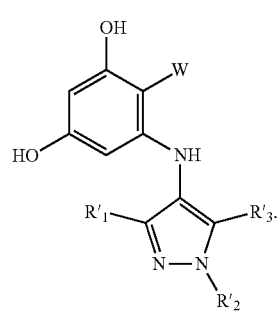
(II-H₂)

PG is a protecting group. X is a halide selected from chlorine, bromine or iodine. $R_1$, $R_2$, $R_3$, $R'_1$, $R'_2$ and $R'_3$ are independently selected from the group consisting of H, OH, protected hydroxyl, —$CO_2H$, amide, alkyl, alkenyl, alkynyl, alkoxy, acyl, cycloalkyl, heterocycle, aryl, or benzyl. W is —$C(O)NR_4R_5$ or oxazol (Ao),

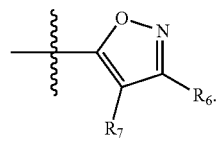

$R_4$ and $R_5$ are independently selected from H, alkyl, alkenyl, alkynyl, acyl, cycloalkyl, heterocycle, aryl, benzyl or $R_4$ and $R_5$ together with the nitrogen to which they are attached form a heterocyclic ring. $R_7$ and $R_8$ independently selected from H, OH, protected hydroxyl, —$CO_2H$, alkyl, alkenyl, alkynyl, alkoxy, acyl, amide, cycloalkyl, heterocycle, aryl, or benzyl. wherein any alkyl, alkenyl, alkynyl, alkoxy, acyl, cycloalkyl, is optionally substituted with one or more substituents independently selected from the group consisting of halogen, —OH, alkyl, O-alkyl, —$NR^AR^B$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —$N(R^E)$-substituting one or more carbons in the carbon chain. Wherein any aryl, benzyl or heteroaryl, whether alone or as part of a substituent group, is optionally substituted with one or more substituents independently selected from the group consisting of halogen, OH, alkyl, O-alkyl, —COOH, —C(O)—$C_{1-4}$ alkyl, —C(O)O—$C_{1-4}$ alkyl, —$NR^CR^D$, —S-alkyl, —SO-alkyl and —$SO_2$-alkyl; $R^A$, $R^B$, $R^C$, $R^D$, and $R^E$ are each independently selected from hydrogen and $C_{1-4}$ alkyl. In some embodiments PG is benzyl (Bn), Methoxymethyl acetal (MOM), Methyl ether, triisopropylsilyl ether (TIPS), [2-(trimethylsilyl)ethoxy]methyl acetal (SEM), or t-butyldimethylsilyl ether (TBS, TBDMS).

In some embodiments the catalyst comprises a Pd(II) or Pd(o) compound. In some embodiments the palladium compound comprises $Pd_2(dba)_3$ or $Pd(OAc)_2$ in the presence of a diphosphorus compound. In some embodiments the solution comprise a solvent selected from one or more of toluene, 1,4-dioxane, tetrahydrofuran, diethyl ether, an alcohol, methyl acetate, water, dimethyl formamide (DMF), acetonitrile, and dimethyl sulfoxide (DMSO). In some embodiments deprotecting comprises a hydrogenation/reduction reaction across an oxygen-PG bond. In some embodiments the solution is heated between 50 and 200 degrees Celsius.

The compounds of Formula (I) or (II) can inhibit Hsp90. Accordingly, in one aspect, provided herein is a method for inhibiting Hsp90 function. Generally, the method comprises contacting Hsp90 with a compound of Formula (I) or (II). In some embodiments the Hsp90 is comprised in a cell and the method further comprises administering the compound to the cell. Methods of administering a compound to a cell are well known in the art and available to one of ordinary skill in the art.

In some embodiments the cell is a fungal cell. In some embodiments the Hsp90 is a fungal isoform. For example, in some embodiments the Hsp90 is a *Candida*, *Aspergillus* or *Cryptococcus* isoform. In some embodiments an additional agent is administered to the cell. In some embodiments the additional agent is an additional anti-fungal agent. The regulation of client proteins by Hsp90 plays an important role in critical cellular processes such as cell cycle control and apoptosis. Dysregulation of Hsp90 is linked to a variety of disorders and diseases. Accordingly, in another aspect, described herein is a method for treating a Hsp90 related disease or disorder in a subject. Generally, the method comprises administering an effective amount of a compound of Formula (I) or (II) to a subject in need thereof.

As used herein, a "Hsp90 related disease or disorder" refers to a disease or disorder characterized by inappropriate Hsp90 activity or over-activity of the Hsp90. Inappropriate activity refers to either; (i) Hsp90 expression in cells which normally do not express Hsp90; (ii) increased Hsp90 expression leading to unwanted cell proliferation, differentiation and/or growth; or, (iii) decreased Hsp90 expression leading to unwanted reductions in cell proliferation, differentiation and/or growth. Over-activity of Hsp90 refers to either amplification of the gene encoding a particular Hsp90 or production of a level of Hsp90 activity which can correlate with a cell proliferation, differentiation and/or growth disorder (that is, as the level of the HSP90 increases, the severity of one or more of the symptoms of the cellular disorder increases).

Exemplary Hsp9 related diseases and disorders, include, but are not limited to, cancers, autoimmune diseases, neurodegenerative diseases, and infectious diseases. In some embodiments, the Hsp90 related disease or disorder is a cancer. In some embodiments, the Hsp90 related disease or disorder is glaucoma.

In some embodiments, the Hsp90 related disease or disorder is an infection, e.g., fungal infection. Accordingly, in some embodiments, the compounds of Formula (I) and/or (II) can be used for inhibiting or treating a fungal infection in a subject in need of treatment. In these embodiments the subject is treated with a therapeutically effective amount of the compound or a pharmaceutical composition including the compound. In some embodiments the fungal infection is a mucosal or an invasive systemic infection by a human fungal pathogen. In some embodiments the fungal infection is caused by a *Candida*, an *Aspergillus* or a *Cryptococcus* species. In some embodiments the fungal infection is caused by *Candida albicans, Candida auris, Aspergillus fumigatus, Cryptococcus neoformans, Cyrptococus gatti* or *Candida glabrata*. In some embodiments the subject is a mammal. In some embodiments the subject is a human.

In some embodiments the fungal infection is caused by *Cryptococcus neoformans* and the compound is selected from (ACSM01348); (ACSM01375); (ACSM01280); (ACSM01301); (BUCMD00420); (BUCMD00433); (ACSM01349); (ACSM01350); (117); (ACSM01351); (116); (95); (119) (94); (ACSM01491); (ACSM01279); (ACSM01371); (123); (120); (122); (109); (118); (111); (110); (ACSM01487) (ACSM01271); (115); (112); (113); (ACSM01476); (114); (83); (ACSM01272); (ACSM01492); (108); (ACSM01130); (BUCMD00429); (107); (58); (93); (91); (104); (BUCMD00467); (ACSM01494); (ACSM01493); or (ACSM01486).

In some embodiments the fungal infection is caused by *Cryptococcus neoformans* and the compound is selected from (ACSM01362); (ACSM01273); (ACSM01268); (ACSM01473); (ACSM01305); (ACSM01269); (106); (ACSM01345); (ACSM01135); or (ACSM01270).

In some embodiments the fungal infection is caused by *Candida albicans* and the compound is selected from (ACSM01348); (BUCMD00433); (131); (132); (130); (ACSM01349); (ACSM01350); (23); (121); or (121).

In some embodiments subject has a compromised immune function, cardiovascular disease, decompensated liver cirrhosis, is undergoing treatment for a burn injury, is undergoing treatment from a surgery, has a GI tract perforation, has pancreatitis, is being ventilated, is undergoing dialysis, has renal failure, is being administered broad-spectrum antibiotics, is receiving parenteral nutrition or is in close contact with vectors for infection such as pigeons. In some embodiments the subject is receiving a treatment for but not limited to rheumatoid arthritis, psoriatic arthritis, myeloproliferative disorders, chronic myeloid leukemia, chronic lymphocytic leukemia, steroid-refractory graft-versus host disease, follicular lymphoma, polycythaemia rubra vera, and Waldenström macroglobulinaemia. In some embodiments the subject is being treated with any one or more of ibrutinib, ruxolitinib, tofacitinib, or idelalisib.

In some embodiments the subject is being treated with one or more additional antifungal agent. For example, wherein the first agent is not effective or is more effective with additional treatment including compound (I) or (II). In some embodiments the treatment includes more than one compound selected from compounds having structures (I) or (II). In some embodiments the additional antifungal agent is an azole antifungal. For example, in some embodiments the azole antifungal is any one or more of, bifonazole, butoconazole, clotrimazole, dconazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, and abafungin. In some embodiments at least one additional anti-fungal agent is an allylamine, such as selected from amorolfin, butenafine, naftifine, and terbinafine. In some embodiments at least one additional anti-fungal agent is an Echinocandins, such as selected from Anidulafungin, Caspofungin, and Micafungin. In some embodiments at least one additional anti-fungal agent is selected from aurones, benzoic acid, ciclopirox, flucytosine, griseofulvin, tolnaftate, undecylenic acid, triacetin, crystal violet, orotomide, miltefosine, nikkomycin, copper(II) sulfate, selenium disulfide, sodium thiosulfate, piroctone olamine, Iodoquinol, clioquinol, acrisorcin, zinc pyrithione and sulfur.

In some embodiments the Hsp90 is a by *Cryptococcus neoformans* isoform and the compound is selected from (ACSM01348); (ACSM01375); (ACSM01280); (ACSM01301); (BUCMD00420); (BUCMD00433); (ACSM01349); (ACSM01350); (117); (ACSM01351); (116); (95); (119) (94); (ACSM01491); (ACSM01279); (ACSM01371); (123); (120); (122); (109); (118); (111); (110); (ACSM01487) (ACSM01271); (115); (112); (113); (ACSM01476); (114); (83); (ACSM01272); (ACSM01492); (108); (ACSM01130); (BUCMD00429); (107); (58); (93); (91); (104); (BUCMD00467); (ACSM01494); (ACSM01493); or (ACSM01486).

In some embodiments the Hsp90 is a by *Cryptococcus neoformans* isoform and the compound is selected from (ACSM01362); (ACSM01273); (ACSM01268); (ACSM01473); (ACSM01305); (ACSM01269); (106); (ACSM01345); (ACSM01135); or (ACSM01270).

In some embodiments the Hsp90 is a *Candida albicans* isoform and the compound is selected from (ACSM01348); (BUCMD00433); (131); (132); (130); (ACSM01349); (ACSM01350); (23); (121); or (121).

The compositions and methods of the invention can be used to treat many different cancers. Specific examples of types of cancers include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated.

In some embodiments, the cancer is an Hsp90 dependent cancer. An "Hsp90" dependent cancer is a cancer whose physiology utilizes Hsp90.

In some embodiments of the various aspects disclosed herein, the composition or method can further comprise administering an additional anti-cancer therapy to the subject. The additional anti-cancer therapy can be selected from the group consisting of surgery, chemotherapy, radiation therapy, thermotherapy, immunotherapy, hormone therapy, laser therapy, and anti-angiogenic therapy, or any combination thereof. For example, additional anti-cancer therapy can comprise administering a standard of care chemotherapeutic to the subject. Non-limiting examples of a standard of care chemotherapeutics or other anti-cancer therapy can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. Additional anti-cancer treatment can further include the use of radiation or radiation therapy. Further, the additional anti-cancer treatment can also include the use of surgical treatments.

In some embodiments, the additional anti-cancer therapy comprises administering a kinase inhibitor, a chemotherapeutic agent, an immunomodulator or any combination thereof, to the subject.

In some embodiments of the various aspects disclosed herein, the treatment is administered to a subject currently receiving standard of care chemotherapeutics or other alternative anti-cancer treatments. Generally, cancer treatment can involve one or more of the treatment options, but not limited to surgery, radiation, chemotherapy, immunotherapy, targeted therapy and hormonal therapy. The single agent therapy or current combination therapies for the treatment of cancer cause side effects such as nausea, rashes, swelling, flu-like symptoms, fatigue, digestive tract problems, allergic reactions and immunosuppression. In some embodiments, the invention described herein provides a more effective treatment of cancer by administering one or more compounds represented by Formula (I) or (II) in combination with other cancer treatments. In some embodiments, the combination therapy induces additive or synergistic therapeutic effect. In some embodiments, the method described herein can reduce or prevent one or more adverse effects or toxicities associated with the administration of a chemotherapeutic agent or radiation therapy. In some embodiments, the method described herein can increase the antitumor activity of a chemotherapeutic agent or radiation therapy or increase the selective cytotoxicity of a chemotherapeutic agent.

The phrase "combination therapy" as described herein means administration of one or more compounds represented by Formula (I) or (II) and a therapeutic agent as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period. The time period may be in minutes, hours, days or weeks depending upon the combination selected.

Combination therapy includes administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be done, for example, by administering to the subject a single pill having a fixed ratio of each therapeutic agent or in multiple, single pills for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered may or may not be important.

Combination therapy also can mean the administration of one or more compounds represented by Formula (I) or (II) in further combination with other compounds and non-drug therapies, such as, but not limited to, surgery or radiation treatment. Where the combination therapy further comprises radiation treatment, the radiation treatment may be conducted at any suitable time so long as a beneficial effect from the co-action of the combination of the therapeutic agents and radiation treatment is achieved.

Some embodiments further comprise pharmaceutical compositions containing a therapeutically effective amount of a compound prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier can take a wide variety of forms depending upon the desired route of administration (e.g. oral, parenteral). Thus, for liquid oral preparations such as suspensions, elixirs, and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives.

To prepare the pharmaceutical compositions according to some embodiments, one or more compounds described herein as the active ingredient is intimately admixed with a pharmaceutical carrier according to conventional pharmaceutical compounding techniques, which carrier can take a wide variety of forms depending of the form of preparation desired for administration, e.g. oral or parenteral such as intramuscular. In preparing the compositions in oral dosage form, any of the usual pharmaceutical media can be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets can be sugar coated or enteric coated by standard techniques. For parenteral administration, the carrier will usually comprise sterile water, through other ingredients, for example, for purposes such as aiding solubility or for preservation, can be included. Injectable suspensions can also be prepared, in which case appropriate liquid carriers, suspending agents and the like can be employed. The pharmaceutical compositions herein will contain, per dosage unit, e.g. tablet, capsule, powder, injection, teaspoonful, and the like, an amount of the active ingredient necessary to deliver an effective dose as described above. The pharmaceutical compositions herein will contain, per unit dosage unit, e.g. tablet, capsule, powder, injection, suppository, teaspoonful, and the like, of from about 0.01 mg to about 1000) mg or any amount or range therein, and can be given at a dosage of from about 0.01 mg/kg/day to about 300 mg/kg/day, or any amount or range therein, for example from about 0.1 mg/kg/day to about 50 mg/kg/day, or any amount or range therein, or for example from about 0.05 mg/kg/day to about 15 mg/kg/day, or any amount or range therein. In some embodiments a recommended starting dosage is from 5 mg/kg/day to about 20 mg/kg/day, or any amount or range therein. In some embodiments the dosage is administered over several smaller dosages, for example a 5 mg/kg/day can be administered in two dosages of 2.5 mg/kg approximately every 12 hours (e.g. 8 am and 8 pm). The dosages, can be varied depending upon the requirement of the patients, the severity of the condition being treated and the compound being employed. The use of either daily administration or post-periodic dosing can be employed.

In some embodiments, these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition can be presented in a form suitable for once-weekly or once-monthly administration; for example, an insoluble salt of the active compound, such as the decanoate salt, can be adapted to provide a depot preparation for intramuscular injection.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the invention, or a pharmaceutically acceptable salt thereof. When referring to these preformulation compositions as homogeneous, it is meant that the active ingredient is dispersed evenly throughout the composition so that the composition can be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the invention. In one embodiment, the solid preformulation composition is subdivided into unit dosage forms containing from about 0.01 mg to about 0.1 mg. In another embodiment, the solid preformulation composition is subdivided into unit dosage forms containing from about 0.05 mg to about 0.5 mg. In another embodiment, the solid preformulation composition is subdivided into unit dosage forms containing from about 0.1 mg to about 1 mg. In another embodiment, the solid preformulation composition is subdivided into unit dosage forms containing from about 0.5 mg to about 5 mg. In another embodiment, the solid preformulation composition is subdivided into unit dosage forms containing from about 1 mg to about 10 mg. In another embodiment, the solid preformulation composition is subdivided into unit dosage forms containing from about 5 mg to about 50 mg. In another embodiment, the solid preformulation composition is subdivided into unit dosage forms containing from about 10 mg to about 100 mg. In another embodiment, the solid preformulation composition is subdivided into unit dosage forms containing from about 50 mg to about 500 mg. In another embodiment, the solid preformulation composition is subdivided into unit dosage forms containing from about 250 mg to about 750 mg. In another embodiment, the solid preformulation composition is subdivided into unit dosage forms containing from about 500 mg to about 1000 mg.

The tablets or pills of the composition according to some embodiments can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol, and cellulose acetate.

The liquid forms in which the compositions can be incorporated for administration orally or by injection include, aqueous solutions, suitably flavored syrups, aqueous or oil suspensions, and flavored emulsions with edible oils such as cottonseed oil, hemp seed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, or gelatin.

In some embodiments, carriers can comprise inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

In some embodiments, the compounds of the invention can be administered in a single daily dose, or the total daily dosage can be administered in divided doses of two, three or four times daily. Furthermore, compounds for the invention can be administered in intranasal form via topical use of suitable intranasal vehicles, or via transdermal skin patches well known to those of ordinary skill in that art. To be administered in the form of a transdermal delivery system, the dosage administration will be continuous rather than intermittent throughout the dosage regimen For example, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum, and the like.

In some embodiments, the liquid forms include any suitably flavored suspending or dispersing agents such as synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition according to some embodiments, a compound prepared according to any of the processes described herein as the active ingredient is intimately admixed with a pharmaceutical carrier according to conventional pharmaceutical compounding techniques, which carrier can take a wide variety of forms depending of the form of preparation desired for administration (e.g. oral or parenteral). Suitable pharmaceutically acceptable carriers are well known in the art. Descriptions of some of these pharmaceutically acceptable carriers can be found in The Handbook of Pharmaceutical Excipients, published by the American Pharmaceutical Association and the Pharmaceutical Society of Great Britain, the entirety of which is incorporated herein by reference.

Methods of formulating pharmaceutical compositions have been described in numerous publications such as "Pharmaceutical Dosage Forms: Tablets", Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc., the entirety of which are incorporated herein by reference.

For oral administration, the compositions are preferably provided in the form of tablets containing, about 0.01 mg, about 0.05 mg, about 0.1 mg, about 0.5 mg, about 1.0 mg, about 2.5 mg, about 5.0 mg, about 10.0 mg, about 15.0 mg, about 25.0 mg, about 50.0 mg, about 100 mg, about 150 mg, about 200 mg, about 250 mg, and/or about 500 mg of the active ingredient for the symptomatic adjustment of the dosage to the patient to be treated. An effective amount of the drug is ordinarily supplied at a dosage level of from about 0.01 mg % kg to about 500 mg/kg of body weight per day, or any amount or range therein. In some embodiments, the range is from about 0.1 to about 50.0 mg/kg of body weight per day, or any amount or range therein. In some embodiments the dosage is from about 0.5 to about 15.0 mg/kg of body weight per day, or any amount or range therein. In some embodiments the dosage is from about 1.0 to about 7.5 mg/kg of body weight per day, or any amount or range therein. In some embodiments the dosage is from about 5 mg/kg/day to about 20 mg/kg/day or any amount or range therein. The compounds can be administered on a regimen of 1 to 4 times per day.

Optimal dosages to be administered can be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known, and generally accepted cell and/or animal models are predictive of the ability of a test compound to treat or prevent a given disorder.

One skilled in the art will further recognize that human clinical trials, including first-in-human, dose ranging, and efficacy trials, in healthy patients and/or those suffering from a given disorder, can be completed according to methods well known in the clinical and medical arts.

Embodiments of various aspects described herein can be defined as in any of the following numbered paragraphs:

1. A compound having the structure of Formula (I) or (II): or stereoisomers, tautomers, or a pharmaceutically acceptable salt or ester thereof, wherein:

$R_{30}$ and $R_{31}$ are independently selected from H, OH, alkyl, alkenyl, alkynyl, alkoxy, acyl, cycloalkyl, heterocycle, aryl, protected hydroxyl, or benzyl;

$R_1$, $R_2$, $R_3$, $R'_1$, $R'_2$ and $R'_3$ are independently selected from the H, OH, protected hydroxyl, —CO$_2$H, amide, alkyl, alkenyl, alkynyl, alkoxy, acyl, cycloalkyl, heterocycle, aryl, or benzyl;

W is —C(O)NR$_4$R$_5$ or —C(O)Z wherein Z is an aryl, heteroaryl, cycloalkyl or hererocyclyoxazol; and W and any one of $R_1$, $R_2$, $R_3$, $R'_1$, $R'_2$ or $R'_3$ can be connected;

$R_4$ and $R_5$ are independently selected from H, alkyl, alkenyl, alkynyl, acyl, cycloalkyl, heterocycle, aryl, benzyl or $R_4$ and $R_5$ together with the nitrogen to which they are attached form a heterocyclic ring;

wherein any alkyl, alkenyl, alkynyl, alkoxy, acyl, amide, cycloalkyl, and heterocycle is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or acyl group optionally includes —O—, —S—, —SO$_2$—, —N(R$^E$)— substituting one or more carbons in the carbon chain, wherein any aryl, benzyl or heteroaryl, whether alone or as part of a substituent group, is optionally substituted with one or more substituents independently selected from the group consisting of halogen, OH, alkyl, O-alkyl, —COOH, —C(O)—C$_{1-4}$ alkyl, —C(O)O—C$_{1-4}$ alkyl, —NR$^C$R$^D$, —S-alkyl, —SO-alkyl and —SO$_2$-alkyl;

wherein $R^A$, $R^B$, $R^C$, $R^D$, and $R^E$ are each independently selected from hydrogen and C$_{1-4}$ alkyl.

2. The compound according to paragraph 1 having structure (I), wherein $R_1$, $R_2$, and $R_3$ are independently selected from H, methyl, ethyl, butyl, phenyl, isopropyl, t-butyl, cyclopropyl, cyclopentyl, cyclohexyl, phenyl-2,3-disubstituted, phenyl-2,5-disubstituted, phenyl-2,4-disubstituted, phenyl-3,4-disubstituted, phenyl-2-methyl, phenyl-4-methyl, phenyl-4-methoxy, phenyl-3-methoxy, phenyl-2-methoxy, phenyl-2-CF$_3$, phenyl-3-methyl, phenyl-2-fluro, phenyl-3-chloro, phenyl-2-OCF$_3$, phenyl-4-fluoro, phenyl-2,6-disubstituted, phenyl-3-fluoro, phenyl-4-t-butyl, phenyl-3-OCF$_3$, phenyl-4-CF$_3$, 2-pyridine, 3-pyridine, 3-furan, phenyl-4-OCF$_3$, —CH$_2$CO$_2$H, —CH$_2$-cyclohexyl, benzyl, benzyl-2-chloro, benzyl-4-CF$_3$, benzyl-4-isopropyl, benzyl-4-methyl, benzyl-2-methyl, benzyl-4-isopropyl, —CH$_2$-2-furan, CH$_2$C(O)NHMe, or benzyl-4-methoxy.

3. The compound according to paragraph 2, wherein the compound has structure (I) and:

$R_1$ is selected from phenyl, methyl, —CH$_2$CO$_2$H, phenyl-4-methoxy, —CH$_2$-cyclohexyl, t-butyl, isopropyl, isobutyl, cyclohexyl, benzyl, benzyl-2-chloro, benzyl-4-CF$_3$, benzyl-4-isopropyl, benzyl-4-methyl, benzyl-2-methyl, benzyl-4-isopropyl, —CH$_2$-2-furan, CH$_2$C(O)NHMe, benzyl-4-methoxy, or cyclopentyl;

$R_2$ is selected from H, methyl, ethyl, t-butyl, phenyl, isopropyl, cyclopropyl, cyclopentyl, cyclohexyl, phenyl-2,3-disubstituted, phenyl-2,5-disubstituted, phenyl-2-methyl, phenyl-3-methyl, phenyl-4-methyl, phenyl-2-methoxy, phenyl-3-methoxy, phenyl-2-CF$_3$, phenyl-4-CF$_3$, phenyl-2-fluro, phenyl-3-chloro, phenyl-2-OCF$_3$, phenyl-3-fluoro, phenyl-4-fluoro, phenyl-2,6-disubstituted, phenyl-4-t-butyl, phenyl-3-OCF$_3$, phenyl-4-OCF$_3$, 2-pyridine, 3-pyridine, or 3-furan;

$R_3$ is selected form H, methyl, isopropyl, phenyl, benzyl.

4. The compound according to paragraph 1 having structure (II), wherein $R'_1$, $R'_2$, and $R'_3$ are independently selected from H, methyl, ethyl, isopropyl, phenyl, phenyl-2,4-disubstituted, phenyl-2,3-disubstituted, phenyl-3,5-disubstituted, phenyl-3,4-disubstituted, phenyl-2-CF$_3$, phenyl-3-CF$_3$, phenyl-2-methoxy, phenyl-3-methyl, phenyl-2-methyl, and —CH$_2$CH$_2$NMe$_2$.

5. The compound according to paragraph 4, wherein the compound has structure (II) and:

$R'_1$ is selected from H, methyl, phenyl-3-CF$_3$, phenyl-2-methoxy, phenyl-2-CF$_3$, phenyl, i-propyl, phenyl-3-methyl, ethyl, phenyl-2-methyl, and —CH$_2$CH$_2$NMe$_2$, $R'_2$ is selected from H, methyl, i-propyl, ethyl phenyl-3-CF$_3$, phenyl-2-methoxy, phenyl-3-methyl, phenyl-2-methoxy, phenyl-2-CF$_3$, phenyl, phenyl-2-methyl, and —CH$_2$CH$_2$NMe$_2$, $R'_3$ is selected from methyl and H.

6. The compound according to paragraph 1, wherein the compound has structure (I) or (II), and W is —C(O)NR$_4$R$_5$.

7. The compound according to paragraph 1, wherein the compound has structure (I) or (II), and where W is —C(O)Z, and where Z is a heterocyclic ring of structure (III);
wherein $R_{10}$, $R_{11}$, $R_{12}$, and $R_{13}$, are independently selected from the group consisting of H, OH, protected hydroxyl, —$CO_2H$, amide, halide, alkyl, alkenyl, alkynyl, alkoxy, acyl, cycloalkyl, heterocycle, aryl, or benzyl; any $R_{10}$, $R_{11}$, $R_{12}$, and $R_{13}$ and carbons to which they are attached can form a spiro or fused ring structure.

8. The compound according to paragraph 1, wherein the compound has structure (I) or (II), and W is —C(O)Z, where Z is a heterocyclic ring of structure (IV);
wherein $B_1$, $B_2$ and $B_3$ are independently $CR_{15}$, $CR_{16}$, $NR_{17}$ or N;
where $R_1$, $R_{16}$, $R_{17}$ are independently selected from the group consisting of H, OH, protected hydroxyl, —$CO_2H$, amide, halide, alkyl, alkenyl, alkynyl, alkoxy, acyl, cycloalkyl, heterocycle, aryl, or benzyl.

9. The compound according to paragraph 8, wherein two of $B_1$, $B_2$ and $B_3$ are $CR_{15}$ and $CR_{16}$, and the remaining $B_1$, $B_2$ or $B_3$ is $NR_{17}$.

10. The compound according to paragraph 8, wherein one of $B_1$, $B_2$ and $B_3$ is $CR_{15}$, one of $B_1$, $B_2$ and $B_3$ is N, and one of $B_1$, $B_2$ and $B_3$ is $NR_{17}$.

11. The compound according to paragraph 1, wherein the compound has structure (I) or (II), and W is —C(O)Z, where Z is a heterocyclic ring of structure (V);
wherein $A_1$ is N, C(O), $NR_{24}$ or $CR_{20}$; $A_2$ is N, C(O), $NR_{24}$ or $CR_{21}$; $A_3$ is N, C(O), NH or $CR_{22}$; $A_4$ is N, C(O), $NR_{24}$ or $CR_{23}$;
$R_{20}$, $R_{21}$, $R_{22}$ and $R_{23}$ are independently selected from the group consisting of H, OH, protected hydroxyl, —$CO_2H$, amide, halide, alkyl, alkenyl, alkynyl, alkoxy, acyl, cycloalkyl, heterocycle, aryl, or benzyl; and
each $R_{24}$ is H, OH, protected hydroxyl, —$CO_2H$, amide, halide, alkyl, alkenyl, alkynyl, alkoxy, acyl, cycloalkyl, heterocycle, aryl, or benzyl.

12. The compound according to paragraph 1, wherein W is an oxazol amide having the structure of (Ao),
wherein $R_7$ and $R_6$ are independently selected from H, OH, protected hydroxyl, —$CO_2H$, alkyl, alkenyl, alkynyl, alkoxy, acyl, amide, cycloalkyl, heterocycle, aryl, or benzyl;
wherein any alkyl, alkenyl, alkynyl, alkoxy, acyl, amide, cycloalkyl, and heterocycle is optionally substituted with one or more substituents independently selected from the group consisting of halogen, —OH, alkyl, O-alkyl, —$NR^IR^J$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —N($R^K$)— substituting one or more carbons in the carbon chain;
wherein $R^I$, $R^J$, and $R^K$ are each independently selected from hydrogen and $C_{1-4}$ alkyl.

13. The compound according to paragraph 1, wherein the compound has structure (I) or (II) and
W is oxazole amide (A30), or
W is —C(O)$NR_4R_5$ wherein $R_4$ and $R_5$ are independently selected from H and ethyl; or methyl and —$CH_2$-3-pyridine; or H and benzyl; or methyl and $CH_2$-oxazole; or methyl and —$CH_2$-pyran; or methyl and —$CH_2$-4-pyridine; or methyl and —$CH_2$-cyclopropyl; or W is —C(O)Z, where Z is a heterocyclic ring selected from:
(A1); (A2); (A3); (A4); (A5); (A6); (A7); (A8); (A9); (A10); (A11); (A12); (A13); (A14); (A15); (A16); (A17); (A18); (A19); (A20); (A21); (A22); (A23); (A24); (A25); (A26); (A28); (A29); (A32); (A33) and (A31).

14. The compound according to paragraph 13, wherein the compound has structure (I), and wherein;
W is oxazole amide ($A_{30}$); or
W is —C(O)$NR_4R_5$ wherein $R_4$ and $R_5$ are independently selected from H and ethyl; or methyl and —$CH_2$-3-pyridine; or H and benzyl; or methyl and $CH_2$Oxazole; or methyl and $CH_2$-pyran; or methyl and —$CH_2$-4-pyridine; or
W is —C(O)Z, where Z is a heterocyclic ring selected from:
(A1); (A2); (A3); (A4); (A5); (A6); (A7); (A8); (A9); (A10); (A11); (A12); (A13); (A14); (A15); (A16); (A17); (A18); (A22); (A23); (A24); (A25); (A26); (A28); and (A29).

15. The compound according to paragraph 13, wherein the compound has structure (II), and W is oxazole amide (A30) having structure; (A30), or
W is —C(O)Z, where Z is a heterocyclic ring selected from; (A1); (A14); (A19); (A15); (A12); (A21); (A11); (A13); (A4); (A10); (A22); and (A23).

16. The compound according to paragraph 1, wherein the compound is a compound selected from Table 1.

17. The compound according to paragraph 1, wherein W is not oxazol (Ao).

18. The compound according to paragraph 1, wherein the compound has structure (I) and is further defined as structure (X); wherein
W is —C(O)Z, where Z is a heterocyclic ring selected from;
($A_1$), ($A_6$), ($A_{24}$); ($A_{32}$), or ($A_{33}$)
$R_1$, $R_6$, $R_7$, $R_8$ are independently selected from H, alkyl, and alkoxy;
wherein any alkyl or alkoxy is optionally substituted with one or more substituents independently selected from the group consisting of halogen, —OH, alkyl, O-alkyl, —$NR^FR^G$, —S-alkyl, —SO— alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —N($R^H$)— substituting one or more carbons in the carbon chain,
wherein $R^F$, $R^G$, and $R^H$ are each independently selected from hydrogen and $C_{1-4}$ alkyl.

19. The compound according to paragraph 18 having structure (X), wherein $R_1$, $R_6$, $R_7$, $R^8$ are independently selected from H, methyl, isopropyl, t-butyl, —$CF_3$, —$OCH_3$, or —$OCF_3$.

20. The compound according to paragraph 18 or 19, wherein $R_6$ and $R_7$ are H.

21. The compound according to any one of paragraphs 18-20, wherein $R_1$ is methyl and $R^8$ is selected from methyl, t-butyl, —$CF_3$, —$OCH_3$, or —$OCF_3$.

22. The compound according to paragraph 18, wherein $R_7$ and $R^8$ are H.

23. The compound according to paragraph 18, wherein $R_1$ is methyl, and $R_6$ is selected from methyl, t-butyl, —$CF_3$, —$OCH_3$, or —$OCF_3$.

24. The compound according to paragraph 18, wherein $R_6$ and $R^8$ are H.

25. The compound according to paragraph 24, wherein $R_1$ is methyl and $R_7$ is methyl, —$CF_3$, or —$OCH_3$.

26. The compound according to paragraph 1, wherein the compound has structure (II) and is further defined as structure (XI), wherein;
W is —C(O)Z, where Z is ($A_1$)
$R'_1$, $R'_3$, $R'_6$, $R'_7$, $R'_8$ are independently selected from H, alkyl, and alkoxy;
wherein any alkyl or alkoxy is optionally substituted with one or more substituents independently selected from the group consisting of halogen, —OH, alkyl, O-alkyl, —$NR^L R^M$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —$N(R^N)$— substituting one or more carbons in the carbon chain, wherein $R^L$, $R^M$, and $R^N$ are each independently selected from hydrogen and $C_{1-4}$ alkyl.

27. The compound according to paragraph 26, wherein;
$R'_1$ and $R'_3$ are independently H or alkyl, and
$R'_6$, $R'_7$ and R's are independently H, alkyl, alkoxy or —$CF_3$.

28. The compound according to paragraph 26 or 27, wherein $R'_6$ is alkoxy or —$CF_3$.

29. The compound according to any one of the above paragraphs, wherein $R_{30}$ and $R_{31}$ are OH.

30. The compounds according to paragraph 1, wherein the compound is:
(ACSM01348); (ACSM01375); (ACSM01280); (ACSM01301); (BUCMD00420); (BUCMD00433); (ACSM01349); (ACSM01350); (117); (ACSM01351); (116); (95); (119); (94); (ACSM01491); (ACSM01279); (ACSM01371); (123); (120); (122); (109); (118); (111); (110); (ACSM01487); (ACSM01271); (115); (112); (113); (ACSM01476); (114); (83); (ACSM01272); (ACSM01492); (108); (ACSM01130); (BUCMD00429); (107); (58); (93); (91); (104); (BUC MD00467); (ACSM01494); (ACSM01493); or (ACSM01486).

31. The compounds according to paragraph 1, wherein the compound is:
(ACSM01362); (ACSM01273); (ACSM01268); (ACSM01473); (ACSM01305); (ACSM0126 9); (106); (ACSM01345); (ACSM01135); or (ACSM01270).

32. The compound according to paragraph 1, wherein the compound is:
(ACSM01348); (BUCMD00433); (131); (132); (130); (ACSM01349); (ACSM01350); (23); (121); or (121).

33. The compound according to paragraph 1;
wherein W and $R_1$, is connected and the compound has the structure of,
(XV); (XVI); (XVII) or (XVIII);
where in (XV) D is N, and
3 of the $A_5$, $A_6$, $A_7$ and $A_8$ are independently $NR_{50}$, $CR_{51}$, and the remaining $A_5$, $A_6$, $A_7$ and $A_8$ is C and is bonded to D by a linker (-----);
wherein in (XVI) D is N, and
2 of the $B_4$, $B_5$, and $B_6$ are independently N, $NR_{50}$, or $CR_{51}$, and the remaining $B_4$, $B_5$, and $B_6$ is C or N and is bonded to D by a linker (-----);
Wherein the linker (-----) is a linking group comprising a chain of 2 to 12 carbons wherein one or more carbons in the chain is substituted with —O—, —S—, —$N(R^R)$—, —$N(R^S)C(O)$—, —$SO_2$—, —C≡C—, —C=C—, and wherein any carbon is optionally substituted with one or more substituents;

$R_{42}$, $R_{43}$, are independently H, —$CO_2H$, amide, halide, alkyl, alkenyl, alkynyl, alkoxy, acyl, cycloalkyl, heterocycle, aryl, or benzyl;
$R_{44}$, $R_{45}$, and $R_{46}$ are independently H, —$CO_2H$, amide, halide, alkyl, alkenyl, alkynyl, alkoxy, acyl, cycloalkyl, heterocycle, aryl, or benzyl; any $R_{44}$, $R_{45}$, and $R_{46}$ and carbons to which they are attached can form a spiro or fused ring structure;
wherein any alkyl or alkoxy is optionally substituted with one or more substituents independently selected from the group consisting of halogen, —OH, alkyl, O-alkyl, —$NR^O R^P$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —$N(R^Q)$-substituting one or more carbons in the carbon chain;
wherein $R^O$, $R^P$, and $R^Q$ are each independently selected from hydrogen and $C_{1-4}$ alkyl.

34. The compound according to paragraph 33 wherein the linker includes;

wherein $R_{47}$ and $R_{48}$ are independently H or alkyl, x is 1 to 10, and y is 1 to 5.

35. The compound according to paragraph 33, wherein the compound has structure (XX), or (XXI).

36. A pharmaceutical composition comprising a compound according to any one of the above paragraphs and a pharmaceutically acceptable carrier, diluent or excipient.

37. A method for preparing a compound having formula (I-$H_2$), the method comprising: providing a solution of a compound having formula (VI) and (VII) in the presence of a catalyst to provide protected product (I'), and de-protecting (I') to afford (I-$H_2$), wherein:
PG is a protecting group;
X is a halide selected from chlorine, bromine or iodine;
$R_1$, $R_2$, $R_3$, $R'_1$, $R'_2$ and $R'_3$ are independently selected from the group consisting of H, OH, protected hydroxyl, —$CO_2H$, amide, alkyl, alkenyl, alkynyl, alkoxy, acyl, cycloalkyl, heterocycle, aryl, or benzyl;
W is —$C(O)NR_4R_5$ or oxazol (Ao),
$R_4$ and $R_5$ are independently selected from H, alkyl, alkenyl, alkynyl, acyl, cycloalkyl, heterocycle, aryl, benzyl or $R_4$ and $R_5$ together with the nitrogen to which they are attached form a heterocyclic ring;
$R_7$ and $R^8$ independently selected from H, OH, protected hydroxyl, —$CO_2H$, alkyl, alkenyl, alkynyl, alkoxy, acyl, amide, cycloalkyl, heterocycle, aryl, or benzyl;
wherein any alkyl, alkenyl, alkynyl, alkoxy, acyl, cycloalkyl, is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or acyl group optionally includes —O—, —S—, —SO$_2$—, —N(R$^E$)— substituting one or more carbons in the carbon chain, wherein any aryl, benzyl or heteroaryl, whether alone or as part of a substituent group, is optionally substituted with one or more substituents independently selected from the group consisting of halogen, OH, alkyl, O-alkyl, —COOH, —C(O)—C$_{1-4}$ alkyl, —C(O)O—C$_{1-4}$ alkyl, —NR$^C$R$^D$, —S-alkyl, —SO-alkyl and —SO$_2$-alkyl;

wherein R$^A$, R$^B$, R$^C$, R$^D$, and R$^E$ are each independently selected from hydrogen and C$_{1-4}$ alkyl.

38. The method according to paragraph 37, wherein PG is benzyl (Bn), Methoxymethyl acetal (MOM), Methyl ether, triisopropylsilyl ether (TIPS), [2-(trimethylsilyl)ethoxy]methyl acetal (SEM), or t-butyldimethylsilyl ether (TBS, TBDMS).

39. The method according to paragraph 37 or 38 wherein the catalyst comprises a Pd(II) or Pd(o) compound.

40. The method according to paragraph 39, wherein the palladium compound comprises Pd$_2$(dba)$_3$ or Pd(OAc)$_2$ in the presence of a diphosphorus compound.

41. The method according to any one of paragraph 37-40 further comprising a base.

42. The method according to any one of paragraph 37-41 wherein the solution comprise a solvent selected from one or more of toluene, 1,4-dioxane, tetrahydrofuran, diethyl ether, an alcohol, methyl acetate, water, dimethyl formamide (DMF), acetonitrile, and dimethyl sulfoxide (DMSO).

43. The method according to any one of paragraphs 37-42, wherein deprotecting comprises a hydrogenation/reduction reaction across an oxygen-PG bond.

44. The method according to any one of paragraphs 37-42, wherein the solution is heated between 50 and 200 degrees Celsius.

45. A method for preparing a compound having formula (I-H$_2$) the method comprising:
providing a solution of a compound having formula (VI) and (VII) in the presence of a noble metal catalyst to provide protected product (II'), and deprotecting (II') to afford (II-H$_2$),
wherein:
PG is a protecting group;
X is a halide selected from chlorine, bromine or iodine;
R$_1$, R$_2$, R$_3$, R'$_1$, R'$_2$ and R'$_3$ are independently selected from the group consisting of H, OH, protected hydroxyl, —CO$_2$H, amide, alkyl, alkenyl, alkynyl, alkoxy, acyl, cycloalkyl, heterocycle, aryl, or benzyl;
W is —C(O)NR$_4$R$_5$ or oxazol (Ao),
R$_4$ and R$_5$ are independently selected from H, alkyl, alkenyl, alkynyl, acyl, cycloalkyl, heterocycle, aryl, benzyl or R$_4$ and R$_5$ together with the nitrogen to which they are attached form a heterocyclic ring;
R$_7$ and R$_6$ independently selected from H, OH, protected hydroxyl, —CO$_2$H, alkyl, alkenyl, alkynyl, alkoxy, acyl, amide, cycloalkyl, heterocycle, aryl, or benzyl;
wherein any alkyl, alkenyl, alkynyl, alkoxy, acyl, cycloalkyl, is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or acyl group optionally includes —O—, —S—, —SO$_2$—, —N(R$^E$)— substituting one or more carbons in the carbon chain, wherein any aryl, benzyl or heteroaryl, whether alone or as part of a substituent group, is optionally substituted with one or more substituents independently selected from the group consisting of halogen, OH, alkyl, O-alkyl, —COOH, —C(O)—C$_{1-4}$ alkyl, —C(O)O—C$_{1-4}$ alkyl, —NR$^C$R$^D$, —S-alkyl, —SO-alkyl and —SO$_2$-alkyl;

wherein R$^A$, R$^B$, R$^C$, R$^D$, and R$^E$ are each independently selected from hydrogen and C$_{1-4}$ alkyl.

46. The method according to paragraph 45, wherein PG is benzyl (Bn), Methoxymethyl acetal (MOM), Methyl ether, triisopropylsilyl ether (TIPS), [2-(trimethylsilyl)ethoxy]methyl acetal (SEM), or t-butyldimethylsilyl ether (TBS, TBDMS).

47. The method according to paragraph 45 or 46 wherein the noble metal catalyst comprises a Pd(II) or Pd(o) compound.

48. The method according to paragraph 47, wherein the palladium compound comprises Pd$_2$(dba)$_3$ or Pd(OAc) in the presence of a diphosphorus compound.

49. The method according to any one of paragraph 45-48 further comprising a base.

50. The method according to any one of paragraph 45-49 wherein the solution comprise a solvent selected from one or more of toluene, 1,4-dioxane, tetrahydrofurane, diethyl ether, an alcohol, methyl acetate, water, dimethyl formamide (DMF), acetonitrile, and dimethyl sulfoxide (DMSO).

51. The method according to any one of claims 45-50, wherein deprotecting comprises a hydrogenation/reduction reaction across an oxygen-PG bond.

52. The method according to any one of claims 45-51, wherein the solution is heated between about 50 and 200 degrees Celsius.

53. A method of inhibiting or treating a fungal infection in a subject in need thereof, the method comprising:
administering to the subject a therapeutically effective amount of the compound of any one of paragraph 1-35 or the pharmaceutical composition of paragraph 36.

54. The method of paragraph 53, wherein the fungal infection is a mucosal or an invasive systemic infection by a human fungal pathogen.

55. The method of paragraph 53 or 54, wherein the fungal infection is caused by a *Candida*, an *Aspergillus* or a *Cryptococcus* species.

56. The method of paragraph 55, wherein the fungal infection is caused by *Candida albicans, Candida auris, Aspergillus fumigatus, Cryptococcus neoformans. Cyrptococus gatti* or *Candida glabrata*.

57. The method of paragraph 53, wherein the fungal infection is caused by *Cryptococcus neoformans* and the compound is selected from a compound of paragraph 30.

58. The method of paragraph 53, wherein the fungal infection is caused by *Cryptococcus neoformans* and the compound is selected from a compound of paragraph 31.

59. The method of paragraph 53, wherein the fungus infection is caused by *Candida albicans* and the compound is selected from a compound of paragraph 32.

60. The method of any one of paragraphs 53-59, wherein the subject is a human.

61. The method of any one of paragraphs 53-60, wherein administration is oral, topical or by direct injection.

62. The method of any one of paragraphs 53-61, wherein the subject has a compromised immune function, cardiovascular disease, decompensated liver cirrhosis, is undergoing treatment for a burn injury, is undergoing treatment from a surgery, has a GI tract perforation, has pancreatitis, is being ventilated, is undergoing dialysis, has renal failure, is being administered broad-spectrum antibiotics, is receiving parenteral nutrition or is in close contact with vectors for infection such as pigeons.
63. The method of any one of paragraphs 53-62, wherein the subject is immunocompromised as a consequence of a pre-existing medical condition including, but not limited to treatment with cancer chemotherapies, stem cell/organ transplantation, or the subject suffers from an immunocompromising viral infection, autoimmune or metabolic disorder.
64. The method of any one of paragraphs 53-63, wherein the subject is receiving a treatment for but not limited to rheumatoid arthritis, psoriatic arthritis, myeloproliferative disorders, chronic myeloid leukemia, chronic lymphocytic leukemia, steroid-refractory graft-versus host disease, follicular lymphoma, polycythaemia rubra vera, and Waldenström macroglobulinaemia.
65. The method of any one of paragraphs 53-64, wherein the subject is being treated with any one or more of ibrutinib, ruxolitinib, tofacitinib, or idelalisib.
66. The method of any one of paragraphs 53-64, wherein the subject is being treated with one or more additional antifungal agent.
67. The method of paragraph 66, wherein the subject has a fungal infection and the fungal infection is resistant to the one or more additional antifungal agent.
68. The method of paragraph 66 or 67, wherein at least one of the additional antifungal agent is an azole antifungal.
69. The method of paragraph 68, wherein the azole antifungal is any one or more of, bifonazole, butoconazole, clotrimazole, dconazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, and abafungin.
70. The method of paragraph 69, wherein at least one additional anti-fungal agent is an allylamine, such as selected from amorolfin, butenafine, naftifine, and terbinafine.
71. The method of any one of paragraphs 61-70, wherein at least one additional anti-fungal agent is an Echinocandins, such as selected from Anidulafungin, Caspofungin, and Micafungin.
72. The method of paragraph 67, wherein at least one additional anti-fungal agent is selected from aurones, benzoic acid, ciclopirox, flucytosine, griseofulvin, tolnaftate, undecylenic acid, triacetin, crystal violet, orotomide, miltefosine, nikkomycin, copper(II) sulfate, selenium disulfide, sodium thiosulfate, piroctone olamine, Iodoquinol, clioquinol, acrisorcin, zinc pyrithione and sulfur.
73. A method of inhibiting Hsp90 function, the method comprising contacting a Hsp90 with at least one compound of any one of paragraphs 1-35.
74. The method of paragraph 73, wherein the Hsp90 is comprised in a cell and the method further comprises administering the compound to the cell.
75. The method of paragraph 73, wherein the cell is a fungal cell.
76. The method of any one of paragraphs 73-75, wherein the Hsp90 is a fungal isoform.
77. The method of paragraph 73, wherein the Hsp90 is a *Candida, Aspergillus* or *Cryptococcus* isoform.
78. The method of paragraph 73, wherein the Hsp90 is a by *Cryptococcus neoformans* isoform and the compound is selected from a compound of paragraph 30.
79. The method of paragraph 73, wherein the Hsp90 is a by *Cryptococcus neoformans* isoform and the compound is selected from a compound of paragraph 31.
80. The method of paragraph 73, wherein the Hsp90 is a *Candida albicans* isoform and the compound is selected from a compound of paragraph 32.
81. The method of any one of paragraphs 63-80, further comprising administering to the cell an additional agent.
82. The method of paragraph 81, wherein the additional agent is an additional anti-fungal agent.
83. A method of inhibiting fungal growth or survival, the method comprising contacting a fungus with one or more of the compounds of any one of paragraph 1-35.
84. A method of treating Hsp90 related disease or disorder in a subject in need thereof, the method comprising:
    administering to the subject a therapeutically effective amount of the compound of any one of paragraph 1-35 or the pharmaceutical composition of paragraph 36.
85. The method according to paragraph 84, wherein the Hsp90 related disease or disorder is selected from the group consisting of cancers, autoimmune diseases, neurodegenerative diseases, infectious diseases and any combinations thereof.
86. The method according to paragraph 84, wherein the Hsp90 related disease or disorder is a fungal infection.
87. The method according to paragraph 86, wherein the fungal infection is a mucosal or an invasive systemic infection by a human fungal pathogen.
88. The method according to paragraph 86 or 87, wherein the fungal infection is caused by a *Candida*, an *Aspergillus* or a *Cryptococcus* species.
89. The method according to paragraph 88, wherein the fungal infection is caused by *Candida albicans, Candida auris, Aspergillus fumigatus, Cryptococcus neoformans. Cyrptococus gatti* or *Candida glabrata*.
90. The method according to any one of paragraphs 84-89, wherein the subject has a compromised immune function, cardiovascular disease, decompensated liver cirrhosis, is undergoing treatment for a burn injury, is undergoing treatment from a surgery, has a GI tract perforation, has pancreatitis, is being ventilated, is undergoing dialysis, has renal failure, is being administered broad-spectrum antibiotics, is receiving parenteral nutrition or is in close contact with vectors for infection.
91. The method of paragraph 90, wherein the subject is immunocompromised as a consequence of a pre-existing medical condition.
92. The method of any one of paragraphs 84-91, wherein the subject is receiving a treatment for rheumatoid arthritis, psoriatic arthritis, myeloproliferative disorders, chronic myeloid leukemia, chronic lymphocytic leukemia, steroid-refractory graft-versus host disease, follicular lymphoma, polycythaemia rubra vera, or Waldenström macroglobulinaemia.

93. The method according to paragraph 84, wherein the Hsp90 related disease or disorder is a cancer.
94. The method according to paragraph 93, further comprising treating the subject with an additional cancer treatment.
95. The method according to paragraph 84, wherein the Hsp90 related disease or disorder is glaucoma.
96. The method according to paragraph 95, further comprising treating the subject with an anti-glaucoma treatment.

The embodiments will be more readily understood by reference to the following examples, which are included merely for purposes of illustration of certain aspects and embodiments of the present invention, and should not be construed as limiting. As such, it will be readily apparent that any of the disclosed specific constructs and experimental plan can be substituted within the scope of the present disclosure.

EXAMPLES

Introduction

The morbidity and mortality caused by fungal infections cripple human health across the globe. Over a billion people are affected by superficial infections, such as ringworm and athlete's foot. Adding to these numbers are the burden of oral and other mucosal infections. Of most concern is the increasing number of invasive systemic infections, which leads to over one million deaths each year[1]. People with compromised immune function, such as patients receiving cancer chemotherapies, organ transplant recipients and those infected with HIV, are most vulnerable to invasive fungal infections. The pathogens responsible for >90% of invasive mycoses are *Candida albicans, Aspergillus fumigatus* and *Cryptococcus neoformans*. Once diagnosed, treatment options are limited to only three major classes of antifungal drugs, notoriously hampered by problems with host toxicity, the emergence of resistance, or limited spectrum of activity [2]. In fact, the only new class of antifungals to reach the clinic in decades has no efficacy against *C. neoformans* and related species [3].

Selective targeting of fungal stress responses provides a promising therapeutic strategy to mitigate resistance and more effectively combat invasive mycoses. The essential molecular chaperone Hsp90 has been extensively validated as a regulator of virulence and antifungal drug resistance in *Candida* and *Aspergillus* species [4, 5]. For instance, in *C. albicans*, genetic depletion or pharmacological inhibition of Hsp90 increases the efficacy of current antifungal drugs, reduces acquired antifungal resistance in clinical isolates, and improves clearance in a mouse model of disseminated candidiasis [6]. Recent studies have demonstrated the critical importance of Hsp90 for *C. neoformans* thermotolerance and shown that Hsp90 inhibition alters capsule assembly and sensitivity to antifungals, influencing virulence of the pathogen [7,8]. While targeting Hsp90 offers a promising but relatively unexplored strategy for antifungal drug development, the chaperone has been intensively explored as a target in oncology. A structurally diverse array of drugs targeting the ATP-binding pocket of human Hsp90 continue to be evaluated for anticancer activity in patients. In contrast, allosteric approaches to targeting the function of Hsp90 at sites other than its N-terminal ATPase have only been explored in preclinical studies, [9] the exception being a putative C-terminal inhibitor (RTA901) which has recently completed Phase I testing in humans (NCT0266693).

Unfortunately, dose-limiting toxicities coupled with relatively limited therapeutic efficacy have so far precluded FDA approval of any N-terminal Hsp90 inhibitor either alone or in combination with other therapeutic agents. In the course of these anticancer drug development and testing campaigns, no effort has been devoted to the pursuit of fungal selectivity and an Hsp90 inhibitor with the properties required for use as an antifungal has yet to be reported.

Fungal selectivity is a crucial feature for an Hsp90 inhibitor to be developed as an antifungal given that Hsp90 is essential in all eukaryotes. Its function supports protein quality control mechanisms, productive folding and the stability of conformationally labile proteins, many involved in key signaling cascades [10]. The chaperoning by Hsp90 of its so-called client proteins is ATP-dependent and coordinated by a suite of co-chaperones and accessory factors that impart client selectivity and help regulate progression through the chaperoning cycle. Although Hsp90 is highly conserved across phylogenetic kingdoms, species-specific variations are observed at the level of conformational flexibility, intrinsic ATPase activity, chaperoning dynamics, and the involvement of specific co-chaperone/accessory proteins [11]. Therefore, despite a very high degree of conservation at the primary sequence level, these important functional differences provide hope that species-selectivity can be achieved, either at the classical N-terminal ATP-binding pocket or alternatively via allosteric inhibitors acting at other sites. [12]

While efforts to achieve species-selectivity are just beginning, the pursuit of human paralog-specific Hsp90 inhibitors has already achieved considerable success. These efforts have been focused on achieving selectivity at the N-terminal nucleotide-binding domain (NBD) across the four family members expressed in humans: Hsp90α, Hsp90β, Trap1 and Grp94 [13, 14]. For example, Blagg and coworkers have described successful efforts to modify the resorcylate scaffold to confer selectivity towards specific human paralogs, including selective Grp94 inhibitors with applications in oncology and glaucoma, [15-19] and more recently, the first Hsp90α-selective inhibitor with applications in cancer [20]. In addition, isoform-selective purine mimetics, such as Hsp90α/β-specific inhibitor TAS—11621 and modified analogs of BIIB021 selectively targeting Trap114 have been described. Modified benzamides resembling SNX-2112 have also been diverted to both Hsp90α/β-specific22 and Trap1-specific23 activities for neurological applications.

Recently the first fungal-selective Hsp90 inhibitors, with activity against the *C. albicans* Hsp90 isoform, based on semi-synthetic oxime-derivatization of the resorcylate macrocycle natural products radicicol (1) and monocillin I (2) were disclosed [11]. For therapeutic applications, fungal-selectivity is critical as current inhibitors targeting host Hsp90 have deleterious effects that preclude their use in the context of systemic infection. A most promising lead from this series, monocillin-derived oxime 3 (CMLD013075) (FIG. 1A), has >25-fold binding selectivity for the *C. albicans* Hsp90 NBD compared to the human ortholog, limits fungal proliferation in whole cell assays, and is less toxic to human cells compared to the non-selective compound radicicol. Importantly, the co-crystal structure of *C. albicans* Hsp90 NBD with 3 (CMLD013075) displayed unique structural rearrangements, including remodeling of the ATP-binding site, N-terminus, and lid region of the fungal chaperone. Aided by structural insights, key residues were identified as critical for the fungal selectivity of this derivative. Encouraged by these findings and using 3 as a point of departure, a structure activity relationship (SAR)- guided efforts to develop fully synthetic, resorcylate inhibitor chemotypes, focusing on selectivity toward both *C. neoformans* and *C. albicans* Hsp90 as reported herein.

Figure 1B:
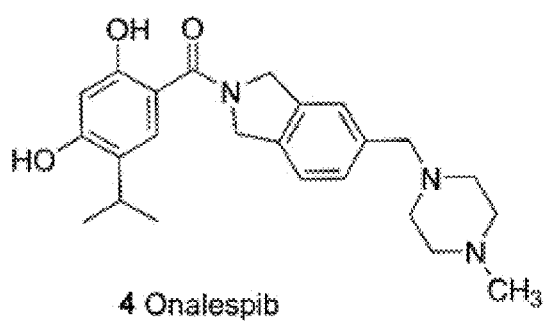
FIG. 1B shows resorcylate Hsp90 inhibitor candidates.
Figure 1B:
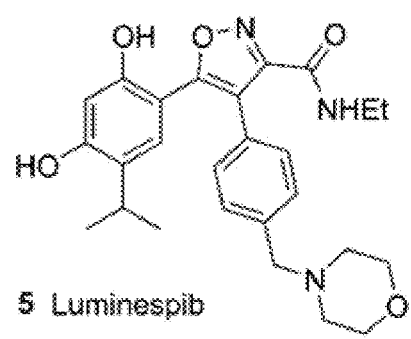
Figure 1B:
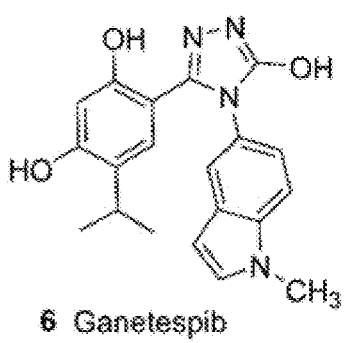
Figure 1B:
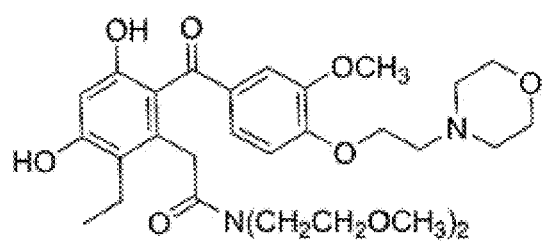
Figure 1C:
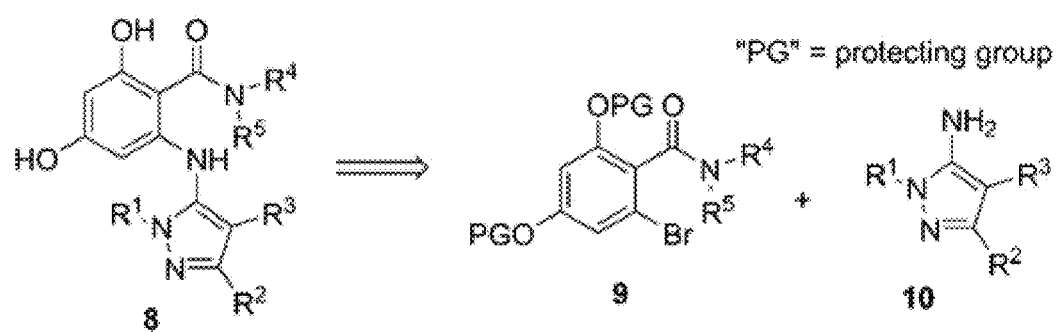
FIG. 1C shows embodiments of Hsp90 inhibitors and retrosynthetic derivation.

Replacement of the macrolactone of radicicol with acyclic isosteres including amides (Onalespib (4)[24-27], oxazoles (Luminespib (5)[28-33], triazolones (Ganetespib (6)[34-42)], and ketones (KW-2478 (7)[43-46] has been a widely successful strategy for the development of multiple classes of synthetic Hsp90 inhibitors currently in clinical evaluation (FIG. 1B). Using our macrocyclic oxime 3 (CMLD013075) as a lead template, our initial efforts focused on the replacement of the selectivity-imparting oxime with a suitable heterocyclic isostere, with the parallel goals of removing the isomerizable oxime (which was postulated could obfuscate selectivity analysis), and reducing rotational degrees of freedom to enhance binding affinity. After evaluating various heterocyclic options for similarity and synthetic tractability, aminopyrazole of general type 8 (FIG. 1C) were selected for initial development. It was hypothesized that a pendant aminopyrazole could project substituents ($R^1/R^2/R^3$) in orientations similar to that of the 3 (CMLD013075) oxime, to impart fungal selectivity in the binding of Hsp90. In addition to the attractiveness of the pyrazole from the standpoint of developability, [47] it is shown herein that structure-activity relationships at three points of diversity ($R/R^2/R^3$) can be elaborated through the coupling of aryl bromide 9 with a combination of commercial and synthetic aminopyrazoles (10).

Results and Discussion

Synthesis of Resorcylate Aminopyrazole Analogs

A synthesis of aminopyrazole resorcylates beging with 1-bromo-3,5-dimethoxybenzene 11 is show by Scheme A. Formylation, de-methylation, MOM protection, and Pinnick oxidation affords carboxylic acid 12, which is then subjected to HATU-mediated amidation with isoindoline to produce amide 13. Isoindoline amide was selected as it is conserved across multiple classes of acyclic resorcylate heat shock protein inhibitors, [48-53] providing a simple, model scaffold on which the selectivity-inducing strategy was evaluated. The aminopyrazole was then installed using Pd-mediated coupling; after a brief exploration of coupling conditions [54] conditions of Pd$_2$(dba)$_3$/Xantphos/NaOPh in dioxane under microwave irradiation[55] was found to be optimal across a wide scope of substrates. Following amination, acid-mediated MOM deprotection produces the desired aminopyrazole-substituted resorcylates.

Scheme A.
First-generation synthetic route to aminopyrazole/isoindoline resorcylate amides.

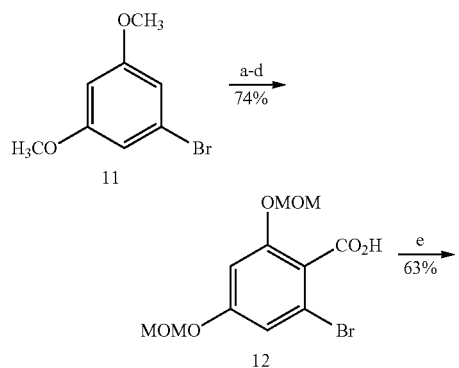

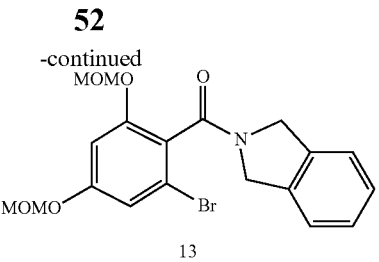

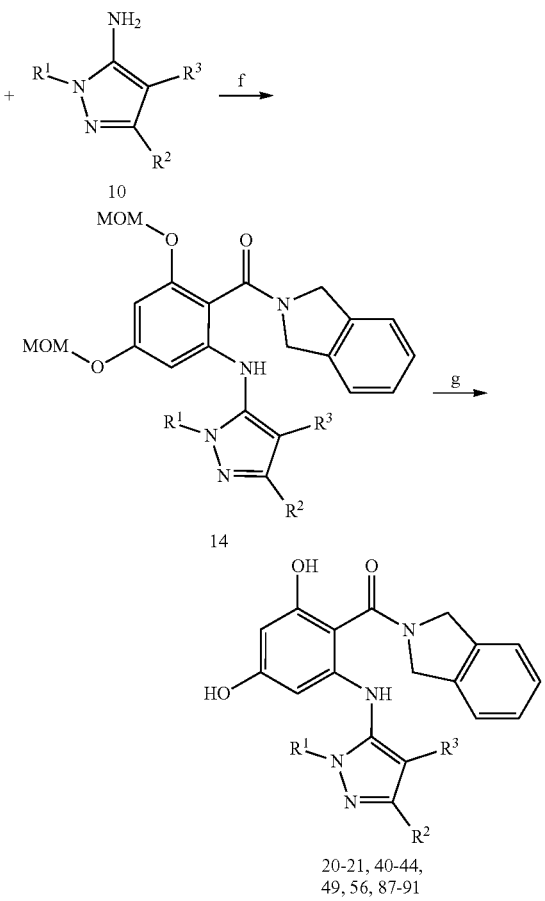

Conditions for Scheme A: a) POCl$_3$, DMF, 100° C.; b) BBr$_3$, CH$_2$Cl$_2$, −78° C. to RT; c) MOMCl, DIPEA, DMF; d) NaOCl$_2$, NaH$_2$PO$_4$.H$_2$O, 2-methyl-2-butene, THF/$^t$BuOH/H$_2$O; e) isoindoline.HCl, HATU, Et$_3$N, THF/CH$_2$Cl$_2$; f) $^t$BuXphos Pd G1 (10 mol %), $^t$BuXPhos (10 mol %), NaO$^t$Bu, $^t$BuOH, or Pd$_2$(dba)$_3$ (4 mol %), Xantphos (8 mol %), NaOPh, dioxane, 60° C. to 120° C., or Pd$_2$(dba)$_3$ (10 mol %), Xantphos (10 mol %), NaOPh, dioxane, 170° C., microwave; g) HCl, methanol, 50° C.

The synthetic sequence of Scheme A was used to explore replacement of the isoindoline amide for several compounds as shown by Scheme B. During the course of analog synthesis, however, it was found that reversing the order of coupling/amidation resulted in a more efficient procedure with improved yields and product purities; the resultant second-generation route is depicted in Scheme C. Following esterification of carboxylic acid 12, the resulting ester 17 was subjected to Pd-mediated coupling with 10 to afford intermediate 18. Following ester hydrolysis, carboxylic acid 19 was subsequently amidated, which was initially performed using the HATU-mediated conditions, and later optimized to employ polymer-supported carbonyldiimidazole (PS-CDI) as a coupling reagent for improved parallel processing. Finally global MOM-deprotection provided the desired products for testing. All tested compounds were purified by mass-targeted HPLC.

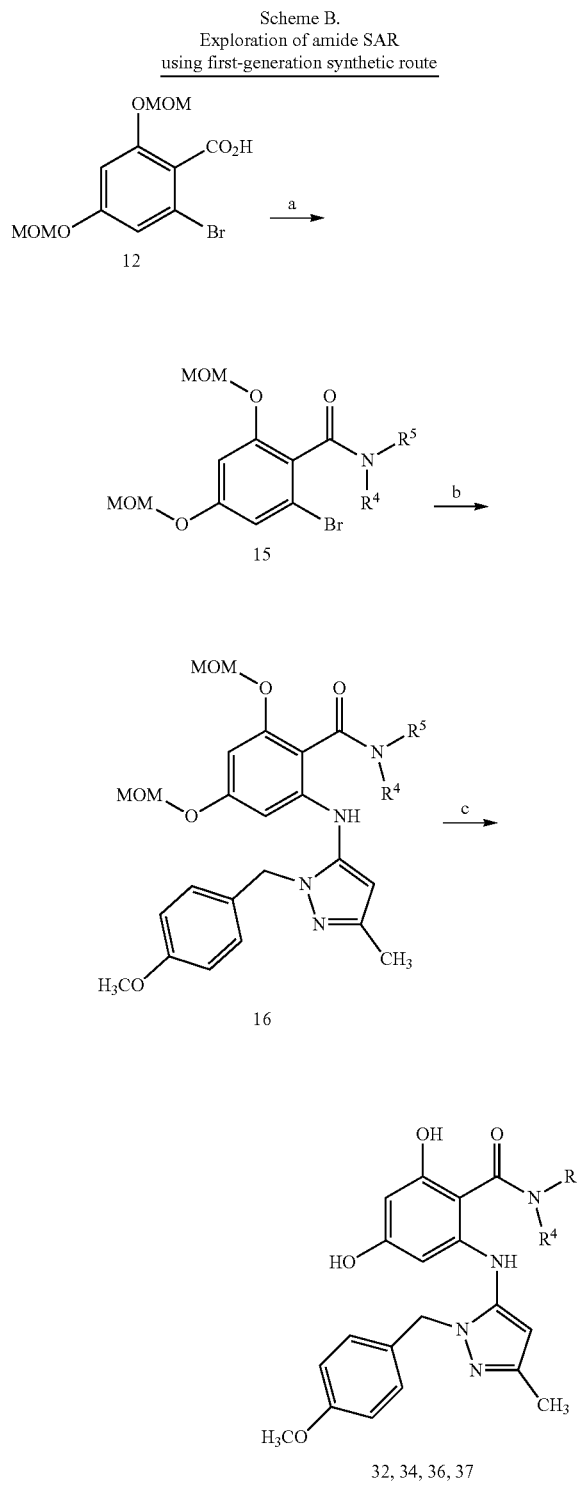

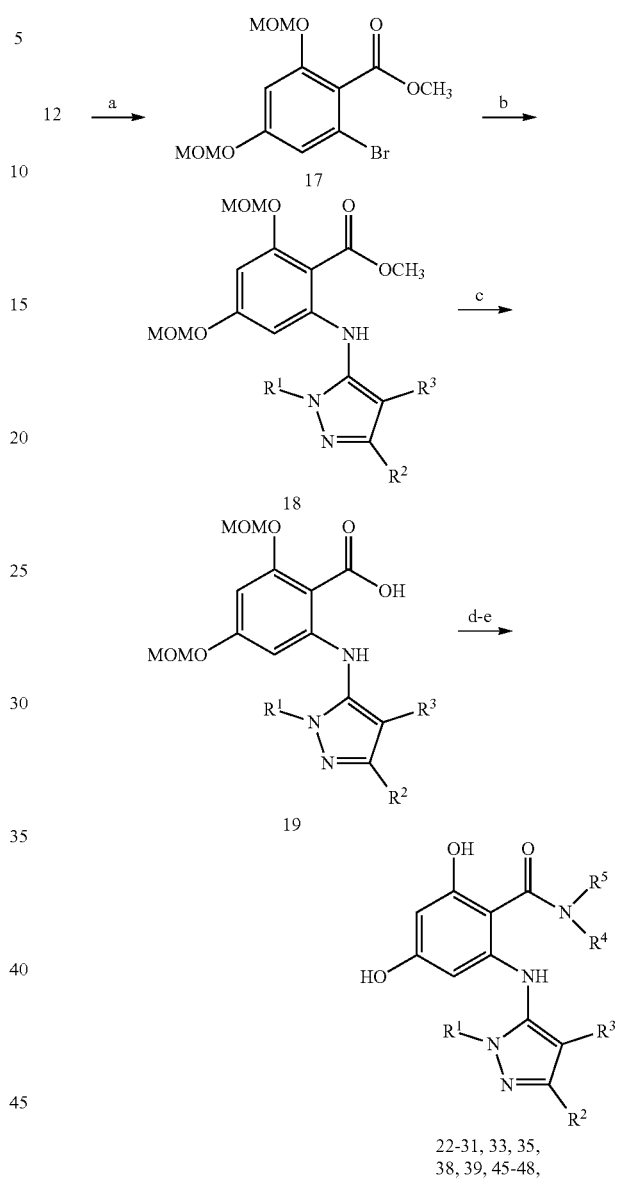

Conditions or Scheme B: a) HNR⁴R⁵, HATU, Et₃N, THF/CH₂Cl₂; b) 10a, Pd₂(dba)₃ (4 mol %), Xantphos (10 mol %), NaOPh, dioxane, 170° C., microwave; c) HCl, methanol, 50° C.

Conditions for Scheme C: a) CH₃I, K₂CO₃, DMF, 80° C.; b) 10, Pd₂(dba)₃ (4 mol %), Xantphos (10 mol %), NaOPh; c) KOH, EtOH, 95° C.; d) HNR⁴R⁵, HATU, Et₃N, CH₂Cl₂/THF, RT or HNR⁴R⁵, PS-CDI, HOBt.xH₂O, Et₃N, THF/CH₂Cl₂; e) HCl, methanol, 50° C.

Measurement of Fungal Hsp90 Binding Affinity and Selectivity

All analogs were assessed for Hsp90 binding affinity using a fluorescence polarization (FP)-based equilibrium competition assay in fungal and human whole cell lysates. Notably, this approach allows for the assessment of compound binding while the target protein is in native complexes with co-chaperones; and, in the case of human cell lysate, in a biologically relevant mix of Hsp90 paralogs. Using lysates, the relative potency and selectivity for fungal Hsp90 was measured versus the entire ensemble of human Hsp90 isoforms in microplate format using small amounts of test materials. To confirm target engagement with an alternative biochemical approach, the most selective analogs were also assessed by protein thermal shift assays using purified recombinant Hsp90 nucleotide binding domains (NBD) of the relevant fungal species. Thermal shift assays were performed under saturating ligand conditions, i.e. equimolar concentrations (10 µM) of protein and ligand. As a result, they provided qualitative evidence of target binding, but not a quantitative measurement of ligand affinity. For quantitation, a ligand dissociation constant ($K_i$) for key compounds was also determined using purified NBDs in FP assays and KD measurements were made by surface plasmon resonance (SPR) using a Biacore instrument. Finally, all analogs were assessed for whole cell antifungal activity against the pathogens C. albicans and C. neoformans. Quantitative dose-response assays were performed for all compounds found to inhibit growth at a concentration ≤50 µM.

N-(para)-methoxybenzyl substituted aminopyrazoles, designed to mimic the parent Candida-selective inhibitor 3 (CMLD013075) were first examined. Systematic alterations to the resorcylate amide, with $R^2$ substitution limited to methyl and phenyl were first made. Initial amide diversification utilized several pyrrolidine/isoindoline-based heterocycles, which are prevalent among resorcylate amide Hsp90 inhibitors reported by Astex and Pfizer (20-21, 26-29, 32-36, 38), [49, 50] as well as new isoindoline isosteres (pyrido- and pyrazolopyrrolidines 22-25). We also pursued a small series of acyclic mono- and disubstituted amides, both new (30-31) and precedented (37, 39) [56] were also pursued. From this initial set, number of compounds having <200 nM $EC_{50}$ values against one or both fungal species were found (Table 2). Consistent with published inhibitors in this space, larger, substituted isoindoline-type moieties (32-36) generally exhibited excellent potency, but with no apparent selectivity for the fungal Hsp90 isoforms. In contrast, it was found that the pairing of smaller heterobicyclic amides with a phenyl group at the $R^2$ position (compounds 21, 23, 25, 27, and 29) afforded modestly fungal-selective compounds; as a general trend, their $R^2$=$CH_3$ analogs (20, 22, 24, 26 and 28) were more potent but nonselective. Activity was mainly relegated to the heterobicyclic amides; the limited set of acyclic and monocyclic amides (30-31, 37-39) were for the most part less active and also nonselective, with the interesting exception of low potency cryptococcal-selective compound 30. Based on these results, and given on the hypothesis that the installation of functionality at the aminopyrazole would be the key driver in imparting selectivity, further studies were conducted with the lower-molecular weight isoindoline, pyridopyrrolidine, and pyrazolopyrrolidine amides, selected to represent both precedented and novel resorcylate amide substitutions with varying basicities.

TABLE 2

Structure-activity relationships for N-(4-methoxybenzyl)-substituted aminopyrazoles, exploring variation of the resorcylate amide with methyl- and phenyl-substitution at $R^2$. Fold-selectivity >5 for any compound is highlighted in *Italics*.

| Entry | Comp. | X' | $R^2$ | C. neoformans $EC_{50}^a$ (µM) | C. neoformans fold-selectivity[b] | C. albicans $EC_{50}^c$ (µM) | C. albicans fold-selectivity[b] |
|---|---|---|---|---|---|---|---|
| 1 | 20 | | $CH_3$ | 0.040 | 0.8 | 0.011 | 0.9 |
| 2 | 21 | isoindoline | Ph | 0.877 | 2.5 | 0.511 | 2.2 |
| 3 | 22 | pyridopyrrolidine | $CH_3$ | 0.087 | 1.2 | 0.184 | 0.4 |
| 4 | 23 | pyridopyrrolidine | Ph | 0.142 | 4.0 | 0.068 | *6.2* |
| 5 | 24 | pyrazolopyrrolidine | $CH_3$ | 0.063 | 1.7 | 0.157 | 0.5 |
| 6 | 25 | pyrazolopyrrolidine | Ph | 0.121 | 2.7 | 0.063 | 3.9 |

TABLE 2-continued

Structure-activity relationships for N-(4-methoxybenzyl)-substituted aminopyrazoles, exploring variation of the resorcylate amide with methyl- and phenyl-substitution at $R^2$. Fold-selectivity >5 for any compound is highlighted in *Italics*.

| Entry | Comp. | X' | $R^2$ | C. neoformans $EC_{50}{}^a$ (μM) | C. neoformans fold-selectivity[b] | C. albicans $EC_{50}{}^c$ (μM) | C. albicans fold-selectivity[b] |
|---|---|---|---|---|---|---|---|
| 7 | 26 | 4-F-isoindolinyl | CH$_3$ | 0.109 | 0.6 | 0.117 | 0.4 |
| 8 | 27 | 4-F-isoindolinyl | Ph | 0.787 | 2.2 | 1.089 | 1.2 |
| 9 | 28 | 5-F-isoindolinyl | CH$_3$ | 0.592 | 0.1 | 0.054 | 0.5 |
| 10 | 29 | 5-F-isoindolinyl | Ph | 0.705 | 2.7 | 1.043 | 1.3 |
| 11 | 30 | N(CH$_3$)CH$_2$-cyclopropyl | CH$_3$ | 1.330 | 5.8 | >9 | — |
| 12 | 31 | N(CH$_3$)CH$_2$-cyclopropyl | Ph | >9 | — | >9 | — |
| 13 | 32 | 5-(4-NHC$_5$H$_9$NCH$_3$)-isoindolinyl | CH$_3$ | 0.096 | 1.0 | 0.171 | 0.4 |
| 14 | 33 | 5-(4-NHC$_5$H$_9$NCH$_3$)-isoindolinyl | Ph | 0.146 | 0.8 | 0.023 | 1.8 |
| 15 | 34 | 5-(OCH$_2$CH$_2$N(CH$_3$)$_2$)-isoindolinyl | CH$_3$ | 0.086 | 1.2 | 0.115 | 0.7 |
| 16 | 35 | 5-(OCH$_2$CH$_2$N(CH$_3$)$_2$)-isoindolinyl | Ph | 0.091 | 0.8 | 0.014 | 1.7 |
| 17 | 36 | 5-(4-methylpiperazinyl)-isoindolinyl | CH$_3$ | 0.115 | 0.9 | 0.143 | 0.6 |
| 18 | 37 | N(CH$_3$)CH$_2$Ph | CH$_3$ | 4.814 | 1.6 | >6 | 0.0 |
| 19 | 38 | pyrrolidinyl | Ph | 0.464 | 2.1 | 0.282 | 1.2 |

TABLE 2-continued

Structure-activity relationships for N-(4-methoxybenzyl)-substituted aminopyrazoles, exploring variation of the resorcylate amide with methyl- and phenyl-substitution at $R^2$. Fold-selectivity >5 for any compound is highlighted in *Italics*.

| Entry | Comp. | X' | $R^2$ | C. neoformans $EC_{50}{}^a$ (µM) | C. neoformans fold-selectivity[b] | C. albicans $EC_{50}{}^c$ (µM) | C. albicans fold-selectivity[b] |
|---|---|---|---|---|---|---|---|
| 20 | 39 | -N(Et)₂ | Ph | >10 | — | >10 | — |

$EC_{50}$ values were determined by FP-based equilibrium competition assay performed in 384-well format using whole cell lysates prepared from *C. neoformans* (a) and *C. albicans* (c) and serial compound dilutions. All determinations were performed in duplicate. To calculate fold-selectivity (b), the $EC_{50}$ value determined in human HepG2 cell lysate was divided by the $EC_{50}$ value determined in fungal cell lysate. The resulting ratio was then normalized to values determined in the same assay for the non-selective inhibitor geldanamycin using lysate of each cell type. Results for key selective compounds were confirmed by repeat assay.

A following series of analogs explored additional $R^2/R^3$ substitutions on the aminopyrazole, again keeping the $R^1$ para-methoxybenzyl group intact (Table 3). For the $R^2$ unsubstituted pyrazoles (40-44), it was found that substitution at $R^3$ was tolerated, but with decreasing potency as steric bulk increased. Several of these compounds also exhibited modest undesired selectivity toward the human isoform. Based on these results, no further exploration of this substitution pattern was conducted. In contrast, and similar to the initial cohort, wider tolerance for substitution at the $R^2$ position with several acyclic (45-48) and cyclic (50-53) aliphatic groups, as well as furan (54-55) substitution was identified. A drop in potency was limited to the bulkier $R^2$=$^t$Bu analog 49. None of the inhibitors exhibited the modest fungal selectivity that had been observed in their $R^2$=Ph substituted counterparts 21, 23 and 25 (Table 2).

TABLE 3

Exploration of SAR at $R^2/R^3$ for $R^1$ = p-methoxybenzyl substituted aminopyrazoles.

40-55

| Entry | Comp. | X' | $R^2$ | $R^3$ | C. neoformans $EC_{50}{}^a$ (µM) | C. neoformans fold-selectivity[b] | C. albicans $EC_{50}{}^c$ (µM) | C. albicans fold-selectivity[b] |
|---|---|---|---|---|---|---|---|---|
| 1 | 40 | A1 | H | H | 0.072 | 0.8 | 0.041 | 1.0 |
| 2 | 41 | A1 | H | CH₃ | 0.094 | 0.3 | 0.022 | 0.7 |
| 3 | 42 | A1 | H | $^i$Pr | 0.396 | 0.4 | 0.147 | 0.5 |
| 4 | 43 | A1 | H | Ph | 1.623 | 1.6 | 0.615 | 2.1 |
| 5 | 44 | A1 | H | Bn | 1.756 | 0.5 | 0.465 | 1.1 |
| 6 | 45 | A6 | Et | H | 0.022 | 0.9 | 0.014 | 0.5 |

TABLE 3-continued

Exploration of SAR at R²/R³ for R¹ = p-methoxybenzyl substituted aminopyrazoles.

| Entry | Comp. | X' | R² | R³ | C. neoformans EC$_{50}$$^a$ (μM) | C. neoformans fold-selectivity$^b$ | C. albicans EC$_{50}$$^c$ (μM) | C. albicans fold-selectivity$^b$ |
|---|---|---|---|---|---|---|---|---|
| 7 | 46 | A24 | | | 0.025 | 0.7 | 0.012 | 0.6 |
| 8 | 47 | A6 | $^i$Pr | H | 0.025 | 1.0 | 0.013 | 0.7 |
| 9 | 48 | A24 | | | 0.023 | 0.8 | 0.009 | 0.8 |
| 10 | 49 | A1 | $^t$Bu | H | 1.026 | 1.4 | 0.816 | 1.0 |
| 11 | 50 | A6 | cyclopropyl | H | 0.026 | 0.9 | 0.014 | 0.6 |
| 12 | 51 | A24 | | | 0.023 | 0.9 | 0.014 | 0.5 |
| 13 | 52 | A6 | cyclopentyl | H | 0.021 | 0.7 | 0.006 | 1.0 |
| 14 | 53 | A24 | | | 0.041 | 0.6 | 0.009 | 1.0 |
| 15 | 54 | A6 | furyl | H | 0.039 | 1.3 | 0.022 | 0.9 |
| 16 | 55 | A24 | | | 0.040 | 0.9 | 0.018 | 0.7 |

Amide substitution (X'):

(A1) isoindoline (A6) pyrrolo-pyridine (A24) pyrrolo-pyrazole

EC$_{50}$ and selectivity values were determined as described for Table 2.

The replacement of the p-methoxybenzyl group at R¹ was next assessed. Initially, this group had been chosen based on analogy to Candida-selective inhibitor 3 (CMLD013075). Our X-ray crystallographic analysis [11] (PDB ID: 6CJP) indicates that the aryl ring participates in a key binding interaction following a major structural rearrangement of the Candida Hsp90 lid region, serving as a donor in an N—H . . . π interaction with *C. albicans* Asn40. However, given the limited scope of radicicol- and monocillin-derived analogs that we previously explored, coupled with a current lack of structural information about the cryptococcal isoform, it is not clear that this group represents an "ideal" binding moiety for either fungal species. As an initial probe, the $R_1$ group across the isoindoline, tetrahydropyrrolopyridine and tetrahydropyrrolopyrazole amides was probed, leaving the $R^2$ and $R^3$ sites unsubstituted. The results for this series are summarized in Table 4. A wide array (aliphatic, aromatic, heteroaromatic) of aminopyrazole substitutions that afforded in most cases sub-125 nM potencies for both fungal species (56, 59, 62-77 and 80-86) were identified, but all were broadly nonselective with the exception of isoindoline 83. This compound was exemplary as the first compound in the aminopyrazole series to exhibit sub-100 nM $EC_{50}$ with greater than 10-fold selectivity. Interestingly, however, in isolated cases the tetrahydropyrrolopyridine and tetrahydropyrrolopyrazole amides diverged from their isoindoline counterparts with a slight decrease in potency (compounds 78-79), which was in some cases coupled with a slight increase in cryptococcal selectivity (57-58 and 60-61). These compounds, bearing aliphatic N-substitutions of varying size, showed 2- to 5-fold selectivity toward *C. neoformans*, with no apparent selectivity toward *C. albicans*.

TABLE 4

Exploring alternative $R^1$ substituents on $R^2/R^3$-unsubstituted aminopyrazoles. Fold selectivity >5 for any compound is highlighted in *Italics*.

| Entry | Comp. | $R^1$ | X | *C. neoformans* $EC_{50}^a$ (μM) | *C. neoformans* fold-selectivity[b] | *C. albicans* $EC_{50}^c$ (μM) | *C. albicans* fold-selectivity[b] |
|---|---|---|---|---|---|---|---|
| 1 | 56 | $CH_3$ | A1 | 0.088 | 1.5 | 0.111 | 0.4 |
| 2 | 57 |  | A6 | 0.286 | 4.4 | 0.624 | 0.7 |
| 3 | 58 |  | A24 | 0.142 | *5.1* | 0.377 | 0.7 |
| 4 | 59 | $^i$Pr | A1 | 0.125 | 1.3 | 0.076 | 0.7 |
| 5 | 60 |  | A6 | 0.250 | 2.6 | 0.309 | 0.7 |
| 6 | 61 |  | A24 | 0.097 | 3.6 | 0.161 | 0.7 |
| 7 | 62 | $^i$Bu | A1 | 0.062 | 1.1 | 0.035 | 0.7 |
| 8 | 63 |  | A6 | 0.103 | 1.7 | 0.117 | 0.6 |
| 9 | 64 |  | A24 | 0.041 | 2.3 | 0.057 | 0.6 |
| 10 | 65 | cyclohexylmethyl | A1 | 0.051 | 0.7 | 0.009 | 1.2 |
| 11 | 66 |  | A6 | 0.026 | 1.7 | 0.015 | 0.9 |
| 12 | 67 |  | A24 | 0.018 | 1.3 | 0.008 | 0.8 |
| 13 | 68 | Ph | A1 | 0.061 | 0.5 | 0.014 | 0.8 |
| 14 | 69 |  | A6 | 0.044 | 0.9 | 0.021 | 0.7 |
| 15 | 70 |  | A24 | 0.037 | 0.8 | 0.015 | 0.8 |
| 16 | 71 | Cy | A1 | 0.087 | 0.4 | 0.013 | 0.9 |
| 17 | 72 |  | A6 | 0.045 | 1.0 | 0.016 | 1.0 |
| 18 | 73 |  | A24 | 0.035 | 1.0 | 0.014 | 1.0 |
| 19 | 74 | Bn | A1 | 0.052 | 0.8 | 0.015 | 0.8 |
| 20 | 75 |  | A6 | 0.043 | 1.1 | 0.018 | 0.8 |
| 21 | 76 |  | A24 | 0.036 | 1.1 | 0.015 | 0.8 |
| 22 | 77 |  | A1 | 0.058 | 1.7 | 0.041 | 0.7 |
| 23 | 78 | pyridylmethyl | A6 | 0.207 | 1.6 | 0.143 | 0.7 |
| 24 | 79 |  | A24 | 0.199 | 1.8 | 0.164 | 0.7 |
| 25 | 80 | furylmethyl | A1 | 0.074 | 0.9 | 0.033 | 0.7 |
| 26 | 81 |  | A6 | 0.106 | 1.2 | 0.080 | 0.6 |
| 27 | 82 |  | A24 | 0.058 | 1.4 | 0.041 | 0.8 |

TABLE 4-continued

Exploring alternative R¹ substituents on R²/R³-unsubstituted aminopyrazoles. Fold selectivity >5 for any compound is highlighted in *Italics*.

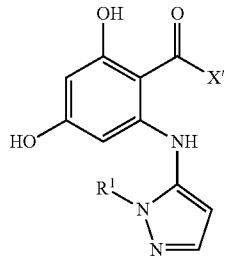

56-86

| Entry | Comp. | R¹ | X | C. neoformans $EC_{50}^{a}$ (μM) | C. neoformans fold-selectivity[b] | C. albicans $EC_{50}^{c}$ (μM) | C. albicans fold-selectivity[b] |
|---|---|---|---|---|---|---|---|
| 28 | 83 | $^{i}$Pr— | A1 | 0.044 | *12.8* | 0.366 | 1.1 |
| 29 | 84 | | A6 | 0.040 | 0.8 | 0.012 | 0.9 |
| 30 | 85 | | A24 | 0.036 | 0.8 | 0.012 | 0.8 |
| 31 | 86 | $F_3C$— | A6 | 0.063 | 0.9 | 0.025 | 0.8 |
| 32 | 87 | | A24 | 0.048 | 1.1 | 0.021 | 0.9 |

$EC_{50}$ an selectivity values were determined as described for Table 2.

The combined modifications of the R N-substitution with additional groups at R² were next examined (Table 5). Again mindful of keeping physicochemical properties such as molecular weight and lipophilicity within an acceptable "druglike" range, a limitation for this series was imposed such that each pyrazole should contain a maximum of one aryl ring at either R¹ or R², but not at both [57]. This series produced a number of analogs with more modest sub-micromolar potency and cryptococcal selectivity greater than 4-fold (91-95). Of these, compounds 94 and 95 also exhibited modest selectivity for *C. albicans* Hsp90 over human Hsp90 paralogs, which was consistent with their early near neighbor analogs 21, 23 and 25 (Table 1).

TABLE 5

Examining varied parings of R¹/R² substitutions on the aminopyrazole ring. Fold selectivity >5 for any compound is highlighted in *Italics*.

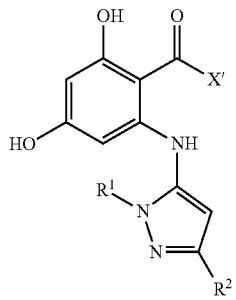

87-99

| Entry | Comp. | X | R¹ | R² | C. neoformans $EC_{50}^{a}$ (μM) | C. neoformans fold-selectivity[b] | C. albicans $EC_{50}^{c}$ (μM) | C. albicans fold-selectivity[b] |
|---|---|---|---|---|---|---|---|---|
| 1 | 88 | A1 | $H_3C$— | $CH_3$ | 0.252 | 0.2 | 0.121 | 0.3 |

TABLE 5-continued

Examining varied parings of $R^1/R^2$ substitutions on the aminopyrazole ring. Fold selectivity >5 for any compound is highlighted in *Italics*.

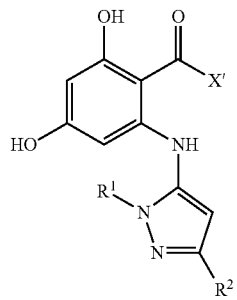

87-99

| Entry | Comp. | X | $R^1$ | $R^2$ | *C. neoformans* $EC_{50}^a$ (μM) | *C. neoformans* fold-selectivity[b] | *C. albicans* $EC_{50}^c$ (μM) | *C. albicans* fold-selectivity[b] |
|---|---|---|---|---|---|---|---|---|
| 2 | 89 | A1 | 2-Cl-benzyl | $CH_3$ | 0.560 | 0.2 | 0.116 | 0.4 |
| 3 | 90 | A1 | 2-CH₃-benzyl | $CH_3$ | 0.700 | 0.2 | 0.134 | 0.4 |
| 4 | 91 | A1 | $CH_3$ | Ph | 0.078 | *9.2* | 0.328 | 0.4 |
| 5 | 92 | A6 | | | 0.127 | *8.2* | 0.395 | 0.8 |
| 6 | 93 | A24 | | | 0.066 | *6.7* | 0.213 | 0.6 |
| 7 | 94 | A6 | $^tBu$ | Ph | 0.517 | *9.7* | 0.379 | 3.9 |
| 8 | 95 | A24 | | | 0.379 | *6.7* | 0.182 | 4.1 |
| 9 | 96 | A6 | cyclohexylmethyl | Ph | 0.615 | 0.4 | 0.059 | 1.7 |
| 10 | 97 | A24 | | | 0.419 | 0.3 | 0.034 | 1.4 |
| 11 | 98 | A6 | $^tBu$ | Ph | 0.315 | 1.7 | 0.100 | 1.6 |
| 12 | 99 | A24 | | | 0.147 | 1.8 | 0.070 | 1.4 |

Amide substitution (X'):

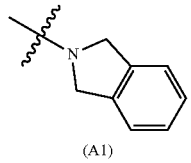

(A1)

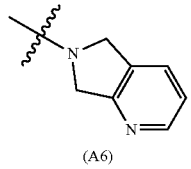

(A6)

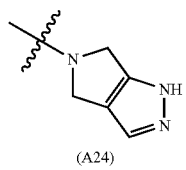

(A24)

EC$_{50}$ an selectivity values were determined as described or Table 1.

Among the initial fungal-selective leads from this effort, compounds 91-93 stood out as having high cryptococcal selectivity without a concomitant loss in cryptococcal potency as seen in earlier analogs. To follow up, an array of analogs N-methylated at R$^1$, probing more diverse aliphatic and aryl substituents at R$^2$ were studied (Table 6).

TABLE 6

Variation of R$^2$ substituent for N-methylated aminopyrazoles yields *C. neoformans*- and *C. albicans*-selective Hsp90 inhibitors with diverging isoform selectivities. Fold selectivities >5 are highlighted in *italics*.

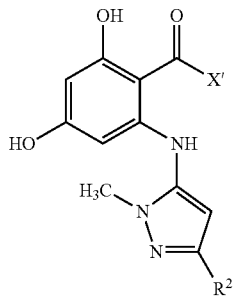

100-132

| Entry | Compound | R$^2$ | X | *C. neoformans* EC$_{50}^a$ (μM) | *C. neoformans* fold-selectivity$^b$ | *C. albicans* EC$_{50}^c$ (μM) | *C. albicans* fold-selectivity$^b$ |
|---|---|---|---|---|---|---|---|
| 1 | 100 | $^i$Pr | A1 | 0.087 | 0.9 | 0.048 | 0.6 |
| 2 | 101 |  | A6 | 0.062 | 1.6 | 0.156 | 0.2 |
| 3 | 102 |  | A24 | 0.040 | 3.0 | 0.094 | 0.5 |
| 4 | 103 | Cy | A1 | 0.156 | 0.7 | 0.033 | 1.4 |
| 5 | 104 |  | A6 | 0.110 | *6.5* | 0.670 | 0.4 |
| 6 | 105 |  | A24 | 0.037 | 3.7 | 0.096 | 0.6 |
| 7 | 106 | 2-MeC$_6$H$_4$ | A1 | 0.065 | *14.1* | 0.599 | 0.7 |
| 8 | 107 |  | A6 | 0.139 | *12.9* | 0.795 | 0.8 |
| 9 | 108 |  | A24 | 0.084 | *12.4* | 0.398 | 0.9 |
| 10 | 109 | 3-MeC$_6$H$_4$ | A1 | 0.267 | *16.3* | 0.573 | 3.0 |
| 11 | 110 |  | A6 | 0.421 | *15.1* | 1.030 | 2.4 |
| 12 | 111 |  | A24 | 0.176 | *14.6* | 0.396 | 2.5 |
| 13 | 112 | 3-MeOC$_6$H$_4$ | A1 | 0.281 | *33.3* | 1.642 | 2.0 |
| 14 | 113 |  | A6 | 0.852 | *27.6* | 5.000 | 1.7 |
| 15 | 114 |  | A24 | 0.244 | *26.5* | 1.881 | 1.3 |
| 16 | 115 | 3-CF$_3$C$_6$H$_4$ | A1 | 4.601 | 3.2 | 2.236 | 2.1 |
| 17 | 116 |  | A6 | 1.523 | *5.5* | 0.594 | 4.4 |
| 18 | 117 |  | A24 | 0.434 | *9.8* | 0.294 | 4.6 |
| 19 | 118 | 4-MeC$_6$H$_4$ | A1 | 1.318 | *6.3* | 1.067 | 2.6 |
| 20 | 119 |  | A6 | 1.781 | *9.5* | 1.779 | 4.0 |
| 21 | 120 |  | A24 | 0.424 | *14.9* | 0.636 | 3.4 |

TABLE 6-continued

Variation of $R^2$ substituent for N-methylated aminopyrazoles yields *C. neoformans*- and *C. albicans*-selective Hsp90 inhibitors with diverging isoform selectivities. Fold selectivities >5 are highlighted in *italics*.

| Entry | Compound | $R^2$ | X | C. neoformans $EC_{50}{}^a$ (µM) | C. neoformans fold-selectivity[b] | C. albicans $EC_{50}{}^c$ (µM) | C. albicans fold-selectivity[b] |
|---|---|---|---|---|---|---|---|
| 22 | 121 | 4-OCH₃-phenyl | A1 | 0.630 | 4.4 | 0.186 | *5.8* |
| 23 | 122 | 4-OCH₃-phenyl | A6 | 1.289 | *6.9* | 1.139 | 3.1 |
| 24 | 123 | 4-OCH₃-phenyl | A24 | 0.489 | *6.8* | 0.376 | 3.4 |
| 25 | 124 | 4-CF₃-phenyl | A | 9.530 | 1.0 | 1.084 | 3.1 |
| 26 | 125 | 4-CF₃-phenyl | B | 5.815 | 0.8 | 0.319 | 4.8 |
| 27 | 126 | 4-CF₃-phenyl | C | 1.385 | 1.1 | 0.103 | 4.9 |
| 28 | 127 | 4-tBu-phenyl | A | >10 | — | 1.197 | 2.1 |
| 29 | 128 | 4-tBu-phenyl | B | 8.337 | 0.4 | 0.237 | 4.5 |
| 30 | 129 | 4-tBu-phenyl | C | 2.262 | 0.5 | 0.071 | *5.0* |
| 31 | 130 | 4-OCF₃-phenyl | A | 5.402 | 1.0 | 0.134 | *15.3* |
| 32 | 131 | 4-OCF₃-phenyl | B | 1.262 | 1.0 | 0.050 | *18.2* |
| 33 | 132 | 4-OCF₃-phenyl | C | 0.514 | 1.3 | 0.016 | *15.9* |

Amide substitution (x'):

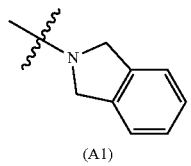

(A1)

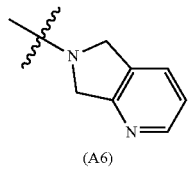

(A6)

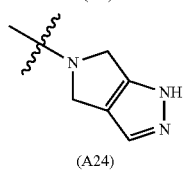

(A24)

EC$_{50}$ an selectivity values were determined as described for Table 2.

This series produced highly selective inhibitors for both the *C. neoformans* and *C. albicans* isoforms of Hsp90. While the exploration of aliphatic substitution was limited, high cryptococcal potency (EC$_{50}$<160 nM), and in some cases modestly *Cryptococcus*-selective compounds (3- to 6.5-fold) were observed with isopropyl (100-102) and cyclohexyl (103-105) substitution at R$^2$. The most highly selective compounds, however, were observed among the R$^2$ arylated analogs, with diverging species-selectivity based on the nature and position of the aryl ring substituent. The ortho-methylated analogs 106-108 displayed slightly enhanced cryptococcal selectivity and similar cryptococcal potency (<150 nM) as compared to their unsubstituted congeners 91-93 (Table 5), with no apparent selectivity and significantly lower potencies (≥400 nM) in lysate of *C. albicans*. Movement of the methyl substituent from ortho- to meta- (compounds 109-111) afforded similarly *Cryptococcus*-selective compounds, albeit with lower potencies. Interestingly, the meta-methoxy substituted 112-114 exhibited a significant improvement in cryptococcal selectivity (27- to 33-fold) despite only modest cryptococcal potency (EC$_{50}$s all >250 nM). Trifluoromethylation at the same meta-position (compounds 115-117), resulted in a dramatic reduction in both cryptococcal selectivity and activity.

Figure 2:
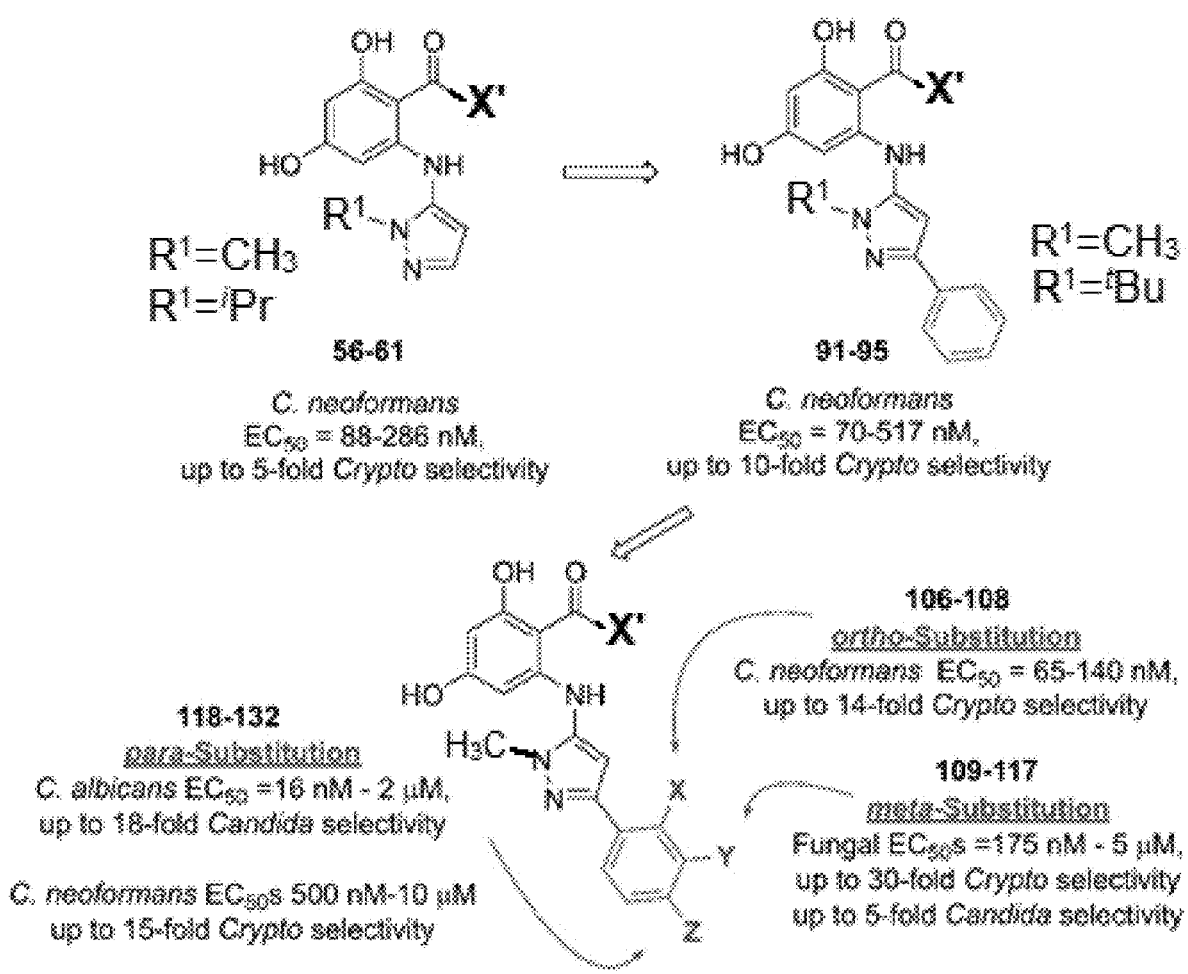
FIG. 2 shows a summary of iterative progression to fungal selective inhibitors with compound according to some embodiments.

Moving from testing in *C. neoformans* lysate to *C. albicans* lysate, the aforementioned meta-substituted compounds 109-117 also exhibited modest selectivity, with the best *Candida*-selectivity observed m-trifluoromethylated analogs 116 and 117 (4.4- and 4.6-fold, respectively). The meta-substituted series also exhibited consistently poor *C. albicans* potencies, with EC$_{50}$ values ranging from ~300 nM to 5 μM. In contrast, improved *C. albicans* selectivities and potencies were observed among the analogs that were para-substituted on the R$^2$ phenyl ring. para-Methylated (119-120) and para-methoxy substituted (121-123) aminopyrazoles exhibited moderate selectivities and, in most cases, equivalently low potencies against both fungal species, with EC$_{50}$ values generally ranging from 0.5-2 μM. Incorporation of larger lipophilic substituents at the para-position such as trifluoromethyl (124-126) and tert-butyl (127-129) further depressed cryptococcal potency, with EC$_{50}$s ranging from 2 to >10 μM and no apparent selectivity. In contrast these compounds (124-129) maintained improved potencies and similar selectivities against *Candida* Hsp90 to their para-methyl- and para-methoxy-counterparts 124-127. This series also highlights what was observed to be an occasional sensitivity to the nature of the amide/aminopyrazole pairing; for example in direct contrast to the cryptococcal potency trends observed with unsubstituted analogs 56-58, pairing of the pyrido- and pyrazolopyrrolidine with the bulkier 3-CF$_3$-Ph (116-117), 4-CF$_3$-Ph (125-126) and 4-$^t$Bu-Ph (128-129) substituents at R$^2$ improved *C. albicans* potency and selectivity relative to their isoindoline counterparts 115, 124 and 127. This trend did not hold, however, for all analogs. Perhaps most intriguingly, the para-trifluoromethoxy substituted compounds 130-132, which were completely nonselective and only modestly potent toward cryptococcal Hsp90, exhibited dramatic improvements in potency toward *C. albicans*, with EC$_{50}$ values ranging from 16-134 nM and 15- to 18-fold *Candida* selectivity. These divergent structure-selectivity trends, wherein ortho/meta-methyl and meta-methoxy compounds exhibited high *Cryptococcus* selectivity and poor *Candida* selectivity, whereas para-trifluoromethoxy substitution rendered high *Candida* selectivity and poor *Cryptococcus* activity, are summarized in FIG. 2.

Relationship of Fungal to Human Selectivity

Figure 3A:
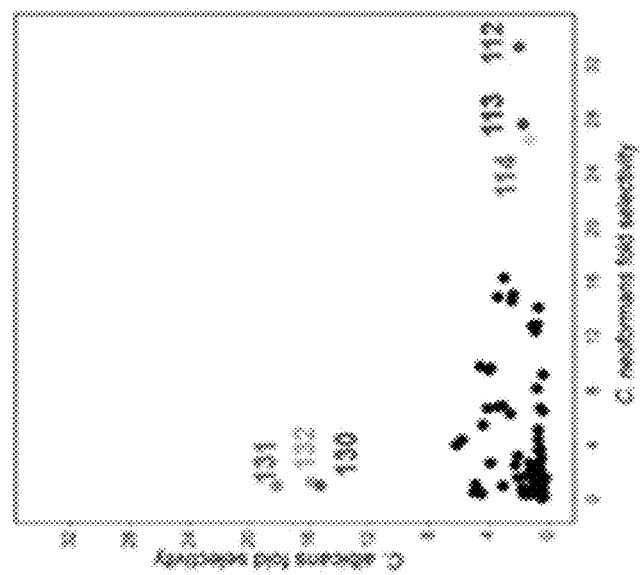
FIG. 3A-3C are scatter plots depicting fungal potency (x-axis) vs. fungal selectivity (y-axis) relationships for aminopyrazoles screened using human cell lysate and lysate of either *C. neoformans*, (FIG. 3A) or *C. albicans*, FIG. 3B).
Figure 3B:
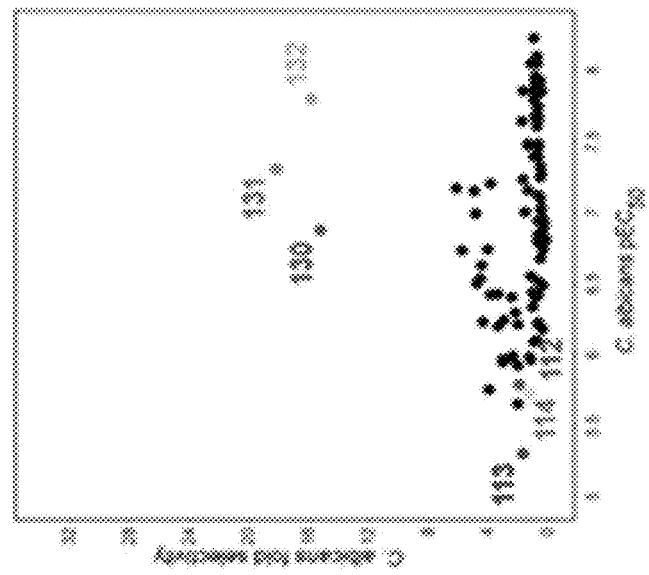
Figure 3C:
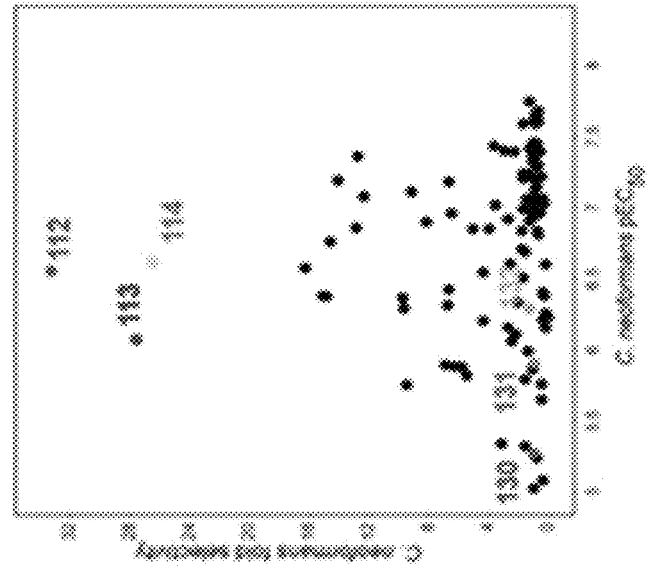

To better understand the phylogenetic origins of the divergent selectivity between fungi, protein:protein BLAST sequence alignments were performed across the different species studied. This analysis indicated that *C. neoformans* and *C. albicans* share 69% sequence identity across the entire Hsp90 protein, and 71% identity across their NBD (residues 1-240). As a comparison, human Hsp90α and Hsp90β share 69% and 67% identity with *C. albicans* Hsp90 across their NBD, respectively. Thus, the two fungal species diverge in primary sequence as greatly from one another as they do from human Hsp90. In light of such sequence divergence, perhaps it is not surprising that while we set out to discriminate against human Hsp90, the potency and selectivity of our synthetic inhibitors also diverged between the two fungal species studied. A graphic summary of inhibitor potency/selectivity relationships found by screening compounds in *C. neoformans* lysate (FIG. 3A) and *C. albicans* lysate (FIG. 3B) highlights the fungal selectivity, while the divergence between compound selectivity in regards to *C. neoformans* vs. *C. albicans* is best demonstrated by plotting the selectivity of compounds for one fungus vs. human against selectivity for the other (FIG. 3C). To more accurately define their potency and selectivity, the activity of 27 compounds with a screening EC$_{50}$<1 μM in lysate of either fungal species was confirmed by repeat testing in two additional experiments, with results provided in Table 7.

TABLE 7

FP-based measurement in whole cell lysates of relative Hsp90 binding affinity and fungal selectivity for resorcylate aminopyrazoles.

| | C. neoformans | | | | C. albicans | | | |
|---|---|---|---|---|---|---|---|---|
| Comp. | Pot.[a] | SEM[b] | Select.[c] | SEM[b] | Pot.[a] | SEM[b] | Select.[c] | SEM |
| 89 | 0.22 | 0.10 | 0.5 | 0.3 | 0.07 | 0.02 | 0.6 | 0.2 |
| 21 | 0.37 | 0.15 | 5.6 | 2.5 | 0.26 | 0.07 | 2.8 | 0.9 |
| 41 | 0.05 | 0.01 | 0.9 | 0.4 | 0.02 | 0.00 | 0.9 | 0.2 |
| 20 | 0.04 | 0.00 | 1.6 | 0.2 | 0.02 | 0.00 | 1 | 0.2 |
| 40 | 0.07 | 0.00 | 1.5 | 0.1 | 0.03 | 0.00 | 1.1 | 0.1 |
| 52 | 0.02 | 0.00 | 1.7 | 0.3 | 0.01 | 0.00 | 1.3 | 0.3 |
| 65 | 0.03 | 0.01 | 2.9 | 1.3 | 0.02 | 0.00 | 1.6 | 0.6 |
| 91 | 0.08 | 0.00 | 16.1 | 3.1 | 0.63 | 0.09 | 0.7 | 0.2 |
| 92 | 0.23 | 0.03 | 11.6 | 3.6 | 1.35 | 0.28 | 0.7 | 0.3 |
| 94 | 0.43 | 0.03 | 26 | 5.6 | 1.61 | 0.36 | 2.5 | 0.9 |
| 98 | 0.20 | 0.03 | 7.7 | 2.7 | 0.37 | 0.08 | 1.5 | 0.6 |
| 106 | 0.06 | 0.00 | 24.2 | 5.1 | 0.64 | 0.04 | 0.8 | 0.2 |

TABLE 7-continued

FP-based measurement in whole cell lysates of relative Hsp90 binding affinity and fungal selectivity for resorcylate aminopyrazoles.

| | C. neoformans | | | | C. albicans | | |
|---|---|---|---|---|---|---|---|
| Comp. | Pot.[a] | SEM[b] | Select.[c] | SEM[b] | Pot.[a] | SEM[b] | Select.[c] | SEM |
| 108 | 0.07 | 0.01 | 20.6 | 5.1 | 0.40 | 0.00 | 1.2 | 0.2 |
| 111 | 0.15 | 0.01 | 58.7 | 15.4 | 0.98 | 0.17 | 3.1 | 1.1 |
| 112 | 0.33 | 0.04 | 34.4 | 9.2 | 1.95 | 0.12 | 2.1 | 0.4 |
| 113 | 0.98 | 0.14 | 14.3 | 2.1 | 6.17 | 0.42 | 0.8 | 0.1 |
| 114 | 0.26 | 0.03 | 40.7 | 12.2 | 2.19 | 0.10 | 1.7 | 0.4 |
| 115 | 3.49 | 0.49 | 3.6 | 0.7 | 2.13 | 0.08 | 2.1 | 0.2 |
| 116 | 1.40 | 0.18 | 7.9 | 2.2 | 0.77 | 0.05 | 5.2 | 1.1 |
| 117 | 0.42 | 0.06 | 13 | 3.8 | 0.35 | 0.02 | 5.6 | 1.1 |
| 118 | 0.84 | 0.17 | 12.5 | 4.3 | 1.20 | 0.07 | 3.1 | 0.6 |
| 121 | 0.78 | 0.12 | 12.5 | 4.3 | 1.35 | 0.06 | 2.6 | 0.6 |
| 122 | 4.52 | 1.10 | 2.9 | 0.8 | 4.62 | 1.03 | 1 | 0.3 |
| 123 | 0.67 | 0.07 | 16 | 4.5 | 1.08 | 0.21 | 3.6 | 1.3 |
| 130 | 5.76 | 0.47 | 2 | 0.4 | 0.68 | 0.16 | 6.1 | 2.1 |
| 131 | 2.22 | 0.40 | 3.4 | 1.2 | 0.20 | 0.05 | 13.2 | 5.2 |
| 132 | 0.64 | 0.09 | 4.8 | 1.7 | 0.07 | 0.02 | 16.2 | 7 |

[a] Mean $EC_{50}$ (µM): Concentration resulting in 50% reduction in maximal polarization signal determined in 3 independent equilibrium competition binding experiments each consisting of duplicate determinations
[b] Standard error of the mean
[c] Mean ratio of $EC_{50}$ values (µM) determined in lysate of human HepG2 cells/indicated fungal species. Results are the mean of 3 independent experiments in each lysate type, each experiment consisting of duplicate determinations FIG. 3A-3C are scatter plots which depict fungal potency (x-axis) vs. fungal selectivity (y-axis) relationships for all aminopyrazoles when screened using human cell lysate and lysate of either C. neoformans (FIG. 3 A) or C. albicans (FIG. 3B). All potencies are reported as the inverse $log_{10}$ of compound $EC_{50}$ ($pEC_{50}$ as measured by FP assay). The scatter plot in FIG. 3C compares compound selectivity patterns between the two fungi. Key fungal-selective compounds for each species (112-114 and 130-132) are highlighted labeled color (113 and 130 or "blue", 114, 131 and 132 are "green", and 112 is "red", where the labels are in the vicinity of the data point) to underscore their divergence in potency and selectivity. Each point represents the mean of duplicate determinations in a single experiment.

Validation of Whole Cell Lysate FP Results

To confirm the FP results obtained in lysate for the most potent and selective compounds, recombinant Candida, Cryptococcus, and human Hsp90 NBDs were preparedly expression and purification in E. coli. Using recombinant proteins, assay-independent nanomolar inhibitory constants (Ki) were defined for these compounds. Binding of the compounds to their relevant NBD by thermal shift denaturation assays was also confirmed. Thermal shift assays were performed under saturating ligand conditions, i.e. equimolar concentrations (10 µM) of protein and ligand. As a result, they can provide only qualitative evidence of target binding, but not a quantitative measurement of ligand affinity. This feature of the thermal shift method is well demonstrated in Table 8, which presents Ki and thermal shift data for both high and low potency compounds. Here, compounds with Ki values of less than 50 nM for a particular NBD increase its ΔTm to a similar extent irrespective of absolute potency. In contrast, lower affinity compounds (Ki>100 nM) fail to increase the Tm of the respective NBD.

TABLE 8

FP-based Ki determinations and protein thermal shift measurements for aminopyrazoles with high- and low-potency in whole cell lysates.

| Compound number | C. neoformans NBD Ki (nM) | C. neoformans NBD ΔTm (° C.) | C. albicans NBD Ki (nM) | C. albicans NBD ΔTm (° C.) |
|---|---|---|---|---|
| 91 | 1.6 | 11 | 13 | 10 |
| 100 | 2.9 | 11 | 8.5 | 9 |
| 106 | 0.8 | 12 | 9.0 | 11 |
| 124 | 190.4 | 1 | 45.9 | 10 |
| 127 | 311.7 | 0 | 28.9 | 12 |

As an orthogonal, highly quantitative approach to FP, we measured the binding affinities of our six lead compounds for C. albicans, C. neoformans and human Hsp90 NBDs by surface plasmon resonance Table 9. The affinity values determined for compounds varied by less than an order of magnitude between the two different experimental techniques. The same pattern of fungal selectivity for compounds demonstrated by FP assay in whole cell lysates was also seen by SPR. The magnitude of selectivity determined by SPR assays compared to FP assays in lysate, however, was reduced. Such a difference might be expected given the absence in SPR assays of native cochaperone-containing complexes and, in the case of human cell lysate, a biologically relevant mix of Hsp90 paralogs.

TABLE 9

Measurement of binding affinities by SPR

| Compound | Biacore KD (nM) | $K_a$ (1/M × s) | $K_d$ (1/s) | Selectivity | Species |
|---|---|---|---|---|---|
| 112 | 126 | 1.38E+04 | 2.79E−03 | 1.8 | C. albicans |
| 113 | 211 | 2.27E+04 | 7.27E−03 | 1.0 | |
| 114 | 86 | 5.62E+04 | 3.99E−03 | 2.9 | |
| 130 | 81 | 1.08E+04 | 2.86E−04 | 13.3 | |
| 131 | 24 | 1.23E+04 | 7.24E−04 | 3.6 | |
| 132 | 9 | 1.56E+04 | 2.31E−04 | 3.4 | |

TABLE 9-continued

Measurement of binding affinities by SPR

| Compound | Biacore KD (nM) | $K_a$ (1/M × s) | $K_d$ (1/s) | Selectivity | Species |
|---|---|---|---|---|---|
| Radicicol | 2 | 1.87E+05 | 5.75E-04 | 0.3 | |
| 112 | 74 | 7.02E+03 | 5.16E-04 | 5.0 | *C.* |
| 113 | 67 | 6.21E+04 | 4.18E-03 | 4.7 | *neoformans* |
| 114 | 22 | 6.31E+04 | 1.40E-03 | 9.2 | |
| 130 | 7 | 2.31E+04 | 1.71E-04 | 47.8 | |
| 131 | 380 | 1.15E+04 | 4.38E-03 | 0.6 | |
| 132 | 214 | 9.78E+03 | 2.09E-03 | 0.2 | |
| Radicicol | 2 | 1.03E+05 | 2.32E-04 | 0.4 | |
| 112 | 365 | 3.14E+03 | 1.15E-03 | | Human |
| 113 | 314 | 1.55E+04 | 4.87E-03 | | |
| 114 | 203 | 1.45E+04 | 2.95E-03 | | |
| 130 | 354 | Not done | Not done | | |
| 131 | 210 | 5.01E+03 | 1.05E-03 | | |
| 132 | 51 | 7.59E+03 | 3.89E-04 | | |
| Radicicol | 1 | 1.66E+05 | 1.35E-04 | | |

Having achieved promising potency and species-selectivity for several compounds at the level of fungal target engagement, the ability of these compounds to inhibit fungal growth was next examined. It was found that minimal inhibitory concentrations (MICs) for most of the potent and selective analogs highlighted in Table 6 were much higher than their $EC_{50}$ values in lysate, generally >50 µM. The disparity between whole cell antifungal activity and the $EC_{50}$ values we determined in FP assays is undoubtedly due to poor permeability/accumulation of the compounds in fungal cells. This common problem in the development of antifungals occurs because the fungal cell wall and membrane as well as the diverse drug efflux pumps expressed by fungi render it a challenge to achieve intracellular concentrations of experimental compounds sufficient to inhibit the function of their targets.

Of the fungal Hsp90-selective compounds tested, only the 14-fold *C. neoformans*-selective analog 106 inhibited growth of the organism below 10 µM (FIG. 4A). While triazole antifungals in current clinical use against *Cryptococcus* do have MICs in excess of this range, they also possess far greater selectivity than we have achieved so far and are much less toxic to human cells. As single agents, the MICs of all our *Candida*-selective compounds were >50 µM. To provide a more sensitive read-out, however, we took advantage of the well-established ability of Hsp90 inhibitors to potentiate the activity of conventional antifungals against drug-resistant isolates of *C. albicans*.[5] Testing compounds 130 and 131 in combination with the widely used antifungal fluconazole, we found an MIC of 12.5 µM for the 15-fold *Candida*-selective analog 130 against a moderately fluconazole-resistant clinical isolate of *C. albicans*. This compound also converted the fungistatic activity of fluconazole to fungicidal against the same isolate, an effect consistent with Hsp90 inhibitory activity (FIG. 4B).

FIG. 4A shows growth inhibition by fungal-selective aminopyrazoles of *C. neoformans* reference strain $H_{99}$ cultured in RPMI 1640 medium at 37° C. FIG. 4B: showsrowth inhibition by fungal-selective aminopyrazoles of a *C. albicans* clinical isolate (CaCi2) with or without a background concentration of 8 µg/mL fluconazole. The effect of 48-hour exposure to inhibitors over a twofold dilution series of concentrations is displayed in heat-map format. Color scale bar: no growth inhibition (green) to complete inhibition (black). Each shaded box represents the mean of technical duplicates. The experiment was repeated as an independent biological replicate to confirm results. Following exposure to compounds, aliquots of the cultures in each well were spotted onto compound-free YPD agar and plates incubated at 30° C. for an additional 24 hours before imaging to assess fungicidal activity (FIG. 4B, right).

Figure 5:
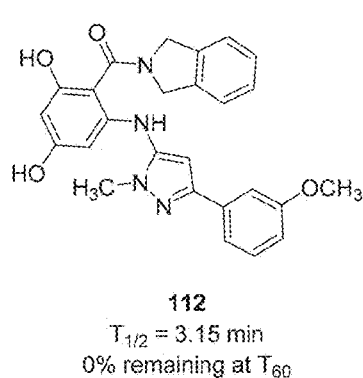
FIG. 5 shows the structure and microsomal stability (mouse liver microsomes) of a panel of fungal-selective inhibitors according to some embodiments.
Figure 5:
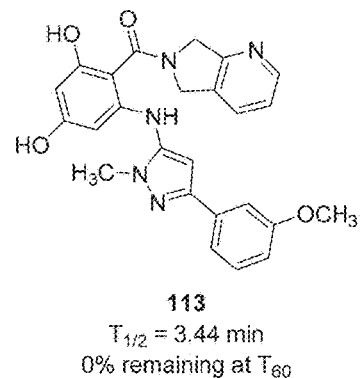
Figure 5:
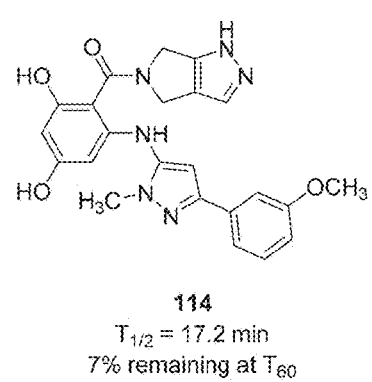
Figure 5:
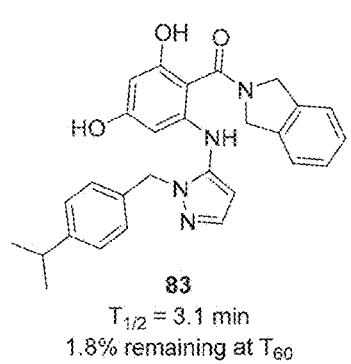
Figure 5:
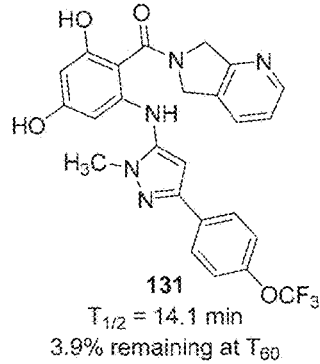
Figure 5:
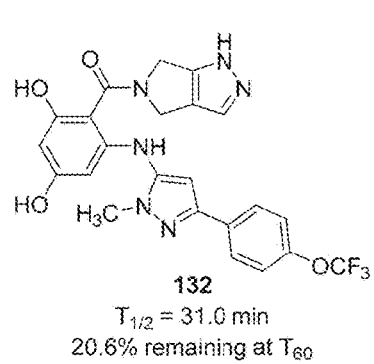
Figure 5:
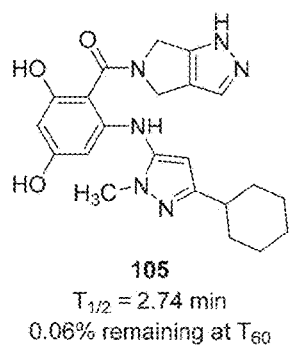
Figure 5:
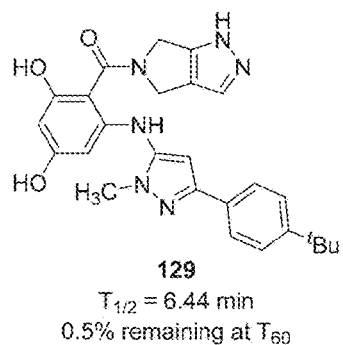
Figure 5:
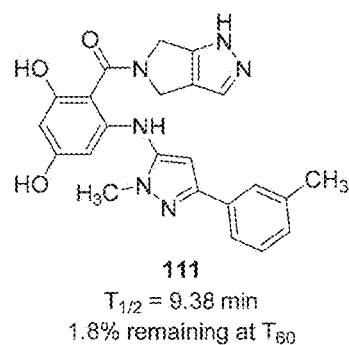

Thus, the whole cell activity of these resorcylate aminopyrazoles remains consistent with an Hsp90-targeted mode of action. Encouraged by this finding and to aid future efforts in developing the scaffold, an initial evaluation of its stability to P450-mediated metabolism in liver microsomes, a major pharmacological liability of our previous fungal-selective macrocyclic oxime 3 (CMLD013075) [11] was performed. Although all the compounds tested suffered from relatively rapid metabolism (FIG. 6 and Table 10), important insights were gained into the basis of their instability. Comparing the half-lives of cryptococcal-selective compounds 112-114 reveals an apparent stabilizing effect of the pyrazolopyrrolidine amide, which is consistent with the previously reported metabolic instability of isoindolines due to oxidation at the 5/6 position[24]. The isoindoline was chosen for this study despite its known downstream pharmacological liabilities, as it represented a low molecular-weight starting point allowing for the methodical assessment of the relative potency and selectivity of different aminopyrazole substitutions. Assessment of additional analogs 105, 111, 129, and 131-132 indicate that additional metabolic liabilities are also likely present at the aminopyrazole, with the para-trifluoromethoxy substitution clearly inhibiting metabolism. Still, the relatively short half-life of compound 132 (31 minutes) underscores the need for further optimization of metabolic stability, in addition to fungal penetration, as we advance in future work to compounds with suitable properties for testing in vivo. Metabolic stability optimization for resorcylate Hsp90 inhibitors via modification of the amide is precedented [24, 50]. FIG. 5 shows microsomal stability (mouse liver microsomes) of a panel of fungal-selective inhibitors. Assays were performed by Charles River Laboratories (Worcester, Mass.).

TABLE 10

Full microsomal stability testing results. Assays performed at Charles River Laboratories (Worcester, MA).

| Compound | $T_{1/2}$ (min) | $CL_{int}$ (mL/min/kg) | % remaining at 15 min | % remaining at 60 min | remaining at 15 min (NADPH-free) |
|---|---|---|---|---|---|
| 83 | 3.1 | 1768 | 3.4% | 1.8% | 109.1% |
| 105 | 2.7 | 1989 | 2.3% | 0% | 103.6% |
| 111 | 9.4 | 582 | 20.2% | 1.8% | 115.3% |
| 112 | 3.2 | 1735 | 3.7% | 0% | 99.3% |
| 113 | 3.4 | 1588 | 4.9% | 0% | 109.2% |
| 114 | 17.2 | 318 | 40.1% | 7.0% | 108.2% |
| 129 | 6.4 | 847 | 21.1% | 0.5% | 97.9% |
| 131 | 14.1 | 387 | 35.5% | 3.9% | 104.1 |
| 132 | 31.0 | 176 | 63.0% | 20.6% | 71.7% |

The factors governing the ability of small molecules to cross cell wall and membrane barriers, avoid active efflux and accumulate within fungi are not well defined. To gain initial insights for the resorcylate aminopyrazoles, the scope of compounds tested in cellulo was expanded to include all biochemically active compounds (FP $EC_{50}$<10 µM) irrespective of their selectivity in cell-free lysates. An additional 83 compounds with diverse physicochemical and structural properties were tested to identify several (21, 27, 29, 49, and 89) with single agent bioactivity against *C. neoformans* (Table 11).

TABLE 11

Aminopyrazoles with whole cell
anti-cryptococcal activity

| Entry | Compound | MIC (μM) | FP EC$_{50}$ (nM) | FP Selectivity |
|---|---|---|---|---|
| 1 | 21 | 6.25 | 877 | 2.5 |
| 2 | 27 | 12.5 | 787 | 2.2 |
| 3 | 29 | 6.25 | 705 | 2.7 |
| 4 | 49 | 12.5 | 1026 | 1.4 |
| 5 | 89 | 25 | 560 | 0.2 |

Minimum inhibitory concentration (MIC) value for compounds against *C. neoformans* (Strain H99) was determined in dose-response format, in technical duplicate. Experiments were conducted in RPMI medium at 37° C. for 48 h. Relative viable cell number was measured by standard dye reduction (resazurin) assay.

The pattern of results suggests that enhancement of lipophilicity through the introduction of halogens or bulky aliphatic moieties can improve whole cell activity. To independently verify that the whole cell activity of these compounds was consistent with an ability to engage Hsp90, the primary FP-based testing of 21, 27, 29, 49 and 89 and 106 was complemented with thermal shift assays using *C. neoformans* NBD (Table 11). Whole cell testing of all biochemically active, but non-selective compounds also revealed three inhibitors (21, 41, and 89) with fungicidal activity in combination with fluconazole against the same clinical isolate of *C. albicans* used in FIGS. 6A and 6B. Analogous to the approach with *Cryptococcus*-active compounds, target engagement for *Candida*-active compounds was confirmed by thermal shift assay using *C. albicans* Hsp90 NBD (Table 12).

Figure 6A:
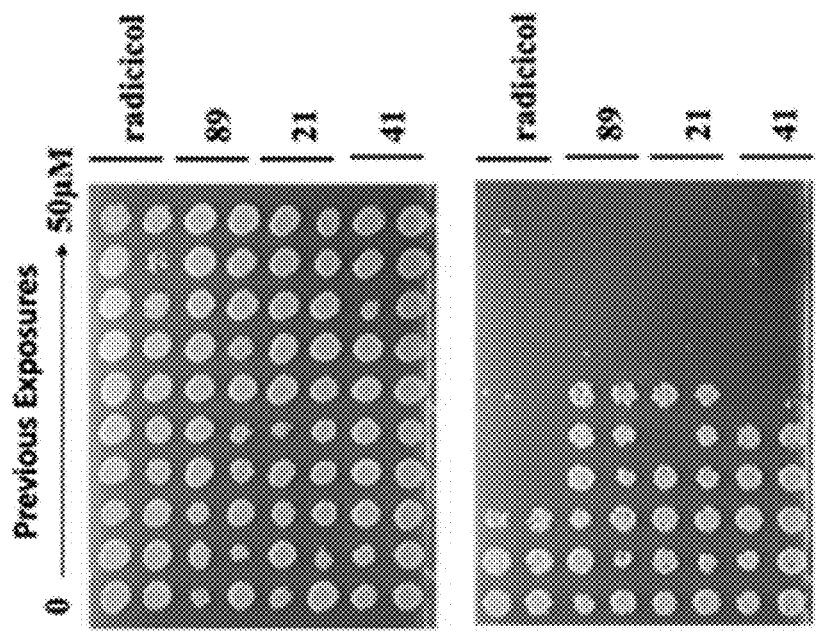
FIG. 6A shows a dose-response assays in liquid medium for fungal-selective inhibitors.
Figure 6B:
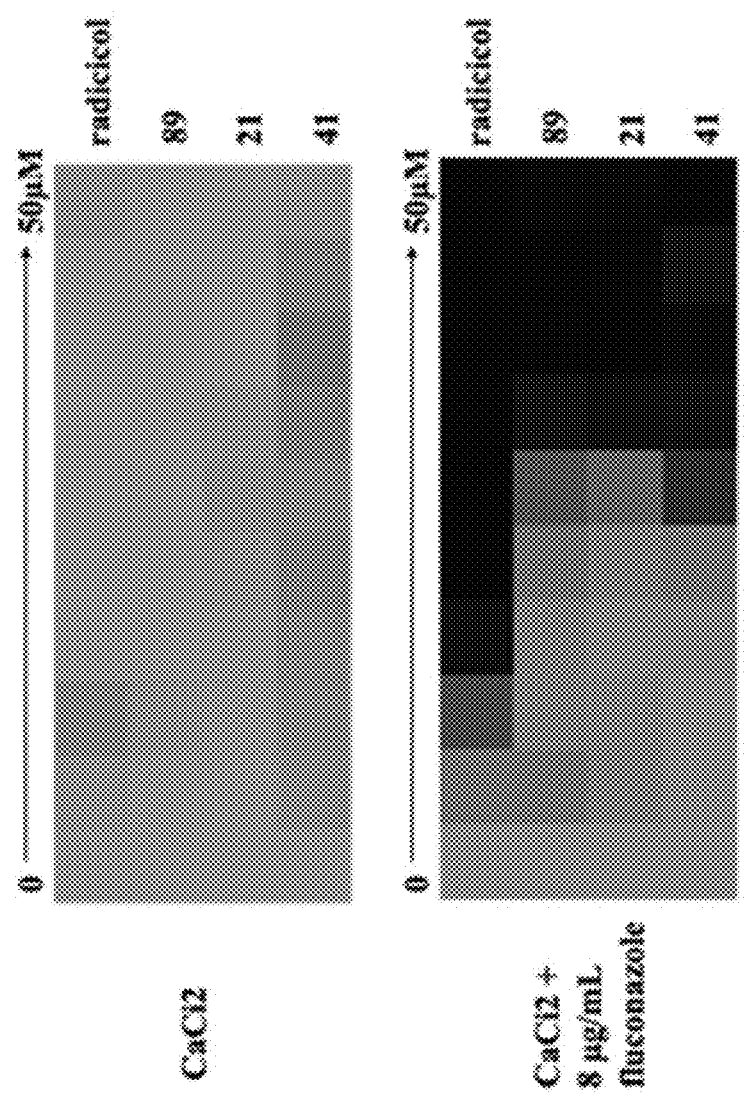
FIG. 6B shows survival of fungi post exposure to fungal-selective inhibitors.

FIG. 6A: Relative growth inhibition by aminopyrazoles of *C. albicans* clinical isolate CaCi2 in RPMI 1640 medium at 37° C., with or without a background concentration of 8 μg/mL fluconazole. The effect of 48-hour exposure to inhibitors over a twofold dilution series of concentrations starting at 50 μM is displayed in heat-map format. Each shaded box represents the mean of technical duplicates. Relative viable cell number was monitored by standard dye reduction assay after 3-hr incubation with resazurin at 37° C. FIG. 6B: Following exposure to compounds, aliquots of the culture in each well were spotted onto compound-free YPD agar and plates incubated at 30° C. for an additional 24 hours before imaging to assess viability. The entire experiment consisting of growth in liquid culture followed by spotting onto YPD agar was repeated once.

TABLE 12

Aminopyrazoles with bioactivity against *C. neoformans* or
*C. albicans* increase thermal stability of the respective
recombinant Hsp90 NBD.

| Fungal NBD | Compound number | ΔTm (° C.) |
|---|---|---|
| | 21 | 14 |
| | 27 | 12 |
| | 29 | 14 |
| *C. neoformans* | 49 | 14 |
| | 89 | 12 |
| | 106 | 12 |
| | 21 | 14 |
| | 41 | 18 |
| *C. albicans* | 89 | 13 |
| | 130 | 9 |

*C. neoformans* or *C. albicans* Hsp90 NBD was combined with equimolar concentrations of the indicated bioactive inhibitors (10 μM) or DMSO control, in technical triplicates. The protein was heated from 25 to 98.6° C. at 0.2° C./5 s in the presence of Sypro Orange dye. All compounds induce an increase in melting temperature relative to the DMSO control, reported as ΔTm.

Macrocyclic Aminopyrazole Analogs

Figure 7:
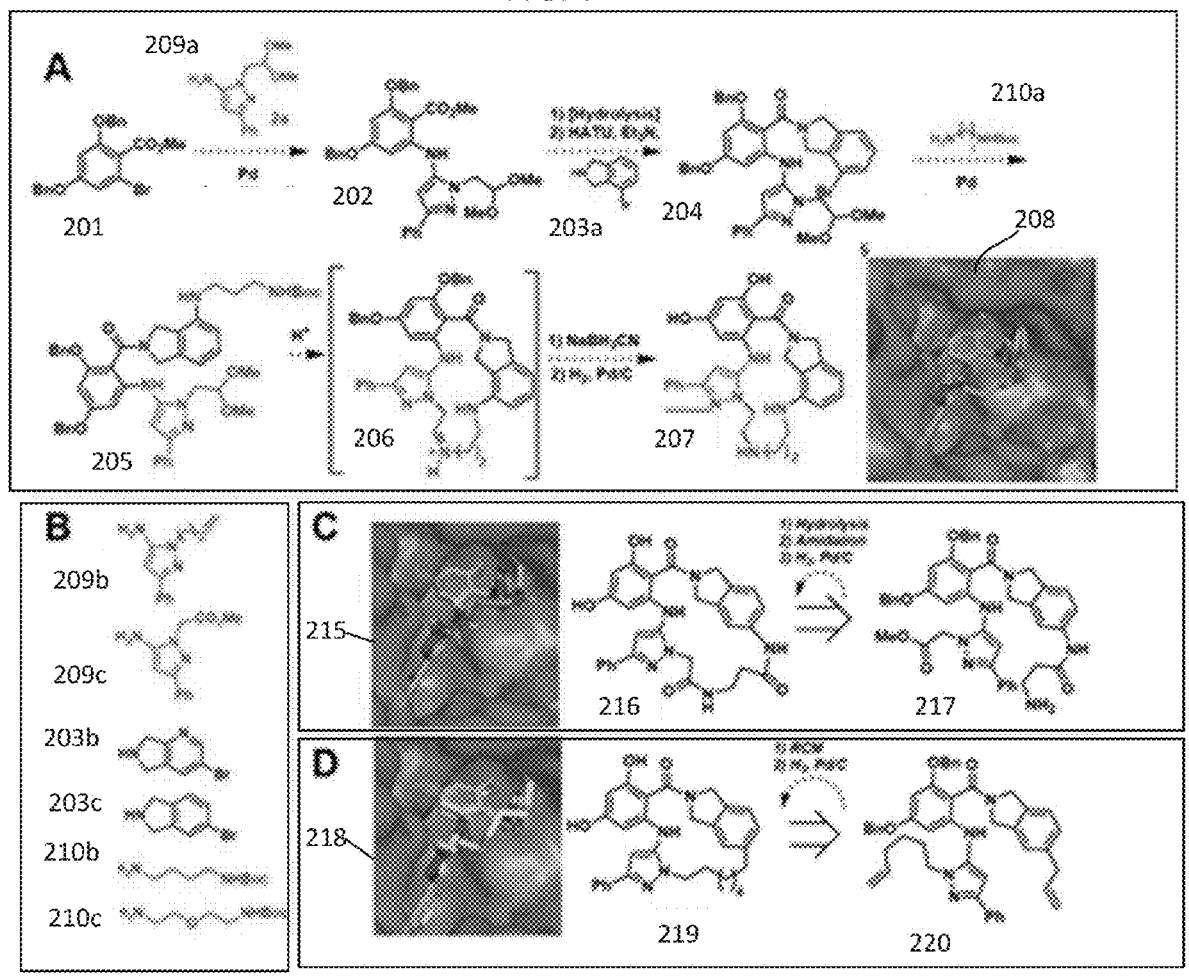
FIG. 7 shows preparative methods for macrocyle compounds. Panel A shows synthetic steps. Panel B shows alternative chemical building blocks. Panel C and Panel D show alternative retrosynthesis for cyclization.

Macrocyclic compounds can be made using the scheme shown by FIG. 7. Panel A shows a synthetic scheme for the preparation of compound 207. Aryl bromide 201 is coupled with aminopyrazole 209a to afford intermediate 202. Hyrolysis and HATU amidiation with isoindoline 203a affords compound 204. Coupling with linker 210a provides compound 205 which is cyclized under acidic conditions providing reactive intermediate 206 which is quenched and reduced to macrocylic compound 207. Compound 207 is shown bound to an Hsp90 portion is complex 208.

Panel B shows some alternative building blocks for the Scheme shown by Panel A. In the first step, the aminopyrazole coupled with 201 can be 209b or 209c, for example. The isoindoline 203a can be replaced, for example, by 203b or 203c. Many different linkers can be used. Here linkers 210b and 210c are shown as additional possible linkers in place of liner 210a.

Panel C shows an alternative retrosynthetic approach for the final cyclization step from 217 to macrocyle 216. Compound 216 is shown bound to an Hsp90 portion in complex 215.

Panel C shows another alternative retrosynthetic approach for the final cyclization step from 220 to 219. Compound 219 is shown bound to an Hsp90 portion in complex 218.

CONCLUSION

Through the iterative design and optimization of a novel aminopyrazole-substituted resorcylate amide chemotype, advanced analogs with markedly improved potency and selectivity for binding to fungal Hsp90 isoforms as compared to their human counterparts have been identified. As fungal selectivity increased, a marked divergence in structure-activity relationship between *C. albicans* and *C. neoformans* becomes evident. Key physicochemical properties have been identified (e.g. structural modification and lipophilicity enhancement through the introduction of halogens or bulky aliphatic moieties) that appear to contribute to improved whole cell activity and metabolic stability.

Experimental Section

Yeast strains and culture conditions. Strains used in this study were *C. albicans* CaCi2 (clinical isolate 2), [58] SC5314, [59] and *C. neoformans* H99. [60] Archives of all fungal strains were maintained at −80° C. in 25% glycerol. Active cultures were maintained on solid (2% agar) yeast extract peptone (YPD, 1% yeast extract, 2% bactopeptone, 2% glucose) at 4° C. for no more than one month. For growth experiments, strains were cultured in YPD medium or in RPMI medium 1640 (Gibco SKU #318000-089, 3.5% MOPS, 2% glucose, pH 7.0), as indicated in figure legends.

Antifungal sensitivity testing. Minimum inhibitory concentrations (MICs) were determined in flat bottom, 96-well plate format using a modified broth microdilution protocol as previously described, [6, 61] except relative viable cell number was monitored by standard dye reduction assay after a 3-hour incubation with resazurin at 37° C. Radicicol and all synthetic analogs were formulated in dimethyl sulfoxide (DMSO, Sigma Aldrich Co.); fluconazole was dissolved in sterile ddH$_2$O. Each compound was tested in duplicate in at least two independent experiments. Minimum inhibitory concentration (MIC) data were quantitatively displayed in heat-map format using the program Java TreeView 1.1.3 (http://jtreeview.sourceforge.net). To test for fungicidal activity, cultures from MIC plates were spotted on YPD agar plates using a spotter (Frogger, V&P Scientific, Inc). Plates were photographed after 24 h of incubation at 30° C.

FP assays. Whole cell lysates were prepared for FP assays as described previously. [11] Total protein concentration of human and yeast lysates was determined by Bradford assay. [6] Titrations of Cy3-labeled geldanamycin (Cy3-GdA) probe and lysate were evaluated to define conditions that resulted in 75% maximal probe polarization with no competitor present. Serial dilutions of test Hsp90 inhibitors were then assayed under these same conditions to monitor loss of fluorescence polarization as an indicator of probe displacement from Hsp90. All determinations were performed in duplicate wells using 384-well black flat-bottom microtiter plates (Greiner Bio-One; 655076). Titrations of test compound in 25 µL of binding buffer (supplemented with 0.1 mg/mL bovine gamma globulin), were mixed with an equal volume of freshly prepared whole-cell lysate spiked with Cy3-GdA (0.1 nM). Plates were incubated at room temperature for 4.5 h to achieve equilibrium binding for the geldanamycin-based probe. Signal in millipolarization (mP) units was measured at an excitation wavelength of 535 nm and emission wavelength of 595 nm in a SpectraMax i3 microplate reader (Molecular Devices) using Softmax Pro software (version 5.4.1). Non-linear 4-parameter curve fitting of raw displacement data was performed in GraphPad Prism 5.0 to determine $EC_{50}$ values as a measure of relative Hsp90-binding affinity. Results were normalized to the value determined for GdA in lysate of each cell type. This experiment was repeated for a set of 27 key compounds for SAR in at least three independent experiments.

FP assays were also performed with purified *C. albicans* and *C. neoformans* Hsp90 NBD for the determination of inhibitory constants ($K_i$) for relevant fungal-selective compounds. Titrations of the Cy3-GdA probe and purified proteins were evaluated to define assay conditions and to determine the dissociation constant $K_d$ of the probe for each NBD. Serial dilutions of test Hsp90 inhibitors were then assayed in triplicate wells under these conditions. Non-linear 4-parameter curve fitting of raw displacement data was performed in GraphPad Prism 5.0 to determine $IC_{50}$ values. Finally, inhibitory constants ($K_i$) were calculated as described previously. [11, 62]

Protein thermal shift assays. Thermal melting curves were determined using a Protein Thermal Shift Kit (ThermoFisher #4462263), employing a CFX384 Real-Time PCR System (Bio-Rad, C1000 Touch Thermal Cycler). Reactions were performed in a final volume of 10 µL, and contained purified *C. albicans* or *C. neoformans* Hsp90 NBD diluted to 250 µg/mL in Buffer HBS-P (GE Healthcare Life Sciences, 0.01 M HEPES pH 7.4, 0.15 M NaCl, 0.005% v/v Surfactant P20) with 10 µM synthetic analog or DMSO control, and 1× Sypro Orange dye solution. Samples were prepared in triplicate in 384-well white plates (Bio-Rad; HSP3805). The instrument was set to melt curve, step 1 (25° C., 2 min) and step 2 (ramp to 98.6° C., increasing 0.2° C. per 5 s cycle). The inflection point of each curve is defined as the protein melting temperature ($T_m$). Temperature shift, $\Delta T_m$, was recorded as the difference between the $T_m$ of the fungal Hsp90 NBD with compound minus $T_m$ of the protein without compound.

NBD expression and purification. Recombinant Hsp90 NBDs were expressed and purified as previously described.

[11] Stock protein solutions in 50% glycerol were stored at −20° C. until dilution into relevant buffers and use for FP and thermal shift assays.

SPR assays. For SPR experiments, Hsp90 NBD expression constructs were modified to encode a C-terminal Avi-Tag™ for site-specific on-column biotinylation with a BirA biotin-ligase kit (Avidity LLC; BirA-500). SPR experiments were performed on a Biacore T200 instrument at 25° C. Biotinylated Hsp90 NBD was diluted to 40 µg/mL and immobilized on a streptavidin chip (Sensor Chip SA, GE Healthcare) at a density of 2000-2500 response units (RU) on the biosensor surface. Binding experiments were done in HBS-P (0.01 M HEPES pH 7.4, 0.15 M NaCl, 0.005% v/v Surfactant P20, GE Healthcare) with 5% DMSO at a flow rate of 40 L/min. Test compounds were injected in two dilutions series, with low concentrations ranging from 6 to 96 nM and high concentrations ranging from 60 to 960 nM, with a 60 s association time and 600 s dissociation time, with the exception of compound 130 for which the injection time was extended to 300 s after observing a very slow on-rate with this molecule. Resulting sensorgrams were analyzed with a fit to a 1:1 binding model, using BIA evaluation software.

Microsome stability testing. The potential susceptibility of compounds to hepatic metabolism was assessed by Charles River Laboratories (Worcester, Mass.) using standard in-house protocols. Compounds were incubated at 1 µM concentration in mixed-gender CD-1 mouse liver microsomes (0.5 mg/mL) in the presence of 2 µM NADPH. Percent compound remaining was measured by LC/MS/MS at six timepoints (0, 15, 30, 60, 90 and 120 min) in duplicate. 7-ethoxycoumarin was utilized as a positive control. In addition, NADPH-free control samples were assessed at two timepoints (0 and 15 m) in duplicate to exclude non-CYP450-mediated decomposition. First-order half-lives are calculated from the equation $T_{1/2}=-0.693/x$, where x is the slope found in the linear fit for the plot of ln(% remaining) versus incubation time. Calculated mouse intrinsic hepatic clearance ($CL_{int}$) in mL/min/kg is extrapolated[63] based on 45 mg microsomes/g liver and 87.5 g liver/kg body weight.

Statistical methods. For FP experiments in support of SAR studies, GraphPad Prism 5.0 was used to perform curve fitting and calculate the concentrations of compounds resulting in 50% reduction in maximal polarization signal ($EC_{50}$). All curve fits demonstrated a correlation coefficient ($R^2$) >0.95 The number of independent experiments performed and the number of technical replicates in each experiment are provided in the legends of figures and tables characterizing the biochemical and biological activities of compounds. In calculating the error of selectivity determinations, the fractional error of measurements in each species was summed to yield a composite error for the derived ratio.

Chemistry Methods.

General Methods. All melting points are uncorrected. $^1$H NMR spectra were recorded at 400 or 500 MHz at ambient temperature. $^{13}$C NMR spectra were recorded at 101 or 126 MHz at ambient temperature. Chemical shifts are reported in parts per million. Data for $^1$H NMR are reported as follows: chemical shift, multiplicity (app=apparent, br=broad, s=singlet, d=doublet, t=triplet, q=quartet, sxt=sextet, hept=heptet, m=multiplet, ovrlp=overlap), coupling constants, and integration. All $^{13}$C NMR spectra were recorded with complete proton decoupling. Analytical thin layer chromatography was performed using 0.25 mm silica gel 60-F plates. Flash column chromatography was performed using 200-400 mesh silica gel (Sorbent Technologies, Inc.). Automated flash chromatography was performed using prepacked columns (SI-HC, puriFlash or Premium Universal, Yamazen) on either an Interchim puriFlash450 or Yamazen Smart Flash EPCLC W-Prep2XY system. All mass-guided preparative HPLC was performed using an acetonitrile: water gradient (mobile phase modified with 0.01% formic acid) on a Waters FractionLynx system equipped with a 600 HPLC pump, a micromass ZQ quadrapole, Waters 996 diode array, and Sedere Sedex 75 ELS detectors, using an XBridge Prep C18 5 μM OBD 19 mm diameter column of either 100 mm or 250 mm length. Isolated yields refer to chromatographically and spectroscopically pure compounds, unless otherwise stated. All reactions were carried out in oven-dried glassware under an argon atmosphere unless otherwise noted. Analytical LC-MS experiments were performed using a Waters Acquity UPLC (ultraperformance liquid chromatography) with a binary solvent manager, SQ mass spectrometer, Waters 2996 PDA (photodiode array) detector, and evaporative light scattering detector (ELSD). All microwave experiments were performed on a CEM Discover microwave reactor, using a sealed 10 or 35 mL vessel with temperatures monitored by an external sensor. All compounds tested in biological assays were determined to be >95% pure by UPLC-MS-ELSD analysis.

General Procedure A: Synthesis of α-Formyl Nitriles.

All α-formyl nitriles used as synthetic precursors for aminopyrazoles 10 were synthesized via a procedure adapted from [64]. To a suspension of potassium tert-butoxide in THF (2.2 equiv, 1.4 M solution in THF) at room temperature was added a mixture of the requisite nitrile (1 equiv) and ethyl formate (1.05 equiv) in THF (6.3 M relative to nitrile) dropwise. After stirring overnight at room temperature, the reaction mixture was diluted with $CH_2Cl_2$ and water. The resulting mixture was adjusted to pH=4 using concentrated HCl (aq.). The layers were separated and aqueous layer was extracted twice with $CH_2Cl_2$. The combined organic layers were washed with brine and dried with anhydrous $MgSO_4$. The salts were removed via gravity filtration and volatile materials were condensed in vacuo. The crude mixture was purified via automated flash chromatography to give the intermediate α-formyl nitrile.

General Procedure B: Synthesis of α,β-unsaturated Nitriles.

All α,β-unsaturated nitriles used as synthetic precursors for aminopyrazoles 10 were generated from commercially-available aldehydes according to the following procedure: To a solution of potassium tert-butoxide (2 M in THF, 1.04 equiv) at 0° C. was added diethyl cyanomethylphosphonate (1.1 equiv) dropwise. After stirring at 0° C. for 1 h, the requisite aldehyde (1 equiv) was added dropwise and the reaction was allowed to warm to room temperature overnight. The reaction mixture was poured into saturated $NH_4Cl$ (aq.) and diluted with ethyl acetate. The layers were separated and the aqueous layer was extracted three times with ethyl acetate. The combined organic layers were washed with brine and dried with anhydrous $Na_2SO_4$. The salts were removed via gravity filtration and condensed in vacuo. The crude mixture was purified via automated flash chromatography to give the intermediate α,β-unsaturated nitrile.

General Procedures C: Syntheses of Aminopyrazoles 10

C1: Procedure adapted from [65]. A suspension of 3-aminocrotonitrile (1.08 equiv) and the requisite hydrazine hydrochloride (1 equiv) in 1 M HCl (aq.) (0.72 M concentration of hydrazine) was refluxed for 3 h. The resulting mixture was diluted with water and extracted twice with ethyl acetate. The aqueous layer was basicified with solid $NaHCO_3$ until solid remained. The aqueous layer was extracted twice with ethyl acetate. The combined organic layers from each extraction sequence were separately washed with brine and dried with anhydrous $Na_2SO_4$. The salts were removed via gravity filtration and the mother liquors were combined and condensed in vacuo. The crude residues were purified via automated flash chromatography.

C2: A mixture of the requisite α-formyl nitrile and 4-(methoxybenzyl)hydrazine hydrochloride (1 equiv) was refluxed overnight in ethanol (0.36 M relative to α-formyl nitrile). The solution was cooled to room temperature and condensed in vacuo. The residue was diluted with $CH_2Cl_2$ and the organic layer was washed twice with saturated $NaHCO_3$ (aq.) and brine. The organic layer was dried with anhydrous $Na_2SO_4$. The salts were removed via gravity filtration and volatile materials were condensed in vacuo. The crude mixture was purified via automated flash chromatography.

C3: Procedure adapted from [65]. To a solution of hydrazine monohydrate (1.03 equiv) in THF (5 M relative to hydrazine) at room temperature was added the requisite α,β-unsaturated nitrile (1.02 equiv) and heated to 40° C. for 2 h. After cooling to room temperature, the requisite aldehyde (1 equiv) was added dropwise. The mixture was heated to 40° C. for an additional 2 h. After cooling to room temperature, volatile materials were condensed in vacuo. The resulting residue was dissolved in ⁱPrOH (4.5 M relative to benzaldehyde). Sodium tert-butoxide (1.03 equiv) was added to the reaction mixture and the resulting suspension was heated to 100° C. for 2.5 h and then stirred overnight at room temperature. The reaction mixture was diluted with water and extracted twice with diethyl ether. The combined organic layers were washed twice with 1 M HCl. The combined 1 M HCl washes were basicified to pH=14 with 50% NaOH (aq.) and extracted with diethyl ether. The second set of ether extractions were combined and washed with brine and dried with anhydrous $Na_2SO_4$. The salts were removed via gravity filtration and volatile materials were condensed in vacuo. The crude mixture was purified via automated flash chromatography.

C4: A solution of requisite oxonitrile (1 equiv) and (4-methoxybenzyl)hydrazine hydrochloride (2 equiv) in EtOH (0.3 M relative to oxonitrile) was heated to reflux overnight. After cooling to room temperature, volatile materials were condensed in vacuo. The residue was dissolved in $CH_2Cl_2$ and saturated $NaHCO_3$ (aq.). The layers were separated and the aqueous layer was extracted twice with $CH_2Cl_2$. The combined organic layers were washed with brine and dried with anhydrous $Na_2SO_4$. The salts were removed via gravity filtration and volatile materials were condensed in vacuo. The crude mixture was purified via automated flash chromatography.

C5: A solution of requisite oxonitrile (1 equiv) and methylhydrazine (1 equiv) in methanol (2 M) were irradiated at 120° C. for 40 min in a microwave reactor. After cooling to room temperature, volatile materials were condensed in vacuo. The crude mixture was purified via automated flash chromatography General Procedures D. Pd-Mediated Coupling of Aryl Bromides to Aminopyrazoles 10.

D1: Inside a nitrogen glovebox were combined aryl bromide (1 equiv), amine 10 (1.1 equiv), tris(dibenzylideneacetone)dipalladium (0.04 equiv), Xantphos (0.08 equiv), sodium phenoxide (1.5 equiv). Dioxane (0.13 M) was added to the mixture and the reaction vessel was capped and removed from the glovebox. After the reaction was heated in an oil bath at 120° C. for 2 h, the reaction was cooled to room temperature and diluted with ethyl acetate. The resulting mixture was washed three times with saturated Na$_2$CO$_3$ (aq.), brine, then dried with anhydrous Na$_2$SO$_4$. The salts were removed via gravity filtration and volatile materials were condensed in vacuo. The crude mixture was purified via automated flash chromatography.

D2: Inside a nitrogen glovebox were combined aryl bromide (1 equiv), amine 10 (1.1 equiv), tris(dibenzylideneacetone)dipalladium (0.04 equiv), Xantphos (0.08 equiv), sodium phenoxide (1.5 equiv) in a 10 mL microwave reaction vessel. Dioxane (0.13 M) was added to the mixture and the reaction vessel was capped and removed from the glovebox. After the reaction was irradiated at 170° C. for 2 h in a microwave reactor, the reaction was cooled to room temperature and diluted with ethyl acetate. The resulting mixture was washed three times with saturated Na$_2$CO$_3$ (aq.), brine, then dried with anhydrous Na$_2$SO$_4$. The salts were removed via gravity filtration and volatile materials were condensed in vacuo. The crude mixture was purified via automated flash chromatography.

General Procedure E. Hydrolysis conditions to generate crude acids 19. To a solution of ester (1 equiv) in EtOH: water (1:1 ratio, 0.06 M) was added potassium hydroxide (9.2 equiv) and then heated to 95° C. for 1 h. After cooling to room temperature, volatile materials were condensed in vacuo. The residue was suspended in saturated NH$_4$Cl (aq.) and CH$_2$Cl$_2$. The layers were separated and the aqueous layer was extracted three times with CH$_2$Cl$_2$. The combined organic layers were washed twice with water, brine and then dried with anhydrous Na$_2$SO$_4$. The salts were removed via gravity filtration and volatile materials were condensed in vacuo. The crude acid 19 was used without further purification.

General Procedure F: Global MOM-Deprotection.

To a solution of amide (1 equiv) in methanol (13.7 mM) was added HCl (2 M, 6.5 equiv). The resulting solution was stirred at 50° C. overnight. After cooling to room temperature, volatile materials were condensed in vacuo. The residue was purified on mass-guided preparative HPLC.

General Procedure G: Amidation of Acids 19.

To a suspension of crude carboxylic acid 19 (1 equiv) and amine (1.5 equiv) in CH$_2$Cl$_2$:THF (1:1 mixture, 0.08-0.09 M) was added triethylamine followed by HATU (1.2 equiv). The suspension was stirred overnight at room temperature and then diluted with CH$_2$Cl$_2$. The reaction mixture was washed with saturated NaHCO$_3$ (aq.), brine and then dried with anhydrous Na$_2$SO$_4$. The salts were removed via gravity filtration and volatile materials were condensed in vacuo. The crude mixture was purified via automated flash chromatography.

General Procedures H:

Tandem PS-CDI-mediated amidation and MOM deprotection of crude acids 19.

H1: To a solution of crude carboxylic acid 19 (1 equiv) and isoindoline hydrochloride (1.5 equiv) in THF: CH$_2$Cl$_2$ (1:1 ratio, 77 mM) was added trimethylamine (4 equiv) followed by HOBt hydrate (1.2 equiv) and PS-Carbodiimide (1.18 mmol/g loading, 1.2 equiv). The suspension was shaken overnight at room temperature. The resin was removed via filtration and the resulting filtrate was washed twice with saturated NaHCO$_3$ (aq.) and once with brine. The organic layer was dried with anhydrous sodium sulfate. The salts were removed via gravity filtration and volatile materials were condensed in vacuo. The resulting residue was dissolved in methanol (20 mM) and HCl (aq.) (2 M, 6.5 equiv) was added to the mixture. The resulting solution was stirred at 50° C. overnight. After cooling to room temperature, volatile materials were condensed in vacuo. The residue was purified on mass-guided preparative HPLC.

H2: Identical to General Procedure H1, except using 6,7-dihydro-5H-pyrrolo[3,4-b]pyridine instead of isoindoline hydrochloride.

H3: Identical to General Procedure H1, except using 1,4,5,6-tetrahydropyrrolo[3,4-c]pyrazole instead of isoindoline hydrochloride.

1-(4-methoxybenzyl)-3-methyl-1H-pyrazol-5-amine (10a)

Synthesized using General Procedure C1 with (4-methoxybenzyl)hydrazine hydrochloride (250 mg, 1.33 mmol) and purified using automated flash chromatography (5% to 25% ethyl acetate in hexanes) to afford 189 mg of 10a as a white/orange solid (66% yield). $^1$H NMR (400 MHz, CDCl$_3$) δ 7.12 (d, J=8.2 Hz, 2H), 6.86 (d, J=8.4 Hz, 2H), 5.37 (s, 1H), 5.08 (s, 2H), 3.80-3.74 (m, 3H), 3.30 (s, 2H), 2.19 (s, 3H). $^{13}$C NMR (101 MHz, CDCl$_3$) δ 159.0, 147.4, 145.2, 129.0, 128.1, 114.2, 91.3, 55.2, 50.8, 13.9. LC/MS (m/z): 218.126 [M+H$^+$]; UPLC t$_R$ 1.04 min.

1-(4-methoxybenzyl)-3-phenyl-1H-pyrazol-5-amine (10b)

A solution of benzoylacetonitrile (350 mg, 2.41 mmol) and (4-methoxybenzyl)hydrazine hydrochloride (910 mg, 4.82 mmol) in ethanol (8 mL) was heated to reflux overnight. After cooling to room temperature, the solution was condensed in vacuo. The residue was dissolved in CH$_2$Cl$_2$ and saturated NaHCO$_3$ (aq.). The layers were separated and the aqueous layer was extracted twice with CH$_2$Cl$_2$. The combined organic layers were washed with brine and dried with anhydrous Na$_2$SO$_4$. The salts were removed via gravity filtration and the volatile materials were condensed in vacuo. The crude mixture was purified via automated flash chromatography (1% to 5% ethyl acetate in CH$_2$Cl$_2$) to afford 498 mg of 10b (74% yield) as a white solid. $^1$H NMR (400 MHz, CDCl$_3$) δ 7.77 (dd, J=8.2, 1.4 Hz, 2H), 7.38 (dd, J=8.4, 6.9 Hz, 2H), 7.29 (d, J=7.4 Hz, 1H), 7.18 (d, J=8.4 Hz, 2H), 6.90-6.80 (m, 2H), 5.90 (s, 1H), 5.24 (s, 2H), 3.78 (s, 3H), 3.44 (s, 2H). $^{13}$C NMR (101 MHz, CDCl$_3$) δ 149.3, 144.5, 134.5, 128.5, 127.2, 125.5, 88.9, 56.2, 32.3, 25.8, 25.3. LC/MS (m/z): 281.203 [M+H$^+$]; UPLC t$_R$ 1.64 min.

1-(4-methoxybenzyl)-4-methyl-1H-pyrazol-5-amine (10c)

2-methyl-3-oxopropanenitrile was synthesized using General Procedure A from propionitrile (0.82 mL, 11.4 mmol) in 6.7% yield after automated flash chromatography (20% to 60% ethyl acetate in hexanes). 2-methyl-3-oxopropanenitrile (64 mg, 0.73 mmol) was subjected to General Procedure C2 to afford 68 mg of 10c as an off-white solid (41% yield) after purification via automated flash chromatography (15% to 85% ethyl acetate in hexanes). $^1$H NMR (400 MHz, CDCl$_3$) δ 7.18 (s, 1H), 7.16-7.07 (m, 2H), 6.85 (d, J=8.6 Hz, 2H), 5.14 (s, 2H), 3.78 (s, 3H), 3.11 (s, 1H), 1.90 (s, 3H). $^{13}$C NMR (101 MHz, CDCl$_3$) δ 159.1, 141.3, 138.7, 128.9, 128.3, 114.2, 100.5, 55.3, 51.4, 7.9. LC/MS (m/z): 218.17 [M+H$^+$]; UPLC t$_R$ 1.11 min.

4-isopropyl-1-(4-methoxybenzyl)-1H-pyrazol-5-amine (10d)

2-formyl-3-methylbutanenitrile was synthesized using General Procedure A from isovaleronitrile (1.20 mL, 11.4 mmol) in 24% yield after automated flash chromatography (10% to 30% acetone in hexanes and 5% to 20% ethyl acetate in $CH_2Cl_2$).

2-formyl-3-methylbutanenitrile (291 mg, 2.62 mmol) was subjected to General Procedure C2 to afford 260 mg of 10d as a white/yellow solid (40% yield) after purification via automated flash chromatography (15% to 55% ethyl acetate in hexanes). $^1$H NMR (400 MHz, $CDCl_3$) δ 7.22 (s, 1H), 7.12 (d, J=8.5 Hz, 2H), 6.86 (d, J=8.6 Hz, 2H), 5.14 (s, 2H), 3.78 (s, 3H), 3.13 (s, 2H), 2.62 (p, J=6.9 Hz, 1H), 1.19 (d, J=6.9 Hz, 6H). 13C NMR (101 MHz, $CDCl_3$) δ 159.1, 140.1, 135.8, 129.0, 128.3, 114.2, 112.4, 55.2, 51.2, 23.7, 23.3. Mp: 74-76° C. LC/MS (m/z): 245.916 [M+H$^+$]; UPLC $t_R$ 1.30 min.

1-(4-Methoxybenzyl)-4-phenyl-1H-pyrazol-5-amine (10e)

Synthesized using General Procedure C2 from 3-oxo-2-phenylpropanenitrile (250 mg, 1.72 mmol) to afford 223 mg of 10e (46% yield) as an off-white solid after purification via automated flash chromatography (4% to 12% ethyl acetate in $CH_2Cl_2$). $^1$H NMR (400 MHz, $CDCl_3$) δ 7.53 (s, 1H), 7.46-7.33 (m, 4H), 7.25-7.11 (m, 3H), 6.88 (d, J=8.5 Hz, 2H), 5.21 (s, 2H), 3.79 (s, 3H), 3.61 (s, 2H). $^{13}$C NMR (101 MHz, $CDCl_3$) δ 159.3, 141.2, 137.3, 133.6, 129.0, 128.4, 128.3, 126.3, 125.6, 114.4, 106.9, 55.3, 51.6. Mp: 154-156° C. LC/MS (m/z): 281.159 [M+H$^+$]; UPLC $t_R$ 1.68 min.

4-benzyl-1-(4-methoxybenzyl)-1H-pyrazol-5-amine (10f)

2-benzyl-3-oxopropanenitrile was synthesized using General Procedure A from 3-phenylpropionitrile (1.50 mL, 11.4 mmol) in 17% yield after automated flash chromatography (10% to 30% acetone in hexanes and 5% to 20% ethyl acetate in $CH_2Cl_2$). 2-benzyl-3-oxopropanenitrile (300 mg, 1.88 mmol) was subjected to General Procedure C2 to afford 152 mg of 10f (27% yield) as a white/brown solid after purification via automated flash chromatography (20% to 60% ethyl acetate in hexanes and 4% to 15% ethyl acetate in $CH_2Cl_2$). $^1$H NMR (400 MHz, $CDCl_3$) δ 7.35-7.15 (m, 5H), 7.11 (d, J=8.3 Hz, 2H), 6.85 (d, J=8.5 Hz, 2H), 5.14 (s, 2H), 3.78 (s, 3H), 3.70 (s, 2H), 3.03 (s, 2H). $^{13}$C NMR (101 MHz, $CDCl_3$) δ 159.2, 141.7, 140.3, 138.7, 128.8, 128.6, 128.3, 126.2, 114.3, 103.9, 55.3, 51.4, 29.7. LC/MS (m/z): 295.186 [M+H$^+$]; UPLC $t_R$ 1.54 min.

3-ethyl-1-(4-methoxybenzyl)-1H-pyrazol-5-amine (10g)

Synthesized using General Procedure C3 from pent-2-enenitrile (239 mg, 2.95 mmol) and p-anisaldehyde (0.353 mL, 2.90 mmol) to afford 131 mg of 10g (19% yield) after purification via automated flash chromatography (10% to 30% acetone in hexanes and 5% to 20% ethyl acetate in $CH_2Cl_2$). $^1$H NMR (400 MHz, $CDCl_3$) δ 7.12 (d, J=8.6 Hz, 2H), 6.85 (d, J=8.7 Hz, 2H), 5.40 (s, 1H), 5.11 (s, 2H), 3.78 (s, 3H), 3.36 (s, 2H), 2.57 (q, J=7.6 Hz, 2H), 1.22 (t, J=7.6 Hz, 3H). $^{13}$C NMR (101 MHz, $CDCl_3$) δ 159.1, 153.6, 144.9, 128.9, 128.1, 114.2, 89.9, 55.3, 50.9, 21.8, 14.0. LC/MS (m/z): 231.933 [M+H$^+$]; UPLC $t_R$ 1.14 min.

3-isopropyl-1-(4-methoxybenzyl)-1H-pyrazol-5-amine (10h)

Synthesized using General Procedure C4 from 4-methyl-3-oxopentanenitrile (100 mg, 0.900 mmol) to afford 278 mg of 10h (>100% yield) as a yellow oil after purification via automated flash chromatography (7% to 20% ethyl acetate in $CH_2Cl_2$). Chromatographed product was impure and was carried forward to the next step without further purification.

3-(tert-butyl)-1-(4-methoxybenzyl)-1H-pyrazol-5-amine (10i)

Synthesized using General Procedure C4 from 4,4-dimethyl-3-oxopentanenitrile (200 mg, 1.60 mmol) and (4-methoxybenzyl)hydrazine hydrochloride (301 mg, 1.60 mmol) to afford 342 mg of 10i (83% yield) as an orange solid after purification via automated flash chromatography (10% to 35% ethyl acetate in hexanes). $^1$H NMR (400 MHz, $CDCl_3$) δ 7.13-7.00 (m, 2H), 6.85 (d, J=8.5 Hz, 2H), 5.44 (s, 1H), 5.12 (s, 2H), 3.78 (s, 3H), 3.25 (s, 2H), 1.29 (s, 9H). $^{13}$C NMR (101 MHz, $CDCl_3$) δ 160.6, 159.0, 144.5, 129.2, 127.9, 114.2, 88.3, 55.2, 50.9, 32.1, 30.5. Mp: 72-74° C. LC/MS (m/z): 261.222 [M+H$^+$]; UPLC $t_R$ 1.30 min.

3-cyclopropyl-1-(4-methoxybenzyl)-1H-pyrazol-5-amine (10j)

Synthesized using General Procedure C4 from 3-cyclopropyl-3-oxopropanenitrile (100 mg, 0.916 mmol) to afford 176 mg of 10j (79% yield) as an off-white solid after purification via automated flash chromatography (7% to 20% ethyl acetate in $CH_2Cl_2$). $^1$H NMR (400 MHz, $CDCl_3$) δ 7.12 (d, J=8.5 Hz, 2H), 6.85 (d, J=8.7 Hz, 2H), 5.20 (s, 1H), 5.10 (s, 2H), 3.78 (s, 3H), 3.35 (s, 2H), 1.93-1.81 (m, 1H), 0.96-0.82 (m, 2H), 0.75-0.59 (m, 2H). $^{13}$C NMR (101 MHz, $CDCl_3$) δ 159.0, 154.0, 145.0, 128.9, 128.1, 114.2, 87.4, 55.2, 50.9, 9.5, 7.7. Mp: 113-114° C. LC/MS (m/z): 245.21 [M+H$^+$]; UPLC $t_R$ 1.19 min.

3-cyclopentyl-1-(4-methoxybenzyl)-1H-pyrazol-5-amine (10k)

3-cyclopentylacrylonitrile was synthesized using General Procedure A from cyclopentanecarboxaldehyde (0.50 mL, 4.7 mmol) to afford 390 mg (68% yield) of a 1:1.4 mixture of E:Z isomers as a colorless oil after purification via automated flash chromatography (1% to 5% ethyl acetate in hexanes). 3-cyclopentylacrylonitrile (387 mg, 3.19 mmol) was subjected to General Procedure C3 with p-anisaldehyde (0.381 mL, 3.14 mmol) to afford 68.7 mg of 10k (8.2% yield) after purification via automated flash chromatography (3% to 15% ethyl acetate in $CH_2Cl_2$). $^1$H NMR (400 MHz, $CDCl_3$) δ 7.10 (d, J=8.5 Hz, 2H), 6.85 (d, J=8.7 Hz, 2H), 5.39 (s, 1H), 5.09 (s, 2H), 3.77 (s, 3H), 3.31 (s, 2H), 3.06-2.89 (m, 1H), 2.09-1.94 (m, 2H), 1.83-1.53 (m, 6H). $^{13}$C NMR (101 MHz, $CDCl_3$) δ 156.4, 144.9, 129.1, 128.2, 114.3, 88.9, 55.3, 51.0, 39.6, 33.5, 25.5. LC/MS (m/z): 272.426 [M+H$^+$]; UPLC $t_R$ 1.08 min.

3-(furan-3-yl)-1-(4-methoxybenzyl)-1H-pyrazol-5-amine (10l)

To a solution of potassium tert-butoxide (2 M in THF, 1.04 equiv) at 0° C. was added diethyl cyanomethylphosphonate (1.1 equiv) dropwise. After stirring at 0° C. for 1 h, 3-furancarboxaldehyde (0.50 mL, 5.8 mmol, 1 equiv) was added dropwise and the reaction was allowed to warm to room temperature overnight. The reaction mixture was poured into saturated $NH_4Cl$ (aq.) and diluted with ethyl acetate. The layers were separated and the aqueous layer was extracted three times with ethyl acetate. The combined organic layers were washed with brine and dried with anhydrous $Na_2SO_4$. The salts were removed via gravity filtration and volatile materials were condensed in vacuo. The crude mixture was purified via automated flash chromatography (4% to 12% ethyl acetate in $CH_2Cl_2$) to afford 3-(furan-3-yl)acrylonitrile 600 mg (88% yield) as an oil in a 3.3:1 mixture of E:Z isomers. 3-(furan-3-yl)acrylonitrile was subjected to General Procedure $C_3$ using p-anisaldehyde (0.605 mL, 4.98 mmol) to afford 292 mg of 10l (22% yield) as a beige solid after purification via automated flash chromatography (3% to 15% ethyl acetate in $CH_2Cl_2$). $^1$H NMR (400 MHz, $CDCl_3$) δ 7.80 (s, 1H), 7.44 (t, J=1.7 Hz, 1H), 7.18 (d, J=8.1 Hz, 2H), 6.87 (d, J=8.5 Hz, 2H), 6.76 (s, 1H), 5.69 (s, 1H), 5.23 (s, 1H), 3.79 (s, 3H), 3.47 (s, 2H). $^{13}$C NMR (101 MHz, $CDCl_3$) δ 161.1, 159.2, 145.3, 143.1, 139.0, 130.1, 128.5, 128.1, 120.3, 114.3, 108.8, 89.3, 55.3, 51.3. Mp: 140-142° C. LC/MS (m/z): 270.176 [M+H$^+$]; UPLC $t_R$ 1.45 min.

3-methyl-1-(4-methylbenzyl)-1H-pyrazol-5-amine (10m)

Synthesized using General Procedure C3 from crotononitrile (0.70 mL, 8.6 mmol) and p-tolualdehyde (1.0 mL, 8.5 mmol) to afford 610 mg of 10m (36% yield) as a yellow solid after purification via automated flash chromatography (5% to 20% ethyl acetate in $CH_2Cl_2$). $^1$H NMR (400 MHz, $CDCl_3$) δ 7.13 (d, J=7.9 Hz, 2H), 7.06 (d, J=7.8 Hz, 2H), 5.37 (s, 1H), 5.11 (s, 2H), 3.29 (s, 2H), 2.32 (s, 3H), 2.19 (s, 3H). $^{13}$C NMR (101 MHz, $CDCl_3$) δ 147.4, 145.6, 137.1, 134.0, 129.4, 126.7, 90.9, 50.8, 21.1, 13.9. Mp: 102-104° C. LC/MS (m/z): 202.158 [M+H$^+$]; UPLC $t_R$ 1.13 min.

3-methyl-1-(2-methylbenzyl)-1H-pyrazol-5-amine (10n)

Synthesized using General Procedure C1 from (2-methylbenzyl)hydrazine hydrochloride (180 mg, 1.33 mmol) to afford 125 mg of 10n (47% yield) as a white solid after purification via automated flash chromatography (5% to 20% ethyl acetate in $CH_2Cl_2$). $^1$H NMR (400 MHz, $CDCl_3$) δ 7.22-7.08 (m, 3H), 6.74 (d, J=7.3 Hz, 1H), 5.41 (s, 1H), 5.13 (s, 2H), 3.36-3.18 (m, 2H), 2.33 (s, 3H), 2.20 (s, 3H). $^{13}$C NMR (101 MHz, $CDCl_3$) δ 147.6, 145.6, 135.4, 135.0, 130.4, 127.5, 126.5, 126.1, 91.1, 74.1, 49.4, 19.1, 14.0. Mp: 84-87° C. LC/MS (m/z): 202.202 [M+H$^+$]; UPLC $t_R$ 1.10 min.

1-(2-chlorobenzyl)-3-methyl-1H-pyrazol-5-amine (10o)

Synthesized using General Procedure C1 from (2-chlorobenzyl)hydrazine dihydrochloride (300 mg, 1.31 mmol) to afford 245 mg of 10o (85% yield) as a white solid after purification via automated flash chromatography (3% to 15% ethyl acetate in $CH_2Cl_2$). $^1$H NMR (400 MHz, $CDCl_3$) δ 7.43-7.33 (m, 1H), 7.24-7.15 (m, 2H), 6.85-6.72 (m, 1H), 5.43 (s, 1H), 5.23 (s, 2H), 3.42 (s, 2H), 2.20 (s, 3H). $^{13}$C NMR (101 MHz, $CDCl_3$) δ 148.2, 145.6, 134.7, 131.9, 129.3, 128.7, 127.9, 127.3, 91.1, 48.3, 14.0. Mp: 97-99° C. LC/MS (m/z): 222.14 [M+H$^+$]; UPLC $t_R$ 1.12 min.

1-methyl-3-phenyl-1H-pyrazol-5-amine (10p)

Synthesized using General Procedure C5 from benzoylacetonitrile (250 mg, 1.72 mmol) to afford 221 mg of 10p (74% yield) as a white solid after purification via automated flash chromatography (25% to 40% ethyl acetate in $CH_2Cl_2$). $^1$H NMR (400 MHz, $CDCl_3$) δ 7.78-7.67 (m, 2H), 7.36 (td, J=7.2, 6.4, 1.3 Hz, 2H), 7.31-7.21 (m, 1H), 5.83 (s, 1H), 3.68 (s, 3H), 3.56 (s, 2H). $^{13}$C NMR (101 MHz, $CDCl_3$) δ 149.7, 145.6, 133.8, 128.5, 127.5, 125.3, 88.5, 34.4. Mp: 127-128° C. LC/MS (m/z): 174.103 [M+H$^+$]; UPLC $t_R$ 1.14 min.

1-(tert-butyl)-3-phenyl-1H-pyrazol-5-amine (10q)

Synthesized using General Procedure C4 from benzoylacetonitrile (250 mg, 1.72 mmol) and tert-butylhydrazine hydrochloride (429 mg, 3.44 mmol) to afford 278 mg of 10q (85% yield) as a yellow solid after purification via automated flash chromatography (7% to 20% ethyl acetate in hexanes). $^1$H NMR (400 MHz, $(CD_3)_2SO$) δ 7.62 (d, J=7.5 Hz, 2H), 7.38-7.27 (m, 2H), 7.26-7.13 (m, 1H), 5.76 (d, J=1.6 Hz, 1H), 4.95 (s, 2H), 1.55 (s, 9H). $^{13}$C NMR (101 MHz, $CDCl_3$) δ 147.5, 145.6, 134.4, 128.5, 127.1, 125.3, 91.3, 58.8, 29.4. Mp: 103-104° C. LC/MS (m/z): 217.2 [M+H$^+$]; UPLC $t_R$ 1.63 min.

1-cyclohexyl-3-phenyl-1H-pyrazol-5-amine (10r)

Synthesized using General Procedure C4 from benzoylacetonitrile (250 mg, 1.72 mmol) and cyclohexylhydrazine hydrochloride (519 mg, 3.44 mmol) to afford 326 mg of 10r (79% yield) as a yellow solid after purification via automated flash chromatography (7% to 20% ethyl acetate in hexanes). $^1$H NMR (400 MHz, $CDCl_3$) δ 7.77 (d, J=7.6 Hz, 2H), 7.36 (t, J=7.5 Hz, 2H), 7.30-7.25 (m, 1H), 5.88 (s, 1H), 3.99 (s, 1H), 3.62 (s, 1H), 2.17-1.84 (m, 7H), 1.72 (d, J=11.5 Hz, 1H), 1.48-1.11 (m, 3H). $^{13}$C NMR (101 MHz, $CDCl_3$) δ 149.3, 144.5, 134.5, 128.5, 127.2, 125.5, 88.9, 56.2, 32.3, 25.8, 25.3. Mp: 126-128° C. LC/MS (m/z): 243.225 [M+H$^+$]; UPLC $t_R$ 1.68 min.

1-isobutyl-3-phenyl-1H-pyrazol-5-amine (10s)

Synthesized using General Procedure C4 from benzoylacetonitrile (100 mg, 0.689 mmol) and isobutylhydrazine hydrochloride (172 mg, 1.38 mmol) to afford 102 mg of 10s (69% yield) after purification via automated flash chromatography (15% to 40% ethyl acetate in hexanes). $^1$H NMR (400 MHz, $CDCl_3$) δ 7.80-7.70 (m, 2H), 7.41-7.32 (m, 2H), 7.32-7.23 (m, 1H), 5.87 (s, 1H), 3.80 (d, J=7.5 Hz, 2H), 3.50 (s, 2H), 2.29 (dt, J=13.8, 6.9 Hz, 1H), 0.97 (d, J=6.7 Hz, 6H).

3-isopropyl-1-methyl-1H-pyrazol-5-amine (10t)

Synthesized using General Procedure C5 from 4-methyl-3-oxopentanenitrile (200 mg, 1.80 mmol) to afford 205 mg of 10s (82% yield) as a purple solid after purification via automated flash chromatography (2% to 6% methanol in $CH_2Cl_2$). $^1$H NMR (400 MHz, $CDCl_3$) δ 5.38 (s, 1H), 3.61 (s, 3H), 3.42 (s, 2H), 2.83 (p, J=7.0 Hz, 1H), 1.21 (d, J=7.1 Hz, 6H). $^{13}$C NMR (101 MHz, $CDCl_3$) δ 157.9, 144.7, 87.8, 33.9, 28.1, 22.9. Mp: 105-107° C. LC/MS (m/z): 140.358 [M+H$^+$].; UPLC $t_R$ 0.37 min.

3-cyclohexyl-1-methyl-1H-pyrazol-5-amine (10u)

Synthesized using General Procedure C5 from 3-cyclohexyl-3-oxopropanenitrile (253 mg, 1.67 mmol) to afford 161 mg of 10u (54% yield) as a clear crystalline solid after recrystallization of the crude material from an ethyl acetate in $CH_2Cl_2$ mixture. $^1$H NMR (400 MHz, $CD_3OD$) δ 5.27 (s, 1H), 3.51 (s, 3H), 2.47-2.32 (m, 1H), 1.93-1.66 (m, 5H), 1.43-1.12 (m, 5H). $^{13}$C NMR (101 MHz, CDCl$_3$) δ 157.1, 144.6, 88.2, 38.0, 33.9, 33.3, 26.4, 26.1. Mp: 170-171° C. LC/MS (m/z): 181.205 [M+H$^+$]; UPLC $t_R$ 1.16 min.

1-methyl-3-(o-tolyl)-1H-pyrazol-5-amine (10v)

Synthesized using General Procedure C5 from 3-(2-methylphenyl)-3-oxopropanenitrile (256 mg, 1.61 mmol) to afford 186 mg of 10v (62% yield) as a brown solid after purification via automated flash chromatography (15% to 40% ethyl acetate in CH$_2$Cl$_2$). $^1$H NMR (400 MHz, CDCl$_3$) δ 7.55-7.45 (m, 1H), 7.23-7.17 (m, 3H), 5.73 (s, 1H), 3.74 (s, 3H), 3.51 (s, 2H), 2.45 (s, 3H). $^{13}$C NMR (101 MHz, CDCl$_3$) δ 150.1, 144.7, 135.9, 133.8, 130.6, 129.0, 127.4, 125.7, 91.8, 34.2, 21.1. Mp: 69-72° C. LC/MS (m/z): 189.145 [M+H$^+$]; UPLC $t_R$ 1.14 min.

1-methyl-3-(m-tolyl)-1H-pyrazol-5-amine (10w)

Synthesized using General Procedure C5 from 3-(3-methylphenyl)-3-oxopropanenitrile (278 mg, 1.75 mmol) to afford 258 mg of 10w (79% yield) as a white solid after purification via automated flash chromatography (15% to 40% ethyl acetate in CH$_2$Cl$_2$). $^1$H NMR (400 MHz, CDCl$_3$) δ 7.58 (s, 1H), 7.49 (d, J=7.7 Hz, 1H), 7.31-7.20 (m, 1H), 7.14-7.03 (m, 1H), 5.86 (s, 1H), 3.73 (d, J=0.8 Hz, 3H), 3.53 (s, 2H), 2.37 (s, 3H). $^{13}$C NMR (101 MHz, CDCl$_3$) δ 149.8, 145.7, 138.1, 133.7, 128.4, 128.2, 125.9, 122.5, 88.5, 34.3, 21.5. Mp: 103-104° C. LC/MS (m/z): 188.396 [M+H$^+$]; UPLC $t_R$ 1.27 min.

3-(3-methoxyphenyl)-1-methyl-1H-pyrazol-5-amine (10x)

Synthesized using General Procedure C5 from 3-(3-methoxyphenyl)-3-oxopropanenitrile (306 mg, 1.75 mmol) to afford 279 mg of 10x (79% yield) as a yellow solid after purification via automated flash chromatography (15% to 45% ethyl acetate in CH$_2$Cl$_2$). $^1$H NMR (400 MHz, CDCl$_3$) δ 7.32-7.24 (m, 3H), 6.86-6.80 (m, 1H), 5.86 (s, 1H), 3.85 (s, 3H), 3.73 (s, 3H), 3.53 (s, 2H). $^{13}$C NMR (101 MHz, CDCl$_3$) δ 159.8, 149.5, 145.8, 135.3, 129.5, 117.9, 113.4, 110.3, 88.6, 74.1, 55.3, 34.3. Mp: 91-92° C. LC/MS (m/z): 205.158 [M+H$^+$]; UPLC $t_R$ 1.21 min.

1-methyl-3-(3-(trifluoromethyl)phenyl)-1H-pyrazol-5-amine (10y)

Synthesized using General Procedure C5 from 3-(trifluoromethyl)benzoylacetonitrile (373 mg, 1.75 mmol) to afford 334 mg of 10y (79% yield) as a white/beige solid after purification via automated flash chromatography (15% to 40% ethyl acetate in CH$_2$Cl$_2$). $^1$H NMR (400 MHz, CDCl$_3$) δ 7.97 (d, J=2.2 Hz, 1H), 7.89 (d, J=7.5 Hz, 1H), 7.48 (dt, J=15.3, 7.7 Hz, 2H), 5.90 (s, 1H), 3.74 (s, 3H), 3.57 (s, 2H). $^{13}$C NMR (101 MHz, CDCl$_3$) δ 148.2, 146.0, 134.7, 130.8 (q, $^2J_{C\text{-}F}$=31.9 Hz), 129.0, 128.4, 128.4, 124.3 (q, $^1J_{C\text{-}F}$=272.4 Hz), 123.9 (q, $^3J_{C\text{-}F}$=4.1 Hz), 121.9 (q, $^3J_{C\text{-}F}$=4.1 Hz), 88.4, 74.1, 34.3. $^{19}$F NMR (376 MHz, CDCl$_3$) δ −62.7. Mp: 87-88° C. LC/MS (m/z): 243.137 [M+H$^+$]; UPLC $t_R$ 1.60 min.

1-methyl-3-(p-tolyl)-1H-pyrazol-5-amine (10z)

Synthesized using General Procedure C5 with 3-(4-methylphenyl)-3-oxopropanenitrile (278 mg, 1.75 mmol) to afford 238 mg of 10z (73% yield) as a white solid after purification via automated flash chromatography (15% to 40% ethyl acetate in CH$_2$Cl$_2$). $^1$H NMR (400 MHz, CDCl$_3$) δ 7.61 (d, J=8.2 Hz, 2H), 7.22-7.09 (m, 2H), 5.84 (s, 1H), 3.72 (s, 3H), 3.52 (s, 2H), 2.35 (s, 3H). Mp: 139-140° C. LC/MS (m/z): 188.396 [M+H$^+$]; UPLC $t_R$ 1.25 min.

3-(4-methoxyphenyl)-1-methyl-1H-pyrazol-5-amine (10aa)

Synthesized using General Procedure C5 with 3-(4-methoxyphenyl)-3-oxopropanenitrile (306 mg, 1.75 mmol) to afford 238 mg of 10aa (67% yield) as an off-white/brown crystalline solid after purification via automated flash chromatography (15% to 45% ethyl acetate in CH$_2$Cl$_2$). $^1$H NMR (400 MHz, (CD$_3$)$_2$SO) δ 7.60-7.47 (m, 2H), 6.91-6.80 (m, 2H), 5.57 (s, 1H), 5.18 (s, 2H), 3.73 (s, 3H), 3.51 (s, 3H). $^{13}$C NMR (101 MHz, CDCl$_3$) δ 159.1, 149.6, 145.5, 126.7, 126.5, 113.9, 88.1, 55.3, 34.3. Mp: 139-142° C. LC/MS (m/z): 204.364 [M+H$^+$]; UPLC $t_R$ 1.15 min.

1-methyl-3-(4-(trifluoromethyl)phenyl)-1H-pyrazol-5-amine (10ab)

Synthesized using General Procedure C5 from 4-(trifluoromethyl)benzoylacetonitrile (373 mg, 1.75 mmol) to afford 326 mg of 10ab (77% yield) as a white solid after purification via automated flash chromatography (15% to 40% ethyl acetate in CH$_2$Cl$_2$). $^1$H NMR (400 MHz, CD$_3$OD) δ 7.84 (d, J=8.1 Hz, 2H), 7.64 (d, J=8.1 Hz, 2H), 5.89 (s, 1H), 3.67 (s, 3H). $^{13}$C NMR (101 MHz, CD$_3$OD) δ 149.8, 149.7, 138.8, 130.1 (q, $^2J_{C\text{-}F}$=32.2 Hz), 126.6, 125.8 (q, $^1J_{C\text{-}F}$=271.1 Hz), 126.4 (q, $^3J_{C\text{-}F}$=3.9 Hz), 88.5, 34.4. $^{19}$F NMR (376 MHz, CD$_3$OD) δ −64.0. Mp: 170-172° C. LC/MS (m/z): 243.137 [M+H$^+$]; UPLC $t_R$ 1.61 min.

3-(4-(tert-butyl)phenyl)-1-methyl-1H-pyrazol-5-amine (10ac)

Synthesized using General Procedure C5 from 3-(4-tert-butylphenyl)-3-oxopropanenitrile (253 mg, 1.26 mmol) to afford 222 mg of 10ac (77% yield) as a white solid after purification via automated flash chromatography (15% to 40% ethyl acetate in CH$_2$Cl$_2$). $^1$H NMR (400 MHz, CDCl$_3$) δ 7.64 (d, J=8.5 Hz, 2H), 7.38 (d, J=8.5 Hz, 2H), 5.85 (s, 1H), 3.72 (s, 3H), 1.33 (s, 9H). $^{13}$C NMR (101 MHz, CDCl$_3$) δ 150.4, 149.7, 145.5, 131.1, 125.4, 125.0, 88.4, 74.1, 34.6, 34.3, 31.4. Mp: 143-145° C. LC/MS (m/z): 231.183 [M+H$^+$]; UPLC $t_R$ 1.59 min.

1-methyl-3-(4-(trifluoromethoxy)phenyl)-1H-pyrazol-5-amine (10ad)

Synthesized using General Procedure C5 from 4-(trifluoromethoxy)benzoyl acetonitrile (400 mg, 1.75 mmol) to afford 362 mg of 10ad (81% yield) as a purple solid after purification via automated flash chromatography (15% to 40% ethyl acetate in CH$_2$Cl$_2$). $^1$H NMR (400 MHz, CDCl$_3$) δ 7.73 (d, J=8.7 Hz, 2H), 7.20 (d, J=7.8 Hz, 2H), 5.85 (s, 1H), 3.73 (s, 3H), 3.55 (s, 2H). $^{13}$C NMR (101 MHz, CDCl$_3$) δ 148.4, 146.0, 132.7, 126.5, 120.5 (q, $^1J_{C\text{-}F}$=256.8 Hz) 121.0, 88.3, 34.2. $^{19}$F NMR (376 MHz, CDCl$_3$) δ −57.8. Mp: 97-99° C. LC/MS (m/z): 259.105 [M+H$^+$]; UPLC $t_R$ 1.62 min.

2-Bromo-4,6-bis(methoxymethoxy)benzoic acid (12)

To a suspension of 2-bromo-4,6-dimethoxybenzaldehyde (3.0 g, 12 mmol) in CH$_2$Cl$_2$ (40 mL) was added a freshly-prepared solution of boron tribromide (3.5 mL, 37 mmol) in CH$_2$Cl$_2$ (10 mL) via cannula over 15 minutes. The reaction was warmed to room temperature and stirred overnight. The reaction mixture was poured into 200 mL ice water and the resulting mixture was extracted four times with ethyl acetate. The combined organic layers were washed with brine and dried with anhydrous Na$_2$SO$_4$. The salts were removed via gravity filtration and volatile materials were condensed in vacuo. The crude mixture was purified via automated flash chromatography (5% to 20% acetone in hexanes) to afford 1.8 g of 2-bromo-4,6-dihydroxybenzaldehyde as a white solid (81% yield). $^1$H NMR (400 MHz, (CD$_3$)$_2$SO) δ 12.18 (s, 1H), 11.33 (s, 1H), 9.96 (s, 1H), 6.69 (d, J=2.2 Hz, 1H), 6.29 (d, J=2.2 Hz, 1H). $^{13}$C NMR (101 MHz, (CD$_3$)$_2$SO) δ 194.5, 165.6, 165.4, 128.2, 113.9, 111.5, 102.3.

To a solution of 2-bromo-4,6-dihydroxybenzaldehyde (1.5 g, 6.9 mmol) and N,N-diisopropylethylamine (4.8 mL, 28 mmol) in DMF (20 mL) at room temperature was chloromethyl methyl ether (2.1 mL, 28 mmol) dropwise. The reaction was stirred at room temperature overnight. The reaction mixture was poured into water and the resulting mixture was extracted four times with Et$_2$O. The combined organic layers were washed twice with water and once with brine and dried with anhydrous Na$_2$SO$_4$. The salts were removed via gravity filtration and volatile materials were condensed in vacuo. The crude mixture was purified via automated flash chromatography (5% to 25% ethyl acetate in hexanes) to afford 2.1 g of 2-bromo-4,6-bis(methoxymethoxy)benzaldehyde as a white solid (93% yield). $^1$H NMR (400 MHz, CDCl$_3$) δ 10.34 (s, 1H), 7.01 (d, J=2.3 Hz, 1H), 6.83 (d, J=2.2 Hz, 1H), 5.26 (s, 2H), 5.20 (s, 2H), 3.51 (s, 3H), 3.48 (s, 3H). $^{13}$C NMR (101 MHz, CDCl$_3$) δ 189.1, 161.9, 161.2, 126.3, 118.3, 115.3, 102.9, 95.0, 94.3, 56.7, 56.5. Mp: 60-64° C.

To a solution of 2-bromo-4,6-bis(methoxymethoxy)benzaldehyde (350 mg, 1.15 mmol) in $^t$BuOH (3.6 mL) and THF (1.3 mL) at room temperature was added a solution of sodium chlorite (80%, 260 mg, 2.29 mmol) and sodium phosphate monobasic monohydrate (791 mg, 5.74 mmol) in water (1.9 mL) dropwise. To the yellow solution was added 2-methyl-2-butene (90%, 1.08 mL, 9.18 mmol). After 25 minutes, the orange solution became faint yellow/colorless and was diluted with ethyl acetate. The layers were separated, and the organic layer was washed three times with saturated NH$_4$Cl (aq.). The organic layer was dried with anhydrous Na$_2$SO$_4$. The salts were removed via gravity filtration and volatile materials were condensed in vacuo. The crude carboxylic acid 12 (364 mg, 99% crude yield) was used in the next step without further purification.

(2-bromo-4,6-bis(methoxymethoxy)phenyl)(isoindolin-2-yl)methanone (13)

To a suspension of benzoic acid 12 (320 mg, 0.997 mmol) and isoindoline hydrochloride (156 mg, 1.49 mmol) in THF (2.9 mL) and CH$_2$Cl$_2$ (2.9 mL) at room temperature was added trimethylamine (0.420 mL, 2.99 mmol) followed by HATU (451 mg, 1.20 mmol). After stirring the suspension was stirred at room temperature, the reaction mixture was diluted with CH$_2$Cl$_2$. The resulting mixture was washed with saturated NaHCO$_3$ (aq.), brine and dried with anhydrous Na$_2$SO$_4$. The salts were removed via gravity filtration and volatile materials were condensed in vacuo. The crude mixture was purified via automated flash chromatography (20% to 50% ethyl acetate in hexanes) to afford 266 mg of 13 as a white solid (63% yield). $^1$H NMR (400 MHz, CDCl$_3$) δ 7.39-7.27 (m, 3H), 7.19-7.14 (m, 1H), 6.99 (d, J=2.1 Hz, 1H), 6.85 (d, J=2.1 Hz, 1H), 5.21-5.10 (m, 4H), 5.07-4.94 (m, 2H), 4.68-4.48 (m, 2H), 3.49 (s, 3H), 3.42 (s, 3H). $^{13}$C NMR (101 MHz, CDCl$_3$) δ 165.6, 158.8, 154.8, 136.3, 136.2, 127.7, 127.5, 123.1, 123.0, 122.5, 119.8, 113.3, 103.1, 94.9, 94.4, 56.4, 56.2, 53.1, 51.7. Mp: 102-104° C. LC/MS (m/z): 422.128 and 424.133 [M+H$^+$]; UPLC t$_R$ 1.97 min.

Isoindolin-2-yl(2-((1-(4-methoxybenzyl)-3-methyl-1H-pyrazol-5-yl)amino)-4,6-bis(methoxymethoxy)phenyl)methanone (14a)

Synthesized using General Procedure D1 from 13 (45 mg, 110 µmol) and 10a (25 mg, 170 µmol). Following silica gel flash chromatography (12% to 40% acetone in hexanes), TMT (18 mg) was added to the isolated residue; the mixture was suspended in toluene (3 mL) and stirred overnight. The suspension was filtered through a plug of Celite® and the filtrate was concentrated using a rotary evaporator to afford 52 mg of 14a (87% yield). $^1$H NMR (400 MHz, CDCl$_3$) δ 7.39-7.24 (m, 3H), 7.16 (d, J=7.1 Hz, 1H), 7.06 (d, J=8.6 Hz, 2H), 6.64 (d, J=8.7 Hz, 2H), 6.44-6.35 (m, 2H), 6.22 (d, J=2.1 Hz, 1H), 5.85 (s, 1H), 5.15 (q, J=6.7 Hz, 2H), 5.07 (d, J=1.3 Hz, 2H), 5.03 (s, 2H), 4.99-4.41 (m, 4H), 3.66 (s, 3H), 3.45 (s, 2H), 3.44 (s, 3H), 2.24 (s, 3H). $^{13}$C NMR (101 MHz, CDCl$_3$) δ 166.8, 159.7, 158.9, 155.3, 147.5, 143.6, 139.3, 136.5, 136.1, 128.6, 128.6, 128.6, 127.7, 127.6, 122.9, 122.5, 113.8, 107.7, 98.5, 96.4, 95.3, 95.0, 94.2, 56.5, 56.2, 55.1, 52.9, 52.0, 51.2, 14.1. LC/MS (m/z): 559.299 [M+H$^+$]; UPLC t$_R$ 1.66 min.

Isoindolin-2-yl(2-((1-(4-methoxybenzyl)-3-phenyl-1H-pyrazol-5-yl)amino)-4,6-bis(methoxymethoxy)phenyl)methanone (14b)

Synthesized using General Procedure D1 from 13 (40 mg, 95 µmol) and 10b (25 mg, 170 µmol). Following silica gel flash chromatography (5% to 30% acetone in hexanes), TMT (18 mg) was added to the isolated residue; the mixture was suspended in toluene (3 mL) and stirred overnight. The suspension was filtered through a plug of Celite® and the filtrate was concentrated using a rotary evaporator to afford 52.6 mg of 14b (89% yield). $^1$H NMR (400 MHz, CDCl$_3$) δ 7.83-7.76 (m, 2H), 7.43-7.23 (m, 5H), 7.18 (d, J=7.2 Hz, 1H), 7.16-7.09 (m, 2H), 6.70-6.61 (m, 2H), 6.48 (s, 1H), 6.42 (d, J=2.1 Hz, 1H), 6.39 (s, 1H), 6.29 (d, J=2.1 Hz, 1H), 5.16 (d, J=7.2 Hz, 4H), 5.06 (s, 2H), 5.01-4.49 (m, 4H), 3.67 (s, 3H), 3.45 (s, 3H), 3.45 (s, 3H). $^{13}$C NMR (101 MHz, CDCl$_3$) δ 166.8, 159.8, 159.0, 155.3, 150.0, 143.5, 140.0, 136.5, 136.1, 133.7, 128.7, 128.5, 128.3, 127.7, 127.6, 127.5, 125.3, 122.9, 122.5, 113.8, 107.8, 96.5, 96.3, 95.3, 95.2, 94.2, 56.5, 56.2, 55.1, 52.9, 52.0, 51.8. LC/MS (m/z): 621.311 [M+H$^+$]; UPLC t$_R$ 2.03 min.

Isoindolin-2-yl(2-((1-(4-methoxybenzyl)-1H-pyrazol-5-yl)amino)-4,6-bis(methoxymethoxy)phenyl)methanone (14c)

Synthesized using General Procedure D2 from 13 (45 mg, 110 µmol) and 1-[(4-methoxyphenyl)methyl]-1H-pyrazol-5-amine (24 mg, 170 µmol). Following silica gel flash chromatography (10% to 45% ethyl acetate in hexanes), TMT (22 mg) was added to the isolated residue; the mixture was suspended in toluene (3 mL) and stirred overnight. The suspension was filtered through a plug of Celite® and the filtrate was concentrated using a rotary evaporator to afford 66 mg of 14c (108% yield). $^1$H NMR (400 MHz, CDCl$_3$) δ 7.31 (ddd, J=16.1, 7.2, 2.0 Hz, 3H), 7.17 (d, J=7.3 Hz, 1H), 7.09 (d, J=8.7 Hz, 2H), 6.66 (d, J=8.7 Hz, 2H), 6.45 (s, 1H), 6.40 (d, J=2.2 Hz, 1H), 6.19 (d, J=2.1 Hz, 1H), 6.05 (d, J=2.0 Hz, 1H), 5.16 (dd, J=9.7, 5.0 Hz, 2H), 5.11 (s, 2H), 5.07-5.01 (m, 2H), 4.99-4.79 (m, 3H), 4.56 (d, J=14.6 Hz, 1H), 3.68 (s, 3H), 3.48-3.39 (m, 6H). $^{13}$C NMR (101 MHz, CDCl$_3$) δ 166.9, 159.8, 159.0, 155.4, 143.8, 138.9, 138.8, 136.6, 136.2, 128.9, 128.4, 128.3, 127.7, 127.6, 123.0, 122.5, 114.3, 113.9, 107.7, 99.2, 96.2, 95.3, 95.3, 94.3, 56.5, 56.2, 55.1, 53.0, 52.1, 51.6. LC/MS (m/z): 545.185 [M+H$^+$]; UPLC t$_R$ 1.67 min.

Isoindolin-2-yl(2-((1-(4-methoxybenzyl)-4-methyl-1H-pyrazol-5-yl)amino)-4,6-bis(methoxymethoxy)phenyl)methanone (14d)

Synthesized using General Procedure D2 from 13 45 mg, 110 µmol) and 10c (25 mg, 120 µmol). Following silica gel flash chromatography (10% to 40% acetone in hexanes), TMT (17 mg) was added to the isolated residue; the mixture was suspended in toluene (3 mL) and stirred overnight. The suspension was filtered through a plug of Celite® and the filtrate was concentrated using a rotary evaporator to afford 49 mg of 14d (82% yield). $^1$H NMR (400 MHz, CDCl$_3$) δ 7.39-7.28 (m, 4H), 7.20 (d, J=7.2 Hz, 1H), 7.07-7.01 (m, 2H), 6.66-6.54 (m, 2H), 6.36 (d, J=2.1 Hz, 1H), 6.09 (s, 1H), 5.71 (d, J=2.1 Hz, 1H), 5.16 (s, 2H), 5.10-4.81 (m, 7H), 4.61 (d, J=14.7 Hz, 1H), 3.68 (s, 3H), 3.46 (s, 3H), 3.42 (s, 3H), 1.86 (s, 3H). $^{13}$C NMR (101 MHz, CDCl$_3$) δ 167.0, 159.9, 158.9, 155.4, 144.6, 139.2, 136.6, 136.3, 135.5, 128.9, 128.9, 127.8, 127.7, 123.1, 122.6, 113.8, 111.5, 107.1, 95.5, 95.3, 94.5, 94.2, 56.6, 56.2, 55.1, 53.1, 52.1, 51.8, 8.3. LC/MS (m/z): 559.166 [M+H$^+$]; UPLC t$_R$ 1.81 min.

Isoindolin-2-yl(2-((4-isopropyl-1-(4-methoxybenzyl)-1H-pyrazol-5-yl)amino)-4,6-bis(methoxymethoxy)phenyl)methanone (14e)

Synthesized using General Procedure D2 from 13 (45 mg, 110 µmol) and 10d (29 mg, 120 µmol). Following silica gel flash chromatography (10% to 30% acetone in hexanes), TMT (15 mg) was added to the isolated residue; the mixture was suspended in toluene (3 mL) and stirred overnight. The suspension was filtered through a plug of Celite® and the filtrate was concentrated using a rotary evaporator to afford 54 mg of 14e (86% yield). $^1$H NMR (400 MHz, CDCl$_3$) δ 7.41 (s, 1H), 7.39-7.27 (m, 3H), 7.21 (d, J=7.2 Hz, 1H), 7.02 (d, J=8.1 Hz, 2H), 6.58 (d, J=8.1 Hz, 2H), 6.35 (d, J=2.2 Hz, 1H), 6.13 (s, 1H), 5.65 (d, J=2.1 Hz, 1H), 5.17 (s, 2H), 5.11-4.83 (m, 7H), 4.62 (d, J=14.7 Hz, 1H), 3.66 (s, 3H), 3.46 (s, 3H), 3.39 (s, 3H), 2.67 (p, J=6.9 Hz, 1H), 1.13 (d, J=6.9 Hz, 3H), 1.08 (d, J=6.9 Hz, 3H). $^{13}$C NMR (101 MHz, CDCl$_3$) δ 167.1, 159.9, 158.9, 155.5, 145.4, 136.6, 136.6, 136.3, 133.9, 129.0, 128.9, 127.7, 127.7, 123.7, 123.1, 122.6, 113.7, 106.9, 95.5, 95.3, 94.5, 94.2, 56.6, 56.1, 55.1, 53.1, 52.1, 51.6, 23.7, 23.6, 23.3. LC/MS (m/z): 587.262 [M+H$^+$]; UPLC t$_R$ 1.96 min.

Isoindolin-2-yl(2-((1-(4-methoxybenzyl)-4-phenyl-1H-pyrazol-5-yl)amino)-4,6-bis(methoxymethoxy)phenyl)methanone (14f)

Synthesized using General Procedure D1 from 13 (40 mg, 95 µmol) and 10e (29 mg, 100 µmol) for 4 h. Following silica gel flash chromatography (5% to 35% acetone in hexanes), TMT (13 mg) was added to the isolated residue; the mixture was suspended in toluene (3 mL) and stirred overnight. The suspension was filtered through a plug of Celite® and the filtrate was concentrated using a rotary evaporator to afford 25 mg of 14f (43% yield). $^1$H NMR (400 MHz, CDCl$_3$) δ 7.79 (s, 1H), 7.41 (dt, J=6.2, 1.3 Hz, 2H), 7.38-7.26 (m, 3H), 7.22-7.02 (m, 6H), 6.65 (d, J=8.3 Hz, 2H), 6.47 (s, 1H), 6.36 (d, J=2.1 Hz, 1H), 5.72 (d, J=2.1 Hz, 1H), 5.24-4.94 (m, 6H), 4.93-4.81 (m, 3H), 4.58 (d, J=14.7 Hz, 1H), 3.68 (s, 3H), 3.47 (s, 3H), 3.34 (s, 3H). $^{13}$C NMR (101 MHz, CDCl$_3$) δ 167.0, 159.9, 159.1, 155.5, 144.3, 137.7, 136.6, 136.2, 134.3, 132.1, 129.2, 128.5, 128.4, 127.8, 127.7, 126.3, 126.1, 123.1, 122.5, 116.7, 113.9, 107.3, 95.8, 95.4, 94.8, 94.2, 56.6, 56.2, 55.2, 53.0, 52.2, 51.9. LC/MS (m/z): 621.311 [M+H$^+$]; UPLC t$_R$ 1.92 min (2-((4-Benzyl-1-(4-methoxybenzyl)-1H-pyrazol-5-yl)amino)-4,6-bis(methoxymethoxy)phenyl)(isoindolin-2-yl)methanone (14g)

Synthesized using General Procedure D1 from 13 (40 mg, 95 µmol) and 10f (31 mg, 100 µmol) for 4 h. Following silica gel flash chromatography (10% to 35% acetone in hexanes), TMT (17 mg) was added to the isolated residue; the mixture was suspended in toluene (3 mL) and stirred overnight. The suspension was filtered through a plug of Celite® and the filtrate was concentrated using a rotary evaporator to afford 45 mg of 14g (75% yield). $^1$H NMR (400 MHz, CDCl$_3$) δ 7.41-7.27 (m, 4H), 7.23-6.96 (m, 7H), 6.68-6.56 (m, 2H), 6.34 (d, J=2.1 Hz, 1H), 6.19 (s, 1H), 5.65 (d, J=2.1 Hz, 1H), 5.16 (d, J=2.4 Hz, 2H), 5.11-4.82 (m, 7H), 4.53 (d, J=14.7 Hz, 1H), 3.69 (s, 3H), 3.61 (d, J=3.5 Hz, 2H), 3.46 (s, 3H), 3.41 (s, 3H). $^{13}$C NMR (101 MHz, CDCl$_3$) δ 167.0, 159.8, 159.0, 155.4, 144.8, 140.2, 139.0, 136.6, 136.3, 135.4, 129.1, 128.7, 128.4, 128.2, 127.7, 127.6, 125.9, 123.0, 122.6, 115.6, 113.8, 106.9, 95.4, 95.3, 94.7, 94.1, 56.6, 56.2, 55.2, 53.0, 52.1, 51.8, 29.8. LC/MS (m/z): 635.292 [M+H$^+$]; UPLC t$_R$ 1.96 min.

(2-((3-(tert-Butyl)-1-(4-methoxybenzyl)-1H-pyrazol-5-yl)amino)-4,6-bis(methoxymethoxy)phenyl)(isoindolin-2-yl)methanone (14h)

Synthesized using General Procedure D1 from 13 (40 mg, 95 µmol) and 10i (27 mg, 100 µmol) for 4 h. Following silica gel flash chromatography (5% to 25% acetone in hexanes), TMT (18 mg) was added to the isolated residue; the mixture was suspended in toluene (3 mL) and stirred overnight. The suspension was filtered through a plug of Celite® and the filtrate was concentrated using a rotary evaporator to afford 45 mg of 14h (79% yield). $^1$H NMR (400 MHz, CDCl$_3$) δ 7.35-7.27 (m, 3H), 7.16 (d, J=7.2 Hz, 1H), 7.03 (d, J=8.5 Hz, 2H), 6.64 (d, J=8.6 Hz, 2H), 6.38 (d, J=2.1 Hz, 1H), 6.33-6.23 (m, 2H), 5.92 (s, 1H), 5.14 (q, J=6.5 Hz, 2H), 5.08 (s, 2H), 5.05 (s, 2H), 4.91 (d, J=14.8 Hz, 1H), 4.84 (s, 2H), 4.51 (d, J=14.6 Hz, 1H), 3.66 (s, 3H), 3.45 (s, 3H), 3.44 (s, 3H), 1.30 (s, 9H). $^{13}$C NMR (101 MHz, CDCl$_3$) δ 166.8, 160.8, 159.8, 158.8, 155.3, 143.7, 138.8, 136.6, 136.2, 128.9, 128.4, 127.7, 127.6, 123.0, 122.5, 113.8, 107.8, 96.5, 95.3, 95.2, 95.1, 94.4, 56.5, 56.2, 55.1, 53.0, 52.0, 51.4, 32.3, 30.5. LC/MS (m/z): 601.331 [M+H$^+$]; UPLC t$_R$ 2.04 min.

(2,4-Bis(methoxymethoxy)-6-((1-methyl-1H-pyrazol-5-yl)amino)phenyl)(isoindolin-2-yl)methanone (14i)

Synthesized using General Procedure D2 from 13 (45 mg, 110 µmol) and 1-methyl-1H-pyrazol-5-amine (11 mg, 120

μmol). Following silica gel flash chromatography (30% to 70% ethyl acetate in $CH_2Cl_2$), TMT (19 mg) was added to the isolated residue; the mixture was suspended in toluene (3 mL) and stirred overnight. The suspension was filtered through a plug of Celite® and the filtrate was concentrated using a rotary evaporator to afford 38 mg of 14i (82% yield). $^1$H NMR (400 MHz, $CDCl_3$) δ 7.43 (d, J=2.0 Hz, 1H), 7.38-7.27 (m, 3H), 7.19 (d, J=6.9 Hz, 1H), 6.64 (s, 1H), 6.43 (d, J=2.2 Hz, 1H), 6.08 (d, J=2.1 Hz, 1H), 6.01 (d, J=2.0 Hz, 1H), 5.21-5.10 (m, 3H), 5.08 (s, 2H), 5.05-4.84 (m, 2H), 4.63 (d, J=14.7 Hz, 1H), 3.68 (s, 3H), 3.45 (s, 3H), 3.45 (s, 3H). $^{13}$C NMR (101 MHz, $CDCl_3$) δ 167.1, 159.9, 155.5, 144.4, 139.3, 138.6, 136.6, 136.1, 127.8, 127.6, 123.1, 122.5, 107.6, 99.1, 96.2, 95.4, 95.2, 94.2, 56.6, 56.3, 53.1, 52.2, 35.0. LC/MS (m/z): 439.33 [M+H$^+$]; UPLC $t_R$ 1.48 min.

Isoindolin-2-yl(2-((1-(4-isopropylbenzyl)-1H-pyrazol-5-yl)amino)-4,6-bis(methoxymethoxy)phenyl)methanone (14j)

Synthesized using General Procedure D2 from 13 (40 mg, 95 μmol) and 1-([4-(propan-2-yl)phenyl]methyl)-1H-pyrazol-5-amine (22 mg, 100 μmol). Following silica gel flash chromatography (10% to 30% acetone in hexanes), TMT (15 mg) was added to the isolated residue; the mixture was suspended in toluene (3 mL) and stirred overnight. The suspension was filtered through a plug of Celite® and the filtrate was concentrated using a rotary evaporator to afford 42 mg of 14j (80% yield). H NMR (400 MHz, $CDCl_3$) δ 7.48 (d, J=2.0 Hz, 1H), 7.35-7.28 (m, 3H), 7.18 (d, J=7.3 Hz, 1H), 7.06 (d, J=8.1 Hz, 2H), 6.98 (d, J=8.2 Hz, 2H), 6.43 (s, 1H), 6.40 (d, J=2.1 Hz, 1H), 6.20 (d, J=2.1 Hz, 1H), 6.06 (d, J=2.0 Hz, 1H), 5.23-5.07 (m, 5H), 5.07-5.00 (m, 2H), 5.00-4.76 (m, 3H), 4.57 (d, J=14.7 Hz, 1H), 3.45 (s, 6H), 2.76 (p, J=6.9 Hz, 1H), 1.14 (d, J=6.9 Hz, 6H). $^{13}$C NMR (101 MHz, $CDCl_3$) δ 166.9, 159.8, 155.4, 148.2, 143.9, 139.0, 138.9, 136.6, 136.2, 133.6, 127.7, 127.6, 127.5, 127.5, 126.7, 123.0, 122.5, 107.7, 99.4, 96.2, 95.3, 95.2, 94.3, 56.6, 56.3, 53.0, 52.1, 51.9, 33.7, 23.9, 23.8. LC/MS (m/z): 557.27 [M+H$^+$]; UPLC $t_R$ 1.93 min

(2,4-Bis(methoxymethoxy)-6-((3-methyl-1-(4-methylbenzyl)-1H-pyrazol-5-yl)amino)phenyl)(isoindolin-2-yl)methanone (14k)

Synthesized using General Procedure D1 from 13 (45 mg, 110 μmol) and 10m (24 mg, 120 μmol) and heated for 3 h. Following silica gel flash chromatography (10% to 35% acetone in hexanes), TMT (15 mg) was added to the isolated residue; the mixture was suspended in toluene (3 mL) and stirred overnight. The suspension was filtered through a plug of Celite® and the filtrate was concentrated using a rotary evaporator to afford 40 mg of 14k (70% yield). $^1$H NMR (400 MHz, $CDCl_3$) δ 7.36-7.27 (m, 3H), 7.16 (d, J=7.2 Hz, 1H), 6.97 (d, J=7.8 Hz, 2H), 6.88 (d, J=7.8 Hz, 2H), 6.39 (d, J=2.1 Hz, 1H), 6.32 (s, 1H), 6.24 (d, J=2.1 Hz, 1H), 5.86 (s, 1H), 5.14 (q, J=6.5 Hz, 2H), 5.07 (d, J=1.3 Hz, 2H), 5.06 (s, 2H), 4.90 (d, J=14.7 Hz, 1H), 4.83 (s, 2H), 4.48 (d, J=14.6 Hz, 1H), 3.46 (s, 3H), 3.43 (s, 3H), 2.24 (s, 3H), 2.17 (s, 3H). $^{13}$C NMR (101 MHz, $CDCl_3$) δ 166.8, 159.8, 155.3, 147.6, 143.7, 139.4, 137.0, 136.6, 136.2, 133.6, 129.2, 127.7, 127.6, 127.0, 122.9, 122.5, 107.8, 98.6, 96.4, 95.3, 95.1, 94.3, 56.5, 56.3, 52.9, 52.0, 51.7, 21.0, 14.2. LC/MS (m/z): 543.332 [M+H$^+$]; UPLC $t_R$ 1.76 min.

(2-((1-(2-Chlorobenzyl)-3-methyl-1H-pyrazol-5-yl)amino)-4,6-bis(methoxymethoxy)phenyl)(isoindolin-2-yl)methanone (14l)

Inside a nitrogen glovebox were combined aryl bromide 13 (45 mg, 110 μmol), amine 10o (26 mg, 170 μmol), tris(dibenzylideneacetone)dipalladium (3.9 mg, 4.3 μmol), Xantphos (6.2 mg, 11 μmol), and sodium phenoxide (19 mg, 160 μmol). Dioxane (0.8 mL) was added to the mixture and the reaction vessel was capped and removed from the glovebox. The reaction vessel was heated at 60° C. for 90 min, 90° C. for 90 min, and then 120° C. for 2.5 h. After cooling to room temperature, the reaction was diluted with ethyl acetate. The resulting mixture was washed three times with saturated $Na_2CO_3$ (aq.), brine, then dried with anhydrous $Na_2SO_4$. The salts were removed via gravity filtration and volatile materials were condensed in vacuo. Following silica gel flash chromatography (10% to 30% acetone in hexanes), TMT (20 mg) was added to the isolated residue; the mixture was suspended in toluene (3 mL) and stirred overnight. The suspension was filtered through a plug of Celite® and the filtrate was concentrated using a rotary evaporator to afford 47 mg of 14l (78% yield). $^1$H NMR (400 MHz, $CDCl_3$) δ 7.34-7.27 (m, 3H), 7.16 (s, 1H), 7.09-6.93 (m, 3H), 6.72-6.62 (m, 1H), 6.39 (d, J=2.1 Hz, 1H), 6.37 (s, 1H), 6.20 (d, J=2.1 Hz, 1H), 5.93 (s, 1H), 5.28-5.01 (m, 6H), 4.86 (d, J=14.5 Hz, 1H), 4.77 (s, 2H), 4.38 (d, J=14.6 Hz, 1H), 3.46 (s, 3H), 3.42 (s, 3H), 2.26 (s, 3H). $^{13}$C NMR (101 MHz, $CDCl_3$) δ 166.8, 159.8, 155.4, 148.4, 143.8, 140.1, 136.6, 136.1, 134.6, 131.8, 129.1, 128.4, 127.7, 127.6, 127.5, 127.0, 122.9, 122.6, 107.9, 99.4, 96.5, 95.3, 95.2, 94.3, 56.5, 56.3, 52.9, 52.0, 49.1, 14.3. LC/MS (m/z): 563.224 [M+H$^+$]; UPLC $t_R$ 1.73 min.

(2,4-Bis(methoxymethoxy)-6-((3-methyl-1-(2-methylbenzyl)-1H-pyrazol-5-yl)amino)phenyl)(isoindolin-2-yl)methanone (14m)

Inside a nitrogen glovebox were combined aryl bromide 13 (45 mg, 110 μmol), amine 10n (28 mg, 140 μmol), $^t$BuXPhos Palladacycle Gen. 1 (7.3 mg, 11 μmol), $^t$BuXphos (4.5 mg, 11 μmol), sodium tert-butoxide (22 mg, 220 μmol). tert-Butanol (0.8 mL) was added to the mixture and the reaction vessel was capped and removed from the glovebox. After stirring at room temperature for 2.5 h, the reaction was quenched with saturated $NH_4Cl$ (aq.). The resulting mixture was extracted four times with ethyl acetate. The combined organic layers were washed with brine and dried with anhydrous $Na_2SO_4$. The salts were removed via gravity filtration and volatile materials were condensed in vacuo. Following silica gel flash chromatography (40% to 80% ethyl acetate in hexanes), TMT (21 mg) was added to the isolated residue; the mixture was suspended in toluene (1.5 mL) and stirred overnight. The suspension was filtered through a plug of Celite® and the filtrate was concentrated using a rotary evaporator to afford 25 mg of 14m (52% yield). $^1$H NMR (400 MHz, $CDCl_3$) δ 7.35-7.28 (m, 3H), 7.21-7.09 (m, 1H), 7.03-6.88 (m, 3H), 6.65 (d, J=7.6 Hz, 1H), 6.39 (d, J=2.1 Hz, 1H), 6.33-6.26 (m, 2H), 5.91 (s, 1H), 5.16-5.03 (m, 7H), 4.85 (d, J=14.7 Hz, 1H), 4.73 (d, J=9.2 Hz, 2H), 4.38 (d, J=14.7 Hz, 1H), 3.46 (s, 3H), 3.42 (s, 3H), 2.25 (s, 3H), 2.18 (s, 3H). $^{13}$C NMR (101 MHz, $CDCl_3$) δ 166.7, 159.7, 155.3, 147.8, 143.6, 140.1, 136.5, 136.2, 135.1, 134.8, 130.2, 127.7, 127.5, 127.2, 126.4, 126.2, 123.0, 122.5, 107.9, 98.3, 96.5, 95.3, 95.2, 94.3, 56.5, 56.3, 52.8, 51.9, 49.6, 19.0, 14.3. LC/MS (m/z): 543.288 [M+H$^+$]; UPLC $t_R$ 1.75 min.

(2,4-Bis(methoxymethoxy)-6-((1-methyl-3-phenyl-1H-pyrazol-5-yl)amino)phenyl)(isoindolin-2-yl)methanone (14n)

Synthesized using General Procedure D2 from 13 (60 mg, 140 μmol) and 10p (27 mg, 160 μmol) and purified via automated flash chromatography (30% to 80% ethyl acetate in CH$_2$Cl$_2$). To QuadraPure™ MPA resin (1.5 mmol/g loading, 68 mg) soaked in CH$_2$Cl$_2$ (1 mL) for 90 min was transferred the purified product using CH$_2$Cl$_2$ (3 mL) and shaken overnight. The suspension was filtered through a plug of Celite® and the filtrate was concentrated using a rotary evaporator to afford 65 mg of 14n (89% yield). $^1$H NMR (400 MHz, CDCl$_3$) δ 7.79-7.70 (m, 2H), 7.41-7.27 (m, 6H), 7.20 (d, J=7.1 Hz, 1H), 6.72 (s, 1H), 6.45 (d, J=2.1 Hz, 1H), 6.34 (s, 1H), 6.18 (d, J=2.1 Hz, 1H), 5.24-5.11 (m, 3H), 5.09 (s, 2H), 5.06-4.86 (m, 2H), 4.65 (d, J=14.7 Hz, 1H), 3.73 (s, 3H), 3.46 (d, J=0.8 Hz, 3H), 3.45 (s, 3H). $^{13}$C NMR (101 MHz, CDCl$_3$) δ 167.1, 160.0, 155.6, 150.0, 144.3, 140.5, 136.6, 136.2, 133.6, 128.6, 128.4, 127.8, 127.6, 127.6, 127.4, 125.2, 123.1, 122.5, 107.7, 96.5, 96.4, 95.4, 95.2, 94.3, 56.6, 56.3, 53.1, 52.3, 35.2. LC/MS (m/z): 516.34 [M+H$^+$]; UPLC $t_R$ 1.88 min.

(2-Bromo-4,6-bis(methoxymethoxy)phenyl)(5-((1-methylpiperidin-4-yl)amino)isoindolin-2-yl)methanone (15a)

Inside a glovebox under a nitrogen atmosphere were combined tert-butyl 5-bromoisoindoline-2-carboxylate (85 mg, 0.29 mmol), tris(dibenzylideneacetone)dipalladium (13 mg, 0.014 mmol), Johnphos (8.5 mg, 0.029 mmol) and sodium tert-butoxide (38 mg, 0.40 mmol) and suspended in toluene (4 mL). 4-Amino-1-methylpiperidine (39 mg mL, 0.34 mmol) was added to the mixture and the reaction vessel was sealed and removed from the glovebox. The reaction mixture was irradiated at 120° C. for 30 minutes in a microwave reactor. After cooling to room temperature, the reaction mixture was diluted with ethyl acetate, washed with brine and dried with anhydrous Na$_2$SO$_4$. The salts were removed via gravity filtration and volatile materials were condensed in vacuo. The crude mixture was purified via silica gel flash chromatography (95:5:1 CH$_2$Cl$_2$:methanol:concentrated NH$_4$OH (aq.)) to afford 47 mg of tert-butyl 5-((1-methylpiperidin-4-yl)amino)isoindoline-2-carboxylate (50% yield). H NMR (400 MHz, CDCl$_3$) 7.01 (dd, J=20.7, 8.1 Hz, 1H), 6.63-6.40 (m, 2H), 4.65-4.42 (m, 4H), 3.33-3.17 (m, 1H), 2.82 (d, J=11.3 Hz, 2H), 2.31 (s, 3H), 2.22-2.02 (m, 4H), 1.50 (s, 9H). $^{13}$C NMR (101 MHz, CDCl$_3$) δ 154.5, 154.4, 146.6, 146.6, 138.4, 138.0, 125.6, 125.3, 123.3, 123.0, 113.1, 106.6, 106.5, 79.2, 54.4, 52.3, 52.0, 51.6, 51.3, 46.1, 32.3, 28.4. LC/MS (m/z): 332.193 [M+H$^+$]; UPLC $t_R$ 1.19 min To a solution of tert-butyl 5-((1-methylpiperidin-4-yl)amino)isoindoline-2-carboxylate (47 mg, 0.14 mmol) from above in CH$_2$Cl$_2$ (0.28 mL) at room temperature was added HCl (4 M in dioxane, 0.45 mL, 1.8 mmol) and stirred overnight. The reaction was then triturated with ether. The suspension was filter and the resulting solid washed with ether to afford 29 mg of N-(1-methylpiperidin-4-yl)isoindolin-5-amine dihydrogenchloride as a viscous gum (66% based on crude mass).

Benzoic acid 12 (68 mg, 0.21 mmol), N-(1-methylpiperidin-4-yl)isoindolin-5-amine dihydrogenchloride salt (64 mg, 0.21 mmol) from above, trimethylamine (0.12 mL, 0.84 mmol) and HATU (95 mg, 0.25 mmol) were reacted using the same procedure for the synthesis of amide 13 to afford 57 mg of 15a (51% yield) after purification via automated flash chromatography (1% to 10% methanol in CH$_2$Cl$_2$). $^1$H NMR (400 MHz, CD$_3$OD) δ 7.15-6.87 (m, 3H), 6.71-6.38 (m, 2H), 5.32-5.13 (m, 4H), 4.89 (s, 3H), 4.86-4.74 (m, 2H), 4.45 (d, J=14.7 Hz, 2H), 3.48 (d, J=1.2 Hz, 2H), 3.42-3.38 (m, 3H), 3.35 (s, 1H), 3.02 (t, J=13.6 Hz, 2H), 2.44 (d, J=11.0 Hz, 4H), 2.17-1.97 (m, 2H), 1.69-1.42 (m, 2H). 13C NMR (101 MHz, CD$_3$OD) δ 166.7, 166.7, 159.3, 159.3, 155.0, 147.8, 147.6, 136.7, 136.5, 123.5, 123.4, 123.1, 122.9, 122.2, 122.1, 119.2, 113.9, 113.7, 112.9, 112.8, 106.4, 106.3, 102.8, 102.8, 94.8, 94.7, 94.3, 55.4, 55.2, 53.7, 53.3, 52.7, 51.6, 51.0, 44.1, 30.7. LC/MS (m/z): 534.114 and 536.099 [M+H$^+$]; UPLC $t_R$ 1.31 min.

(2-Bromo-4,6-bis(methoxymethoxy)phenyl)(5-(2-(dimethylamino)ethoxy)isoindolin-2-yl)methanone (15b)

A suspension of tert-butyl 5-hydroxyisoindoline-2-carboxylate (250 mg, 1.06 mmol), 2-chloro-N,N-dimethylethylamine hydrochloride (367 mg, 2.55 mmol), and cesium carbonate (1.73 g, 5.31 mmol) in MeCN (4 mL) was heated overnight at 90° C. The mixture was cooled to room temperature and diluted with 15% methanol in CH$_2$Cl$_2$. The resulting mixture was washed twice with water and once with brine and dried with anhydrous Na$_2$SO$_4$. The salts were removed via gravity filtration and volatile materials were condensed in vacuo. The crude mixture was purified via automated flash chromatography (5% to 10% methanol in CH$_2$Cl$_2$) to afford 165 mg of tert-butyl 5-(2-(dimethylamino)ethoxy)isoindoline-2-carboxylate (51% yield). H NMR (400 MHz, CDCl$_3$) δ 7.12 (dd, J=20.9, 8.3 Hz, 1H), 6.88-6.72 (m, 2H), 4.60 (t, J=15.2 Hz, 4H), 4.05 (td, J=5.7, 2.0 Hz, 2H), 2.74 (t, J=5.7 Hz, 2H), 2.35 (s, 6H), 1.51 (s, 9H). $^{13}$C NMR (101 MHz, CDCl$_3$) δ 158.4, 158.4, 154.3, 154.3, 138.5, 138.1, 129.2, 128.8, 123.2, 123.0, 114.3, 114.0, 108.3, 108.2, 79.4, 66.0, 58.1, 52.2, 52.0, 51.6, 51.2, 45.7, 28.4. LC/MS (m/z): 307.139 [M+H$^+$]; UPLC $t_R$ 1.18 min.

To a solution of tert-butyl 5-(2-(dimethylamino)ethoxy)isoindoline-2-carboxylate from above (135 mg, 0.441 mmol) in CH$_2$Cl$_2$ (0.88 mL) at room temperature was added HCl (4 M in dioxane, 1.4 mL, 5.6 mmol) and stirred overnight. The reaction was then triturated with ether. The suspension was filter and the resulting solid washed with ether to afford 103 mg 2-(Isoindolin-5-yloxy)-N,N-dimethylethane-1-amine dihydrochloride as a solid (84% based on crude mass).

Benzoic acid 12 (38 mg, 0.12 mmol), 2-(isoindolin-5-yloxy)-N,N-dimethylethane-1-amine dihydrochloride salt from above (33 mg, 0.12 mmol), trimethylamine (0.066 mL, 0.47 mmol) and HATU (54 mg, 0.14 mmol) were reacted using the same procedure for the synthesis of amide 13 to afford 60 mg of 15b (75% yield) after purification via automated flash chromatography (1% to 8% methanol in CH$_2$Cl$_2$). H NMR (400 MHz, CDCl$_3$) δ 7.14 (dd, J=75.4, 8.4 Hz, 1H), 6.98 (t, J=2.0 Hz, 1H), 6.94-6.66 (m, 3H), 5.25-5.05 (m, 4H), 4.92 (dd, J=7.9, 3.4 Hz, 2H), 4.50 (q, J=13.3 Hz, 2H), 4.09 (dt, J=20.4, 5.5 Hz, 2H), 3.57-3.45 (m, 3H), 3.41 (s, 3H), 3.18 (q, J=7.3 Hz, 4H), 2.87 (dt, J=16.3, 5.6 Hz, 2H), 2.46 (s, 3H), 2.42 (s, 3H), 1.34 (t, J=7.3 Hz, 4H). LC/MS (m/z): 509.062 and 511.047 [M+H$^+$]; UPLC $t_R$ 1.29 min.

(2-Bromo-4,6-bis(methoxymethoxy)phenyl)(5-(4-methylpiperazin-1-yl)isoindolin-2-yl)methanone (15c)

Procedure adapted from [66]. Inside a glovebox under a nitrogen atmosphere were combined tert-butyl 5-bromoisoindoline-2-carboxylate (300 mg, 1.01 mmol), tris(dibenzylideneacetone)dipalladium (46.1 mg, 0.0503 mmol), Xantphos (29.1 mg, 0.0503 mmol) and sodium tert-butoxide (145 mg, 1.51 mmol) and suspended in toluene (3 mL). 1-Methylpiperazine (0.134 mL, 1.21 mmol) was added to the mixture and the reaction vessel was sealed and removed from the glovebox. After heating at 100° C. overnight, the reaction mixture was cooled to room temperature and diluted with ethyl acetate. The organic mixture was washed with brine and dried with anhydrous Na$_2$SO$_4$. The salts were removed via gravity filtration and volatile materials were condensed in vacuo. The crude mixture was purified via automated flash chromatography (1% to 7% methanol in CH$_2$Cl$_2$) to afford 259 mg of tert-butyl 5-(4-methylpiperazin-1-yl)isoindoline-2-carboxylate (81% yield). $^1$H NMR (400 MHz, CDCl$_3$) δ 7.12 (dd, J=20.8, 8.3 Hz, 1H), 6.92-6.75 (m, 2H), 4.70-4.46 (m, 4H), 3.19 (d, J=5.1 Hz, 4H), 2.58 (t, J=5.0 Hz, 4H), 2.35 (s, 3H), 1.51 (s, 9H). $^{13}$C NMR (101 MHz, CDCl$_3$) δ 154.3, 154.3, 151.0, 138.1, 137.7, 128.2, 127.9, 122.9, 122.7, 115.8, 115.6, 110.0, 109.8, 79.2, 54.8, 52.3, 52.0, 51.6, 51.3, 49.4, 49.3, 45.9, 28.3. LC/MS (m/z): 318.167 [M+H$^+$]; UPLC $t_R$ 1.04 min.

To a solution of tert-butyl 5-(4-methylpiperazin-1-yl) isoindoline-2-carboxylate from above (259 mg, 0.816 mmol) in CH$_2$Cl$_2$ (1.6 mL) at room temperature was added HCl (4 M in dioxane, 2.59 mL, 10.4 mmol) and stirred overnight. The reaction was then triturated with ether. The suspension was filter and the resulting solid washed with ether to afford 262 mg of crude 5-(4-methylpiperazin-1-yl) isoindoline dihydrochloride salt (110% crude yield).

Benzoic acid 12 (133 mg, 0.374 mmol), 5-(4-methylpiperazin-1-yl)isoindoline dihydrochloride salt from above (106 mg, 0.365 mmol), trimethylamine (0.208 mL, 1.49 mmol) and HATU (169 mg, 0.448 mmol) were reacted using the same procedure for the synthesis of amide 13 to afford 132 mg of 15c (68% yield) after purification via automated flash chromatography (1% to 8% methanol in CH$_2$Cl$_2$). $^1$H NMR (400 MHz, CDCl$_3$) δ 7.23 (d, J=8.6 Hz, 1H), 7.04 (d, J=8.3 Hz, 1H), 6.98 (dd, J=2.1, 1.5 Hz, 1H), 6.96-6.82 (m, 3H), 5.30 (s, 1H), 5.23-5.07 (m, 4H), 4.93 (d, J=13.0 Hz, 2H), 4.61-4.39 (m, 2H), 3.49 (d, J=0.9 Hz, 3H), 3.41 (d, J=2.0 Hz, 3H), 3.27-3.12 (m, 5H), 2.64 (dt, J=9.5, 4.7 Hz, 4H), 2.40 (d, J=7.0 Hz, 3H), 1.39 (t, J=7.3 Hz, 2H). $^{13}$C NMR (101 MHz, CDCl$_3$) δ 165.7, 165.6, 158.8, 154.8, 151.3, 151.2, 137.2, 137.2, 127.1, 127.1, 123.5, 123.0, 122.7, 119.7, 116.5, 116.0, 113.2, 113.2, 110.4, 109.8, 103.1, 103.0, 94.9, 94.8, 94.4, 77.2, 56.4, 56.2, 54.8, 53.4, 52.7, 51.9, 51.2, 49.1, 49.1, 47.0, 47.0, 45.7, 8.7. LC/MS (m/z): 520.089 and 522.073 [M+H$^+$]; UPLC $t_R$ 1.25 min.

N-benzyl-2-bromo-4,6-bis(methoxymethoxy)-N-methylbenzamide (15d)

The product was synthesized using the same procedure for the synthesis of amide 13. The reaction with benzoic acid 12 (0.68 g, 2.1 mmol), N-benzylmethylamine (0.41 mL, 3.2 mmol), trimethylamine (0.59 mL, 4.2 mmol) and HATU (0.96 g, 2.5 mmol) to afford 0.55 g of 15d as a colorless oil (61% yield) after purification via automated flash chromatography (20% to 40% ethyl acetate in hexanes and 5% to 10% ethyl acetate in CH$_2$Cl$_2$). Isomer 1: $^1$H NMR (400 MHz, CDCl$_3$) δ 7.42 (d, J=7.5 Hz, 1H), 7.32 (dt, J=20.9, 8.2 Hz, 4H), 6.96 (d, J=2.1 Hz, 1H), 6.79 (d, J=2.1 Hz, 1H), 5.29-5.08 (m, 6H), 5.03-4.59 (m, 2H), 3.47 (s, 3H), 3.43 (s, 3H), 2.75 (s, 3H). Isomer 2: $^1$H NMR (400 MHz, CDCl$_3$) δ 7.42 (d, J=7.5 Hz, 1H), 7.32 (dt, J=20.9, 8.2 Hz, 4H), 6.96 (d, J=2.1 Hz, 1H), 6.82 (d, J=2.2 Hz, 1H), 5.29-5.08 (m, 5H), 4.52-4.25 (m, 2H), 3.45 (s, 3H), 3.43 (s, 3H), 3.01 (s, 3H). LC/MS (m/z): 424.069 and 426.010 [M+H$^+$]; UPLC $t_R$ 1.69 min.

(2-((1-(4-Methoxybenzyl)-3-methyl-1H-pyrazol-5-yl)amino)-4,6-bis(methoxymethoxy)phenyl)(5-((1-methylpiperidin-4-yl)amino)isoindolin-2-yl)methanone (16a)

Synthesized using General Procedure D2 from 15a (56.9 mg, 106 μmol) and 10a (25.4 mg, 117 μmol) in dioxane. The crude mixture was purified via automated flash chromatography (2% to 10% methanol in CH$_2$Cl$_2$). To QuadraPure™ MPA resin (1.5 mmol/g loading, 45 mg) soaked in CH$_2$Cl$_2$ (2 mL) for 30 min was transferred the purified product using CH$_2$Cl$_2$ (3 mL) and shaken overnight. The suspension was filtered through a plug of Celite® and the filtrate was concentrated using a rotary evaporator to afford 41.8 mg of 16a (59% yield). $^1$H NMR (400 MHz, CDCl$_3$) δ 7.14-6.91 (m, 3H), 6.66 (dd, J=8.6, 1.5 Hz, 2H), 6.53 (q, J=8.9, 8.2 Hz, 2H), 6.41-6.16 (m, 3H), 5.84 (s, 1H), 5.23-5.09 (m, 2H), 5.09-4.97 (m, 4H), 4.88-4.67 (m, 3H), 4.43 (t, J=13.1 Hz, 1H), 3.68 (d, J=1.5 Hz, 3H), 3.51-3.39 (m, 6H), 3.26 (d, J=28.2 Hz, 1H), 2.83 (d, J=13.5 Hz, 2H), 2.30 (d, J=8.8 Hz, 4H), 2.24 (s, 3H), 2.18-1.95 (m, 4H), 1.49 (d, J=11.8 Hz, 1H). $^{13}$C NMR (101 MHz, CDCl$_3$) δ 166.8, 166.7, 159.7, 158.9, 155.3, 147.6, 147.6, 147.1, 146.9, 143.7, 139.3, 137.8, 137.5, 128.7, 128.7, 128.7, 124.8, 124.5, 123.6, 123.2, 113.9, 113.9, 113.5, 113.4, 108.0, 107.9, 106.8, 106.3, 98.7, 98.6, 96.4, 96.4, 95.3, 95.3, 95.1, 95.0, 94.3, 56.5, 56.5, 56.2, 55.1, 55.1, 54.5, 53.2, 52.6, 52.2, 51.6, 51.3, 49.6, 46.2, 46.2, 32.4, 14.2. LC/MS (m/z): 671.282 [M+H$^+$]; UPLC $t_R$ 1.45 min.

(5-(2-(Dimethylamino)ethoxy)isoindolin-2-yl)(2-((1-(4-methoxybenzyl)-3-methyl-1H-pyrazol-5-yl)amino)-4,6-bis(methoxymethoxy)phenyl)methanone (16b)

Synthesized using General Procedure D2 from 15b (41.9 mg, 82.3 μmol) and 10a (19.7 mg, 90.5 μmol) in dioxane (0.8 mL). The crude mixture was purified via automated flash chromatography (1% to 8% methanol in CH$_2$Cl$_2$). To QuadraPure™ MPA resin (1.5 mmol/g loading, 34 mg) soaked in CH$_2$Cl$_2$ (2 mL) for 30 min was transferred the purified product using CH$_2$Cl$_2$ (3 mL) and shaken overnight. The suspension was filtered through a plug of Celite® and the filtrate was concentrated in vacuo to afford 37.7 mg of 16b (71% yield). $^1$H NMR (400 MHz, CDCl$_3$) δ 7.21 (d, J=8.4 Hz, 1H), 7.05 (t, J=8.8 Hz, 2H), 6.90-6.79 (m, 2H), 6.72-6.59 (m, 2H), 6.37 (dd, J=7.7, 3.6 Hz, 2H), 6.22 (d, J=2.4 Hz, 1H), 5.84 (s, 1H), 5.14 (q, J=7.1 Hz, 2H), 5.04 (d, J=12.2 Hz, 4H), 4.92-4.67 (m, 3H), 4.46 (t, J=12.8 Hz, 1H), 4.05 (dt, J=18.9, 5.7 Hz, 2H), 3.67 (s, 3H), 3.44 (s, 3H), 3.43 (s, 3H), 2.74 (dt, J=11.6, 5.6 Hz, 2H), 2.35 (s, 3H), 2.33 (s, 3H), 2.23 (s, 3H). $^{13}$C NMR (101 MHz, CDCl$_3$) δ 166.8, 166.8, 159.7, 158.9, 158.9, 158.8, 155.3, 147.6, 143.7, 139.3, 137.9, 137.5, 128.7, 128.6, 128.5, 128.2, 127.7, 126.4, 125.8, 125.3, 123.7, 123.3, 121.5, 120.7, 114.8, 114.5, 113.9, 108.6, 108.5, 107.8, 98.6, 96.4, 95.3, 95.3, 95.1, 94.3, 66.3, 66.2, 58.2, 58.2, 56.5, 56.5, 56.2, 55.1, 53.1, 52.5, 52.2, 51.5, 51.3, 45.8, 45.8, 14.2. LC/MS (m/z): 646.275 [M+H$^+$]; UPLC $t_R$ 1.47 min.

(2-((1-(4-Methoxybenzyl)-3-methyl-1H-pyrazol-5-yl)amino)-4,6-bis(methoxymethoxy)phenyl)(5-(4-methylpiperazin-1-yl)isoindolin-2-yl)methanone (16c)

Synthesized using General Procedure D2 from 15c (41 mg, 79 µmol) and 10a (19 mg, 87 µmol) in dioxane (0.8 mL). The crude mixture was purified via automated flash chromatography (1% to 7% methanol in CH$_2$Cl$_2$). To QuadraPure™ MPA resin (1.5 mmol/g loading, 34 mg) soaked in CH$_2$Cl$_2$ (2 mL) for 30 min was transferred the purified product using CH$_2$Cl$_2$ (3 mL) and shaken overnight. The suspension was filtered through a plug of Celite® and the filtrate was concentrated in vacuo to afford 39 mg of 16c (75% yield). $^1$H NMR (400 MHz, CDCl$_3$) δ 7.22-6.99 (m, 3H), 6.94-6.82 (m, 2H), 6.71-6.58 (m, 2H), 6.40-6.31 (m, 2H), 6.21 (dd, J=5.1, 2.1 Hz, 1H), 5.84 (s, 1H), 5.19-5.08 (m, 2H), 5.08-4.97 (m, 4H), 4.91-4.71 (m, 3H), 4.46 (t, J=13.0 Hz, 1H), 3.67 (d, J=3.6 Hz, 3H), 3.51-3.40 (m, 6H), 3.29-3.10 (m, 4H), 2.59 (dt, J=10.0, 4.7 Hz, 4H), 2.36 (d, J=7.7 Hz, 3H), 2.24 (s, 3H). $^{13}$C NMR (101 MHz, CDCl$_3$) δ 166.8, 166.7, 159.7, 158.9, 155.3, 151.5, 151.4, 147.6, 143.7, 139.3, 137.7, 137.3, 128.7, 128.7, 128.7, 127.5, 127.3, 123.4, 123.0, 116.4, 116.1, 113.9, 110.3, 109.8, 107.9, 107.8, 98.7, 98.6, 96.4, 95.3, 95.3, 95.1, 95.0, 94.3, 56.5, 56.2, 55.1, 55.0, 55.0, 55.0, 53.2, 52.6, 52.3, 51.6, 51.3, 49.5, 49.5, 46.1, 46.1, 14.2. LC/MS (m/z): 657.301 [M+H$^+$]; UPLC $t_R$ 0.89 min.

N-Benzyl-2-((1-(4-methoxybenzyl)-3-methyl-1H-pyrazol-5-yl)amino)-4,6-bis(methoxymethoxy)-N-methylbenzamide (16d)

Synthesized using General Procedure D2 from 15d (30 mg, 71 µmol) and 10a (17 mg, 78 µmol). Following silica gel flash chromatography (10% to 35% acetone in hexanes), TMT (15 mg) was added to the isolated residue; the mixture was suspended in toluene (3 mL) and stirred overnight. The suspension was filtered through a plug of Celite® and the filtrate was concentrated using a rotary evaporator to afford 39 mg 16d (98% yield). $^1$H NMR (400 MHz, CDCl$_3$) δ 7.35-7.07 (m, 8H), 7.06-6.97 (m, 1H), 6.87-6.74 (m, 2H), 6.43-6.30 (m, 1H), 6.23 (dd, J=15.2, 2.1 Hz, 1H), 5.84 (d, J=12.4 Hz, 1H), 5.19-4.96 (m, 7H), 4.65-4.17 (m, 1H), 3.72 (d, J=6.6 Hz, 3H), 3.46-3.35 (m, 6H), 2.91-2.78 (m, 3H), 2.27 (s, 3H). $^{13}$C NMR (101 MHz, CDCl$_3$) δ 168.0, 168.0, 159.6, 159.6, 159.0, 155.2, 155.0, 147.7, 147.6, 144.2, 144.1, 139.9, 139.5, 136.8, 136.4, 128.9, 128.8, 128.7, 128.7, 128.6, 128.6, 128.1, 127.7, 127.6, 127.4, 114.2, 114.1, 114.0, 106.9, 106.5, 98.4, 97.5, 97.0, 96.4, 95.0, 94.9, 94.9, 94.3, 94.3, 94.2, 91.4, 56.5, 56.3, 56.2, 56.2, 55.3, 55.2, 54.8, 51.2, 51.0, 50.9, 50.4, 35.8, 32.4, 14.3. LC/MS (m/z): 561.284 [M+H$^+$]; UPLC $t_R$ 1.80 min.

Methyl 2-bromo-4,6-bis(methoxymethoxy)benzoate (17)

To a suspension of benzoic acid 12 (1.26 g, 3.93 mmol) and K$_2$CO$_3$ (0.951 g, 6.88 mmol) in DMF (39 mL) at room temperature was added iodomethane (0.428 mL, 6.88 mmol) dropwise. The suspension was heated to 80° C. and stirred for 1 h. After cooling to room temperature, the reaction was quenched with saturated NH$_4$Cl (aq.). The resulting mixture was extracted 4 times with ether. The combined organic layers were washed twice with water, brine and then dried with anhydrous Na$_2$SO$_4$. The salts were removed via gravity filtration and volatile materials were condensed in vacuo. The crude mixture was purified via automated flash chromatography (5% to 20% ethyl acetate in hexanes twice) to afford 1.02 g of 17 (77% yield) as a clear colorless oil. $^1$H NMR (400 MHz, CDCl$_3$) δ 6.94 (d, J=2.1 Hz, 1H), 6.79 (d, J=2.1 Hz, 1H), 5.15 (s, 2H), 5.14 (s, 2H), 3.92 (s, 3H), 3.46 (s, 6H). $^{13}$C NMR (101 MHz, CDCl$_3$) δ 166.5, 159.0, 155.6, 120.7, 119.9, 113.0, 102.8, 94.7, 94.4, 56.3, 56.2, 52.6. LC/MS (m/z): [M+H$^+$]; UPLC $t_R$ min (dH-109-763).

Methyl 2-((1-(4-methoxybenzyl)-3-methyl-1H-pyrazol-5-yl)amino)-4,6-bis(methoxymethoxy)benzoate (18a)

Synthesized using General Procedure D2 from 17 (130 mg, 390 µmol) and 10a (93 mg, 430 µmol). Following silica gel flash chromatography (20% to 60% ethyl acetate in hexanes and 15% to 50% ethyl acetate in hexanes), TMT (59 mg) was added to the isolated residue; the mixture was suspended in toluene (3 mL) and stirred overnight. The suspension was filtered through a plug of Celite® and the filtrate was concentrated using a rotary evaporator to afford 161 mg of 18a (88% yield). $^1$H NMR (400 MHz, CDCl$_3$) δ 8.64 (s, 1H), 7.17-7.10 (m, 2H), 6.82-6.73 (m, 2H), 6.24 (d, J=2.3 Hz, 1H), 6.10 (d, J=2.3 Hz, 1H), 5.88 (s, 1H), 5.17 (s, 2H), 5.06 (s, 2H), 5.03 (s, 2H), 3.84 (s, 3H), 3.76 (s, 3H), 3.52 (s, 3H), 3.42 (s, 3H), 2.27 (s, 3H). $^{13}$C NMR (101 MHz, CDCl$_3$) δ 168.7, 161.3, 159.7, 158.9, 149.2, 147.7, 138.9, 128.9, 128.8, 113.9, 99.9, 99.5, 95.2, 95.0, 95.0, 93.9, 56.4, 56.2, 55.1, 51.8, 51.1, 14.2. LC/MS (m/z): 473.16 [M+H$^+$]; UPLC $t_R$ 1.70 min.

Methyl 2-((1-(4-methoxybenzyl)-3-phenyl-1H-pyrazol-5-yl)amino)-4,6-bis(methoxymethoxy)benzoate (18b)

Synthesized using General Procedure D2 from 17 (203 mg, 606 µmol) and 10b (186 mg, 666 µmol). Following silica gel flash chromatography (7% to 25% ethyl acetate in hexanes), TMT (115 mg) was added to the isolated residue; the mixture was suspended in toluene (4 mL) and stirred overnight. The suspension was filtered through a plug of Celite® and the filtrate was concentrated using a rotary evaporator to afford 270 mg of 18b (84% yield). $^1$H NMR (400 MHz, CDCl$_3$) δ 8.70 (s, 1H), 7.85-7.76 (m, 2H), 7.44-7.36 (m, 2H), 7.31 (d, J=7.4 Hz, 1H), 7.20 (d, J=8.7 Hz, 2H), 6.80 (d, J=8.7 Hz, 2H), 6.42 (d, J=0.7 Hz, 1H), 6.26 (d, J=2.3 Hz, 1H), 6.15 (d, J=2.3 Hz, 1H), 5.19 (s, 2H), 5.18 (s, 2H), 5.01 (s, 2H), 3.85 (s, 3H), 3.76 (s, 3H), 3.53 (s, 3H), 3.41 (s, 3H), 1.56 (s, 3H). $^{13}$C NMR (101 MHz, CDCl$_3$) δ 168.7, 161.4, 159.7, 159.0, 150.2, 149.0, 139.6, 133.7, 128.9, 128.5, 128.5, 127.5, 125.3, 113.9, 100.1, 97.3, 95.2, 95.2, 95.1, 93.9, 56.4, 56.3, 55.1, 51.8, 51.6. LC/MS (m/z): 535.438 [M+H$^+$]; UPLC $t_R$ 2.01 min Methyl 2-((3-ethyl-1-(4-methoxybenzyl)-1H-pyrazol-5-yl)amino)-4,6-bis(methoxymethoxy)benzoate (18c)

Synthesized using General Procedure D2 from 17 (100 mg, 298 µmol) and 10g (75.9 mg, 328 µmol). Following silica gel flash chromatography (15% to 40% ethyl acetate in hexanes), TMT (40 mg) was added to the isolated residue; the mixture was suspended in toluene (3 mL) and stirred overnight. The suspension was filtered through a plug of Celite® and the filtrate was concentrated using a rotary evaporator to afford 123 mg of 18c (85% yield). $^1$H NMR (400 MHz, CDCl$_3$) δ 7.16 (s, 2H), 6.80 (d, J=8.3 Hz, 2H), 6.25 (s, 1H), 6.14 (s, 1H), 5.93 (s, 1H), 5.17 (s, 2H), 5.11 (s, 2H), 5.03 (s, 2H), 3.83 (s, 3H), 3.76 (s, 3H), 3.52 (s, 3H), 3.42 (s, 3H), 2.65 (q, J=7.7 Hz, 2H), 1.25 (t, J=7.6 Hz, 3H). $^{13}$C NMR (101 MHz, CDCl$_3$) δ 168.7, 161.4, 159.7, 159.0, 153.9, 149.2, 138.9, 128.9, 128.9, 113.9, 100.0, 98.0, 95.3, 95.1, 94.0, 56.4, 56.3, 55.2, 51.8, 51.2, 22.1, 13.9. LC/MS (m/z): 487.318 [M+H$^+$]; UPLC $t_R$ 1.80 min.

Methyl 2-((3-isopropyl-1-(4-methoxybenzyl)-1H-pyrazol-5-yl)amino)-4,6-bis(methoxymethoxy)benzoate (18d)

Synthesized using General Procedure D2 from 17 100 mg, 298 μmol) and 10h (80.5 mg, 328 μmol). Following silica gel flash chromatography (12% to 35% ethyl acetate in hexanes), TMT (42 mg) was added to the isolated residue; the mixture was suspended in toluene (3 mL) and stirred overnight. The suspension was filtered through a plug of Celite® and the filtrate was concentrated using a rotary evaporator to afford 112 mg of 18d (75% yield). $^1$H NMR (400 MHz, CDCl$_3$) δ 8.59 (s, 1H), 7.14 (d, J=8.2 Hz, 2H), 6.86-6.71 (m, 2H), 6.24 (d, J=2.2 Hz, 1H), 6.13 (s, 1H), 5.93 (s, 1H), 5.17 (s, 2H), 5.10 (s, 2H), 5.01 (s, 2H), 3.82 (s, 3H), 3.76 (s, 3H), 3.51 (s, 3H), 3.42 (s, 3H), 2.97 (p, J=6.9 Hz, 1H), 1.27 (d, J=6.9 Hz, 6H). 13C NMR (101 MHz, CDCl$_3$) δ 168.6, 161.4, 159.7, 159.0, 158.3, 149.2, 138.8, 129.0, 128.8, 113.9, 100.1, 96.5, 95.3, 95.2, 95.2, 94.0, 56.4, 56.2, 55.2, 51.8, 51.2, 28.3, 22.9. LC/MS (m/z): 501.344 [M+H$^+$]; UPLC $t_R$ 1.89 min.

Methyl 2-((3-cyclopropyl-1-(4-methoxybenzyl)-1H-pyrazol-5-yl)amino)-4,6-bis(methoxymethoxy)benzoate (18e)

Synthesized using General Procedure D2 from 17 (100 mg, 298 μmol) and 10j (80.0 mg, 328 μmol). Following silica gel flash chromatography (8% to 50% ethyl acetate in hexanes), TMT (44 mg) was added to the isolated residue; the mixture was suspended in toluene (3 mL) and stirred overnight. The suspension was filtered through a plug of Celite® and the filtrate was concentrated using a rotary evaporator to afford 133 mg of 18e (89% yield). $^1$H NMR (400 MHz, CDCl$_3$) δ 8.62 (s, 1H), 7.15 (d, J=8.2 Hz, 2H), 6.85-6.73 (m, 2H), 6.24 (d, J=2.2 Hz, 1H), 6.11 (s, 1H), 5.72 (s, 1H), 5.16 (s, 2H), 5.07 (s, 2H), 5.02 (s, 2H), 3.82 (s, 3H), 3.76 (s, 3H), 3.51 (s, 3H), 3.42 (s, 3H), 1.93 (dq, J=8.8, 5.1, 4.4 Hz, 1H), 0.90 (dd, J=7.7, 5.5 Hz, 2H), 0.77-0.63 (m, 2H). $^{13}$C NMR (101 MHz, CDCl$_3$) δ 168.7, 161.4, 159.7, 159.0, 154.3, 149.1, 138.9, 128.9, 128.9, 113.9, 100.0, 95.7, 95.3, 95.2, 94.0, 56.4, 56.3, 55.2, 51.8, 51.2, 9.7, 7.9. LC/MS (m/z): 499.315 [M+H$^+$]; UPLC $t_R$ 1.81 min.

Methyl 2-((3-cyclopentyl-1-(4-methoxybenzyl)-1H-pyrazol-5-yl)amino)-4,6-bis(methoxymethoxy)benzoate (18f)

Synthesized using General Procedure D2 from 17 (81 mg, 240 μmol) and 10k (67 mg, 240 μmol) in dioxane (1.2 mL). Following silica gel flash chromatography (8% to 25% ethyl acetate in hexanes), TMT (36 mg) was added to the isolated residue; the mixture was suspended in toluene (3 mL) and stirred overnight. The suspension was filtered through a plug of Celite® and the filtrate was concentrated using a rotary evaporator to afford 90 mg of 18f (71% yield). $^1$H NMR (400 MHz, CDCl$_3$) δ 8.60 (s, 1H), 7.15 (d, J=8.2 Hz, 2H), 6.80 (d, J=8.6 Hz, 2H), 6.24 (s, 1H), 6.15 (s, 1H), 5.92 (s, 1H), 5.17 (s, 2H), 5.10 (s, 2H), 5.02 (s, 2H), 3.82 (s, 3H), 3.76 (s, 3H), 3.51 (s, 3H), 3.42 (s, 3H), 3.08 (t, J=8.1 Hz, 1H), 2.06 (s, 2H), 1.83-1.45 (m, 6H). $^{13}$C NMR (101 MHz, CDCl$_3$) δ 168.6, 161.4, 159.7, 159.0, 156.6, 149.2, 138.9, 129.0, 128.8, 113.9, 100.1, 97.0, 95.3, 95.2, 95.2, 94.0, 56.4, 56.3, 55.2, 51.8, 51.2, 39.6, 33.4, 25.4. LC/MS (m/z): 527.366 [M+H$^+$]; UPLC $t_R$ 2.02 min.

Methyl 2-((3-(furan-3-yl)-1-(4-methoxybenzyl)-1H-pyrazol-5-yl)amino)-4,6-bis(methoxymethoxy)benzoate (18g)

Synthesized using General Procedure D2 from 17 (88.4 mg, 328 μmol) and 101 (88.4 mg, 328 μmol). Following silica gel flash chromatography (12% to 35% ethyl acetate in hexanes), TMT (44 mg) was added to the isolated residue; the mixture was suspended in toluene (3 mL) and stirred overnight. The suspension was filtered through a plug of Celite® and the filtrate was concentrated using a rotary evaporator to afford 111 mg of 18g (71% yield). $^1$H NMR (400 MHz, CDCl$_3$) δ 8.68 (s, 1H), 7.77 (dd, J=1.6, 0.9 Hz, 1H), 7.45 (t, J=1.7 Hz, 1H), 7.17 (d, J=8.6 Hz, 2H), 6.85-6.78 (m, 2H), 6.76 (dd, J=1.9, 0.9 Hz, 1H), 6.26 (d, J=2.3 Hz, 1H), 6.22-6.18 (m, 1H), 6.14 (d, J=2.2 Hz, 1H), 5.18 (s, 2H), 5.16 (s, 2H), 5.02 (s, 2H), 3.84 (s, 3H), 3.76 (s, 3H), 3.52 (s, 3H), 3.41 (s, 3H). $^{13}$C NMR (101 MHz, CDCl$_3$) δ 168.7, 161.4, 159.8, 159.1, 149.0, 143.7, 143.2, 139.5, 139.1, 128.9, 128.6, 120.2, 113.9, 108.8, 100.2, 97.6, 95.3, 95.3, 95.2, 94.0, 56.5, 56.3, 55.2, 51.9, 51.6. LC/MS (m/z): 524.279 [M+H$^+$]; UPLC $t_R$ 1.81 min.

Methyl 2,4-bis(methoxymethoxy)-6-((1-methyl-1H-pyrazol-5-yl)amino)benzoate (18h)

Synthesized using General Procedure D2 from 17 (100 mg, 207 μmol) and 1-methyl-1H-pyrazol-5-amine (31.9 mg, 328 μmol). Following silica gel flash chromatography (10% to 35% ethyl acetate in hexanes), TMT (30 mg) was added to the isolated residue; the mixture was suspended in toluene (3 mL) and stirred overnight. The suspension was filtered through a plug of Celite® and the filtrate was concentrated using a rotary evaporator to afford 80.6 mg of 18h (77% yield). $^1$H NMR (400 MHz, CDCl$_3$) δ 8.95 (s, 1H), 7.47 (d, J=2.0 Hz, 1H), 6.27 (d, J=2.3 Hz, 1H), 6.08 (dd, J=8.0, 2.1 Hz, 2H), 5.18 (s, 2H), 5.07 (s, 2H), 3.91 (s, 3H), 3.73 (s, 3H), 3.52 (s, 3H), 3.42 (s, 3H). $^{13}$C NMR (101 MHz, CDCl$_3$) δ 169.1, 161.6, 160.0, 149.5, 139.0, 138.6, 99.4, 95.3, 95.2, 94.6, 93.9, 56.5, 56.3, 52.0, 35.0. LC/MS (m/z): 353.233 [M+H$^+$]; UPLC $t_R$ 1.34 min.

Methyl 2-((1-isopropyl-1H-pyrazol-5-yl)amino)-4,6-bis(methoxymethoxy)benzoate (18i)

Synthesized using General Procedure D2 from 17 (150 mg, 448 μmol) and 1-(propan-2-yl)-1H-pyrazol-5-amine (61.6 mg, 492 μmol). Following silica gel flash chromatography (10% to 30% ethyl acetate in hexanes), TMT (47 mg) was added to the isolated residue; the mixture was suspended in toluene (3 mL) and stirred overnight. The suspension was filtered through a plug of Celite® and the filtrate was concentrated using a rotary evaporator to afford 124 mg of 18i (73% yield). $^1$H NMR (400 MHz, CDCl$_3$) δ

8.84 (s, 1H), 7.53 (d, J=1.9 Hz, 1H), 6.24 (d, J=2.3 Hz, 1H), 6.05 (dd, J=5.1, 2.0 Hz, 2H), 5.18 (s, 2H), 5.05 (s, 2H), 4.48 (p, J=6.6 Hz, 1H), 3.91 (s, 3H), 3.52 (d, J=1.2 Hz, 3H), 3.40 (d, J=0.8 Hz, 3H), 1.45 (d, J=6.6 Hz, 6H). $^{13}$C NMR (101 MHz, CDCl$_3$) δ 169.2, 161.6, 160.0, 150.4, 138.6, 137.4, 100.2, 99.4, 95.3, 95.1, 94.5, 93.9, 56.4, 56.2, 51.9, 48.6, 22.4. LC/MS (m/z): 381.329 [M+H$^+$]; UPLC $t_R$ 1.61 min.

Methyl 2-((1-isobutyl-1H-pyrazol-5-yl)amino)-4,6-bis(methoxymethoxy)benzoate (18j)

Synthesized using General Procedure D2 from 17 (150 mg, 448 μmol) and 1-(2-methylpropyl)-1H-pyrazol-5-amine (68.3 mg, 492 μmol). Following silica gel flash chromatography (12% to 33% ethyl acetate in hexanes), TMT (50 mg) was added to the isolated residue; the mixture was suspended in toluene (3 mL) and stirred overnight. The suspension was filtered through a plug of Celite® and the filtrate was concentrated using a rotary evaporator to afford 136 mg of 18j (77% yield). $^1$H NMR (400 MHz, CDCl$_3$) δ 8.93 (s, 1H), 7.50 (d, J=2.0 Hz, 1H), 6.25 (d, J=2.3 Hz, 1H), 6.18 (d, J=2.3 Hz, 1H), 6.07 (d, J=1.9 Hz, 1H), 5.18 (s, 2H), 5.06 (s, 2H), 3.90 (s, 3H), 3.80 (d, J=7.4 Hz, 2H), 3.52 (s, 3H), 3.42 (s, 3H), 2.22 (hept, J=7.0 Hz, 1H), 0.90 (d, J=6.7 Hz, 6H). $^{13}$C NMR (101 MHz, CDCl$_3$) δ 169.1, 161.6, 160.0, 149.7, 138.9, 138.6, 99.6, 99.2, 95.3, 95.2, 94.7, 93.9, 56.4, 56.2, 55.1, 51.9, 29.4, 19.9. LC/MS (m/z): 395.355 [M+H$^+$]; UPLC $t_R$ 1.73 min.

Methyl 2-((1-(cyclohexylmethyl)-1H-pyrazol-5-yl)amino)-4,6-bis(methoxymethoxy)benzoate (18k)

Synthesized using General Procedure D2 from 17 (139 mg, 415 μmol) and 1-(cyclohexylmethyl)-1H-pyrazol-5-amine (81.8 mg, 456 μmol). Following silica gel flash chromatography (8% to 25% ethyl acetate in hexanes), TMT (44 mg) was added to the isolated residue; the mixture was suspended in toluene (3 mL) and stirred overnight. The suspension was filtered through a plug of Celite® and the filtrate was concentrated using a rotary evaporator to afford 130 mg of 18k (72% yield) as a yellow oil. $^1$H NMR (400 MHz, CDCl$_3$) δ 8.88 (s, 1H), 7.49 (d, J=2.0 Hz, 1H), 6.25 (d, J=2.3 Hz, 1H), 6.16 (d, J=2.3 Hz, 1H), 6.09-5.97 (m, 1H), 5.18 (s, 2H), 5.06 (s, 2H), 3.91 (s, 3H), 3.82 (d, J=7.3 Hz, 2H), 3.53 (s, 3H), 3.41 (s, 3H), 1.91 (tt, J=7.5, 3.7 Hz, 1H), 1.75-1.54 (m, 6H), 1.32-1.07 (m, 3H), 0.96 (q, J=11.8 Hz, 1H). $^{13}$C NMR (101 MHz, CDCl$_3$) δ 169.1, 161.6, 159.7, 149.7, 139.0, 138.6, 99.7, 99.1, 95.3, 95.2, 94.7, 93.9, 56.4, 56.3, 53.9, 51.9, 38.5, 30.6, 26.3, 25.7. LC/MS (m/z): 435.405 [M+H$^+$]; UPLC $t_R$ 1.93 min.

Methyl 2,4-bis(methoxymethoxy)-6-((1-phenyl-1H-pyrazol-5-yl)amino)benzoate (18l)

Synthesized using General Procedure D2 from 17 (150 mg, 448 μmol) and 1-phenyl-1H-pyrazol-5-amine (78.4 mg, 492 μmol). Following silica gel flash chromatography (12% to 33% ethyl acetate in hexanes), TMT (47 mg) was added to the isolated residue; the mixture was suspended in toluene (3 mL) and stirred overnight. The suspension was filtered through a plug of Celite® and the filtrate was concentrated using a rotary evaporator to afford 132 mg of 18l (71% yield) as a yellow oil. $^1$H NMR (400 MHz, CDCl$_3$) δ 8.99 (s, 1H), 7.66 (d, J=2.0 Hz, 1H), 7.60-7.53 (m, 2H), 7.49-7.40 (m, 2H), 7.38-7.32 (m, 1H), 6.46 (d, J=2.3 Hz, 1H), 6.30-6.19 (m, 2H), 5.16 (s, 2H), 5.09 (s, 2H), 3.79 (s, 3H), 3.50 (s, 3H), 3.43 (s, 3H). $^{13}$C NMR (101 MHz, CDCl$_3$) δ 168.6, 161.5, 159.7, 148.2, 140.3, 139.3, 138.5, 129.2, 127.6, 124.0, 100.5, 99.1, 95.7, 95.2, 95.2, 94.0, 56.4, 56.3, 51.9. LC/MS (m/z): 415.292 [M+H$^+$]; UPLC $t_R$ 1.67 min.

Methyl 2-((1-cyclohexyl-1H-pyrazol-5-yl)amino)-4,6-bis(methoxymethoxy)benzoate (18m)

Synthesized using General Procedure D2 from 17 (150 mg, 448 μmol) and 1-cyclohexyl-1H-pyrazol-5-amine (81.4 mg, 492 μmol). Following silica gel flash chromatography (10% to 30% ethyl acetate in hexanes), TMT (60 mg) was added to the isolated residue; the mixture was suspended in toluene (3 mL) and stirred overnight. The suspension was filtered through a plug of Celite® and the filtrate was concentrated using a rotary evaporator to afford 152 mg of 18m (81% yield) as a clear yellow oil. H NMR (400 MHz, CDCl$_3$) δ 8.84 (s, 2H), 7.51 (d, J=1.9 Hz, 2H), 6.24 (d, J=2.3 Hz, 2H), 6.13-5.96 (m, 1H), 5.19 (s, 1H), 5.05 (s, 2H), 4.09-3.97 (m, 1H), 3.91 (s, 3H), 3.53 (d, J=1.0 Hz, 3H), 3.40 (s, 3H), 1.99-1.81 (m, 7H), 1.72-1.64 (m, 1H), 1.46-1.06 (m, 2H). $^{13}$C NMR (101 MHz, CDCl$_3$) δ 169.2, 161.6, 160.0, 150.4, 138.5, 137.6, 99.9, 99.5, 95.3, 95.1, 94.5, 93.8, 56.4, 56.3, 56.2, 51.9, 32.7, 25.6, 25.2. LC/MS (m/z): 421.379 [M+H$^+$]; UPLC $t_R$ 1.83 min.

Methyl 2-((1-benzyl-1H-pyrazol-5-yl)amino)-4,6-bis(methoxymethoxy)benzoate (18n)

Synthesized using General Procedure D2 from 17 (140 mg, 418 μmol) and 1-benzyl-1H-pyrazol-5-amine (79.6 mg, 460 μmol). Following silica gel flash chromatography (10% to 30% ethyl acetate in hexanes), TMT (44 mg) was added to the isolated residue; the mixture was suspended in toluene (3 mL) and stirred overnight. The suspension was filtered through a plug of Celite® and the filtrate was concentrated using a rotary evaporator to afford 116 mg of 18n (65% yield) as a yellow oil. $^1$H NMR (400 MHz, CDCl$_3$) δ 8.69 (s, 1H), 7.54 (d, J=2.0 Hz, 1H), 7.31-7.23 (m, 3H), 7.22-7.17 (m, 2H), 6.25 (d, J=2.3 Hz, 1H), 6.11 (d, J=2.0 Hz, 1H), 6.09 (d, J=2.3 Hz, 1H), 5.20 (s, 2H), 5.17 (s, 2H), 5.01 (s, 2H), 3.82 (s, 3H), 3.51 (s, 3H), 3.41 (s, 3H). $^{13}$C NMR (101 MHz, CDCl$_3$) δ 168.7, 161.4, 159.8, 149.3, 139.2, 138.9, 136.5, 128.6, 127.7, 127.6, 100.2, 100.0, 95.3, 95.3, 94.9, 93.9, 56.5, 56.3, 52.0, 51.9. LC/MS (m/z): 429.362 [M+H$^+$]; UPLC $t_R$ 1.71 min.

Methyl 2,4-bis(methoxymethoxy)-6-((1-(pyridin-3-ylmethyl)-1H-pyrazol-5-yl)amino)benzoate (18o)

Synthesized using General Procedure D2 from 17 (150 mg, 448 μmol) and 1-(pyridin-3-ylmethyl)-1H-pyrazol-5-amine (85.8 mg, 492 μmol) and purified via silica gel flash chromatography (10% to 30% acetone in CH$_2$Cl$_2$). To QuadraPure™ MPA resin (1.5 mmol/g loading, 192 mg) soaked in CH$_2$Cl$_2$ (3 mL) for 30 min was transferred the purified product using CH$_2$Cl$_2$ (2 mL) and shaken overnight. The suspension was filtered through a plug of Celite® and the filtrate was concentrated using a rotary evaporator to afford 135 mg of 18o (71% yield) as a brown oil. $^1$H NMR (400 MHz, CDCl$_3$) δ 8.61 (s, 1H), 7.31 (dd, J=8.5, 7.3 Hz, 2H), 7.18 (dd, J=8.5, 1.3 Hz, 2H), 7.07-6.99 (m, 1H), 6.59 (d, J=2.2 Hz, 1H), 6.26 (d, J=2.3 Hz, 1H), 5.18 (s, 2H), 5.08 (s, 2H), 3.88 (s, 3H), 3.52 (s, 3H), 3.43 (s, 3H). $^{13}$C NMR (101 MHz, CDCl$_3$) δ 168.8, 160.9, 159.4, 148.1, 141.1, 129.3, 123.0, 121.5, 101.8, 95.7, 95.2, 95.2, 94.0, 56.4, 56.2, 51.9. LC/MS (m/z): 429.582 [M+H$^+$]; UPLC $t_R$ 1.16 min.

Methyl 2-((1-(furan-2-ylmethyl)-1H-pyrazol-5-yl)amino)-4,6-bis(methoxymethoxy)benzoate (18p)

Synthesized using General Procedure D2 from 17 (150 mg, 448 μmol) and 1-(furan-2-ylmethyl)-1H-pyrazol-5-amine (80.3 mg, 492 μmol). Following silica gel flash chromatography (12% to 35% ethyl acetate in hexanes), TMT (60 mg) was added to the isolated residue; the mixture was suspended in toluene (3 mL) and stirred overnight. The suspension was filtered through a plug of Celite® and the filtrate was concentrated using a rotary evaporator to afford 145 mg of 18p (78% yield) as a yellow oil. $^1$H NMR (400 MHz, CDCl$_3$) δ 8.85 (s, 1H), 7.51 (d, J=1.9 Hz, 1H), 7.41-7.33 (m, 1H), 6.35-6.28 (m, 2H), 6.28 (d, J=2.2 Hz, 1H), 6.17 (d, J=2.2 Hz, 1H), 6.09 (d, J=2.0 Hz, 1H), 5.19 (s, 4H), 5.05 (s, 2H), 3.90 (s, 3H), 3.52 (d, J=0.9 Hz, 3H), 3.42 (d, J=0.9 Hz, 3H). $^{13}$C NMR (101 MHz, CDCl$_3$) δ 168.8, 161.4, 159.8, 149.4, 149.2, 142.8, 139.3, 139.0, 110.4, 108.7, 100.2, 99.9, 95.4, 95.3, 95.0, 93.9, 56.4, 56.3, 51.9, 44.7. LC/MS (m/z): 419.35 [M+H$^+$]; UPLC $t_R$ 1.57 min.

Methyl 2-((1-(4-isopropylbenzyl)-1H-pyrazol-5-yl)amino)-4,6-bis(methoxymethoxy)benzoate (18q)

Synthesized using General Procedure D2 from 17 (80 mg, 240 μmol) and 1-([4-(propan-2-yl)phenyl]methyl)-1H-pyrazol-5-amine (57 mg, 270 μmol). Following silica gel flash chromatography (7% to 25% ethyl acetate in hexanes), TMT (21 mg) was added to the isolated residue; the mixture was suspended in toluene (3 mL) and stirred overnight. The suspension was filtered through a plug of Celite® and the filtrate was concentrated using a rotary evaporator to afford 55 mg of 18q (49% yield) as a yellow oil. $^1$H NMR (400 MHz, CDCl$_3$) δ 8.67 (s, 1H), 7.52 (d, J=2.0 Hz, 1H), 7.14 (s, 4H), 6.24 (d, J=2.3 Hz, 1H), 6.10 (t, J=2.2 Hz, 2H), 5.17 (s, 2H), 5.16 (s, 2H), 5.00 (s, 2H), 3.83 (s, 3H), 3.52 (s, 3H), 3.41 (s, 3H), 2.85 (p, J=7.0 Hz, 1H), 1.20 (d, J=6.9 Hz, 6H). $^{13}$C NMR (101 MHz, CDCl$_3$) δ 168.7, 161.4, 159.8, 149.3, 148.3, 139.1, 138.8, 133.8, 127.7, 126.7, 100.1, 100.0, 95.3, 95.3, 94.9, 93.9, 56.4, 56.3, 51.9, 51.7, 33.8, 23.9. LC/MS (m/z): 470.381 [M+H$^+$]; UPLC $t_R$ 1.96 min.

Methyl 2,4-bis(methoxymethoxy)-6-((1-(4-(trifluoromethyl)benzyl)-1H-pyrazol-5-yl)amino)benzoate (18r)

Inside a nitrogen glovebox were combined aryl bromide 17 (145 mg, 432 μmol), 1-([4-(trifluoromethyl)phenyl]methyl)-1H-pyrazol-5-amine hydrochloride (100 mg, 360 μmol), tris(dibenzylideneacetone)dipalladium (16.5 mg, 18.0 μmol). Xantphos (25.0 mg, 43.2, μmol) and sodium phenoxide (155 mg, 1.33 mmol). Dioxane (3.4 mL) was added to the mixture and the reaction vessel was capped and removed from the glovebox. After the reaction was irradiated at 170° C. for 2 h in a microwave reactor, the reaction was cooled to room temperature and diluted with ethyl acetate. The resulting mixture was washed three times with saturated Na$_2$CO$_3$ (aq.), brine, then dried with anhydrous Na$_2$SO$_4$. The salts were removed via gravity filtration and volatile materials were condensed in vacuo. Following silica gel flash chromatography (10% to 40% ethyl acetate in hexanes), TMT (30 mg) was added to the isolated residue; the mixture was suspended in toluene (3 mL) and stirred overnight. The suspension was filtered through a plug of Celite® and the filtrate was concentrated using a rotary evaporator to afford 66 mg of 18r (37% yield) as a yellow oil. $^1$H NMR (400 MHz, CDCl$_3$) δ 8.78 (s, 1H), 7.55 (d, J=1.9 Hz, 1H), 7.53 (d, J=8.1 Hz, 2H), 7.29 (d, J=8.0 Hz, 2H), 6.25 (d, J=2.3 Hz, 1H), 6.13 (d, J=1.9 Hz, 1H), 6.04 (d, J=2.3 Hz, 1H), 5.26 (s, 2H), 5.17 (s, 2H), 5.01 (s, 2H), 3.83 (s, 3H), 3.51 (s, 3H), 3.40 (s, 3H). $^{13}$C NMR (101 MHz, CDCl$_3$) δ 168.9, 161.5, 159.9, 149.2, 140.4, 140.4, 139.5, 139.1, 129.9 (q, $^2J_{C-F}$=32.6 Hz), 127.9, 125.6 (q, $^3J_{C-F}$=3.7 Hz), 124.0 (q, $^1J_{C-F}$=272.0 Hz), 100.4, 99.9, 95.4, 95.3, 94.8, 93.9, 56.4, 56.3, 51.9, 51.5. $^{19}$F NMR (376 MHz, CDCl$_3$) δ −62.6. LC/MS (m/z): 497.33 [M+H$^+$]; UPLC $t_R$ 1.88 min.

Methyl 2,4-bis(methoxymethoxy)-6-((1-methyl-3-phenyl-1H-pyrazol-5-yl)amino)benzoate (18s)

Synthesized using General Procedure D2 from 17 (50 mg, 150 μmol) and 10p (28 mg, 160 μmol). Following silica gel flash chromatography (10% to 35% MTBE in hexanes), TMT (21 mg) was added to the isolated residue; the mixture was suspended in toluene (3 mL) and stirred overnight. The suspension was filtered through a plug of Celite® and the filtrate was concentrated using a rotary evaporator to afford 55 mg of 18s (86% yield). $^1$H NMR (400 MHz, CDCl$_3$) δ 9.01 (s, 1H), 7.81-7.72 (m, 2H), 7.48-7.34 (m, 2H), 7.34-7.27 (m, 1H), 6.51-6.36 (m, 1H), 6.29 (d, J=2.3 Hz, 1H), 6.18 (d, J=2.2 Hz, 1H), 5.20 (s, 2H), 5.08 (s, 2H), 3.92 (s, 3H), 3.78 (s, 3H), 3.53 (s, 3H), 3.42 (s, 3H). $^{13}$C NMR (101 MHz, CDCl$_3$) δ 161.7, 160.1, 150.1, 149.4, 140.1, 133.6, 128.6, 127.6, 125.3, 99.8, 96.6, 95.3, 95.3, 94.9, 94.0, 56.5, 56.3, 52.0, 35.2. LC/MS (m/z): 429.23 [M+H$^+$]; UPLC $t_R$ 1.76 min.

Methyl 2-((1-(tert-butyl)-3-phenyl-1H-pyrazol-5-yl)amino)-4,6-bis(methoxymethoxy)benzoate (18t)

Synthesized using General Procedure D2 from 17 (69.4 mg, 207 μmol) and 10q (49.0 mg, 227 μmol) in dioxane (1.6 mL). Following silica gel flash chromatography (7% to 20% MTBE in hexanes), TMT (29 mg) was added to the isolated residue; the mixture was suspended in toluene (3 mL) and stirred overnight. The suspension was filtered through a plug of Celite® and the filtrate was concentrated using a rotary evaporator to afford 65.5 mg of 18t (68% yield). $^1$H NMR (400 MHz, CDCl$_3$) δ 8.91 (s, 1H), 7.83-7.73 (m, 2H), 7.47-7.35 (m, 2H), 7.33-7.22 (m, 1H), 6.47-6.38 (m, 1H), 6.28-6.19 (m, 2H), 5.19 (s, 2H), 5.05 (s, 2H), 3.91 (s, 3H), 3.54 (s, 3H), 3.40 (s, 3H), 1.68 (s, 9H). $^{13}$C NMR (101 MHz, CDCl$_3$) δ 169.3, 161.6, 160.0, 150.4, 147.8, 139.2, 134.1, 128.5, 127.3, 125.2, 100.0, 99.3, 95.4, 95.0, 94.7, 94.0, 59.8, 56.5, 56.3, 51.9, 29.8. LC/MS (m/z): 471.263 [M+H$^+$]; UPLC $t_R$ 2.15 min.

Methyl 2-((1-cyclohexyl-3-phenyl-1H-pyrazol-5-yl)amino)-4,6-bis(methoxymethoxy)benzoate (18u)

Synthesized using General Procedure D2 from 17 (100 mg, 298 μmol) and 10r (79.2 mg, 323 μmol). Following silica gel flash chromatography (8% to 25% MTBE in hexanes), TMT (44 mg) was added to the isolated residue; the mixture was suspended in toluene (3 mL) and stirred overnight. The suspension was filtered through a plug of Celite® and the filtrate was concentrated using a rotary evaporator to afford 111 mg of 18u (75% yield). $^1$H NMR (400 MHz, CDCl$_3$) δ 8.89 (s, 1H), 7.84-7.75 (m, 2H), 7.38 (t, J=7.7 Hz, 2H), 7.30-7.27 (m, 1H), 6.40-6.33 (m, 1H), 6.26 (d, J=2.3 Hz, 1H), 6.17 (d, J=2.3 Hz, 1H), 5.20 (s, 2H), 5.05 (s, 2H), 4.07 (td, J=11.2, 5.5 Hz, 1H), 3.92 (s, 3H), 3.54 (s, 3H), 3.40 (s, 3H), 2.12-1.87 (m, 6H), 1.74-1.66 (m, 1H), 1.47-1.16 (m, 3H).

Methyl 2-((1-isobutyl-3-phenyl-1H-pyrazol-5-yl)amino)-4,6-bis(methoxymethoxy)benzoate (18v)

Synthesized using General Procedure D2 from 17 (100 mg, 298 µmol) and 10s (66.4 mg, 308 µmol). Following silica gel flash chromatography (7% to 20% ethyl acetate in hexanes), TMT (42 mg) was added to the isolated residue; the mixture was suspended in toluene (3 mL) and stirred overnight. The suspension was filtered through a plug of Celite® and the filtrate was concentrated using a rotary evaporator to afford 118 mg of 18v (84% yield). $^1$H NMR (400 MHz, CDCl$_3$) δ 9.05 (s, 1H), 7.84-7.78 (m, 2H), 7.40 (t, J=7.6 Hz, 2H), 7.30 (t, J=7.3 Hz, 1H), 6.40 (s, 1H), 6.29 (d, J=2.1 Hz, 2H), 5.20 (s, 2H), 5.08 (s, 2H), 3.92 (s, 3H), 3.88 (d, J=7.4 Hz, 2H), 3.54 (s, 3H), 3.42 (s, 3H), 2.40-2.21 (m, 1H), 0.94 (d, J=6.7 Hz, 6H). $^{13}$C NMR (101 MHz, CDCl$_3$) δ 169.2, 161.6, 160.0, 150.0, 149.6, 140.0, 133.8, 128.6, 127.5, 125.4, 99.7, 96.4, 95.3, 95.2, 95.0, 94.0, 56.5, 56.3, 55.2, 52.0, 29.5, 20.0. LC/MS (m/z): 471.307 [M+H$^+$]; UPLC $t_R$ 2.05 min.

Methyl 2-((3-isopropyl-1-methyl-1H-pyrazol-5-yl)amino)-4,6-bis(methoxymethoxy)benzoate (18w)

Synthesized using General Procedure D2 from 17 (150 mg, 448 µmol) an amine 10t (68.5 mg, 492 µmol). Following silica gel flash chromatography (15% to 45% ethyl acetate in hexanes), TMT (55 mg) was added to the isolated residue; the mixture was suspended in toluene (3 mL) and stirred overnight. The suspension was filtered through a plug of Celite® and the filtrate was concentrated using a rotary evaporator to afford 129 mg of 18w (78% yield) as a yellow oil. $^1$H NMR (400 MHz, CDCl$_3$) δ 6.26 (d, J=2.3 Hz, 1H), 6.14 (d, J=2.2 Hz, 1H), 5.89 (s, 1H), 5.18 (s, 2H), 5.08 (s, 2H), 3.89 (d, J=0.9 Hz, 3H), 3.66 (s, 3H), 3.52 (d, J=0.6 Hz, 3H), 3.43 (d, J=0.6 Hz, 3H), 2.92 (p, J=6.9 Hz, 1H), 1.26 (d, J=7.0 Hz, 6H). $^{13}$C NMR (101 MHz, CDCl$_3$) δ 169.1, 161.6, 159.9, 158.1, 149.5, 139.1, 99.7, 95.8, 95.3, 95.1, 94.9, 94.0, 56.4, 56.2, 51.9, 34.6, 28.3, 22.8. LC/MS (m/z): 395.355 [M+H$^+$]; UPLC $t_R$ 1.68 min.

Methyl 2-((3-cyclohexyl-1-methyl-1H-pyrazol-5-yl)amino)-4,6-bis(methoxymethoxy)benzoate (18x)

Synthesized using General Procedure D2 from 17 (150 mg, 448 µmol) an amine 10u (88.3 mg, 492 µmol). Following silica gel flash chromatography (15% to 40% ethyl acetate in hexanes), TMT (42 mg) was added to the isolated residue; the mixture was suspended in toluene (3 mL) and stirred overnight. The suspension was filtered through a plug of Celite® and the filtrate was concentrated using a rotary evaporator to afford 108 mg of 18x (56% yield) as a clear yellow oil. $^1$H NMR (400 MHz, CDCl$_3$) δ 8.87 (s, 1H), 6.26 (d, J=2.3 Hz, 1H), 6.12 (d, J=2.3 Hz, 1H), 5.87 (s, 1H), 5.18 (s, 2H), 5.07 (s, 2H), 3.89 (s, 3H), 3.66 (s, 3H), 3.52 (s, 3H), 3.43 (s, 3H), 2.64-2.50 (m, 1H), 2.05-1.90 (m, 2H), 1.86-1.75 (m, 2H), 1.75-1.62 (m, 1H), 1.50-1.15 (m, 4H). $^{13}$C NMR (101 MHz, CDCl$_3$) δ 169.0, 161.6, 159.9, 157.3, 149.5, 139.0, 99.7, 96.1, 95.3, 95.1, 94.9, 94.0, 56.4, 56.2, 51.9, 38.1, 34.6, 33.2, 26.4, 26.1. LC/MS (m/z): 435.405 [M+H$^+$]; UPLC $t_R$ 1.97 min.

Methyl 2,4-bis(methoxymethoxy)-6-((1-methyl-3-(o-tolyl)-1H-pyrazol-5-yl)amino)benzoate (18y)

Synthesized using General Procedure D2 from 17 (150 mg, 448 µmol) and 10v (92.2 mg, 492 µmol). Following silica gel flash chromatography (10% to 30% ethyl acetate in hexanes), TMT (48 mg) was added to the isolated residue; the mixture was suspended in toluene (3 mL) and stirred overnight. The suspension was filtered through a plug of Celite® and the filtrate was concentrated using a rotary evaporator to afford 139 mg of 18y (70% yield) as a clear yellow oil. $^1$H NMR (400 MHz, CDCl$_3$) δ 7.59 (s, 1H), 7.27-7.21 (m, 2H), 6.30-6.16 (m, 3H), 5.20 (s, 2H), 5.08 (s, 2H), 3.92 (s, 3H), 3.79 (s, 3H), 3.53 (s, 3H), 3.42 (s, 3H), 2.48 (s, 3H). $^{13}$C NMR (101 MHz, CDCl$_3$) δ 169.2, 161.7, 160.0, 150.4, 149.5, 139.2, 135.8, 133.5, 130.7, 129.0, 127.6, 125.8, 99.7, 95.3, 95.3, 94.7, 94.0, 56.5, 56.3, 52.0, 35.1, 21.1. LC/MS (m/z): 443.388 [M+H$^+$]; UPLC $t_R$ 1.93 min.

Methyl 2,4-bis(methoxymethoxy)-6-((1-methyl-3-(m-tolyl)-1H-pyrazol-5-yl)amino)benzoate (18z)

Synthesized using General Procedure D2 from 17 (170 mg, 570 µmol) and 10w (104 mg, 558 µmol). Following silica gel flash chromatography (10% to 30% ethyl acetate in hexanes), TMT (66 mg) was added to the isolated residue; the mixture was suspended in toluene (3 mL) and stirred overnight. The suspension was filtered through a plug of Celite® and the filtrate was concentrated using a rotary evaporator to afford 155 mg of 18z (69% yield) as a yellow oil. $^1$H NMR (400 MHz, CDCl$_3$) δ 8.99 (s, 1H), 7.63 (s, 1H), 7.55 (d, J=7.8 Hz, 1H), 7.29 (d, J=7.7 Hz, 1H), 7.12 (d, J=7.6 Hz, 1H), 6.42-6.32 (m, 1H), 6.29 (d, J=2.3 Hz, 1H), 6.17 (d, J=2.3 Hz, 1H), 5.20 (s, 2H), 5.08 (s, 2H), 3.92 (s, 3H), 3.77 (s, 3H), 3.53 (s, 3H), 3.42 (s, 3H), 2.39 (s, 3H). $^{13}$C NMR (101 MHz, CDCl$_3$) δ 169.2, 161.7, 160.1, 150.2, 149.5, 140.1, 138.2, 133.5, 128.5, 128.4, 125.8, 122.5, 99.8, 96.7, 95.3, 95.2, 94.9, 94.0, 56.5, 56.3, 52.0, 35.1, 21.5.

Methyl 2,4-bis(methoxymethoxy)-6-((3-(3-methoxyphenyl)-1-methyl-1H-pyrazol-5-yl)amino)benzoate (18aa)

Synthesized using General Procedure D2 from 17 (150 mg, 448 µmol) and 10x (100 mg, 492 µmol). Following silica gel flash chromatography (10% to 40% ethyl acetate in hexanes), TMT (64 mg) was added to the isolated residue; the mixture was suspended in toluene (3 mL) and stirred overnight. The suspension was filtered through a plug of Celite® and the filtrate was concentrated using a rotary evaporator to afford 161 mg of 18aa (79% yield) as a yellow oil. $^1$H NMR (400 MHz, CDCl$_3$) δ 9.02 (s, 1H), 7.39-7.29 (m, 3H), 6.86 (dd, J=7.8, 2.2 Hz, 1H), 6.39 (s, 1H), 6.30 (dd, J=2.3, 1.0 Hz, 1H), 6.18 (t, J=2.4 Hz, 1H), 5.20 (s, 2H), 5.08 (s, 2H), 3.92 (s, 3H), 3.87 (s, 3H), 3.78 (d, J=2.1 Hz, 3H), 3.53 (s, 3H), 3.43 (s, 3H). 13C NMR (101 MHz, CDCl$_3$) δ 169.2, 161.7, 160.1, 159.9, 149.9, 149.4, 140.1, 135.0, 129.6, 117.9, 113.7, 110.2, 99.8, 96.8, 95.3, 95.2, 94.9, 93.9, 56.5, 56.3, 55.3, 52.0, 35.2. LC/MS (m/z): 459.399 [M+H$^+$]; UPLC $t_R$ 1.85 min.

Methyl 2,4-bis(methoxymethoxy)-6-((1-methyl-3-(3-(trifluoromethyl)phenyl)-1H-pyrazol-5-yl)amino)benzoate (18ab)

Synthesized using General Procedure D2 from 17 (150 mg, 448 µmol) and 10y (119 mg, 492 µmol). Following silica gel flash chromatography (10% to 30% ethyl acetate in hexanes), TMT (65 mg) was added to the isolated residue; the mixture was suspended in toluene (3 mL) and stirred overnight. The suspension was filtered through a plug of Celite® and the filtrate was concentrated using a rotary evaporator to afford 165 mg of 18ab (74% yield) as a yellow oil. $^1$H NMR (400 MHz, CDCl$_3$) δ 9.09 (s, 1H), 8.04 (s, 1H), 7.95 (d, J=7.5 Hz, 1H), 7.58-7.43 (m, 2H), 6.47-6.40 (m, 1H), 6.31 (d, J=2.3 Hz, 1H), 6.20 (d, J=2.3 Hz, 1H), 5.20 (s, 2H), 5.09 (s, 2H), 3.92 (s, 3H), 3.79 (s, 3H), 3.53 (s, 3H), 3.43 (s, 3H). $^{13}$C NMR (101 MHz, CDCl$_3$) δ 169.2, 161.7, 160.1, 149.2, 148.6, 140.6, 134.5, 130.9 (q, $^2J_{C-F}$=32.2 Hz), 129.0, 128.4, 124.2 (q, $^1J_{C-F}$=272.4 Hz), 124.1 (q, $^3J_{C-F}$=3.8 Hz), 122.0 (q, $^3J_{C-F}$=3.9 Hz), 99.8, 96.5, 95.4, 95.3, 94.9, 94.0, 56.4, 56.3, 52.0, 35.2. $^{19}$F NMR (376 MHz, CDCl$_3$) δ −62.7. LC/MS (m/z): 497.286 [M+H$^+$]; UPLC $t_R$ 2.09 min.

Methyl 2,4-bis(methoxymethoxy)-6-((1-methyl-3-(p-tolyl)-1H-pyrazol-5-yl)amino)benzoate (18ac)

Synthesized using General Procedure D2 from 17 (150 mg, 448 μmol) and 10z (92.2 mg, 492 μmol). Following silica gel flash chromatography (10% to 30% ethyl acetate in hexanes), TMT (59 mg) was added to the isolated residue; the mixture was suspended in toluene (3 mL) and stirred overnight. The suspension was filtered through a plug of Celite® and the filtrate was concentrated using a rotary evaporator to afford 160 mg of 18ac (81% yield) as a yellow oil. $^1$H NMR (400 MHz, CDCl$_3$) δ 8.98 (s, 1H), 7.66 (d, J=7.9 Hz, 2H), 7.20 (d, J=7.9 Hz, 2H), 6.36 (s, 1H), 6.29 (d, J=2.2 Hz, 1H), 6.18 (d, J=2.3 Hz, 1H), 5.19 (s, 2H), 5.08 (s, 2H), 3.91 (d, J=0.9 Hz, 3H), 3.76 (s, 3H), 3.53 (s, 3H), 3.42 (s, 3H), 2.37 (s, 3H). $^{13}$C NMR (101 MHz, CDCl$_3$) δ 169.2, 161.7, 160.1, 150.2, 149.5, 140.0, 137.3, 130.8, 129.3, 125.2, 99.8, 96.4, 95.3, 95.2, 94.9, 94.0, 56.5, 56.3, 52.0, 35.1, 21.2. LC/MS (m/z): 443.388 [M+H$^+$]; UPLC $t_R$ 1.94 min.

Methyl 2,4-bis(methoxymethoxy)-6-((3-(4-methoxyphenyl)-1-methyl-1H-pyrazol-5-yl)amino)benzoate (18ad)

Synthesized using General Procedure D2 from 17 (150 mg, 448 μmol) and 10aa (100 mg, 492 μmol). Following silica gel flash chromatography (15% to 45% ethyl acetate in hexanes), TMT (57 mg) was added to the isolated residue; the mixture was suspended in toluene (3 mL) and stirred overnight. The suspension was filtered through a plug of Celite® and the filtrate was concentrated using a rotary evaporator to afford 161 mg of 18ad (78% yield) as a yellow oil. $^1$H NMR (400 MHz, CDCl$_3$) δ 8.98 (s, 1H), 7.70 (d, J=8.6 Hz, 2H), 6.93 (d, J=8.6 Hz, 2H), 6.32 (s, 1H), 6.29 (d, J=2.3 Hz, 1H), 6.18 (d, J=2.3 Hz, 1H), 5.19 (s, 2H), 5.08 (s, 2H), 3.92 (s, 3H), 3.84 (s, 3H), 3.75 (s, 3H), 3.53 (s, 3H), 3.42 (s, 3H). $^{13}$C NMR (101 MHz, CDCl$_3$) δ 169.1, 161.7, 160.1, 159.3, 150.0, 149.5, 140.0, 126.5, 126.5, 114.0, 99.7, 96.1, 95.3, 95.2, 94.9, 94.0, 56.5, 56.3, 55.3, 52.0, 35.0. LC/MS (m/z): 459.354 [M+H$^+$]; UPLC $t_R$ 1.80 min.

Methyl 2,4-bis(methoxymethoxy)-6-((1-methyl-3-(4-(trifluoromethyl)phenyl)-1H-pyrazol-5-yl)amino)benzoate (18ae)

Synthesized using General Procedure D2 from 17 (150 mg, 448 μmol) and 10ab (119 mg, 492 μmol). Following silica gel flash chromatography (10% to 30% ethyl acetate in hexanes), TMT (60 mg) was added to the isolated residue; the mixture was suspended in toluene (3 mL) and stirred overnight. The suspension was filtered through a plug of Celite® and the filtrate was concentrated using a rotary evaporator to afford 180 mg of 18ae (81% yield) as a clear oil. $^1$H NMR (400 MHz, CDCl$_3$) δ 9.09 (s, 1H), 7.88 (d, J=8.1 Hz, 2H), 7.64 (d, J=8.1 Hz, 2H), 6.45 (s, 1H), 6.31 (d, J=2.3 Hz, 1H), 6.19 (d, J=2.2 Hz, 1H), 5.20 (s, 2H), 5.09 (s, 2H), 3.92 (s, 3H), 3.79 (s, 3H), 3.53 (s, 3H), 3.43 (s, 3H). $^{13}$C NMR (101 MHz, CDCl$_3$) δ 169.2, 161.7, 160.1, 149.2, 148.6, 140.5, 137.0, 137.0, 129.3 (q, $^2J_{C-F}$=32.3 Hz), 128.8, 125.53 (q, $^3J_{C-F}$=3.8 Hz), 124.3 (q, $^1J_{C-F}$=271.8 Hz), 123.0, 120.3, 99.8, 96.8, 95.4, 95.3, 94.9, 94.0, 56.5, 56.3, 52.0, 35.3. $^{19}$F NMR (376 MHz, CDCl$_3$) δ −62.4. LC/MS (m/z): 497.33 [M+H$^+$]; UPLC $t_R$ 2.06 min.

Methyl 2-((3-(4-(tert-butyl)phenyl)-1-methyl-1H-pyrazol-5-yl)amino)-4,6-bis(methoxymethoxy)benzoate (18af)

Synthesized using General Procedure D2 from 17 (150 mg, 448 μmol) and 10ac (113 mg, 492 μmol). Following silica gel flash chromatography (10% to 30% ethyl acetate in hexanes), TMT (58 mg) was added to the isolated residue; the mixture was suspended in toluene (3 mL) and stirred overnight. The suspension was filtered through a plug of Celite® and the filtrate was concentrated using a rotary evaporator to afford 174 mg of 18af (80% yield) as a clear oil. $^1$H NMR (400 MHz, CDCl$_3$) δ 8.98 (s, 1H), 7.70 (d, J=8.2 Hz, 2H), 7.42 (d, J=8.2 Hz, 2H), 6.37 (s, 1H), 6.28 (d, J=2.2 Hz, 1H), 5.19 (s, 2H), 5.07 (s, 2H), 3.92 (s, 2H), 3.76 (s, 3H), 3.53 (s, 3H), 3.42 (s, 3H), 1.34 (s, 9H). $^{13}$C NMR (101 MHz, CDCl$_3$) δ 169.2, 161.7, 160.0, 150.6, 150.1, 149.5, 140.0, 130.8, 129.0, 128.2, 125.5, 125.3, 125.0, 99.7, 96.5, 95.3, 95.2, 94.9, 94.0, 56.5, 56.3, 52.0, 35.1, 34.6, 31.3. LC/MS (m/z): 485.377 [M+H$^+$]; UPLC $t_R$ 2.20 min.

Methyl 2,4-bis(methoxymethoxy)-6-((1-methyl-3-(4-(trifluoromethoxy)phenyl)-1H-pyrazol-5-yl)amino)benzoate (18ag)

Synthesized using General Procedure D2 from 17 (150 mg, 448 μmol) and 10ad (127 mg, 492 μmol). Following silica gel flash chromatography (12% to 33% ethyl acetate in hexanes), TMT (66 mg) was added to the isolated residue; the mixture was suspended in toluene (3 mL) and stirred overnight. The suspension was filtered through a plug of Celite® and the filtrate was concentrated using a rotary evaporator to afford 183 mg of 18ag (80% yield) as a white/yellow solid. $^1$H NMR (400 MHz, CDCl$_3$) δ 9.04 (s, 1H), 7.83-7.71 (m, 2H), 7.25-7.19 (m, 2H), 6.41-6.34 (m, 1H), 6.30 (d, J=2.3 Hz, 1H), 6.17 (d, J=2.2 Hz, 1H), 5.20 (s, 2H), 5.08 (s, 2H), 3.92 (s, 3H), 3.77 (s, 3H), 3.53 (s, 3H), 3.43 (s, 3H). $^{13}$C NMR (101 MHz, CDCl$_3$) δ 169.2, 161.7, 160.1, 149.3, 148.8, 140.4, 132.5, 126.6, 121.1, 120.5 (q, J=256.9 Hz), 99.8, 96.5, 95.3, 95.3, 94.9, 94.0, 56.4, 56.3, 52.0, 35.2. $^{19}$F NMR (376 MHz, CDCl$_3$) δ −57.8. LC/MS (m/z): 513.296 [M+H$^+$]; UPLC $t_R$ 2.04 min.

2-((1-(4-Methoxybenzyl)-3-methyl-1H-pyrazol-5-yl)amino)-4-(methoxymethoxy)-6-((methoxymethyl)peroxy)benzoic acid (19a)

Ester 18a (105 mg, 0.222 mmol) was hydrolyzed using General Procedure E to afford 95.1 mg of crude acid 19a (93% crude yield).

2-((1-(4-Methoxybenzyl)-3-phenyl-1H-pyrazol-5-yl)amino)-4-(methoxymethoxy)-6-((methoxymethyl)peroxy)benzoic acid (19b)

Ester 18b (267 mg, 500 μmol) was hydrolyzed using General Procedure E to afford 235 mg of crude acid 19b (90% crude yield).

2-((3-Ethyl-1-(4-methoxybenzyl)-1H-pyrazol-5-yl)amino)-4,6-bis(methoxymethoxy)benzoic acid (19c)

Ester 18c (123 mg, 253 μmol) was hydrolyzed using General Procedure E to afford 112 mg of crude acid 19c (94% crude yield).

2-((3-Isopropyl-1-(4-methoxybenzyl)-1H-pyrazol-5-yl)amino)-4,6-bis(methoxymethoxy)benzoic acid (19d)

Ester 18d (112 mg, 224 μmol) was hydrolyzed using General Procedure E to afford 111 mg of crude acid 19d (102% crude yield).

2-((3-Cyclopropyl-1-(4-methoxybenzyl)-1H-pyrazol-5-yl)amino)-4,6-bis(methoxymethoxy)benzoic acid (19e)

Ester 18e (132 mg, 265 μmol) was hydrolyzed using General Procedure E to afford 118 mg of crude acid 19e (92% crude yield).

2-((3-Cyclopentyl-1-(4-methoxybenzyl)-1H-pyrazol-5-yl)amino)-4,6-bis(methoxymethoxy)benzoic acid (19f)

Ester 18f (90.1 mg, 171 μmol) was hydrolyzed using General Procedure E to afford 90 mg of crude acid 19f (103% crude yield).

2-((3-(Furan-3-yl)-1-(4-methoxybenzyl)-1H-pyrazol-5-yl)amino)-4,6-bis(methoxymethoxy)benzoic acid (19g)

Ester 18g (110 mg, 210 μmol) was hydrolyzed using General Procedure E to afford 104 mg of crude acid 19g (97% crude yield).

2,4-Bis(methoxymethoxy)-6-((1-methyl-1H-pyrazol-5-yl)amino)benzoic acid (19h)

Ester 18h (79.8 mg, 227 μmol) was hydrolyzed using General Procedure E to afford 27.6 mg of crude acid 19h (36% crude yield).

2-((1-Isopropyl-1H-pyrazol-5-yl)amino)-4,6-bis(methoxymethoxy)benzoic acid (19i)

Ester 18i (124 mg, 327 μmol) was hydrolyzed using General Procedure E to afford 98.8 mg of crude acid 19i (83% crude yield).

2-((1-Isobutyl-1H-pyrazol-5-yl)amino)-4,6-bis(methoxymethoxy)benzoic acid (19j)

Ester 18j (135 mg, 343 μmol) was hydrolyzed using General Procedure E to afford 119 mg of crude acid 19j (91% crude yield).

2-((1-(Cyclohexylmethyl)-1H-pyrazol-5-yl)amino)-4,6-bis(methoxymethoxy)benzoic acid (19k)

Ester 18k (125 mg, 288 μmol) was hydrolyzed using General Procedure E to afford 105 mg of crude acid 19k (87% crude yield).

2,4-Bis(methoxymethoxy)-6-((1-phenyl-1H-pyrazol-5-yl)amino)benzoic acid (19l)

Ester 18l (131 mg, 317 μmol) was hydrolyzed using General Procedure E to afford 114 mg of crude acid 19l (90% crude yield).

2-((1-Cyclohexyl-1H-pyrazol-5-yl)amino)-4,6-bis(methoxymethoxy)benzoic acid (19m)

Ester 18m (152 mg, 362 μmol) was hydrolyzed using General Procedure E to afford 152 mg of crude acid 19m (103% crude yield).

2-((1-Benzyl-1H-pyrazol-5-yl)amino)-4,6-bis(methoxymethoxy)benzoic acid (19n)

Ester 18n (115 mg, 269 μmol) was hydrolyzed using General Procedure E to afford 106 mg of crude acid 19n (95% crude yield).

2,4-Bis(methoxymethoxy)-6-((1-(pyridin-3-ylmethyl)-1H-pyrazol-5-yl)amino)benzoic acid (19)

Ester 18o (135 mg, 315 μmol) was hydrolyzed using General Procedure E to afford 90.1 mg of crude acid 19o (69% crude yield).

2-((1-(Furan-2-ylmethyl)-1H-pyrazol-5-yl)amino)-4,6-bis(methoxymethoxy)benzoic acid (19p)

Ester 18p (145 mg, 347 μmol) was hydrolyzed using General Procedure E to afford 128 mg of crude acid 19p (91% crude yield).

2-((1-(4-Isopropylbenzyl)-1H-pyrazol-5-yl)amino)-4,6-bis(methoxymethoxy)benzoic acid (19q)

Ester 18q (55.1 mg, 117 μmol) was hydrolyzed using General Procedure E to afford 47.9 mg of crude acid 19q (90% crude yield).

2,4-Bis(methoxymethoxy)-6-((1-(4-(trifluoromethyl)benzyl)-1H-pyrazol-5-yl)amino)benzoic acid (19r)

Ester 18r (66 mg, 133 μmol) was hydrolyzed using General Procedure E to afford 57 mg of crude acid 19r (89% crude yield).

2,4-Bis(methoxymethoxy)-6-((1-methyl-3-phenyl-1H-pyrazol-5-yl)amino)benzoic acid (19s)

Ester 18s (65.7 mg, 154 μmol) was hydrolyzed using General Procedure E to afford 64.1 mg of crude acid 19s (101% crude yield).

2-((1-(tert-Butyl)-3-phenyl-1H-pyrazol-5-yl)amino)-4,6-bis(methoxymethoxy)benzoic acid (19t)

Ester 18t (65.5 mg, 140 μmol) was hydrolyzed using General Procedure E to afford 62.2 mg of crude acid 19t (98% crude yield).

2-((1-Cyclohexyl-3-phenyl-1H-pyrazol-5-yl)amino)-4,6-bis(methoxymethoxy)benzoic acid (19u)

Ester 18u (111 mg, 224 µmol) was hydrolyzed using General Procedure E to afford 104 mg of crude acid 19u (96% crude yield).

2-((1-Isobutyl-3-phenyl-1H-pyrazol-5-yl)amino)-4,6-bis(methoxymethoxy)benzoic acid (19v)

Ester 18v (118 mg, 251 µmol) was hydrolyzed using General Procedure E to afford 112 mg of crude acid 19v (98% crude yield).

2-((3-Isopropyl-1-methyl-1H-pyrazol-5-yl)amino)-4,6-bis(methoxymethoxy)benzoic acid (19w)

Ester 18w (124 mg, 316 µmol) was hydrolyzed using General Procedure E to afford 124 mg of crude acid 19w (104% crude yield).

2-((3-Cyclohexyl-1-methyl-1H-pyrazol-5-yl)amino)-4,6-bis(methoxymethoxy)benzoic acid (19x)

Ester 18x (105 mg, 242 µmol) was hydrolyzed using General Procedure E to afford 102 mg of crude acid 19x (101% crude yield).

2,4-Bis(methoxymethoxy)-6-((1-methyl-3-(o-tolyl)-1H-pyrazol-5-yl)amino)benzoic acid (19y)

Ester 18y (138 mg, 313 µmol) was hydrolyzed using General Procedure E to afford 133 mg of crude acid 19y (100% crude yield).

2,4-Bis(methoxymethoxy)-6-((1-methyl-3-(m-tolyl)-1H-pyrazol-5-yl)amino)benzoic acid (19z)

Ester 18z (154 mg, 349 µmol) was hydrolyzed using General Procedure E to afford 166 mg of crude acid 19z (112% crude yield).

2,4-Bis(methoxymethoxy)-6-((3-(3-methoxyphenyl)-1-methyl-1H-pyrazol-5-yl)amino)benzoic acid (19aa)

Ester 18aa (161 mg, 352 µmol) was hydrolyzed using General Procedure E to afford 142 mg of crude acid 19aa (91% crude yield).

2,4-Bis(methoxymethoxy)-6-((1-methyl-3-(3-(trifluoromethyl)phenyl)-1H-pyrazol-5-yl)amino)benzoic acid (19ab)

Ester 18ab (161 mg, 325 µmol) was hydrolyzed using General Procedure E to afford 152 mg of crude acid 19ab (97% crude yield).

2,4-Bis(methoxymethoxy)-6-((1-methyl-3-(p-tolyl)-1H-pyrazol-5-yl)amino)benzoic acid (19ac)

Ester 18ac (146 mg, 331 µmol) was hydrolyzed using General Procedure E to afford 142 mg of crude acid 19ac (100% crude yield).

2,4-Bis(methoxymethoxy)-6-((3-(4-methoxyphenyl)-1-methyl-1H-pyrazol-5-yl)amino)benzoic acid (19ad)

Ester 18ad (155 mg, 339 µmol) was hydrolyzed using General Procedure E to afford 144 mg of crude acid (96% crude yield).

2,4-Bis(methoxymethoxy)-6-((1-methyl-3-(4-(trifluoromethyl)phenyl)-1H-pyrazol-5-yl)amino)benzoic acid (19ae)

Ester 18ae (174 mg, 351 µmol) was hydrolyzed using General Procedure E to afford 174 mg of crude acid 19ae (105% crude yield).

2-((3-(4-(tert-Butyl)phenyl)-1-methyl-1H-pyrazol-5-yl)amino)-4,6-bis(methoxymethoxy)benzoic acid (19af)

Ester 18af (167 mg, 345 µmol) was hydrolyzed using General Procedure E to afford 138 mg of crude acid 19af (85% crude yield).

2,4-Bis(methoxymethoxy)-6-((1-methyl-3-(4-(trifluoromethoxy)phenyl)-1H-pyrazol-5-yl)amino)benzoic acid (19ag)

Ester 18ag (175 mg, 342 µmol) was hydrolyzed using General Procedure E to afford 156 mg of crude acid 19ag (92% crude yield).

4-(2,3-dihydro-1H-isoindole-2-carbonyl)-5-((1-((4-methoxyphenyl)methyl)-3-methyl-1H-pyrazol-5-yl)amino)benzene-1,3-diol (20)

Amide 14a (38 mg, 68 µmol) was deprotected using General Procedure F to afford 24 mg of 20 (74% yield). $^1$H NMR (400 MHz, (CD$_3$)$_2$SO) δ 9.66 (s, 1H), 9.31 (s, 1H), 7.45-7.13 (m, 3H), 7.13-6.92 (m, 3H), 6.68 (d, J=8.5 Hz, 1H), 5.85 (d, J=2.1 Hz, 1H), 5.78 (s, 1H), 5.71 (d, J=2.0 Hz, 1H), 4.89 (s, 2H), 4.72 (s, 2H), 3.62 (s, 3H), 2.03 (s, 3H). 13C NMR (126 MHz, (CD$_3$)$_2$SO) δ 166.6, 159.2, 158.4, 155.4, 146.0, 143.8, 143.7, 140.1, 129.3, 128.8, 127.2, 122.8, 113.6, 103.7, 98.0, 94.3, 92.8, 55.0, 50.0, 40.4, 13.9. LC/MS (m/z): 471.207 [M+H$^+$]; UPLC $t_R$ 1.31 min.

4-(2,3-dihydro-1H-isoindole-2-carbonyl)-5-((1-((4-methoxyphenyl)methyl)-3-phenyl-1H-pyrazol-5-yl)amino)benzene-1,3-diol (21)

Amide 14b was deprotected using General Procedure F (52.6 mg, 84.7 µmol) to afford 25.9 mg of 21 (57% yield). $^1$H NMR (400 MHz, CD$_3$OD) δ 7.75-7.66 (m, 2H), 7.42-7.32 (m, 3H), 7.32-7.21 (m, 5H), 7.06 (d, J=8.7 Hz, 2H), 6.65 (d, J=8.7 Hz, 2H), 6.46 (s, 1H), 5.93 (dd, J=14.2, 2.1 Hz, 2H), 5.17 (s, 2H), 4.96-4.59 (m, 4H), 3.63 (s, 3H). $^{13}$C NMR (126 MHz, (CD$_3$)$_2$SO) δ 166.6, 159.4, 158.5, 155.6, 148.7, 143.6, 141.2, 136.6 (br), 133.5, 129.0, 128.8, 128.5, 127.4, 127.3, 124.8, 122.8, 113.7, 104.0, 96.1, 94.6, 93.0, 55.0, 50.6, 40.4. LC/MS (m/z): 533.257 [M+H$^+$]; UPLC $t_R$ 1.63 min.

5-((1-((4-Methoxyphenyl)methyl)-3-methyl-1H-pyrazol-5-yl)amino)-4-(5H,6H,7H-pyrrolo[3,4-b]pyridine-6-carbonyl)benzene-1,3-diol (22)

Crude acid 19a (31.7 mg, 69.3 µmol) was coupled with 6,7-dihydro-5H-pyrrolo[3,4-b]pyridine dihydrochloride (20.1 mg, 104 µmol), and triethylamine (72 µL, 520 µmol) using General Procedure G to give 21.8 mg of MOM-protected intermediate (56% yield) after purification via automated flash chromatography (10% to 50% acetone in CH$_2$Cl$_2$). $^1$H NMR (400 MHz, CDCl$_3$) δ 8.56-8.42 (m, 1H), 7.67-7.43 (m, 1H), 7.21 (ddd, J=13.1, 7.7, 4.9 Hz, 1H), 7.06 (ddd, J=9.9, 6.0, 2.6 Hz, 2H), 6.70-6.57 (m, 2H), 6.45 (d, J=2.5 Hz, 1H), 6.39 (dd, J=7.5, 2.1 Hz, 1H), 6.23 (dd, J=13.2, 2.1 Hz, 1H), 5.84 (s, 1H), 5.30-4.72 (m, 9H), 4.61-4.41 (m, 1H), 3.68 (d, J=2.8 Hz, 3H), 3.44 (dd, J=4.3, 2.0 Hz, 6H), 2.23 (d, J=3.1 Hz, 3H). $^{13}$C NMR (101 MHz, CDCl$_3$) δ 167.2, 167.2, 159.9, 159.0, 158.9, 157.6, 157.2, 155.4, 155.4, 149.4, 149.3, 147.6, 147.6, 143.9, 143.8, 139.4, 139.2, 131.0, 130.6, 130.3, 129.9, 128.8, 128.6, 128.5, 122.5, 122.4, 113.9, 113.8, 107.1, 98.5, 98.5, 96.5, 95.4, 95.3, 95.1, 95.1, 94.3, 94.2, 56.6, 56.5, 56.3, 56.2, 55.2, 55.1, 53.8, 53.4, 52.6, 51.4, 51.3, 51.3, 50.5, 29.3, 14.2, 14.2. LC/MS (m/z): 560.225 [M+H$^+$]; UPLC $t_R$ 1.41 min The MOM-protected intermediate (21.8 mg, 39.0 µmol) was deprotected using General Procedure F to afford 3.0 mg of 22 (16% yield) after purification using mass-guided preparative HPLC. $^1$H NMR (400 MHz, CD$_3$OD) δ 8.44 (d, J=5.0 Hz, 1H), 7.76 (s, 1H), 7.40-7.30 (m, 1H), 7.00 (d, J=8.7 Hz, 2H), 6.66 (d, J=8.7 Hz, 2H), 5.96-5.85 (m, 2H), 5.83 (d, J=2.1 Hz, 1H), 5.04 (s, 2H), 4.96-4.43 (m, 4H), 3.65 (s, 3H), 2.13 (s, 3H). LC/MS (m/z): 472.234 [M+H$^+$]; UPLC $t_R$ 1.12 min.

5-((1-((4-Methoxyphenyl)methyl)-3-phenyl-1H-pyrazol-5-yl)amino)-4-(5H,6H,7H-pyrrolo[3,4-b]pyridine-6-carbonyl)benzene-1,3-diol (23)

Acid 19b (31.7 mg, 69.3 µmol) was coupled with 6,7-dihydro-H-pyrrolo[3,4-b]pyridine dihydrochloride (20.1 mg, 104 µmol), and triethylamine (72 µL, 520 µmol) using General Procedure G to give 43.2 mg of MOM-protected intermediate (77% yield) after purification via automated flash chromatography (4% to 40% acetone in hexanes and 0% to 3% methanol in CH$_2$Cl$_2$). $^1$H NMR (400 MHz, CDCl$_3$) δ 8.57-8.40 (m, 1H), 7.78 (dq, J=6.4, 1.4 Hz, 2H), 7.66-7.46 (m, 1H), 7.42-7.34 (m, 2H), 7.33-7.18 (m, 2H), 7.18-7.06 (m, 2H), 6.73-6.58 (m, 2H), 6.53 (d, J=4.4 Hz, 1H), 6.46-6.34 (m, 2H), 6.30 (dd, J=18.9, 2.1 Hz, 1H), 5.16 (d, J=17.6 Hz, 4H), 5.06 (d, J=3.8 Hz, 2H), 5.02-4.78 (m, 3H), 4.56 (d, J=16.2 Hz, 1H), 3.69 (d, J=3.1 Hz, 3H), 3.52-3.40 (m, 6H). LC/MS (m/z): 622.237 [M+H$^+$]; UPLC $t_R$ 1.71 min.

The MOM-protected intermediate (43.2 mg, 69.5 µmol) was deprotected using General Procedure F to afford 11.5 mg of 23 (31% yield) after purification using mass-guided preparative HPLC. H NMR (500 MHz, CD$_3$OD) δ 8.40 (d, J=5.1 Hz, 1H), 7.75 (d, J=7.5 Hz, 1H), 7.72-7.63 (m, 2H), 7.38-7.30 (m, 2H), 7.30-7.20 (m, 1H), 7.15-7.04 (m, 2H), 6.73-6.66 (m, 2H), 6.45 (s, 1H), 6.01-5.90 (m, 1H), 5.19 (s, 2H), 4.99-4.49 (m, 4H), 3.65 (s, 2H), 2.65 (s, 3H). LC/MS (m/z): 535.173 [M+H$^+$]; UPLC $t_R$ 1.40 min.

5-((1-((4-Methoxyphenyl)methyl)-3-methyl-1H-pyrazol-5-yl)amino)-4-(1H,4H,5H,6H-pyrrolo[3,4-c]pyrazole-5-carbonyl)benzene-1,3-diol (24)

Acid 19a (39 mg, 85 µmol) was coupled with 1H,4H,5H,6H-pyrrolo[3,4-c]pyrazole (14 mg, 130 µmol), and triethylamine (24 µL, 170 µmol) using General Procedure G to give 28.1 mg of MOM-protected intermediate (60% yield) after purification via automated flash chromatography (15% to 60% acetone in CH$_2$Cl$_2$). $^1$H NMR (400 MHz, CDCl$_3$) δ 7.36-7.17 (m, 2H), 7.13-6.98 (m, 2H), 6.73-6.61 (m, 2H), 6.43-6.31 (m, 2H), 6.20 (d, J=2.1 Hz, 1H), 5.84 (d, J=2.3 Hz, 1H), 5.20-5.10 (m, 2H), 5.09-4.97 (m, 4H), 4.77-4.56 (m, 3H), 4.31 (dd, J=13.6, 7.2 Hz, 1H), 3.68 (d, J=1.0 Hz, 3H), 3.48-3.38 (m, 6H), 2.23 (s, 3H). $^{13}$C NMR (101 MHz, CDCl$_3$) δ 167.4, 159.8, 159.7, 159.0, 158.9, 155.2, 147.6, 143.6, 139.4, 139.3, 128.7, 128.6, 128.6, 128.6, 113.9, 113.9, 107.7, 107.6, 98.7, 98.6, 96.5, 96.4, 95.2, 95.1, 95.1, 94.2, 56.5, 56.5, 56.2, 55.1, 55.1, 53.7, 51.2, 51.2, 46.6, 46.4, 45.6, 45.3, 29.2, 14.1. LC/MS (m/z): 549.199 [M+H$^+$]; UPLC $t_R$ 1.28 min.

The MOM-protected intermediate (28.1 mg, 51.2 µmol) was deprotected using General Procedure F to afford 3.6 mg of 24 (15% yield) after purification using mass-guided preparative HPLC. $^1$H NMR (400 MHz, CD$_3$OD) δ 7.44 (s, 1H), 7.06-6.95 (m, 2H), 6.75-6.65 (m, 2H), 5.95-5.87 (m, 2H), 5.82 (d, J=2.1 Hz, 1H), 5.03 (s, 2H), 4.77-4.22 (m, 4H), 3.68 (s, 3H), 2.65 (s, 3H), 2.15 (s, 3H). LC/MS (m/z): 461.207 [M+H$^+$]; UPLC $t_R$ 0.94 min.

5-((1-((4-Methoxyphenyl)methyl)-3-phenyl-1H-pyrazol-5-yl)amino)-4-(1H,4H,5H,6H-pyrrolo[3,4-c]pyrazole-5-carbonyl)benzene-1,3-diol (25)

Acid 19b (90 mM in 1:1 CH$_2$Cl$_2$:THF, 1.0 mL, 90 µmol) was coupled with 1H,4H,5H,6H-pyrrolo[3,4-c]pyrazole (15 mg, 140 µmol), and triethylamine (25 µL, 180 µmol) using General Procedure G to give 33 mg of MOM-protected intermediate (61% yield) after purification via automated flash chromatography (10% to 40% acetone in CH$_2$Cl$_2$). $^1$H NMR (400 MHz, CDCl$_3$) δ 7.85-7.75 (m, 2H), 7.39 (t, J=7.6 Hz, 2H), 7.29 (t, J=7.5 Hz, 1H), 7.16 (d, J=8.2 Hz, 2H), 6.76-6.65 (m, 2H), 6.50-6.35 (m, 3H), 6.29 (dd, J=8.7, 1.9 Hz, 1H), 5.15 (s, 1H), 5.05 (s, 2H), 4.83-4.50 (m, 3H), 4.35 (t, J=12.4 Hz, 1H), 3.71 (dd, J=2.1, 0.9 Hz, 3H), 3.45 (s, 3H), 3.44 (s, 3H). $^{13}$C NMR (101 MHz, CDCl$_3$) δ 167.4, 159.8, 159.8, 159.0, 158.9, 155.2, 150.1, 143.4, 143.4, 140.1, 140.0, 133.6, 128.7, 128.5, 128.3, 128.2, 127.6, 125.3, 113.9, 113.9, 107.7, 107.7, 96.6, 96.4, 95.3, 95.2, 94.2, 56.5, 56.5, 56.2, 55.1, 55.1. LC/MS (m/z): 611.255 [M+H$^+$]; UPLC $t_R$ 1.61 min.

The MOM-protected intermediate (33.5 mg, 54.9 µmol) was deprotected using General Procedure F to afford 7.2 mg of 25 (25% yield) after purification using mass-guided preparative HPLC. $^1$H NMR (500 MHz, CD$_3$OD) δ 7.71 (dd, J=8.0, 1.4 Hz, 2H), 7.46-7.31 (m, 3H), 7.30-7.21 (m, 1H), 7.13-7.00 (m, 2H), 6.75-6.68 (m, 2H), 6.46 (s, 1H), 5.92 (dd, J=17.4, 2.1 Hz, 2H), 5.18 (s, 2H), 4.77-4.17 (m, 4H), 3.68 (d, J=0.6 Hz, 3H). LC/MS (m/z): 523.132 [M+H$^+$]; UPLC $t_R$ 1.31 min.

4-(4-Fluoro-2,3-dihydro-1H-isoindole-2-carbonyl)-5-((1-((4-methoxyphenyl)methyl)-3-methyl-1H-pyrazol-5-yl)amino)benzene-1,3-diol (26)

Acid 19a (30 mg, 66 µmol) was coupled with 4-fluoroisoindoline (13 mg, 98 µmol), and triethylamine (18 µL, 130 µmol) using General Procedure G to give 38 mg of MOM-protected intermediate (78% yield) after purification via automated flash chromatography (10% to 45% acetone in hexanes). $^1$H NMR (400 MHz, CDCl$_3$) δ 7.30 (dd, J=7.9, 5.2 Hz, 1H), 7.17-7.03 (m, 2H), 7.03-6.88 (m, 1H), 6.72-6.61 (m, 2H), 6.46-6.33 (m, 2H), 6.25 (dd, J=13.2, 2.1 Hz, 1H), 5.85 (d, J=2.5 Hz, 1H), 5.16 (dd, J=9.5, 3.3 Hz, 2H), 5.06 (d, J=10.6 Hz, 4H), 5.00-4.76 (m, 3H), 4.53 (d, J=14.9 Hz, 1H), 3.68 (d, J=7.4 Hz, 3H), 3.49-3.38 (m, 6H), 2.24 (s, 3H). $^{19}$F NMR (376 MHz, CDCl$_3$) δ −117.44 (dd, J=9.1, 5.1 Hz), −117.90 (dd, J=9.1, 5.0 Hz). $^{13}$C NMR (101 MHz, CDCl$_3$) δ 167.0, 166.8, 159.9, 159.9, 159.0, 158.9, 156.8, 156.5, 155.3, 147.6, 147.6, 143.8, 143.7, 140.0, 139.9, 139.5, 139.5, 139.3, 139.3, 129.9, 129.9, 129.8, 128.7, 128.6, 128.5, 123.4, 118.7, 118.6, 118.2, 114.3, 114.1, 114.1, 114.0, 113.9, 113.9, 107.5, 107.2, 98.5, 98.3, 96.5, 95.4, 95.3, 95.1, 95.1, 94.3, 56.6, 56.3, 55.1, 55.1, 53.0, 52.3, 51.4, 51.3, 50.0, 49.2, 14.2. LC/MS (m/z): 578.22 [M+H$^+$]; UPLC $t_R$ 1.65 min.

The MOM-protected intermediate (27.5 mg, 47.7 μmol) was deprotected using General Procedure F to afford 6.9 mg of 26 (30% yield) after purification using mass-guided preparative HPLC. $^1$H NMR (400 MHz, CD$_3$OD) δ 7.33 (q, J=7.7 Hz, 1H), 7.09 (s, 1H), 7.04-6.94 (m, 3H), 6.66 (d, J=8.7 Hz, 2H), 5.96-5.87 (m, 2H), 5.84 (d, J=2.1 Hz, 1H), 5.03 (s, 2H), 4.92-4.53 (m, 4H), 3.64 (s, 3H), 2.13 (s, 3H). LC/MS (m/z): 489.214 [M+H$^+$]; UPLC $t_R$ 1.36 min.

4-(4-Fluoro-2,3-dihydro-1H-isoindole-2-carbonyl)-5-((1-((4-methoxyphenyl)methyl)-3-phenyl-1H-pyrazol-5-yl)amino)benzene-1,3-diol (27)

Acid 19b (90 mM in 1:1 CH$_2$Cl$_2$:THF, 1.0 mL, 90 μmol) was coupled with 4-fluoroisoindoline (17 mg, 140 μmol), and triethylamine (25 μL, 180 μmol) using General Procedure G to give 42 mg of MOM-protected intermediate (72% yield) after purification via automated flash chromatography (8% to 30% acetone in hexanes). $^1$H NMR (400 MHz, CDCl$_3$) δ 7.86-7.73 (m, 2H), 7.39 (t, J=7.7 Hz, 2H), 7.35-7.23 (m, 2H), 7.19-7.08 (m, 3H), 6.98 (dt, J=12.5, 8.4 Hz, 1H), 6.73-6.65 (m, 2H), 6.52 (d, J=3.3 Hz, 1H), 6.46-6.37 (m, 2H), 6.32 (dd, J=16.3, 2.1 Hz, 1H), 5.29 (s, 1H), 5.25-5.11 (m, 4H), 5.07 (s, 2H), 5.03-4.81 (m, 3H), 4.56 (dd, J=14.7, 5.9 Hz, 1H), 3.69 (d, J=8.1 Hz, 3H), 3.48-3.43 (m, 6H). $^{19}$F NMR (376 MHz, CDCl$_3$) δ −117.44 (dd, J=9.1, 4.9 Hz), −117.88 (dd, J=9.4, 5.1 Hz). $^{13}$C NMR (101 MHz, CDCl$_3$) δ 166.9, 166.8, 160.0, 159.9, 159.3, 159.1, 159.0, 156.8, 155.4, 150.1, 150.1, 143.7, 143.5, 140.0, 140.0, 139.9, 139.5, 133.7, 130.0, 129.9, 129.8, 128.7, 128.7, 128.6, 128.4, 128.2, 127.6, 125.4, 123.6, 123.4, 123.3, 123.1, 118.6, 118.2, 114.3, 114.2, 114.1, 114.0, 113.9, 113.9, 107.6, 107.3, 96.6, 96.3, 96.0, 95.4, 95.3, 95.3, 95.3, 94.3, 94.3, 56.6, 56.3, 55.1, 55.1, 53.1, 52.3, 51.9, 51.8, 50.0, 49.3. LC/MS (m/z): 639.306 [M+H$^+$]; UPLC $t_R$ 2.00 min.

The MOM-protected intermediate (41.7 mg, 65.3 μmol) was deprotected using General Procedure F to afford 19.2 mg of 27 (53% yield) after purification using mass-guided preparative HPLC. $^1$H NMR (500 MHz, CD$_3$OD) δ 7.76-7.52 (m, 3H), 7.41-7.20 (m, 4H), 7.06 (d, J=8.5 Hz, 3H), 6.98 (t, J=8.8 Hz, 1H), 6.74-6.62 (m, 2H), 6.46 (d, J=0.9 Hz, 1H), 5.93 (ddd, J=14.0, 2.1, 0.9 Hz, 2H), 5.18 (s, 2H), 4.93-4.53 (m, 4H), 3.64 (d, J=0.9 Hz, 3H). $^{13}$C NMR (126 MHz, (CD$_3$)$_2$SO) δ 166.6, 159.5, 158.5, 157.2 (d, J$_{C-F}$=244.1 Hz), 155.7, 148.7, 143.7, 141.2, 133.5, 129.9 (d, 3J$_{C-F}$=4.8 Hz), 129.0, 128.7, 128.5, 127.3, 124.7, 123.1 (br), 119.1, 113.67 (app d, ovrlp), 113.63, 103.7, 96.2, 94.6, 93.2, 54.9, 50.5, 40.4. LC/MS (m/z): 551.250 [M+H$^+$]; UPLC $t_R$ 1.65 min.

4-(5-Fluoro-2,3-dihydro-1H-isoindole-2-carbonyl)-5-((1-((4-methoxyphenyl)methyl)-3-methyl-1H-pyrazol-5-yl)amino)benzene-1,3-diol (28)

Acid 19a (31.1 mg, 68.0 μmol) was coupled with 5-fluoroisoindoline hydrochloride (17.7 mg, 102 μmol), and triethylamine (28 μL, 204 μmol) using General Procedure G to give 33.3 mg of MOM-protected intermediate (85% yield) after purification via automated flash chromatography (20% to 50% ethyl acetate in hexanes). $^1$H NMR (400 MHz, CDCl$_3$) δ 7.17-6.80 (m, 4H), 6.66 (dd, J=8.6, 1.8 Hz, 2H), 6.43-6.34 (m, 2H), 6.24 (dd, J=2.1, 0.7 Hz, 1H), 5.85 (s, 1H), 5.15 (q, J=6.6 Hz, 2H), 5.05 (dd, J=11.3, 1.7 Hz, 4H), 4.96-4.74 (m, 3H), 4.55-4.40 (m, 1H), 3.68 (s, 3H), 3.51-3.37 (m, 6H), 2.24 (s, 3H). $^{19}$F NMR (376 MHz, CDCl$_3$) δ −114.63--114.72 (m), −114.72--114.83 (m). $^{13}$C NMR (101 MHz, CDCl$_3$) δ 166.9, 166.8, 163.9, 163.8, 161.4, 161.3, 159.9, 159.9, 158.9, 155.3, 155.3, 147.6, 143.8, 143.7, 139.3, 138.6, 138.6, 138.3, 138.2, 132.0, 131.7, 128.7, 128.7, 128.6, 124.3, 124.2, 123.8, 123.7, 115.1, 115.0, 114.9, 114.8, 113.9, 110.3, 110.1, 109.8, 109.6, 107.5, 107.5, 98.5, 98.4, 96.5, 95.4, 95.3, 95.1, 94.3, 56.6, 56.3, 55.1, 55.1, 52.9, 52.3, 52.0, 52.0, 51.5, 51.3, 14.2. LC/MS (m/z): 577.206 [M+H$^+$]; UPLC $t_R$ 1.71 min.

The MOM-protected intermediate (29.9 mg, 51.9 μmol) was deprotected using General Procedure F to afford 9.1 mg of 28 (36% yield) after purification using mass-guided preparative HPLC. $^1$H NMR (400 MHz, CD$_3$OD) δ 7.25 (s, 1H), 7.07-6.91 (m, 4H), 6.72-6.57 (m, 2H), 5.93-5.84 (m, 2H), 5.83 (d, J=2.1 Hz, 1H), 5.03 (s, 2H), 4.91-4.48 (m, 4H), 3.65 (s, 3H), 2.14 (d, J=6.9 Hz, 4H). LC/MS (m/z): 489.244 [M+H$^+$]; UPLC $t_R$ 1.34 min 4-(5-Fluoro-2,3-dihydro-1H-isoindole-2-carbonyl)-5-((1-((4-methoxyphenyl)methyl)-3-phenyl-1H-pyrazol-5-yl)amino)benzene-1,3-diol (29)

Acid 19b (90 mM in 1:1 CH$_2$Cl$_2$:THF, 1.0 mL, 90 μmol) was coupled with 5-fluoroisoindoline hydrochloride (23 mg, 140 μmol), and triethylamine (38 μL, 270 μmol) using General Procedure G to give 39 mg of MOM-protected intermediate (68% yield) after purification via automated flash chromatography (8% to 30% acetone in hexanes). $^1$H NMR (400 MHz, CDCl$_3$) δ 7.83-7.74 (m, 2H), 7.38 (dd, J=8.4, 6.9 Hz, 2H), 7.32-7.27 (m, 1H), 7.12 (ddd, J=11.7, 7.9, 3.6 Hz, 2H), 7.04-6.80 (m, 2H), 6.72-6.59 (m, 2H), 6.48 (d, J=5.9 Hz, 1H), 6.43-6.36 (m, 2H), 6.30 (t, J=1.9 Hz, 1H), 5.16 (d, J=9.5 Hz, 4H), 5.06 (s, 2H), 4.98-4.73 (m, 3H), 4.57-4.43 (m, 1H), 3.69 (s, 3H), 3.50-3.38 (m, 6H). $^{13}$C NMR (101 MHz, CDCl$_3$) δ 166.8, 166.8, 163.9, 163.8, 161.5, 161.4, 159.9, 159.9, 159.0, 155.4, 155.4, 150.1, 143.6, 143.6, 140.0, 140.0, 138.6, 138.5, 138.3, 138.2, 133.7, 132.0, 132.0, 131.7, 131.7, 128.7, 128.6, 128.6, 128.4, 128.3, 127.6, 125.4, 124.3, 124.2, 123.9, 123.8, 115.1, 115.0, 114.9, 114.8, 113.9, 110.3, 110.1, 109.8, 109.6, 107.6, 107.6, 96.7, 96.2, 96.2, 95.4, 95.4, 95.3, 94.3, 56.6, 56.3, 55.1, 55.1, 52.9, 52.4, 52.0, 51.8, 51.5. LC/MS (m/z): 639.306 [M+H$^+$]; UPLC $t_R$ 1.98 min.

The MOM-protected intermediate (39.3 mg, 61.5 μmol) was deprotected using General Procedure F to afford 6.6 mg of 29 (19% yield) after purification using mass-guided preparative HPLC. $^1$H NMR (500 MHz, CD$_3$OD) δ 7.72-7.60 (m, 2H), 7.34 (dd, J=8.4, 6.9 Hz, 2H), 7.28-7.22 (m, 1H), 7.21 (s, 1H), 7.08-7.00 (m, 2H), 6.98 (dd, J=9.0, 7.0 Hz, 2H), 6.72-6.64 (m, 2H), 6.45 (s, 1H), 5.93 (dd, J=12.7, 2.1 Hz, 2H), 5.17 (s, 2H), 4.97-4.43 (m, 4H), 3.65 (s, 3H). $^{13}$C NMR (126 MHz, (CD$_3$)$_2$SO) δ 166.5, 161.8 (d, $^1$J$_{C-F}$=241.3 Hz), 159.4, 158.5, 155.6, 148.7, 143.6, 141.2, 133.4, 129.0, 128.8, 128.5, 127.3, 124.7, 124.5 (d, 3J$_{C-F}$=9.5 Hz), 114.3 (d, $^2$J$_{C-F}$=22.9 Hz), 113.6, 110.0 (d, $^2$J$_{C-F}$=22.9 Hz), 103.9, 96.2, 94.6, 93.1, 55.0, 50.5, 40.4. LC/MS (m/z): 551.250 [M+H$^+$]; UPLC $t_R$ 1.64 min.

N-(Cyclopropylmethyl)-2,4-dihydroxy-6-((1-((4-methoxyphenyl)methyl)-3-methyl-1H-pyrazol-5-yl)amino)-N-methylbenzamide (30)

Acid 19a (49 mg, 110 μmol) was coupled with (cyclopropylmethyl)methylamine (27 mg, 320 μmol), and triethylamine (30 μL, 210 μmol) using General Procedure G to give 43 mg of MOM-protected intermediate (76% yield) after purification via automated flash chromatography (10% to 35% acetone in hexanes). $^1$H NMR (400 MHz, CDCl$_3$) δ 7.19-7.07 (m, 2H), 6.80 (t, J=8.6 Hz, 2H), 6.43-6.26 (m, 1H), 6.25-6.15 (m, 1H), 5.84 (d, J=8.5 Hz, 1H), 5.19-4.92 (m, 6H), 3.75 (d, J=4.1 Hz, 3H), 3.50-3.30 (m, 7H), 3.10-2.87 (m, 3H), 2.31-2.17 (m, 3H), 1.07--0.15 (m, 2H). $^{13}$C NMR (101 MHz, CDCl$_3$) δ 167.5, 167.2, 159.5, 159.4, 159.0, 159.0, 155.0, 154.7, 147.7, 147.6, 143.9, 143.9, 139.7, 139.6, 128.9, 128.8, 128.8, 128.7, 114.0, 113.9, 107.4, 107.2, 98.3, 97.9, 96.6, 96.4, 95.0, 95.0, 94.8, 94.7, 94.3, 94.3, 56.4, 56.3, 56.2, 56.2, 55.4, 55.2, 55.2, 51.1, 51.0, 36.2, 32.4, 14.2, 9.9, 9.2, 3.9, 3.5, 3.4, 3.4. LC/MS (m/z): 525.249 [M+H$^+$]; UPLC t$_R$ 1.66 min The MOM-protected intermediate (42.7 mg, 81.4 μmol) was deprotected using General Procedure F to afford 19.2 mg of 30 (54% yield) after purification using mass-guided preparative HPLC. $^1$H NMR (400 MHz, CD$_3$OD) δ 7.07 (d, J=8.7 Hz, 2H), 6.83 (d, J=8.7 Hz, 2H), 5.89 (s, 1H), 5.87-5.79 (m, 2H), 5.05 (s, 2H), 3.74 (s, 3H), 3.19 (dd, J=6.9, 4.6 Hz, 2H), 3.02 (s, 3H), 2.20 (s, 4H), 0.99-0.82 (m, 1H), 0.53-0.32 (m, 2H), 0.12 (ddt, J=37.2, 9.5, 4.8 Hz, 2H). LC/MS (m/z): 437.213 [M+H$^+$]; UPLC t$_R$ 1.28 min.

N-(Cyclopropylmethyl)-2,4-dihydroxy-6-((1-((4-methoxyphenyl)methyl)-3-phenyl-1H-pyrazol-5-yl)amino)-N-methylbenzamide (31)

Acid 19b (90 mM in 1:1 CH$_2$Cl$_2$:THF, 1.0 mL, 90 μmol) was coupled with (cyclopropylmethyl)methylamine (23 mg, 270 μmol), and triethylamine (25 μL, 180 μmol) using General Procedure G to give 40 mg of MOM-protected intermediate (75% yield) after purification via automated flash chromatography (8% to 30% acetone in hexanes). $^1$H NMR (400 MHz, CDCl$_3$) δ 7.80 (dt, J=8.2, 1.6 Hz, 2H), 7.39 (t, J=7.6 Hz, 2H), 7.33-7.27 (m, 1H), 7.22 (dd, J=8.8, 2.6 Hz, 2H), 6.87-6.71 (m, 2H), 6.41-6.31 (m, 2H), 6.30-6.24 (m, 1H), 5.29-5.09 (m, 4H), 5.03 (s, 2H), 3.76 (d, J=4.5 Hz, 3H), 3.50-3.30 (m, 7H), 3.17-2.92 (m, 4H), 1.04--0.10 (m, 3H). $^{13}$C NMR (101 MHz, CDCl$_3$) δ 167.4, 167.2, 159.5, 159.4, 159.1, 159.1, 155.1, 154.8, 150.1, 150.1, 143.8, 143.7, 140.5, 140.3, 133.8, 133.7, 128.9, 128.9, 128.5, 128.5, 128.4, 127.6, 125.4, 114.0, 114.0, 107.5, 107.3, 96.8, 96.6, 96.0, 95.5, 95.1, 95.0, 94.8, 94.3, 94.3, 56.4, 56.4, 56.3, 56.2, 55.2, 55.2, 51.6, 51.6, 51.1, 36.2, 32.5, 10.0, 9.3, 3.9, 3.5, 3.5, 3.4. LC/MS (m/z): 587.306 [M+H$^+$]; UPLC t$_R$ 1.95 min The MOM-protected intermediate (39.8 mg, 54.9 μmol) was deprotected using General Procedure F to afford 5.7 mg of 19b (17% yield) after purification using mass-guided preparative HPLC. $^1$H NMR (500 MHz, CD$_3$OD) δ 7.78-7.73 (m, 2H), 7.38 (dd, J=8.3, 7.0 Hz, 2H), 7.32-7.26 (m, 1H), 7.18-7.12 (m, 2H), 6.87-6.81 (m, 2H), 6.45 (s, 1H), 5.93 (d, J=2.1 Hz, 1H), 5.88 (d, J=2.1 Hz, 1H), 5.20 (s, 2H), 3.75 (s, 3H), 3.26-3.15 (m, 2H), 3.03 (s, 3H), 0.99-0.84 (m, 1H), 0.50-0.33 (m, 2H), 0.12 (ddq, J=42.7, 9.6, 4.8 Hz, 2H). LC/MS (m/z): 499.182 [M+H$^+$]; UPLC t$_R$ 1.60 min

5-((1-((4-methoxyphenyl)methyl)-3-methyl-1H-pyrazol-5-yl)amino)-4-(5-((1-methylpiperidin-4-yl)amino)-2,3-dihydro-1H-isoindole-2-carbonyl)benzene-1,3-diol (32)

Amide 16a (41.8 mg, 62.3 μmol) was deprotected using General Procedure F to afford 3.3 mg of 32 (9.1% yield) after purification using mass-guided preparative HPLC. $^1$H NMR (400 MHz, CD$_3$OD) δ 8.52 (s, 1H), 7.08-6.94 (m, 3H), 6.63 (d, J=8.7 Hz, 4H), 5.91 (d, J=2.1 Hz, 1H), 5.88 (s, 1H), 5.82 (d, J=2.0 Hz, 1H), 5.01 (s, 3H), 4.84-4.29 (m, 4H), 3.64 (s, 3H), 3.51 (s, 1H), 3.03-2.81 (m, 4H), 2.72 (s, 3H), 2.65 (s, 1H), 2.14 (s, 5H), 1.66 (s, 1H). LC/MS (m/z): 583.336 [M+H$^+$]; UPLC t$_R$ 0.88 min.

5-((1-((4-Methoxyphenyl)methyl)-3-phenyl-1H-pyrazol-5-yl)amino)-4-(5-((1-methylpiperidin-4-yl)amino)-2,3-dihydro-1H-isoindole-2-carbonyl)benzene-1,3-diol (33)

Acid 19b 77 mM in 1:1 CH$_2$Cl$_2$:THF, 1.0 mL, 77 μmol) was coupled with N-(1-methylpiperidin-4-yl)isoindolin-5-amine dihydrogenchloride (25 mg, 81 μmol), and triethylamine (85 μL, 610 μmol) using General Procedure G to give 35 mg of MOM-protected intermediate (59% yield) after purification via silica gel flash chromatography (96:4:1 CH$_2$Cl$_2$:methanol:conc. NH$_{40}$H (aq.)). $^1$H NMR (400 MHz, CDCl$_3$) δ 7.79 (d, J=7.6 Hz, 2H), 7.38 (t, J=7.5 Hz, 2H), 7.30 (d, J=7.2 Hz, 1H), 7.21-7.05 (m, 2H), 6.71-6.61 (m, 2H), 6.60-6.46 (m, 1H), 6.40 (dd, J=12.6, 10.4 Hz, 3H), 6.26 (dd, J=8.6, 2.1 Hz, 1H), 5.15 (d, J=6.9 Hz, 4H), 5.05 (d, J=2.0 Hz, 2H), 4.81 (dt, J=21.1, 14.4 Hz, 3H), 3.68 (d, J=1.6 Hz, 3H), 3.47-3.35 (m, 6H), 2.81 (s, 1H), 2.30 (d, J=8.6 Hz, 3H), 2.20-1.92 (m, 3H), 1.49 (d, J=11.6 Hz, 1H). 13C NMR (101 MHz, CDCl$_3$) δ 166.8, 166.7, 159.7, 159.0, 155.4, 150.1, 147.1, 147.0, 143.5, 140.0, 137.8, 137.5, 133.7, 128.8, 128.5, 128.4, 127.6, 125.4, 124.8, 124.5, 123.7, 123.2, 113.9, 113.6, 113.4, 106.8, 106.3, 96.5, 96.4, 95.3, 94.3, 56.5, 56.3, 55.1, 54.5, 52.6, 52.2, 51.8, 51.6, 46.2, 32.4. LC/MS (m/z): 733.603 [M+H$^+$]; UPLC t$_R$ 1.45 min The MOM-protected intermediate (34.7 mg, 47.4 μmol) was deprotected using General Procedure F to afford 7.7 mg of 33 (25% yield) after purification using mass-guided preparative HPLC. $^1$H NMR (400 MHz, CD$_3$OD) δ 8.52 (s, 1H), 7.76-7.63 (m, 2H), 7.42-7.22 (m, 3H), 7.10-6.94 (m, 2H), 6.71-6.60 (m, 3H), 6.55 (s, 1H), 6.44 (s, 1H), 5.92 (dd, J=16.0, 2.1 Hz, 1H), 5.15 (s, 2H), 4.83-4.43 (m, 4H), 3.64 (s, 3H), 3.52 (s, 1H), 3.36 (d, J=14.5 Hz, 2H), 2.99 (s, 2H), 2.76 (s, 3H), 2.18 (d, J=14.2 Hz, 2H), 1.68 (s, 2H). LC/MS (m/z): 645.481 [M+H$^+$]; UPLC t$_R$ 1.21 min

4-(5-(2-(Dimethylamino)ethoxy)-2,3-dihydro-1H-isoindole-2-carbonyl)-5-((1-((4-methoxyphenyl)methyl)-3-methyl-1H-pyrazol-5-yl)amino)benzene-1,3-diol (34)

Amide 16b (37.7 mg, 58.4 μmol) was deprotected using General Procedure F to afford 8.2 mg of 34 (25% yield) after purification using mass-guided preparative HPLC. $^1$H NMR (400 MHz, CD$_3$OD) δ 8.52 (s, 1H), 7.19 (s, 1H), 7.02-6.96 (m, 2H), 6.93 (d, J=8.7 Hz, 2H), 6.65 (d, J=8.7 Hz, 2H), 5.92 (d, J=2.1 Hz, 1H), 5.88 (s, 1H), 5.83 (d, J=2.1 Hz, 1H), 5.02 (s, 3H), 4.85-4.45 (m, 3H), 4.22 (t, J=5.3 Hz, 2H), 3.65 (s, 3H), 3.25-3.18 (m, 2H), 2.70 (s, 7H), 2.65 (s, 5H), 2.13 (s, 3H). LC/MS (m/z): 558.328 [M+H$^+$]; UPLC t$_R$ 0.90 min.

4-(5-(2-(Dimethylamino)ethoxy)-2,3-dihydro-1H-isoindole-2-carbonyl)-5-((1-((4-methoxyphenyl)methyl)-3-phenyl-1H-pyrazol-5-yl)amino)benzene-1,3-diol (35)

To a suspension of crude carboxylic acid 19b (57 mg, 110 μmol) and 2-(isoindolin-5-yloxy)-N,N-dimethylethan-1-amine dihydrochloride (24 mg, 86 μmol) in CH$_2$Cl$_2$ (0.7 mL) and THF (0.7 mL) was added triethylamine (60 μL, 430 μmol) followed by HATU (26 mg, 69 μmol). After the suspension was stirred overnight at room temperature, additional 2-(isoindolin-5-yloxy)-N,N-dimethylethan-1-amine dihydrochloride (12 mg, 43 μmol), triethylamine (60 μL, 430 μmol) and HATU (13 mg, 34 μmol) were added to the reaction. After stirring overnight, the reaction was diluted with $CH_2Cl_2$. The reaction mixture was washed with saturated $NaHCO_3$ (aq.), brine and then dried with anhydrous $Na_2SO_4$. The salts were removed via gravity filtration and volatile materials were condensed in vacuo. The crude mixture was purified via automated flash chromatography (2% to 5% methanol in $CH_2Cl_2$) to afford 47 mg of MOM-protected intermediate (60% yield). $^1$H NMR (400 MHz, $CDCl_3$) δ 7.82-7.73 (m, 2H), 7.38 (t, J=7.6 Hz, 2H), 7.30 (d, J=7.1 Hz, 1H), 7.23-7.01 (m, 3H), 6.91-6.80 (m, 1H), 6.66 (d, J=8.6 Hz, 2H), 6.45 (d, J=5.8 Hz, 1H), 6.42-6.33 (m, 2H), 6.28 (dd, J=3.4, 2.1 Hz, 1H), 5.16 (d, J=7.4 Hz, 4H), 5.05 (d, J=1.9 Hz, 2H), 4.95-4.73 (m, 3H), 4.55-4.43 (m, 1H), 4.07 (dt, J=17.1, 5.6 Hz, 2H), 3.68 (d, J=1.0 Hz, 3H), 3.44 (t, J=1.4 Hz, 6H), 2.80 (dt, J=9.2, 5.5 Hz, 2H), 2.40 (s, 3H), 2.38 (s, 3H). $^{13}$C NMR (101 MHz, $CDCl_3$) δ 166.8, 166.8, 159.8, 159.1, 158.8, 158.7, 155.4, 150.1, 143.6, 140.1, 138.0, 137.6, 133.8, 128.7, 128.5, 128.4, 127.5, 125.4, 123.7, 123.3, 114.8, 114.6, 114.0, 108.8, 108.6, 108.0, 96.7, 96.4, 95.4, 94.4, 66.0, 58.1, 56.5, 56.2, 55.1, 53.1, 52.5, 52.2, 51.8, 51.5, 45.7. LC/MS (m/z): 708.551 [M+H$^+$]; UPLC $t_R$ 1.45 min.

To a solution of the resulting MOM-protected intermediate (46.7 mg, 66.0 μmol) in methanol (6.4 mL) at room temperature was added HCl (aq.) (2 M, 0.21 mL, 420 μmol) and stirred at 50° C. overnight. Additional HCl (aq.) (2 M, 0.21 mL, 420 μmol) was added to the reaction mixture and stirred at 50° C. overnight. The reaction was cooled the room temperature and volatile materials were condensed in vacuo. The crude residue was purified using mass-guided preparative HPLC to afford 29.2 mg of 35 (71% yield). $^1$H NMR (400 MHz, $CD_3OD$) δ 7.68 (dt, J=6.4, 1.3 Hz, 2H), 7.37-7.28 (m, 2H), 7.28-7.20 (m, 1H), 7.16 (d, J=8.6 Hz, 1H), 7.10-6.99 (m, 2H), 6.97-6.79 (m, 2H), 6.74-6.59 (m, 2H), 6.43 (s, 1H), 5.94 (dd, J=14.2, 2.0 Hz, 2H), 5.16 (s, 2H), 4.85-4.45 (m, 4H), 4.25 (t, J=5.1 Hz, 2H), 3.64 (s, 3H), 3.41 (t, J=4.9 Hz, 2H), 3.34 (s, 1H), 2.84 (s, 6H). LC/MS (m/z): 620.473 [M+H$^+$]; UPLC $t_R$ 1.20 min.

5-((1-((4-Methoxyphenyl)methyl)-3-methyl-1H-pyrazol-5-yl)amino)-4-[5-(4-methylpiperazin-1-yl)-2,3-dihydro-1H-isoindole-2-carbonyl)benzene-1,3-diol (36)

Amide 16c (38.8 mg, 59.1 μmol) was deprotected using General Procedure F to afford 14.6 mg of 36 (43% yield) after purification using mass-guided preparative HPLC. $^1$H NMR (400 MHz, $CD_3OD$) δ 7.04-6.92 (m, 4H), 6.68-6.58 (m, 2H), 5.92 (d, J=2.1 Hz, 1H), 5.88 (s, 1H), 5.83 (d, J=2.1 Hz, 1H), 5.01 (s, 3H), 4.68 (d, J=59.6 Hz, 4H), 3.63 (s, 3H), 3.30 (dt, J=3.7, 1.9 Hz, 4H), 3.01 (d, J=5.1 Hz, 4H), 2.66-2.61 (m, 3H), 2.13 (s, 3H). LC/MS (m/z): 569.311 [M+H$^+$]; UPLC $t_R$ 0.77 min.

N-Benzyl-2,4-dihydroxy-6-((1-((4-methoxyphenyl)methyl)-3-methyl-1H-pyrazol-5-yl)amino)-N-methylbenzamide (37)

Amide 16d (39.1 mg, 69.7 μmol) was deprotected using General Procedure F to afford 12.6 mg of 37 (38% yield) after purification using mass-guided preparative HPLC. $^1$H NMR (400 MHz, $CD_3OD$) δ 7.19 (q, J=4.2, 3.4 Hz, 5H), 7.10-7.02 (m, 2H), 6.83-6.73 (m, 2H), 5.95-5.82 (m, 3H), 5.04 (s, 2H), 4.53 (d, J=14.7 Hz, 2H), 3.70 (s, 3H), 2.84 (s, 3H), 2.21 (s, 3H). LC/MS (m/z): 473.16 [M+H$^+$]; UPLC $t_R$ 1.49 min.

5-((1-((4-Methoxyphenyl)methyl)-3-phenyl-1H-pyrazol-5-yl)amino)-4-(pyrrolidine-1-carbonyl)benzene-1,3-diol (38)

Acid 19b (31.5 mg, 60.6 μmol) was coupled with pyrrolidine (6.5 mg, 91 μmol), and triethylamine (17 μL, 120 μmol) using General Procedure G to give 22.6 mg of MOM-protected intermediate (65% yield) after purification via automated flash chromatography (30% to 60% ethyl acetate in hexanes, 10% to 20% ethyl acetate in $CH_2Cl_2$, and 10% to 30% acetone in hexanes). $^1$H NMR (400 MHz, $CDCl_3$) δ 7.83-7.76 (m, 2H), 7.39 (t, J=7.6 Hz, 2H), 7.29 (t, J=7.3 Hz, 1H), 7.25-7.16 (m, 2H), 6.86-6.74 (m, 2H), 6.69 (s, 1H), 6.40-6.32 (m, 2H), 6.28 (d, J=2.1 Hz, 1H), 5.26-5.09 (m, 4H), 5.03 (s, 2H), 3.76 (s, 3H), 3.47 (s, 6H), 3.42 (s, 3H), 3.21 (s, 1H), 2.80 (s, 3H), 1.90 (d, J=6.3 Hz, 3H), 1.76 (s, 1H). $^{13}$C NMR (101 MHz, $CDCl_3$) δ 166.1, 159.5, 159.1, 155.3, 150.1, 143.5, 140.4, 133.8, 129.0, 128.5, 127.6, 125.4, 114.0, 108.5, 96.6, 95.7, 95.3, 95.2, 94.3, 56.4, 56.2, 55.2, 51.6, 47.5, 45.6, 25.8, 24.5. LC/MS (m/z): 573.457 [M+H$^+$]; UPLC $t_R$ 1.87 min The MOM-protected intermediate (22.6 mg, 39.5 μmol) was deprotected using General Procedure F to afford 8.5 mg of 38 (44% yield) after purification using mass-guided preparative HPLC. $^1$H NMR (400 MHz, $CD_3OD$) δ 7.82-7.66 (m, 2H), 7.38 (dd, J=8.2, 6.8 Hz, 2H), 7.32-7.24 (m, 1H), 7.14 (s, 2H), 6.85 (d, J=8.7 Hz, 2H), 6.45 (s, 1H), 5.89 (d, J=4.1 Hz, 2H), 5.19 (s, 2H), 3.75 (s, 3H), 3.41-3.23 (m, 5H), 1.98-1.69 (m, 4H). LC/MS (m/z): 485.377 [M+H$^+$]; UPLC $t_R$ 1.53 min.

N,N-Diethyl-2,4-dihydroxy-6-((1-((4-methoxyphenyl)methyl)-3-phenyl-1H-pyrazol-5-yl)amino)benzamide (39)

Acid 19b (35.6 mg, 68.5 μmol) was coupled with diethylamine (7.5 mg, 100 μmol), and triethylamine (19 μL, 140 μmol) using General Procedure G to give 25.2 mg of MOM-protected intermediate (64% yield) after purification via automated flash chromatography (20% to 50% ethyl acetate in hexanes and 10% to 30% ethyl acetate in hexanes). $^1$H NMR (400 MHz, $CDCl_3$) δ 7.85-7.76 (m, 2H), 7.43-7.36 (m, 2H), 7.33-7.28 (m, 1H), 7.24-7.14 (m, 2H), 6.81 (d, J=8.7 Hz, 2H), 6.38-6.36 (m, 1H), 6.35 (d, J=2.1 Hz, 1H), 6.27 (d, J=2.1 Hz, 1H), 6.11 (s, 1H), 5.29-5.10 (m, 4H), 5.02 (s, 2H), 3.76 (s, 3H), 3.64 (dq, J=13.7, 6.9 Hz, 1H), 3.46 (s, 3H), 3.42 (s, 3H), 3.33 (dp, J=14.3, 7.1 Hz, 2H), 3.18 (dq, J=14.3, 7.1 Hz, 1H), 1.14 (t, J=7.1 Hz, 3H), 1.02 (t, J=7.1 Hz, 3H). $^{13}$C NMR (101 MHz, $CDCl_3$) δ 166.9, 159.3, 159.1, 154.7, 150.2, 143.4, 140.5, 133.7, 128.8, 128.5, 128.5, 127.6, 125.4, 114.1, 108.2, 96.8, 95.8, 95.1, 95.0, 94.3, 56.4, 56.2, 55.2, 51.5, 43.0, 39.0, 14.3, 12.9. LC/MS (m/z): 575.485 [M+H$^+$]; UPLC $t_R$ 1.95 min.

The MOM-protected intermediate (25.4 mg, 44.2 μmol) was deprotected using General Procedure F to afford 13.5 mg of 39 (63% yield) after purification using mass-guided preparative HPLC. $^1$H NMR (400 MHz, $CD_3OD$) δ 7.79-7.71 (m, 2H), 7.38 (td, J=7.3, 6.4, 1.3 Hz, 2H), 7.32-7.26 (m, 1H), 7.21-7.10 (m, 2H), 6.94-6.78 (m, 2H), 6.44 (s, 1H), 5.91 (dd, J=14.7, 2.1 Hz, 2H), 5.19 (s, 2H), 3.75 (s, 3H), 3.43

(dq, J=14.1, 7.1 Hz, 2H), 3.36-3.24 (m, 2H), 1.07 (t, J=7.1 Hz, 6H). LC/MS (m/z): 487.406 [M+H$^+$]; UPLC $t_R$ 1.61 min.

4-(2,3-Dihydro-1H-isoindole-2-carbonyl)-5-((1-((4-methoxyphenyl)methyl)-1H-pyrazol-5-yl)amino)benzene-1,3-diol (40)

Amide 14c (62.4 mg, 114 μmol) was deprotected using General Procedure F to afford 23.8 mg of 40 (46% yield) after purification using mass-guided preparative HPLC. $^1$H NMR (400 MHz, CD$_3$OD) δ 7.43 (d, J=2.1 Hz, 1H), 7.28 (s, 4H), 7.02-6.96 (m, 2H), 6.67-6.59 (m, 2H), 6.10 (d, J=2.1 Hz, 1H), 5.92 (d, J=2.1 Hz, 1H), 5.77 (d, J=2.1 Hz, 1H), 5.10 (s, 2H), 4.98-4.56 (m, 4H), 3.63 (s, 3H). $^{13}$C NMR (126 MHz, (CD$_3$)$_2$SO) δ 166.6, 159.3, 158.5, 155.5, 143.7, 143.6, 139.73, 139.66, 138.1, 129.1, 128.8, 127.3, 122.8, 122.8, 113.6, 103.3, 98.8, 94.4, 92.6, 55.0, 50.4, 40.4. LC/MS (m/z): 457.227 [M+H$^+$]; UPLC $t_R$ 1.30 min.

4-(2,3-Dihydro-1H-isoindole-2-carbonyl)-5-((1-((4-methoxyphenyl)methyl)-4-methyl-1H-pyrazol-5-yl)amino)benzene-1,3-diol (41)

Amide 14d (49.1 mg, 87.9 μmol) was deprotected using General Procedure F to afford 12.2 mg of 41 (30% yield) after purification using mass-guided preparative HPLC $^1$H NMR (400 MHz, CD$_3$OD) δ 7.31 (d, J=14.5 Hz, 5H), 6.98 (d, J=8.6 Hz, 2H), 6.65-6.54 (m, 3H), 5.87 (d, J=2.1 Hz, 1H), 5.34 (d, J=2.0 Hz, 1H), 5.03 (s, 2H), 4.94-4.73 (m, 4H), 3.63 (s, 3H), 1.90 (s, 3H). $^{13}$C NMR (126 MHz, (CD$_3$)$_2$SO) δ 166.6, 159.3, 158.4, 155.5, 144.4, 138.4, 136.7 (br), 136.6, 129.4, 128.9, 127.3, 122.9, 113.5, 109.9, 103.4, 93.8, 91.6, 55.0, 50.5, 40.4, 8.3. LC/MS (m/z): 471.251 [M+H$^+$]; UPLC $t_R$ 1.34 min.

4-(2,3-Dihydro-1H-isoindole-2-carbonyl)-5-((1-((4-methoxyphenyl)methyl)-4-(propan-2-yl)-1H-pyrazol-5-yl)amino)benzene-1,3-diol (42)

Amide 14e (53.7 mg, 91.5 μmol) was deprotected using General Procedure F to afford 22.4 mg of 42 (49% yield) after purification using mass-guided preparative HPLC. $^1$H NMR (400 MHz, CD$_3$OD) δ 7.39 (s, 1H), 7.29 (s, 4H), 6.98 (d, J=8.2 Hz, 2H), 6.62-6.50 (m, 3H), 5.88 (d, J=2.1 Hz, 1H), 5.31 (d, J=2.1 Hz, 1H), 5.00 (s, 2H), 4.97-4.70 (m, 4H), 3.61 (s, 3H), 2.73 (p, J=6.9 Hz, 1H), 1.14 (d, J=6.9 Hz, 6H). LC/MS (m/z): 499.255 [M+H$^+$]; UPLC $t_R$ 1.47 min.

4-(2,3-Dihydro-1H-isoindole-2-carbonyl)-5-((1-((4-methoxyphenyl)methyl)-4-phenyl-1H-pyrazol-5-yl)amino)benzene-1,3-diol (43)

Amide 14f (25.4 mg, 40.9 μmol) was deprotected using General Procedure F to afford 15.0 mg of 43 (69% yield) after purification using mass-guided preparative HPLC. $^1$H NMR (400 MHz, CD$_3$OD) δ 7.81 (s, 1H), 7.50-7.44 (m, 2H), 7.33-7.16 (m, 9H), 7.10 (dd, J=13.6, 7.6 Hz, 3H), 6.65 (d, J=8.2 Hz, 2H), 5.87 (d, J=2.1 Hz, 1H), 5.37 (d, J=2.1 Hz, 1H), 5.12 (s, 2H), 3.65 (s, 3H). LC/MS (m/z): 533.257 [M+H$^+$]; UPLC $t_R$ 1.53 min.

5-((4-Benzyl-1-((4-methoxyphenyl)methyl)-1H-pyrazol-5-yl)amino)-4-(2,3-dihydro-1H-isoindole-2-carbonyl)benzene-1,3-diol (44)

Amide 14g (45.3 mg, 71.4 μmol) was deprotected using General Procedure F to afford 23.5 mg of 44 (60% yield) after purification using mass-guided preparative HPLC. $^1$H NMR (400 MHz, CD$_3$OD) δ 7.29 (d, J=4.5 Hz, 5H), 7.09 (d, J=5.6 Hz, 4H), 7.04-6.95 (m, 3H), 6.67-6.56 (m, 3H), 5.88 (d, J=2.1 Hz, 1H), 5.36 (d, J=2.1 Hz, 1H), 5.05 (s, 2H), 4.96-4.57 (m, 4H), 3.68-3.59 (m, 5H). LC/MS (m/z): 547.17 [M+H$^+$]; UPLC $t_R$ 1.70 min.

(5,7-dihydro-6H-pyrrolo[3,4-b]pyridin-6-yl)(2-((3-ethyl-1-(4-methoxybenzyl)-1H-pyrazol-5-yl)amino)-4,6-dihydroxyphenyl)methanone (45)

Acid 19c (51.7 mg, 110 μmol) was coupled with 6,7-dihydro-5H-pyrrolo[3,4-b]pyridine dihydrochloride (31.7 mg, 164 μmol), and triethylamine (115 μL, 822 μmol) using General Procedure G to give 33.2 mg of MOM-protected intermediate (53% yield) after purification via silica gel flash chromatography (1% to 4% methanol in CH$_2$Cl$_2$) and manual flash chromatography (20:80:1 CH$_2$Cl$_2$:ethyl acetate:conc. NH$_{40}$H (aq.))$^1$H NMR (400 MHz, CDCl$_3$) δ 8.57-8.41 (m, 1H), 7.21 (ddd, J=13.4, 7.6, 4.9 Hz, 1H), 7.08 (dd, J=8.4, 5.9 Hz, 2H), 6.67 (dd, J=8.7, 3.2 Hz, 2H), 6.47 (d, J=2.8 Hz, 1H), 6.40 (dd, J=8.3, 2.1 Hz, 1H), 6.26 (dd, J=11.8, 2.1 Hz, 1H), 5.88 (d, J=2.1 Hz, 1H), 5.22-5.00 (m, 6H), 4.99-4.78 (m, 3H), 4.52 (d, J=15.5 Hz, 1H), 3.69 (d, J=2.6 Hz, 3H), 3.45 (dd, J=4.4, 1.7 Hz, 6H), 2.61 (qd, J=7.7, 1.9 Hz, 2H), 1.29-1.14 (m, 3H). $^{13}$C NMR (101 MHz, CDCl$_3$) δ 167.2, 167.1, 159.9, 159.0, 158.9, 157.6, 157.2, 155.4, 155.3, 153.7, 153.7, 149.4, 149.3, 143.8, 143.7, 139.4, 139.2, 131.0, 130.6, 130.3, 129.9, 128.8, 128.6, 128.6, 128.5, 122.5, 122.4, 113.9, 113.8, 107.1, 96.9, 96.8, 96.6, 95.4, 95.2, 95.2, 95.1, 94.3, 94.3, 56.6, 56.5, 56.2, 56.2, 55.2, 55.1, 53.4, 52.5, 51.4, 51.4, 51.3, 50.5, 22.0, 13.9. LC/MS (m/z): 574.383 [M+H$^+$]; UPLC $t_R$ 1.51 min.

The MOM-protected intermediate (33.2 mg, 57.9 μmol) was deprotected using General Procedure F to afford 22.9 mg of 45 (81% yield) after purification using mass-guided preparative HPLC. $^1$H NMR (400 MHz, CD$_3$OD) δ 8.43 (dd, J=5.0, 1.5 Hz, 1H), 7.74 (s, 1H), 7.33 (dd, J=7.8, 5.0 Hz, 1H), 7.06-6.95 (m, 2H), 6.65 (d, J=8.7 Hz, 2H), 5.93 (d, J=3.1 Hz, 2H), 5.83 (d, J=2.1 Hz, 1H), 5.05 (s, 2H), 4.97-4.48 (m, 4H), 3.64 (s, 3H), 2.51 (q, J=7.6 Hz, 2H), 1.17 (t, J=7.6 Hz, 3H). LC/MS (m/z): 486.259 [M+H$^+$]; UPLC $t_R$ 1.16 min.

5-((3-Ethyl-1-((4-methoxyphenyl)methyl)-1H-pyrazol-5-yl)amino)-4-(1H,4H,5H,6H-pyrrolo[3,4-c]pyrazole-5-carbonyl)benzene-1,3-diol (46)

Acid 19c (54.0 mg, 115 μmol) was coupled with 1H,4H, 5H,6H-pyrrolo[3,4-c]pyrazole (18.8 mg, 172 μmol), and triethylamine (32 μL, 230 μmol) using General Procedure G to give 26.9 mg of MOM-protected intermediate (42% yield) after purification via silica gel flash chromatography (12% to 35% acetone in CH$_2$Cl$_2$) and manual flash chromatography (96:4 CH$_2$Cl$_2$:methanol). $^1$H NMR (400 MHz, CDCl$_3$) δ 7.08 (d, J=8.6 Hz, 2H), 6.70 (d, J=8.7 Hz, 2H), 6.38 (dd, J=7.1, 2.1 Hz, 1H), 6.32 (d, J=13.6 Hz, 1H), 6.24 (dd, J=4.2, 2.1 Hz, 1H), 5.88 (d, J=1.7 Hz, 1H), 5.15 (td, J=7.3, 5.2 Hz, 2H), 5.06 (d, J=2.5 Hz, 4H), 4.82-4.59 (m, 3H), 4.32 (t, J=12.4 Hz, 1H), 3.71 (d, J=1.8 Hz, 3H), 3.50-3.39 (m, 6H), 2.62 (q, J=7.6 Hz, 2H), 1.23 (t, J=7.6 Hz, 3H). $^{13}$C NMR (101 MHz, CDCl$_3$) δ 167.4, 159.8, 159.8, 159.0, 158.9, 155.2, 153.8, 143.6, 139.3, 139.2, 128.8, 128.6, 128.6, 118.3, 117.8, 113.9, 113.9, 107.7, 107.6, 97.1, 97.0, 96.6, 95.3, 95.2, 94.3, 56.5, 56.2, 55.2, 55.2, 51.3, 46.6, 46.4, 45.6, 45.3, 22.0, 13.9. LC/MS (m/z): 563.401 [M+H$^+$]; UPLC $t_R$ 1.39 min.

The MOM-protected intermediate (26.9 mg, 47.8 μmol) was deprotected using General Procedure F to afford 15.3 mg of 46 (67% yield) after purification using mass-guided preparative HPLC. ¹H NMR (400 MHz, CD₃OD) δ 7.43 (s, 1H), 7.00 (d, J=8.7 Hz, 2H), 6.69 (d, J=8.7 Hz, 2H), 5.98-5.89 (m, 2H), 5.82 (d, J=2.1 Hz, 1H), 5.04 (s, 2H), 4.83-4.28 (m, 4H), 3.67 (s, 3H), 2.53 (q, J=7.6 Hz, 2H), 1.19 (t, J=7.6 Hz, 3H). LC/MS (m/z): 475.321 [M+H⁺]; UPLC $t_R$ 1.04 min 5-((1-((4-Methoxyphenyl)methyl)-3-(propan-2-yl)-1H-pyrazol-5-yl)amino)-4-(5H,6H,7H-pyrrolo[3,4-b]pyridine-6-carbonyl)benzene-1,3-diol (47)

Acid 19d (53.2 mg, 110 μmol) was coupled with 6,7-dihydro-5H-pyrrolo[3,4-b]pyridine dihydrochloride (31.7 mg, 164 μmol), and triethylamine (115 μL, 822 μmol) using General Procedure G to give 44.1 mg of MOM-protected intermediate (68% yield) after purification via silica gel flash chromatography (1% to 4% methanol in CH₂Cl₂) and manual flash chromatography (20:80:1 CH₂Cl₂:ethyl acetate:conc. NH₄OH (aq.)). ¹H NMR (400 MHz, CDCl₃) δ 8.59-8.42 (m, 1H), 7.56 (dd, J=66.5, 7.7 Hz, 1H), 7.25-7.17 (m, 1H), 7.08 (dd, J=8.3, 5.8 Hz, 2H), 6.68 (dd, J=8.7, 2.9 Hz, 2H), 6.48 (d, J=9.5 Hz, 1H), 6.40 (dd, J=9.2, 2.1 Hz, 1H), 6.29 (dd, J=10.5, 2.0 Hz, 1H), 5.89 (d, J=3.2 Hz, 1H), 5.24-5.01 (m, 6H), 5.01-4.71 (m, 3H), 4.52 (d, J=15.3 Hz, 1H), 3.69 (d, J=2.7 Hz, 3H), 3.45 (d, J=1.4 Hz, 3H), 3.44 (d, J=1.9 Hz, 3H), 2.94 (p, J=6.9 Hz, 1H), 1.25 (d, J=6.8 Hz, 6H). ¹³C NMR (101 MHz, CDCl₃) δ 167.2, 167.1, 160.0, 159.0, 158.8, 158.2, 158.2, 157.6, 157.2, 155.4, 155.3, 149.4, 149.3, 143.8, 143.7, 139.2, 139.0, 131.0, 130.6, 129.9, 128.8, 128.6, 128.5, 128.5, 122.5, 122.4, 113.9, 113.8, 107.2, 107.2, 96.7, 95.4, 95.3, 95.2, 95.2, 95.1, 94.4, 94.3, 56.6, 56.5, 56.2, 56.2, 55.2, 55.1, 53.4, 52.5, 51.4, 51.4, 51.3, 50.5, 28.3, 22.8. LC/MS (m/z): 588.408 [M+H⁺]; UPLC $t_R$ 1.61 min.

The MOM-protected intermediate (44.1 mg, 71.0 μmol) was deprotected using General Procedure F to afford 24.8 mg of 47 (66% yield) after purification using mass-guided preparative HPLC. ¹H NMR (400 MHz, CD₃OD) δ 8.43 (dd, J=5.0, 1.5 Hz, 1H), 7.74 (s, 1H), 7.33 (dd, J=7.8, 5.0 Hz, 1H), 6.98 (d, J=8.7 Hz, 2H), 6.65 (d, J=8.7 Hz, 2H), 5.99-5.87 (m, 2H), 5.83 (d, J=2.1 Hz, 1H), 5.06 (s, 2H), 4.97-4.49 (m, 4H), 3.63 (s, 3H), 2.84 (hept, J=6.9 Hz, 1H), 1.20 (d, J=6.9 Hz, 6H). LC/MS (m/z): 500.285 [M+H⁺]; UPLC $t_R$ 1.25 min.

5-((1-((4-Methoxyphenyl)methyl)-3-(propan-2-yl)-1H-pyrazol-5-yl)amino)-4-(1H,4H,5H,6H-pyrrolo[3,4-c]pyrazole-5-carbonyl)benzene-1,3-diol (48)

Acid 19d (57.5 mg, 118 μmol) was coupled with 1H,4H,5H,6H-pyrrolo[3,4-c]pyrazole (19.4 mg, 178 μmol), and triethylamine (33 μL, 240 μmol) using General Procedure G to give 23.2 mg of MOM-protected intermediate (34% yield) after purification via silica gel flash chromatography (12% to 35% acetone in CH₂Cl₂) and manual flash chromatography (96:4 CH₂Cl₂:methanol). ¹H NMR (400 MHz, CDCl₃) δ 7.40-7.19 (m, 1H), 7.09 (d, J=8.1 Hz, 2H), 6.70 (d, J=8.4 Hz, 2H), 6.44-6.27 (m, 2H), 6.26 (t, J=2.1 Hz, 1H), 5.89 (d, J=2.2 Hz, 1H), 5.21-5.00 (m, 6H), 4.78-4.57 (m, 3H), 4.38-4.22 (m, 1H), 3.71 (d, J=1.4 Hz, 3H), 3.44 (d, J=1.3 Hz, 6H), 2.94 (p, J=6.9 Hz, 1H), 1.25 (dd, J=7.0, 2.2 Hz, 6H). ¹³C NMR (101 MHz, CDCl₃) δ 167.4, 159.8, 159.8, 159.0, 158.9, 158.2, 155.2, 143.5, 143.4, 139.3, 139.2, 128.7, 128.6, 113.9, 113.9, 107.8, 107.7, 96.7, 96.6, 95.5, 95.4, 95.3, 95.2, 94.4, 56.5, 56.2, 55.2, 55.1, 51.3, 51.3, 46.6, 46.4, 45.6, 45.3, 28.3, 22.8. LC/MS (m/z): 577.382 [M+H⁺]; UPLC $t_R$ 1.47 min.

The MOM-protected intermediate (23.2 mg, 40.2 μmol) was deprotected using General Procedure F to afford 15.3 mg of 48 (78% yield) after purification using mass-guided preparative HPLC. ¹H NMR (400 MHz, CD₃OD) δ 7.43 (s, 1H), 7.05-6.92 (m, 2H), 6.74-6.63 (m, 2H), 5.99-5.88 (m, 2H), 5.82 (d, J=2.1 Hz, 1H), 5.05 (s, 2H), 4.79-4.22 (m, 4H), 3.67 (s, 3H), 2.85 (h, J=6.9 Hz, 1H), 1.21 (d, J=6.9 Hz, 6H). LC/MS (m/z): 489.303 [M+H⁺]; UPLC $t_R$ 1.13 min.

(2-((3-(tert-Butyl)-1-(4-methoxybenzyl)-1H-pyrazol-5-yl)amino)-4,6-dihydroxyphenyl)(isoindolin-2-yl)methanone (49)

Amide 14h (45.0 mg, 74.9 μmol) was deprotected using General Procedure F to afford 12.5 mg of 49 (33% yield) after purification using mass-guided preparative HPLC. ¹H NMR (400 MHz, CD₃OD) δ 7.33-7.17 (m, 4H), 6.93 (d, J=8.7 Hz, 2H), 6.61 (d, J=8.7 Hz, 2H), 5.98 (s, 1H), 5.91 (d, J=2.1 Hz, 1H), 5.82 (d, J=2.1 Hz, 1H), 5.07 (s, 2H), 4.93-4.56 (m, 4H), 3.61 (s, 3H), 1.26 (s, 9H). ¹³C NMR (126 MHz, (CD₃)₂SO) δ 166.6, 159.32, 159.27, 158.4, 155.5, 143.7, 139.8, 136.7 (br), 129.4, 128.5, 127.2, 122.8, 113.6, 103.8, 94.6, 94.4, 92.9, 54.9, 50.2, 40.4, 31.9, 30.3. LC/MS (m/z): 513.208 [M+H⁺]; UPLC $t_R$ 1.73 min (2-((3-cyclopropyl-1-(4-methoxybenzyl)-1H-pyrazol-5-yl)amino)-4,6-dihydroxyphenyl)(5,7-dihydro-6H-pyrrolo[3,4-b]pyridin-6-yl)methanone (50)

Acid 19e (52.5 mg, 109 μmol) was coupled with 6,7-dihydro-5H-pyrrolo[3,4-b]pyridine dihydrochloride (31.5 mg, 163 μmol), and triethylamine (114 μL, 814 μmol) using General Procedure G to give 43.7 mg of MOM-protected intermediate (69% yield) after purification via automated flash system (1% to 4% methanol in CH₂Cl₂) and manual flash chromatography (20:80:1 CH₂Cl₂:ethyl acetate:conc. NH₄OH (aq.)). ¹H NMR (400 MHz, CDCl₃) δ 8.56-8.44 (m, 1H), 7.68-7.40 (m, 1H), 7.25-7.16 (m, 1H), 7.08 (dd, J=8.5, 5.0 Hz, 2H), 6.67 (dd, J=8.7, 2.6 Hz, 2H), 6.48 (d, J=7.3 Hz, 1H), 6.40 (dd, J=8.9, 2.1 Hz, 1H), 6.29-6.20 (m, 1H), 5.69 (s, 1H), 5.24-4.97 (m, 7H), 5.00-4.79 (m, 3H), 4.51 (d, J=15.8 Hz, 1H), 3.69 (d, J=2.2 Hz, 3H), 3.45 (d, J=1.5 Hz, 3H), 3.44 (d, J=1.8 Hz, 3H), 1.89 (dtd, J=8.9, 5.6, 5.2, 2.8 Hz, 1H), 0.89 (dd, J=8.6, 2.0 Hz, 2H), 0.68 (dd, J=5.2, 2.4 Hz, 2H). ¹³C NMR (101 MHz, CDCl₃) δ 167.2, 167.1, 159.9, 159.0, 158.9, 157.5, 157.2, 155.4, 155.3, 154.2, 154.1, 149.4, 149.3, 143.6, 143.6, 139.5, 139.3, 131.0, 130.6, 130.3, 129.9, 128.7, 128.6, 128.5, 128.5, 122.5, 122.4, 113.9, 113.8, 107.2, 107.2, 96.7, 95.4, 95.3, 95.2, 95.2, 94.6, 94.5, 94.3, 94.3, 56.6, 56.5, 56.3, 56.2, 55.2, 55.1, 53.4, 52.5, 51.4, 51.4, 51.3, 50.5, 9.6, 7.9. LC/MS (m/z): 586.38 [M+H⁺]; UPLC $t_R$ 1.46 min.

The MOM-protected intermediate (43.7 mg, 74.6 μmol) was deprotected using General Procedure F to afford 25.3 mg of 50 (68% yield) after purification using mass-guided preparative HPLC. ¹H NMR (400 MHz, CD₃OD) δ 8.43 (dd, J=5.1, 1.5 Hz, 1H), 7.74 (s, 1H), 7.33 (dd, J=7.7, 5.0 Hz, 1H), 7.03-6.90 (m, 2H), 6.72-6.57 (m, 2H), 5.92 (d, J=2.1 Hz, 1H), 5.81 (d, J=2.1 Hz, 1H), 5.74 (s, 1H), 5.03 (s, 2H), 4.94-4.44 (m, 4H), 3.64 (s, 4H), 1.78 (tt, J=8.4, 5.0 Hz, 1H), 0.83 (dd, J=8.5, 2.1 Hz, 2H), 0.61 (dd, J=5.1, 2.0 Hz, 2H). LC/MS (m/z): 498.3 [M+H⁺]; UPLC $t_R$ 1.19 min

5-((3-Cyclopropyl-1-((4-methoxyphenyl)methyl)-1H-pyrazol-5-yl)amino)-4-(1H,4H,5H,6H-pyrrolo[3,4-c]pyrazole-5-carbonyl)benzene-1,3-diol (51)

Acid 19e (59.7 mg, 123 µmol) was coupled with 1H,4H,5H,6H-pyrrolo[3,4-c]pyrazole (20.2 mg, 185 µmol), and triethylamine (34 µL, 250 µmol) using General Procedure G to give 31.4 mg of MOM-protected intermediate (44% yield) after purification via automated flash system (12% to 35% acetone in $CH_2Cl_2$) and manual flash chromatography (96:4 $CH_2Cl_2$:methanol). $^1$H NMR (400 MHz, $CDCl_3$) δ 7.08 (d, J=8.4 Hz, 2H), 6.75-6.63 (m, 2H), 6.38 (dd, J=7.1, 2.1 Hz, 1H), 6.29 (d, J=15.5 Hz, 1H), 6.22 (dd, J=5.2, 2.1 Hz, 1H), 5.69 (s, 1H), 5.21-5.09 (m, 2H), 5.04 (d, J=4.3 Hz, 5H), 4.78-4.65 (m, 2H), 4.64 (s, 1H), 4.30 (t, J=12.6 Hz, 1H), 3.71 (d, J=2.1 Hz, 3H), 3.48-3.37 (m, 6H), 1.89 (td, J=8.6, 4.3 Hz, 1H), 0.89 (dd, J=8.5, 2.2 Hz, 2H), 0.76-0.57 (m, 1H). $^{13}$C NMR (101 MHz, $CDCl_3$) δ 167.4, 159.8, 159.8, 159.0, 158.9, 155.2, 154.2, 143.5, 139.4, 139.3, 128.7, 128.6, 128.6, 128.6, 118.2, 117.7, 113.9, 113.9, 107.7, 107.7, 96.6, 95.3, 95.2, 94.9, 94.8, 94.3, 56.5, 56.5, 56.2, 55.2, 55.1, 51.3, 46.6, 46.4, 45.6, 45.3, 9.7, 7.9. LC/MS (m/z): 575.397 [M+H$^+$]; UPLC $t_R$ 1.41 min.

The MOM-protected intermediate (31.4 mg, 54.6 µmol) was deprotected using General Procedure F to afford 17.7 mg of 51 (67% yield) after purification using mass-guided preparative HPLC. H NMR (400 MHz, $CD_3OD$) δ 7.43 (s, 1H), 6.99 (d, J=8.7 Hz, 2H), 6.69 (d, J=8.7 Hz, 2H), 5.90 (d, J=2.1 Hz, 1H), 5.80 (d, J=2.1 Hz, 1H), 5.74 (s, 1H), 5.02 (s, 2H), 4.77-4.18 (m, 4H), 3.67 (s, 4H), 1.82 (tt, J=8.4, 5.0 Hz, 1H), 0.86 (dd, J=8.5, 2.1 Hz, 2H), 0.64 (dd, J=5.1, 2.1 Hz, 2H). LC/MS (m/z): 487.318 [M+H$^+$]; UPLC $t_R$ 1.08 min.

5-((3-Cyclopentyl-1-((4-methoxyphenyl)methyl)-1H-pyrazol-5-yl)amino)-4-(5H,6H,7H-pyrrolo[3,4-b]pyridine-6-carbonyl)benzene-1,3-diol (52)

Acid 19f (44.7 mg, 87.4 µmol) was coupled with 6,7-dihydro-5H-pyrrolo[3,4-b]pyridine dihydrochloride (25.3 mg, 131 µmol), and triethylamine (91.4 µL, 655 µmol) using General Procedure G to give 41.2 mg of MOM-protected intermediate (77% yield) after purification via automated flash system (1% to 4% methanol in $CH_2Cl_2$) and manual flash chromatography (55:45:1 $CH_2Cl_2$:ethyl acetate:conc. $NH_{40}H$ (aq.) to 40:60:1 $CH_2Cl_2$:ethyl acetate:conc. $NH_{40}H$ (aq.)). $^1$H NMR (400 MHz, $CDCl_3$) δ 8.58-8.38 (m, 1H), 7.68-7.38 (m, 1H), 7.24-7.15 (m, 1H), 7.08 (dd, J=8.4, 5.7 Hz, 2H), 6.67 (dd, J=8.7, 3.0 Hz, 2H), 6.46 (d, J=6.2 Hz, 1H), 6.40 (dd, J=8.6, 2.1 Hz, 1H), 6.29 (dd, J=11.1, 2.1 Hz, 1H), 5.88 (d, J=2.7 Hz, 1H), 5.27-4.98 (m, 6H), 4.98-4.78 (m, 3H), 4.51 (d, J=15.6 Hz, 1H), 3.69 (d, J=2.7 Hz, 3H), 3.45 (dd, J=5.0, 1.7 Hz, 6H), 3.04 (t, J=8.2 Hz, 1H), 2.03 (d, J=9.1 Hz, 2H), 1.85-1.33 (m, 6H). $^{13}$C NMR (101 MHz, $CDCl_3$) δ 167.2, 159.9, 158.8, 157.6, 157.2, 156.5, 156.5, 155.4, 155.3, 149.4, 149.3, 143.8, 143.7, 139.3, 139.1, 131.0, 130.6, 130.3, 129.9, 128.8, 128.6, 128.6, 128.5, 122.5, 122.4, 113.9, 113.8, 107.1, 96.6, 95.8, 95.7, 95.4, 95.2, 95.2, 95.1, 94.4, 94.3, 56.6, 56.5, 56.2, 56.2, 55.2, 55.1, 53.4, 51.4, 51.3, 50.5, 39.5, 33.4, 25.4. LC/MS (m/z): 614.431 [M+H$^+$]; UPLC $t_R$ 1.72 min The MOM-protected intermediate (40.8 mg, 66.5 µmol) was deprotected using General Procedure F to afford 22.9 mg of 52 (66% yield) after purification using mass-guided preparative HPLC. $^1$H NMR (400 MHz, $CD_3OD$) δ 8.43 (dd, J=4.9, 1.5 Hz, 1H), 7.74 (s, 1H), 7.33 (dd, J=7.8, 5.1 Hz, 1H), 6.98 (d, J=8.7 Hz, 2H), 6.65 (d, J=8.7 Hz, 2H), 5.92 (d, J=2.6 Hz, 2H), 5.83 (d, J=2.1 Hz, 1H), 5.05 (s, 2H), 4.88 (s, 9H), 3.64 (s, 3H), 2.92 (d, J=8.1 Hz, 1H), 1.96 (s, 2H), 1.80-1.48 (m, 6H). $^{13}$C NMR (101 MHz, $(CD_3)_2SO$) δ 166.8, 159.5, 158.4, 157.3, 155.6, 154.8, 148.8, 143.9, 140.0, 131.3, 129.4, 128.7, 122.4, 113.6, 103.4, 95.8, 94.4, 93.0, 55.0, 50.1, 40.4, 32.7, 24.9 LC/MS (m/z): 526.308 [M+H$^+$]; UPLC $t_R$ 1.36 min

5-((3-Cyclopentyl-1-((4-methoxyphenyl)methyl)-1H-pyrazol-5-yl)amino)-4-(1H,4H,5H,6H-pyrrolo[3,4-c]pyrazole-5-carbonyl)benzene-1,3-diol (53)

Acid 19f (45.3 mg, 88.6 µmol) was coupled with 1H,4H,5H,6H-pyrrolo[3,4-c]pyrazole (14.5 mg, 133 µmol), and triethylamine (35 µL, 180 µmol) using General Procedure G to give 27.1 mg of MOM-protected intermediate (51% yield) after purification via automated flash system (12% to 35% acetone in $CH_2Cl_2$) and manual flash chromatography (96:4 $CH_2Cl_2$:methanol). $^1$H NMR (400 MHz, $CDCl_3$) δ 7.15-6.99 (m, 2H), 6.70 (d, J=8.2 Hz, 2H), 6.44-6.29 (m, 2H), 6.27 (q, J=1.9 Hz, 1H), 5.88 (d, J=2.2 Hz, 1H), 5.24-4.95 (m, 6H), 4.78-4.58 (m, 3H), 4.31 (t, J=12.4 Hz, 1H), 3.71 (t, J=1.4 Hz, 3H), 3.44 (d, J=1.5 Hz, 6H), 3.06 (q, J=8.1 Hz, 1H), 2.04 (s, 2H), 1.82-1.48 (m, 6H). $^{13}$C NMR (101 MHz, $CDCl_3$) δ 167.4, 159.8, 159.8, 159.0, 158.9, 156.5, 156.5, 155.2, 143.4, 139.4, 139.3, 128.7, 128.6, 113.9, 113.9, 107.8, 107.7, 96.7, 96.7, 95.9, 95.8, 95.3, 95.3, 94.4, 56.5, 56.2, 55.2, 55.1, 51.3, 51.3, 46.6, 46.4, 45.6, 45.3, 39.5, 33.4, 33.4, 25.4. LC/MS (m/z): 603.404 [M+H$^+$]; UPLC $t_R$ 1.59 min.

The MOM-protected intermediate (27.1 mg, 45.0 µmol) was deprotected using General Procedure F to afford 16.1 mg of 53 (70% yield) after purification using mass-guided preparative HPLC. $^1$H NMR (400 MHz, $CD_3OD$) δ 7.42 (s, 1H), 6.99 (d, J=8.7 Hz, 2H), 6.69 (d, J=8.7 Hz, 2H), 6.01-5.87 (m, 2H), 5.82 (d, J=2.1 Hz, 1H), 5.05 (s, 2H), 4.82-4.24 (m, 4H), 3.67 (s, 3H), 2.92 (s, 1H), 1.98 (d, J=10.7 Hz, 2H), 1.87-1.43 (m, 6H). LC/MS (m/z): 515.325 [M+H$^+$]; UPLC $t_R$ 1.25 min.

5-((3-(Furan-3-yl)-1-((4-methoxyphenyl)methyl)-1H-pyrazol-5-yl)amino)-4-(5H,6H,7H-pyrrolo[3,4-b]pyridine-6-carbonyl)benzene-1,3-diol (54)

Acid 19g (52.5 mg, 103 µmol) was coupled with 6,7-dihydro-H-pyrrolo[3,4-b]pyridine dihydrochloride (29.8 mg, 155 µmol), and triethylamine (108 µL, 773 µmol) using General Procedure G to give 48.6 mg of MOM-protected intermediate (77% yield) after purification via automated flash system (0% to 3% methanol in $CH_2Cl_2$) and manual flash chromatography (55:45:1 $CH_2Cl_2$:ethyl acetate:conc. $NH_{40}H$ (aq.) to 40:60:1 $CH_2Cl_2$:ethyl acetate:conc. $NH_{40}H$ (aq.)). $^1$H NMR (400 MHz, $CDCl_3$) δ 8.51 (dd, J=21.5, 4.9 Hz, 1H), 7.75 (q, J=1.2 Hz, 1H), 7.70-7.61 (m, 1H), 7.48 (d, J=7.8 Hz, 1H), 7.44 (q, J=1.7 Hz, 1H), 7.24-7.16 (m, 1H), 7.12 (dd, J=8.7, 6.7 Hz, 2H), 6.74 (dd, J=1.9, 0.9 Hz, 1H), 6.73-6.59 (m, 2H), 6.53 (d, J=5.5 Hz, 1H), 6.42 (d, J=7.9, 2.1 Hz, 1H), 6.29 (dd, J=15.9, 2.1 Hz, 1H), 6.16 (d, J=2.0 Hz, 1H), 5.16 (dd, J=11.1, 7.1 Hz, 5H), 5.07 (d, J=2.5 Hz, 3H), 5.01-4.78 (m, 4H), 4.53 (d, J=15.1 Hz, 1H), 3.69 (d, J=3.1 Hz, 4H), 3.47-3.42 (m, 6H), 2.80 (s, 3H). $^{13}$C NMR (101 MHz, $CDCl_3$) δ 167.2, 167.1, 160.0, 159.1, 159.0, 157.4, 157.1, 155.5, 155.4, 149.3, 149.2, 143.5, 143.5, 143.3, 143.2, 143.2, 140.0, 139.8, 139.1, 131.1, 130.7, 130.3, 129.9, 128.6, 128.6, 128.4, 128.2, 122.5, 122.5, 120.1, 113.9, 113.9, 108.7, 107.2, 96.7, 96.3, 95.4, 95.3, 95.3, 94.3, 94.2, 56.6, 56.6, 56.3, 56.3, 55.2, 55.2, 53.4, 52.5, 51.7, 51.6, 51.4, 50.6, 47.4, 38.6, 8.7. LC/MS (m/z): 612.358 [M+H$^+$]; UPLC t$_R$ 1.55 min.

The MOM-protected intermediate (48.6 mg, 79.5 µmol) was deprotected using General Procedure F to afford 28.7 mg of 54 (69% yield) after purification using mass-guided preparative HPLC. $^1$H NMR (400 MHz, CD$_3$OD) δ 8.39 (dd, J=5.0, 1.5 Hz, 1H), 7.76 (dd, J=1.6, 0.8 Hz, 1H), 7.70 (s, 1H), 7.46 (t, J=1.7 Hz, 1H), 7.29 (dd, J=7.8, 5.0 Hz, 1H), 7.04 (d, J=8.7 Hz, 2H), 6.72-6.59 (m, 3H), 6.26 (s, 1H), 5.95 (d, J=2.1 Hz, 1H), 5.91 (d, J=2.1 Hz, 1H), 5.14 (s, 2H), 5.02-4.45 (m, 4H). LC/MS (m/z): 524.279 [M+H$^+$]; UPLC t$_R$ 1.25 min.

5-((3-(Furan-3-yl)-1-((4-methoxyphenyl)methyl)-1H-pyrazol-5-yl)amino)-4-(1H,4H,5H,6H-pyrrolo[3,4-c]pyrazole-5-carbonyl)benzene-1,3-diol (55)

Acid 19g (51.7 mg, 101 µmol) was coupled with 1H,4H, 5H,6H-pyrrolo[3,4-c]pyrazole (16.6 mg, 152 µmol), and triethylamine (28 µL, 200 µmol) using General Procedure G to give 33.3 mg of MOM-protected intermediate (55% yield) after purification via automated flash system (10% to 30% acetone in CH$_2$Cl$_2$) and manual flash chromatography (96:4 CH$_2$Cl$_2$:methanol). $^1$H NMR (400 MHz, CDCl$_3$) δ 7.81 (s, 1H), 7.48-7.31 (m, 1H), 7.17 (d, J=7.8 Hz, 2H), 6.80-6.66 (m, 3H), 6.43 (d, J=8.6 Hz, 1H), 6.31 (s, 1H), 6.16 (d, J=2.4 Hz, 1H), 5.16 (d, J=11.2 Hz, 4H), 5.06 (s, 2H), 4.86-4.55 (m, 3H), 4.33 (s, 1H), 3.72 (d, J=1.9 Hz, 3H), 3.51-3.35 (m, 6H). 13C NMR (101 MHz, CDCl$_3$) δ 167.4, 159.8, 159.8, 159.1, 159.0, 155.3, 143.5, 143.3, 143.3, 140.0, 140.0, 139.1, 139.1, 128.7, 128.3, 128.2, 120.1, 114.0, 113.9, 108.8, 107.9, 107.8, 96.7, 96.6, 96.5, 95.4, 95.3, 94.3, 56.5, 56.3, 55.2, 55.2, 51.6, 46.6, 46.5, 45.6, 45.4. LC/MS (m/z): 601.331 [M+H$^+$]; UPLC t$_R$ 1.35 min The MOM-protected intermediate (32.9 mg, 55.8 µmol) was deprotected using General Procedure F to afford 18.9 mg of 55 (67% yield) after purification using mass-guided preparative HPLC. $^1$H NMR (400 MHz, CD$_3$OD) δ 7.84-7.78 (m, 1H), 7.49 (t, J=1.7 Hz, 1H), 7.41 (s, 1H), 7.05 (d, J=8.7 Hz, 2H), 6.76-6.66 (m, 3H), 6.27 (s, 1H), 5.93 (d, J=2.1 Hz, 1H), 5.89 (d, J=2.1 Hz, 1H), 5.14 (s, 2H), 4.79-4.27 (m, 4H), 3.67 (s, 3H). LC/MS (m/z): 513.296 [M+H$^+$]; UPLC t$_R$ 1.15 min.

(2,4-dihydroxy-6-((1-methyl-1H-pyrazol-5-yl)amino)phenyl)(isoindolin-2-yl)methanone (56)

Amide 14i (37.0 mg, 84.4 µmol) was deprotected using General Procedure F to afford 17.1 mg of 56 (58% yield) after purification using mass-guided preparative HPLC. $^1$H NMR (400 MHz, CD$_3$OD) δ 7.36 (d, J=2.0 Hz, 1H), 7.28 (s, 4H), 6.03 (d, J=2.1 Hz, 1H), 5.92 (d, J=2.1 Hz, 1H), 5.61 (d, J=2.1 Hz, 1H), 5.07-4.70 (m, 4H), 3.64 (s, 3H). LC/MS (m/z): 351.292 [M+H$^+$]; UPLC t$_R$ 1.09 min.

5-((1-Methyl-1H-pyrazol-5-yl)amino)-4-(5H,6H,7H-pyrrolo[3,4-b]pyridine-6-carbonyl)benzene-1,3-diol (57)

Acid 19h (27.6 mg, 81.8 µmmol) was coupled with 6,7-dihydro-5H-pyrrolo[3,4-b]pyridine dihydrochloride (23.7 mg, 123 µmol), and triethylamine (86 µL, 610 µmol) using General Procedure G to give 13.3 mg of MOM-protected intermediate (37% yield) after purification via an automated flash system (1% to 5% methanol in CH$_2$Cl$_2$) and manual flash chromatography (60:40:1 CH$_2$Cl$_2$:acetone: conc. NH$_4$OH (aq.)). $^1$H NMR (400 MHz, CDCl$_3$) δ 8.52 (dd, J=19.1, 5.0 Hz, 1H), 7.77-7.50 (m, 1H), 7.44 (d, J=2.0 Hz, 1H), 7.26 (s, 1H), 6.79 (d, J=15.3 Hz, 1H), 6.45 (dd, J=10.5, 2.1 Hz, 1H), 6.13 (dd, J=4.4, 2.1 Hz, 1H), 6.03 (d, J=2.2 Hz, 1H), 5.18 (d, J=9.2 Hz, 3H), 5.11-4.81 (m, 4H), 4.79-4.53 (m, 1H), 3.70 (s, 3H), 3.46 (s, 3H), 3.45 (s, 3H). $^{13}$C NMR (101 MHz, CDCl$_3$) δ 167.5, 160.1, 160.1, 157.6, 157.2, 155.7, 155.6, 149.5, 149.3, 144.6, 144.4, 138.6, 131.1, 130.6, 129.9, 122.6, 122.4, 106.9, 99.0, 96.3, 96.2, 95.5, 95.3, 95.3, 95.2, 94.3, 94.2, 56.6, 56.6, 56.3, 56.2, 53.5, 52.7, 51.5, 50.7, 35.1. LC/MS (m/z): 440.426 [M+H$^+$]; UPLC t$_R$ 1.13 min The MOM-protected intermediate (13.3 mg, 30.3 µmol) was deprotected using General Procedure F to afford 5.1 mg of 57 (48% yield) after purification using mass-guided preparative HPLC. $^1$H NMR (400 MHz, CD$_3$OD) δ 8.44 (dd, J=5.1, 1.5 Hz, 1H), 7.80 (d, J=7.7 Hz, 1H), 7.36 (d, J=2.0 Hz, 2H), 6.03 (d, J=2.1 Hz, 1H), 5.92 (d, J=2.1 Hz, 1H), 5.62 (d, J=2.1 Hz, 1H), 4.90 (s, 4H), 3.65 (s, 3H). LC/MS (m/z): 352.218 [M+H$^+$]; UPLC t$_R$ 0.77 min.

5-((1-Methyl-1H-pyrazol-5-yl)amino)-4-(1H,4H,5H, 6H-pyrrolo[3,4-c]pyrazole-5-carbonyl)benzene-1,3-diol (58)

Acid 19h (16.8 mg, 49.8 µmmol) was coupled with 1H,4H,5H,6H-pyrrolo[3,4-c]pyrazole (8.2 mg, 75 µmol), and triethylamine (14 µL, 100 µmol) using General Procedure G to afford 4.2 mg of MOM-protected intermediate (20% yield) after purification via automated flash system (1% to 5% methanol in CH$_2$Cl$_2$). $^1$H NMR (400 MHz, CDCl$_3$) δ 7.43 (d, J=2.0 Hz, 1H), 7.34 (d, J=46.2 Hz, 1H), 6.59 (d, J=7.2 Hz, 1H), 6.42 (dd, J=8.2, 2.1 Hz, 1H), 6.07 (d, J=2.1 Hz, 1H), 6.01 (t, J=1.9 Hz, 1H), 5.16 (q, J=6.3, 4.9 Hz, 2H), 5.07 (d, J=2.5 Hz, 2H), 4.98-4.64 (m, 3H), 4.42 (dd, J=13.5, 6.5 Hz, 1H), 3.67 (s, 3H), 3.45 (s, 3H), 3.43 (d, J=1.6 Hz, 3H). LC/MS (m/z): 429.318 [M+H$^+$]; UPLC t$_R$ 1.03 min.

The MOM-protected intermediate (4.2 mg, 9.8 µmol) was deprotected using General Procedure F to afford 2.3 mg of 58 (69% yield) after purification using mass-guided preparative HPLC. $^1$H NMR (400 MHz, CD$_3$OD) δ 7.45 (s, 1H), 7.38 (d, J=2.1 Hz, 1H), 6.04 (d, J=2.1 Hz, 1H), 5.91 (d, J=2.1 Hz, 1H), 5.60 (d, J=2.1 Hz, 1H), 4.80-4.43 (m, 4H), 3.65 (s, 3H). LC/MS (m/z): 341.235 [M+H$^+$]; UPLC t$_R$ 0.66 min.

4-(2,3-Dihydro-1H-isoindole-2-carbonyl)-5-((1-(propan-2-yl)-1H-pyrazol-5-yl)amino)benzene-1,3-diol (59)

To a mixture of carboxylic acid 19i (34.9 mg, 95.5 µmmol) and isoindoline hydrochloride (22.3 mg, 143 µmol) in THF (0.62 mL) and CH$_2$Cl$_2$ (0.62 mL) was added triethylamine (53 µL, 380 µmol) followed by PyBOP (59.7, 115 µmol). After the reaction was stirred at room temperature overnight, the reaction mixture was diluted with CH$_2$Cl$_2$. The reaction mixture was washed twice with saturated NaHCO$_3$ (aq.), once with brine and then dried with anhydrous Na$_2$SO$_4$. The salts were removed via gravity filtration and volatile materials were condensed in vacuo. The crude residue was dissolved in methanol (4.8) and HCl (2 M, 310 µL, 620 µmol) was added to the resulting mixture. The reaction was stirred at 50° C. overnight. After cooling to room temperature, volatile materials were condensed in vacuo. The crude residue was purified using mass-guided preparative HPLC to afford 8.7 mg of 59 (24% yield over 2 steps). $^1$H NMR (400 MHz, CD$_3$OD) δ 7.43 (d, J=2.0 Hz, 1H), 7.29 (d, J=1.7 Hz, 4H), 6.03 (d, J=2.0 Hz, 1H), 5.89 (d, J=2.1 Hz, 1H), 5.60-5.55 (m, 1H), 4.90 (s, 4H), 4.55 (p, J=6.7 Hz, 1H), 1.36 (d, J=6.7 Hz, 6H). LC/MS (m/z): 379.344 [M+H$^+$]; UPLC $t_R$ 1.25 min

(5,7-dihydro-6H-pyrrolo[3,4-b]pyridin-6-yl)(2,4-dihydroxy-6-((1-isopropyl-1H-pyrazol-5-yl)amino)phenyl)methanone (60)

Synthesized using the same procedure for the synthesis of 59 with 19i (37.6 mg, 103 μmol), 6,7-dihydro-5H-pyrrolo[3,4-b]pyridine dihydrochloride (29.8 mg, 154 μmol) and triethylamine (110 μL, 770 μmol) followed by MOM deprotection with HCl (2 M, 330 μL, 670 μmol) in methanol at 50° C. overnight to afford 6.6 mg of 60 (17% yield) after purification using mass-guided preparative HPLC. $^1$H NMR (400 MHz, CD$_3$OD) δ 8.55 (s, 1H), 8.45 (d, J=4.8 Hz, 1H), 7.82 (d, J=7.4 Hz, 1H), 7.43 (d, J=1.6 Hz, 1H), 7.36 (dd, J=7.4, 4.8 Hz, 1H), 6.04 (d, J=1.6 Hz, 1H), 5.90 (d, J=2.0 Hz, 1H), 5.59 (d, J=2.0 Hz, 1H), 4.65-4.53 (m, 2H), 1.67 (d, J=6.6 Hz, 6H). LC/MS (m/z): 380.359 [M+H$^+$]; UPLC $t_R$ 0.93 min.

5-((1-(Propan-2-yl)-1H-pyrazol-5-yl)amino)-4-(1H,4H,5H,6H-pyrrolo[3,4-c]pyrazole-5-carbonyl)benzene-1,3-diol (61)

Synthesized using the same procedure for the synthesis of 59 with 19i (36.7 mg, 100 μmol), 1H,4H,5H,6H-pyrrolo[3,4-c]pyrazole (16.4 mg, 151 μmol) and triethylamine (28 μL, 200 μmol) followed by MOM deprotection with HCl (2 M, 330 μL, 650 μmol) in methanol at 50° C. overnight to afford 11.7 mg of 61 (32% yield) after purification using mass-guided preparative HPLC. $^1$H NMR (400 MHz, CD$_3$OD) δ 7.45 (t, J=2.8 Hz, 2H), 6.04 (d, J=2.0 Hz, 1H), 5.88 (d, J=2.1 Hz, 1H), 5.56 (d, J=2.1 Hz, 1H), 4.80-4.42 (m, 5H), 1.37 (d, J=6.6 Hz, 6H). LC/MS (m/z): 369.332 [M+H$^+$]; UPLC $t_R$ 0.82 min.

4-(2,3-Dihydro-1H-isoindole-2-carbonyl)-5-((1-(2-methylpropyl)-1H-pyrazol-5-yl)amino)benzene-1,3-diol (62)

Carboxylic acid 19j (45 mg, 120 μmol) was subjected to General Procedure H$_1$ to afford 17 mg of 62 (37% yield) after purification using mass-guided preparative HPLC. $^1$H NMR (400 MHz, CD$_3$OD) δ 7.40 (d, J=2.0 Hz, 1H), 7.28 (s, 4H), 6.06 (d, J=2.0 Hz, 1H), 5.92 (d, J=2.1 Hz, 1H), 5.74 (d, J=2.1 Hz, 1H), 5.14-4.69 (m, 4H), 3.75 (d, J=7.6 Hz, 2H), 3.34 (s, 2H), 2.09 (dh, J=12.5, 6.3, 5.9 Hz, 1H), 0.79 (d, J=6.7 Hz, 6H). LC/MS (m/z): 393.238 [M+H$^+$]; UPLC $t_R$ 1.38 min

5-((1-(2-Methylpropyl)-1H-pyrazol-5-yl)amino)-4-(5H,6H,7H-pyrrolo[3,4-b]pyridine-6-carbonyl)benzene-1,3-diol (63)

Carboxylic acid 19j (46 mg, 120 μmol) was subjected to General Procedure H$_2$ to afford 4.7 mg of 63 (9.9% yield) after purification using mass-guided preparative HPLC. $^1$H NMR (400 MHz, CD$_3$OD) δ 8.44 (dd, J=5.2, 1.5 Hz, 1H), 7.80 (d, J=7.7 Hz, 1H), 7.40 (d, J=2.0 Hz, 1H), 7.35 (dd, J=7.8, 5.0 Hz, 1H), 6.06 (d, J=2.0 Hz, 1H), 5.92 (d, J=2.1 Hz, 1H), 5.75 (d, J=2.1 Hz, 1H), 5.04-4.57 (m, 4H), 3.77 (d, J=7.5 Hz, 2H), 2.12 (hept, J=7.0 Hz, 1H), 0.81 (d, J=6.7 Hz, 6H). LC/MS (m/z): 394.341 [M+H$^+$]; UPLC $t_R$ 1.08 min.

5-((1-(2-Methylpropyl)-1H-pyrazol-5-yl)amino)-4-(1H,4H,5H,6H-pyrrolo[3,4-c]pyrazole-5-carbonyl)benzene-1,3-diol (64)

Carboxylic acid 19j (46 mg, 120 μmol) was subjected to General Procedure H$_3$ to afford 13.2 mg of 64 (28% yield) after purification using mass-guided preparative HPLC. $^1$H NMR (400 MHz, CD$_3$OD) δ 7.46 (s, 1H), 7.42 (d, J=2.0 Hz, 1H), 6.06 (d, J=2.1 Hz, 1H), 5.91 (d, J=2.1 Hz, 1H), 5.72 (d, J=2.1 Hz, 1H), 4.88 (s, 4H), 3.76 (d, J=7.5 Hz, 2H), 2.12 (p, J=6.9 Hz, 1H), 0.81 (d, J=6.7 Hz, 6H). LC/MS (m/z): 383.27 [M+H$^+$]; UPLC $t_R$ 0.95 min.

5-((1-(Cyclohexylmethyl)-1H-pyrazol-5-yl)amino)-4-(2,3-dihydro-1H-isoindole-2-carbonyl)benzene-1,3-diol (65)

Carboxylic acid 19k (30.9 mg, 73.4 μmol) was subjected to General Procedure H$_1$ to afford 12.4 mg of 65 (39% yield) after purification using mass-guided preparative HPLC $^1$H NMR (400 MHz, CD$_3$OD) δ 7.40 (d, J=2.1 Hz, 1H), 7.29 (s, 5H), 6.06 (d, J=2.1 Hz, 1H), 5.92 (d, J=2.0 Hz, 1H), 5.69 (d, J=2.0 Hz, 1H), 5.10-4.65 (m, 4H), 3.75 (d, J=7.4 Hz, 2H), 1.77 (ddd, J=11.1, 7.5, 3.6 Hz, 1H), 1.63-1.40 (m, 5H), 1.16-0.72 (m, 5H). $^{13}$C NMR (126 MHz, 2:1 (CD$_3$)$_2$SO: CD$_3$OD) δ 167.6, 159.8, 155.8, 144.4, 140.4, 138.1, 136.9, 127.7, 123.1, 104.0, 99.5, 94.6, 92.9, 53.7, 40.4, 38.3, 30.4, 26.1, 25.5. LC/MS (m/z): 433.596 [M+H$^+$]; UPLC $t_R$ 1.46 min.

5-((1-(Cyclohexylmethyl)-1H-pyrazol-5-yl)amino)-4-(5H,6H,7H-pyrrolo[3,4-b]pyridine-6-carbonyl)benzene-1,3-diol (66)

Synthesized using General Procedure H$_2$ from carboxylic acid 19k (36.4 mg, 86.8 μmol) was subjected to General Procedure H$_2$ to afford 13.8 mg of 66 (37% yield) after purification using mass-guided preparative HPLC $^1$H NMR (400 MHz, CD$_3$OD) δ 8.44 (dd, J=5.0, 1.4 Hz, 1H), 7.81 (d, J=7.7 Hz, 1H), 7.40 (d, J=2.0 Hz, 1H), 7.36 (dd, J=7.8, 5.0 Hz, 1H), 6.06 (d, J=2.0 Hz, 1H), 5.93 (d, J=2.0 Hz, 1H), 5.71 (d, J=2.1 Hz, 1H), 4.89 (s, 4H), 3.77 (d, J=7.4 Hz, 2H), 1.86-1.72 (m, 1H), 1.68-1.39 (m, 5H), 1.18-0.74 (m, 5H). LC/MS (m/z): 434.39 [M+H$^+$]; UPLC $t_R$ 1.22 min.

5-((1-(Cyclohexylmethyl)-1H-pyrazol-5-yl)amino)-4-(1H,4H,5H,6H-pyrrolo[3,4-c]pyrazole-5-carbonyl)benzene-1,3-diol (67)

The product 67 was synthesized following General Procedure H$_3$ from carboxylic acid 19k (37.2 mg, 88.7 μmol) was subjected to General Procedure H$_3$ to afford 14.8 mg of 67 (40% yield) after purification using mass-guided preparative HPLC $^1$H NMR (400 MHz, CD$_3$OD) δ 7.46 (s, 1H), 7.41 (d, J=2.0 Hz, 1H), 6.06 (d, J=2.0 Hz, 1H), 5.92 (d, J=2.0 Hz, 1H), 5.69 (d, J=2.1 Hz, 1H), 5.04-4.38 (m, 4H), 3.76 (d, J=7.4 Hz, 2H), 1.79 (ddq, J=11.3, 7.4, 3.7 Hz, 1H), 1.67-1.43 (m, 5H), 1.18-0.76 (m, 5H). LC/MS (m/z): 423.363 [M+H$^+$]; UPLC $t_R$ 1.08 min.

4-(2,3-Dihydro-1H-isoindole-2-carbonyl)-5-((1-phenyl-1H-pyrazol-5-yl)amino]benzene-1,3-diol (68)

Synthesized using General Procedure H$_1$ from carboxylic acid 19l (42 mg, 110 μmol) was subjected to General Procedure H$_1$ to afford 2.4 mg of 68 (5.5% yield) after purification using mass-guided preparative HPLC. $^1$H NMR (400 MHz, CD$_3$OD) δ 7.61 (d, J=2.0 Hz, 1H), 7.49-7.40 (m, 2H), 7.34-7.16 (m, 8H), 6.26 (d, J=2.0 Hz, 1H), 5.89 (d, J=2.1 Hz, 1H), 5.85 (d, J=2.1 Hz, 1H), 4.98-4.42 (m, 4H). LC/MS (m/z): 413.307 [M+H$^+$]; UPLC $t_R$ 1.39 min.

5-((1-Phenyl-1H-pyrazol-5-yl)amino)-4-(5H,6H,7H-pyrrolo[3,4-b]pyridine-6-carbonyl)benzene-1,3-diol (69)

Synthesized using General Procedure H$_2$ from carboxylic acid 19l (43 mg, 110 μmol) was subjected to General Procedure H$_2$ to afford 5.1 mg of 69 (11% yield) after purification using mass-guided preparative HPLC. $^1$H NMR (400 MHz, CD$_3$OD) δ 8.45 (d, J=5.0 Hz, 1H), 7.77 (s, 1H), 7.61 (d, J=2.0 Hz, 1H), 7.50-7.41 (m, 2H), 7.39-7.29 (m, 3H), 7.29-7.18 (m, 1H), 6.26 (d, J=2.0 Hz, 1H), 5.91-5.84 (m, 2H), 5.12-4.44 (m, 4H). LC/MS (m/z): 414.277 [M+H$^+$]; UPLC $t_R$ 1.08 min.

5-((1-Phenyl-1H-pyrazol-5-yl)amino)-4-(1H,4H,5H,6H-pyrrolo[3,4-c]pyrazole-5-carbonyl)benzene-1,3-diol (70)

Synthesized using General Procedure H$_3$ from carboxylic acid 19l (44 mg, 110 μmol) was subjected to General Procedure H$_3$ to afford 6.6 mg of 70 (15% yield) after purification using mass-guided preparative HPLC. $^1$H NMR (400 MHz, CD$_3$OD) δ 7.62 (d, J=2.0 Hz, 1H), 7.52-7.41 (m, 3H), 7.39-7.24 (m, 3H), 6.26 (d, J=2.0 Hz, 1H), 5.85 (dd, J=17.7, 2.1 Hz, 2H), 4.73-4.07 (m, 4H). LC/MS (m/z): 403.295 [M+H$^+$]; UPLC $t_R$ 0.97 min.

5-((1-Cyclohexyl-1H-pyrazol-5-yl)amino)-4-(2,3-dihydro-1H-isoindole-2-carbonyl)benzene-1,3-diol (71)

Synthesized using General Procedure H$_1$ from carboxylic acid 19m (48.8 mg, 120 μmol) was subjected to General Procedure H$_1$ to afford 18.3 mg of 71 (36% yield) after purification using mass-guided preparative HPLC. $^1$H NMR (400 MHz, CD$_3$OD) δ 7.41 (d, J=2.0 Hz, 1H), 7.37-7.20 (m, 4H), 6.03 (d, J=2.0 Hz, 1H), 5.90 (d, J=2.1 Hz, 1H), 5.59 (d, J=2.1 Hz, 1H), 5.03-4.76 (m, 4H), 4.09 (d, J=11.4 Hz, 1H), 1.98-1.71 (m, 9H), 1.63 (d, J=10.8 Hz, 1H), 1.23 (dd, J=26.4, 15.1 Hz, 2H). LC/MS (m/z): 419.041 [M+H$^+$]; UPLC $t_R$ 1.46 min 5-((1-Cyclohexyl-1H-pyrazol-5-yl)amino)-4-(5H,6H,7H-pyrrolo[3,4-b]pyridine-6-carbonyl)benzene-1,3-diol (72)

Synthesized using General Procedure H$_2$ from carboxylic acid 19m (54.4 mg, 134 μmol) was subjected to General Procedure H$_2$ to afford 14.3 mg of 72 (25% yield) after purification using mass-guided preparative HPLC. $^1$H NMR (400 MHz, CD$_3$OD) δ 8.44 (dd, J=5.1, 1.5 Hz, 1H), 7.86-7.74 (m, 1H), 7.40 (d, J=2.0 Hz, 1H), 7.36 (dd, J=7.8, 5.0 Hz, 1H), 6.03 (d, J=2.0 Hz, 1H), 5.90 (d, J=2.1 Hz, 1H), 5.61 (d, J=2.1 Hz, 1H), 4.88 (s, 4H), 4.12 (dt, J=11.3, 6.4 Hz, 1H), 1.96-1.71 (m, 7H), 1.71-1.59 (m, 1H), 1.44-1.08 (m, 3H). LC/MS (m/z): 420.32 [M+H$^+$]; UPLC $t_R$ 1.18 min.

5-((1-Cyclohexyl-1H-pyrazol-5-yl)amino)-4-(1H,4H,5H,6H-pyrrolo[3,4-c]pyrazole-5-carbonyl)benzene-1,3-diol (73)

Synthesized using General Procedure H$_3$ from carboxylic acid 19m (58.8 mg, 145 μmol) was subjected to General Procedure H$_3$ to afford 22.5 mg of 73 (38% yield) after purification using mass-guided preparative HPLC. $^1$H NMR (400 MHz, CD$_3$OD) δ 7.46 (s, 1H), 7.43 (d, J=2.0 Hz, 1H), 6.04 (d, J=2.0 Hz, 1H), 5.89 (d, J=2.1 Hz, 1H), 5.58 (d, J=2.1 Hz, 1H), 4.80-4.43 (m, 4H), 4.11 (dt, J=10.9, 6.4 Hz, 1H), 1.92-1.72 (m, 7H), 1.71-1.61 (m, 1H), 1.44-1.12 (m, 3H). LC/MS (m/z): 409.337 [M+H$^+$]; UPLC $t_R$ 1.05 min.

5-((1-Benzyl-1H-pyrazol-5-yl)amino)-4-(2,3-dihydro-1H-isoindole-2-carbonyl)benzene-1,3-diol (74)

Acid 19n (42.1 mg, 102 μmol) was subjected to General Procedure H$_1$ to afford 3.3 mg of 74 (7.6% yield) after purification using mass-guided preparative HPLC. $^1$H NMR (400 MHz, CD$_3$OD) δ 7.45 (d, J=2.0 Hz, 1H), 7.34-7.18 (m, 4H), 7.10 (dd, J=4.0, 2.5 Hz, 3H), 7.03 (dd, J=6.8, 3.0 Hz, 2H), 6.12 (d, J=2.1 Hz, 1H), 5.92 (d, J=2.1 Hz, 1H), 5.79 (d, J=2.1 Hz, 1H), 5.18 (s, 2H), 5.01-4.52 (m, 4H). LC/MS (m/z): 427.333 [M+H$^+$]; UPLC $t_R$ 1.37 min.

5-((1-Benzyl-1H-pyrazol-5-yl)amino)-4-(5H,6H,7H-pyrrolo[3,4-b]pyridine-6-carbonyl)benzene-1,3-diol (75)

Acid 19n (42.6 mg, 103 μmol) was subjected to General Procedure H$_2$ to afford 2.9 mg of 75 (6.6% yield) after purification using mass-guided preparative HPLC. $^1$H NMR (400 MHz, CD$_3$OD) δ 8.44 (d, J=5.1 Hz, 1H), 7.76 (s, 1H), 7.45 (d, J=2.0 Hz, 1H), 7.41-7.31 (m, 1H), 7.17-6.99 (m, 5H), 6.13 (d, J=2.1 Hz, 1H), 5.92 (d, J=2.1 Hz, 1H), 5.79 (d, J=2.1 Hz, 1H), 5.19 (s, 2H), 5.05-4.11 (m, 4H). LC/MS (m/z): 428.347 [M+H$^+$]; UPLC $t_R$ 1.08 min.

5-((1-Benzyl-1H-pyrazol-5-yl)amino)-4-(1H,4H,5H,6H-pyrrolo[3,4-c]pyrazole-5-carbonyl)benzene-1,3-diol (76)

Acid 19n (43 mg, 100 μmol) was subjected to General Procedure H$_3$ to afford 5.0 mg of 76 (12% yield) after purification using mass-guided preparative HPLC. $^1$H NMR (400 MHz, CD$_3$OD) δ 7.51-7.33 (m, 2H), 7.15 (dd, J=5.2, 1.9 Hz, 4H), 7.06 (dd, J=6.9, 2.7 Hz, 2H), 6.12 (d, J=2.0 Hz, 1H), 5.91 (d, J=2.1 Hz, 1H), 5.78 (d, J=2.1 Hz, 1H), 5.19 (s, 3H), 4.80-4.21 (m, 4H). LC/MS (m/z): 417.321 [M+H$^+$]; UPLC $t_R$ 0.96 min.

4-(2,3-Dihydro-1H-isoindole-2-carbonyl)-5-((1-((pyridin-3-yl)methyl)-1H-pyrazol-5-yl)amino)benzene-1,3-diol (77)

Acid 19o (41.5 mg, 100 μmol) was subjected to General Procedure H$_1$ to afford 4.0 mg of 77 (9.3% yield) after purification using mass-guided preparative HPLC. $^1$H NMR (400 MHz, CD$_3$OD) δ 8.32 (d, J=6.5 Hz, 2H), 7.61 (d, J=1.9 Hz, 1H), 7.47 (d, J=2.0 Hz, 1H), 7.25 (d, J=18.7 Hz, 6H), 6.13 (d, J=2.0 Hz, 1H), 5.91 (d, J=2.1 Hz, 1H), 5.64 (d, J=2.1 Hz, 1H), 5.25 (s, 2H), 5.00-4.41 (m, 4H). LC/MS (m/z): 428.347 [M+H$^+$]; UPLC $t_R$ 0.98 min.

5-((1-((Pyridin-3-yl)methyl)-1H-pyrazol-5-yl)amino)-4-(5H,6H,7H-pyrrolo[3,4-b]pyridine-6-carbonyl)benzene-1,3-diol (78)

Acid 19o (42.4 mg, 102 μmol) was subjected to General Procedure H$_2$ to afford 2.5 mg of 78 (5.7% yield) after purification using mass-guided preparative HPLC. $^1$H NMR (400 MHz, CD$_3$OD) δ 8.44 (d, J=5.1 Hz, 1H), 8.38-8.29 (m, 2H), 7.75-7.59 (m, 2H), 7.46 (d, J=2.1 Hz, 1H), 7.41-7.32 (m, 1H), 7.32-7.19 (m, 2H), 6.13 (d, J=2.0 Hz, 1H), 5.91 (d, J=2.1 Hz, 1H), 5.64 (d, J=2.0 Hz, 1H), 5.27 (s, 2H), 5.04-4.49 (m, 4H). LC/MS (m/z): 429.362 [M+H$^+$]; UPLC t$_R$ 0.76 min.

5-((1-((Pyridin-3-yl)methyl)-1H-pyrazol-5-yl)amino)-4-(1H,4H,5H,6H-pyrrolo[3,4-c]pyrazole-5-carbonyl)benzene-1,3-diol (79)

Acid 19o (46.6 mg, 112 μmol) was subjected to General Procedure H$_3$ to afford 4.2 mg of 79 (9.0% yield) after purification using mass-guided preparative HPLC. $^1$H NMR (400 MHz, CD$_3$OD) δ 8.40 (dd, J=5.0, 1.6 Hz, 1H), 8.39-8.31 (m, 2H), 7.67-7.56 (m, 1H), 7.49 (d, J=2.1 Hz, 1H), 7.36 (ddd, J=7.9, 4.9, 0.9 Hz, 1H), 6.09 (d, J=2.0 Hz, 1H), 5.77 (s, 2H), 5.27 (s, 2H), 5.01-4.45 (m, 4H). LC/MS (m/z): 418.335 [M+H$^+$]; UPLC t$_R$ 0.63 min.

4-(2,3-Dihydro-1H-isoindole-2-carbonyl)-5-((1-((furan-2-yl)methyl)-1H-pyrazol-5-yl)amino)benzene-1,3-diol (80)

Acid 19p (47.1 mg, 117 μmol) was subjected to General Procedure H$_1$ to afford 12.7 mg of 80 (26% yield) after purification using mass-guided preparative HPLC. $^1$H NMR (400 MHz, CD$_3$OD) δ 7.40 (d, J=2.0 Hz, 1H), 7.26 (d, J=11.9 Hz, 5H), 6.23 (t, J=1.6 Hz, 2H), 6.08 (d, J=2.0 Hz, 1H), 5.94 (d, J=2.1 Hz, 1H), 5.15 (s, 2H), 5.00-4.65 (m, 4H). LC/MS (m/z): 417.321 [M+H$^+$]; UPLC t$_R$ 1.29 min.

5-((1-((Furan-2-yl)methyl)-1H-pyrazol-5-yl)amino)-4-(5H,6H,7H-pyrrolo[3,4-b]pyridine-6-carbonyl)benzene-1,3-diol (81)

Acid 19p (49.6 mg, 123 μmol) was subjected to General Procedure H$_2$ to afford 7.6 mg of 81 (15% yield) after purification using mass-guided preparative HPLC. $^1$H NMR (400 MHz, CD$_3$OD) δ 8.44 (dd, J=5.1, 1.4 Hz, 1H), 7.85-7.70 (m, 1H), 7.40 (d, J=2.1 Hz, 1H), 7.35 (dd, J=7.8, 5.0 Hz, 1H), 7.28 (dd, J=1.8, 0.9 Hz, 1H), 6.25 (dd, J=3.2, 1.3 Hz, 2H), 6.08 (d, J=2.1 Hz, 1H), 5.94 (d, J=2.1 Hz, 1H), 5.79 (d, J=2.1 Hz, 1H), 5.16 (s, 2H), 5.03-4.72 (m, 4H). LC/MS (m/z): 418.291 [M+H$^+$]; UPLC t$_R$ 0.98 min.

5-((1-((Furan-2-yl)methyl)-1H-pyrazol-5-yl)amino)-4-(1H,4H,5H,6H-pyrrolo[3,4-c]pyrazole-5-carbonyl)benzene-1,3-diol (82)

Acid 19p (55.5 mg, 138 μmol) was subjected to General Procedure H$_3$ to afford 8.5 mg of 82 (15% yield) after purification using mass-guided preparative HPLC. $^1$H NMR (400 MHz, CD$_3$OD) δ 7.45 (s, 1H), 7.41 (d, J=2.1 Hz, 1H), 7.34-7.27 (m, 1H), 6.26 (t, J=1.4 Hz, 2H), 6.08 (d, J=2.0 Hz, 1H), 5.93 (d, J=2.1 Hz, 1H), 5.78 (d, J=2.1 Hz, 1H), 5.16 (s, 2H), 4.80-4.33 (m, 4H). LC/MS (m/z): 407.308 [M+H$^+$]; UPLC t$_R$ 0.89 min.

(2,4-Dihydroxy-6-((1-(4-isopropylbenzyl)-1H-pyrazol-5-yl)amino)phenyl)(isoindolin-2-yl)methanone (83)

Amide 14j (42.1 mg, 75.6 μmol) was deprotected using General Procedure F to afford 7.8 mg of 83 (22% yield) after purification using mass-guided preparative HPLC. $^1$H NMR (400 MHz, CD$_3$OD) δ 7.45 (d, J=2.1 Hz, 1H), 7.29 (s, 4H), 6.96 (d, J=1.0 Hz, 4H), 6.11 (d, J=2.1 Hz, 1H), 5.92 (d, J=2.1 Hz, 1H), 5.75 (d, J=2.1 Hz, 1H), 5.13 (s, 2H), 4.95-4.59 (m, 4H), 2.72 (p, J=6.9 Hz, 1H), 1.11 (d, J=6.9 Hz, 6H). LC/MS (m/z): 469.234 [M+H$^+$]; UPLC t$_R$ 1.59 min 5-((1-((4-(Propan-2-yl)phenyl)methyl)-1H-pyrazol-5-yl)amino)-4-(5H,6H,7H-pyrrolo[3,4-b]pyridine-6-carbonyl)benzene-1,3-diol (84)

Acid 19q (24.6 mg, 54.0 μmmol) was coupled with 6,7-dihydro-5H-pyrrolo[3,4-b]pyridine dihydrochloride (15.6 mg, 81.0 μmol), and triethylamine (57 μL, 410 μmol) using General Procedure G to give 20.7 mg of MOM-protected intermediate (69% yield) after purification via an automated flash system (25% to 70% ethyl acetate in hexanes). $^1$H NMR (400 MHz, CDCl$_3$) δ 8.51 (ddd, J=19.6, 5.0, 1.5 Hz, 1H), 7.67-7.44 (m, 2H), 7.21 (ddd, J=12.8, 7.7, 4.9 Hz, 1H), 7.07 (dd, J=8.2, 3.7 Hz, 2H), 7.00 (dd, J=8.2, 3.3 Hz, 2H), 6.51 (d, J=6.0 Hz, 1H), 6.40 (dd, J=6.7, 2.1 Hz, 1H), 6.20 (dd, J=17.0, 2.1 Hz, 1H), 6.12-6.01 (m, 1H), 5.24-5.09 (m, 4H), 5.05 (d, J=3.9 Hz, 2H), 4.93 (dt, J=25.1, 13.4 Hz, 3H), 4.57 (dd, J=15.1, 7.2 Hz, 1H), 3.44 (t, J=1.9 Hz, 6H), 2.83-2.71 (m, 1H), 1.14 (d, J=6.9 Hz, 6H). $^{13}$C NMR (101 MHz, CDCl$_3$) δ 167.3, 167.2, 160.0, 157.6, 157.2, 155.5, 155.4, 149.4, 149.3, 148.5, 148.2, 144.0, 139.0, 138.9, 133.7, 133.6, 133.0, 130.6, 130.3, 129.9, 127.5, 126.7, 126.7, 126.6, 122.5, 122.4, 106.9, 99.3, 99.2, 96.3, 96.2, 95.4, 95.3, 95.3, 95.2, 94.3, 94.2, 56.6, 56.6, 56.3, 56.2, 53.4, 52.6, 51.9, 51.9, 51.5, 50.6, 33.7, 23.9. LC/MS (m/z): 558.417 [M+H$^+$]; UPLC t$_R$ 1.60 min.

The MOM-protected intermediate (20 mg, 36 μmol) was deprotected using General Procedure F to afford 8.5 mg of 84 (50% yield) after purification using mass-guided preparative HPLC. $^1$H NMR (400 MHz, CD$_3$D) 8.44 (dd, J=5.1, 1.5 Hz, 1H), 7.77 (s, 1H), 7.44 (d, J=2.1 Hz, 1H), 7.35 (dd, J=7.8, 5.0 Hz, 1H), 6.99 (s, 4H), 6.11 (d, J=2.1 Hz, 1H), 5.92 (d, J=2.1 Hz, 1H), 5.73 (d, J=2.1 Hz, 1H), 5.14 (s, 2H), 4.89 (s, 25H), 2.73 (p, J=6.9 Hz, 1H), 1.11 (d, J=6.9 Hz, 6H). LC/MS (m/z): 470.381 [M+H$^+$]; UPLC t$_R$ 1.36 min.

5-((1-((4-(Propan-2-yl)phenyl)methyl)-1H-pyrazol-5-yl)amino)-4-(1H,4H,5H,6H-pyrrolo[3,4-c]pyrazole-5-carbonyl)benzene-1,3-diol (85)

Acid 19q (27.7 mg, 60.8 μmmol) was coupled with 1H,4H,5H,6H-pyrrolo[3,4-c]pyrazole (10 mg, 109 μmol), and triethylamine (17 μL, 120 μmol) using General Procedure G to give 17.2 mg of MOM-protected intermediate (52% yield) after purification via automated flash system (2% to 5% methanol in CH$_2$Cl$_2$) and manual flash chromatography (40:59:1 CH$_2$Cl$_2$:ethyl acetate:saturated NH$_4$OH (aq.)). $^1$H NMR (400 MHz, CDCl$_3$) δ 7.49 (d, J=2.0 Hz, 1H), 7.32 (d, J=43.7 Hz, 1H), 7.09 (d, J=7.8 Hz, 2H), 7.04 (d, J=8.1 Hz, 2H), 6.45-6.31 (m, 2H), 6.20 (dd, J=3.7, 2.1 Hz, 1H), 6.07 (d, J=1.9 Hz, 1H), 5.24-5.08 (m, 4H), 5.04 (s, 2H), 4.69 (d, J=20.0 Hz, 2H), 4.36 (dd, J=13.5, 8.5 Hz, 1H), 3.50-3.33 (m, 6H), 2.80 (q, J=7.0, 6.5 Hz, 1H), 1.16 (dd, J=7.0, 1.7 Hz, 6H). $^{13}$C NMR (101 MHz, CDCl$_3$) δ 167.4, 159.9, 159.8, 155.3, 148.4, 148.2, 143.8, 139.1, 139.0, 138.9, 133.6, 133.6, 127.5, 126.7, 126.7, 107.6, 99.4, 99.3, 96.3, 95.3, 95.3, 94.2, 56.5, 56.2, 51.8, 46.6, 33.7, 23.9, 23.9. LC/MS (m/z): 547.434 [M+H$^+$]; UPLC t$_R$ 1.53 min.

The MOM-protected intermediate (17.2 mg, 31.5 μmol) was deprotected using General Procedure F to afford 7.5 mg of 85 (52% yield) after purification using mass-guided preparative HPLC. $^1$H NMR (400 MHz, CD$_3$OD) δ 7.45 (d, J=2.0 Hz, 2H), 7.08-6.91 (m, 4H), 6.11 (d, J=2.0 Hz, 1H), 5.91 (t, J=1.4 Hz, 1H), 5.74 (d, J=2.0 Hz, 1H), 5.14 (s, 2H), 4.80-4.36 (m, 4H), 2.77 (p, J=6.9 Hz, 1H), 1.14 (d, J=6.9 Hz, 6H). LC/MS (m/z): 459.354 [M+H$^+$]; UPLC $t_R$ 1.23 min.

4-(5H,6H,7H-Pyrrolo[3,4-b]pyridine-6-carbonyl)-5-((1-((4-(trifluoromethyl)phenyl)methyl)-1H-pyrazol-5-yl)amino]benzene-1,3-diol (86)

Acid 19r (35.1 mg, 65 µmol) was subjected to General Procedure H$_2$ to afford 10.3 mg of 86 (32% yield) after purification using mass-guided preparative HPLC. $^1$H NMR (400 MHz, CD$_3$OD) δ 8.43 (dd, J=5.0, 1.4 Hz, 1H), 7.75 (s, 1H), 7.52-7.42 (m, 3H), 7.34 (dd, J=7.8, 5.0 Hz, 1H), 7.25 (d, J=8.0 Hz, 2H), 6.14 (d, J=2.1 Hz, 1H), 5.92 (d, J=2.0 Hz, 1H), 5.68 (d, J=2.1 Hz, 1H), 5.28 (s, 2H), 5.07-4.44 (m, 4H). LC/MS (m/z): 496.316 [M+H$^+$]; UPLC $t_R$ 1.31 min

4-(1H,4H,5H,6H-Pyrrolo[3,4-c]pyrazole-5-carbonyl)-5-((1-((4-(trifluoromethyl)phenyl)methyl)-1H-pyrazol-5-yl)amino]benzene-1,3-diol (87)

Acid 19r (31.6 mg, 66 µmol) was subjected to General Procedure H$_3$ to afford 10.6 mg of 87 (33% yield) after purification using mass-guided preparative HPLC. $^1$H NMR (400 MHz, CD$_3$OD) δ 7.54-7.38 (m, 4H), 7.25 (d, J=8.0 Hz, 2H), 6.14 (d, J=2.0 Hz, 1H), 5.91 (d, J=2.1 Hz, 1H), 5.67 (d, J=2.1 Hz, 1H), 5.28 (s, 2H), 4.82-4.20 (m, 4H). $^{19}$F NMR (376 MHz, CD$_3$OD) δ −64.1. LC/MS (m/z): 485.289 [M+H$^+$]; UPLC $t_R$ 1.20 min.

4-(2,3-Dihydro-1H-isoindole-2-carbonyl)-5-((3-methyl-1-((4-methylphenyl)methyl)-1H-pyrazol-5-yl)amino)benzene-1,3-diol (88)

Amide 14k (40.4 mg, 74.5 µmol) was deprotected using General Procedure F to afford 28.8 mg of 88 (85% yield) after purification using mass-guided preparative HPLC. $^1$H NMR (400 MHz, CD$_3$OD) δ 7.29 (d, J=8.8 Hz, 4H), 6.89 (s, 4H), 5.96-5.88 (m, 2H), 5.85 (d, J=2.1 Hz, 1H), 5.05 (s, 2H), 4.95-4.46 (m, 4H), 2.14 (s, 3H), 2.13 (s, 3H). LC/MS (m/z): 455.208 [M+H$^+$]; UPLC $t_R$ 1.55 min.

5-((1-((2-Chlorophenyl)methyl)-3-methyl-1H-pyrazol-5-yl)amino)-4-(2,3-dihydro-1H-isoindole-2-carbonyl)benzene-1,3-diol (89)

Amide 14l (46.5 mg, 82.3 µmol) was deprotected using General Procedure F to afford 30.4 mg of 89 (78% yield) after purification using mass-guided preparative HPLC. $^1$H NMR (400 MHz, CD$_3$OD) δ 7.31-7.19 (m, 4H), 7.17-7.11 (m, 1H), 7.10-6.99 (m, 2H), 6.64-6.53 (m, 1H), 5.97 (s, 1H), 5.92 (d, J=2.1 Hz, 1H), 5.88 (d, J=2.1 Hz, 1H), 5.20 (s, 2H), 4.85-4.29 (m, 4H), 2.14 (s, 3H). $^{13}$C NMR (126 MHz, (CD$_3$)$_2$SO) δ 166.4, 159.2, 155.5, 146.7, 143.7, 141.3, 136.5, 135.0, 131.3, 129.0, 128.8, 128.6, 127.2, 127.1, 122.8, 104.1, 98.4, 94.5, 93.1, 48.0, 40.4, 13.9. LC/MS (m/z): 475.573 [M+H$^+$]; UPLC $t_R$ 1.41 min

4-(2,3-Dihydro-1H-isoindole-2-carbonyl)-5-((3-methyl-1-((2-methylphenyl)methyl)-1H-pyrazol-5-yl)amino)benzene-1,3-diol (90)

Amide 14m (21.3 mg, 39.3 µmol) was deprotected using General Procedure F to afford 9.7 mg of 90 (54% yield) after purification using mass-guided preparative HPLC. $^1$H NMR (400 MHz, CD$_3$OD) δ 7.28 (dt, J=7.1, 3.6 Hz, 2H), 7.22 (d, J=7.4 Hz, 2H), 7.01-6.94 (m, 2H), 6.91-6.83 (m, 1H), 6.49 (d, J=7.6 Hz, 1H), 5.97-5.93 (m, 2H), 5.92 (d, J=2.1 Hz, 1H), 5.11 (s, 2H), 4.82-4.32 (m, 4H), 2.16 (s, 3H), 2.14 (s, 3H). LC/MS (m/z): 455.164 [M+H$^+$]; UPLC $t_R$ 1.51 min.

4-(2,3-Dihydro-1H-isoindole-2-carbonyl)-5-((1-methyl-3-phenyl-1H-pyrazol-5-yl)amino]benzene-1, 3-diol (91)

Amide 14n (65.0 mg, 126 µmol) was deprotected using General Procedure F to afford 32.8 mg of 91 (61% yield) after purification using mass-guided preparative HPLC. $^1$H NMR (400 MHz, CD$_3$OD) δ 7.70-7.53 (m, 2H), 7.34-7.27 (m, 2H), 7.24 (s, 5H), 6.35 (s, 1H), 5.95 (d, J=2.1 Hz, 1H), 5.78 (d, J=2.1 Hz, 1H), 5.03-4.71 (m, 4H), 3.69 (s, 3H). $^{13}$C NMR (101 MHz, CD$_3$OD) δ 170.2, 161.6, 157.5, 151.6, 145.8, 143.7, 137.7, 134.7, 129.7, 128.9, 128.8, 126.4, 123.9, 105.3, 98.3, 95.9, 95.2, 40.6, 35.3. LC/MS (m/z): 428.347 [M+H$^+$]; UPLC $t_R$ 1.58 min

5-((1-Methyl-3-phenyl-1H-pyrazol-5-yl)amino)-4-(5H,6H,7H-pyrrolo[3,4-b]pyridine-6-carbonyl)benzene-1,3-diol (92)

Acid 19s (44.1 mg, 107 µmmol) was coupled with 6,7-dihydro-5H-pyrrolo[3,4-b]pyridine dihydrochloride (30.9 mg, 160 µmol), and triethylamine (110 µL, 800 µmol) using General Procedure G to give 48.3 mg of MOM-protected intermediate (88% yield) after purification via an automated flash system (0% to 4% methanol in CH$_2$Cl$_2$) and manual chromatography (70:30:1 CH$_2$Cl$_2$:acetone:saturated NH$_4$OH (aq.)). $^1$H NMR (400 MHz, CDCl$_3$) δ 8.61-8.46 (m, 1H), 7.75 (ddd, J=8.3, 2.5, 1.3 Hz, 2H), 7.63 (dd, J=51.9, 7.7 Hz, 1H), 7.38 (ddd, J=7.9, 6.8, 2.1 Hz, 2H), 7.32-7.27 (m, 1H), 6.81 (s, 1H), 6.47 (dd, J=7.4, 2.1 Hz, 1H), 6.34 (s, 1H), 6.26-6.16 (m, 1H), 5.19 (d, J=10.6 Hz, 3H), 5.10 (d, J=0.9 Hz, 3H), 4.99-4.83 (m, 1H), 4.75-4.51 (m, 1H), 3.74 (s, 3H), 3.47 (s, 3H), 3.46-3.42 (m, 3H). $^{13}$C NMR (101 MHz, CDCl$_3$) δ 169.2, 161.6, 160.0, 150.4, 149.7, 138.6, 134.1, 128.5, 127.3, 125.4, 99.6, 97.2, 95.4, 95.1, 94.8, 93.9, 56.7, 56.5, 56.3, 52.0, 32.7, 25.7, 25.2. LC/MS (m/z): 516.251 [M+H$^+$]; UPLC $t_R$ 1.43 min.

The MOM-protected intermediate (48.3 mg, 94 µmol) was deprotected using General Procedure F to afford 25 mg of 92 (62% yield) after purification using mass-guided preparative HPLC. $^1$H NMR (400 MHz, CD$_3$OD) δ 8.34 (dd, J=5.0, 1.5 Hz, 1H), 7.68 (dd, J=7.8, 1.4 Hz, 1H), 7.61-7.53 (m, 2H), 7.34-7.14 (m, 4H), 6.35 (s, 1H), 5.96 (d, J=2.1 Hz, 1H), 5.82 (d, J=2.1 Hz, 1H), 5.01-4.60 (m, 4H), 3.72 (s, 3H). $^{13}$C NMR (101 MHz, CD$_3$OD) δ 170.4, 161.8, 158.2, 157.6, 151.4, 149.6, 146.1, 144.0, 134.6, 133.4, 129.7, 128.8, 126.3, 124.3, 111.5, 104.9, 98.2, 96.0, 95.7, 40.6, 35.3. LC/MS (m/z): 428.259 [M+H$^+$]; UPLC $t_R$ 1.11 min.

5-((1-Methyl-3-phenyl-1H-pyrazol-5-yl)amino)-4-(1H,4H,5H,6H-pyrrolo[3,4-c]pyrazole-5-carbonyl)benzene-1,3-diol (93)

Acid 19s (64.1 mg, 155 µmmol) was coupled with 1H,4H,5H,6H-pyrrolo[3,4-c]pyrazole (25 mg, 230 µmol), and triethylamine (43 µL, 310 µmol) using General Procedure G to give 17.2 mg of MOM-protected intermediate (52% yield) as a solid after purification via automated flash system (20% to 60% acetone in CH$_2$Cl$_2$). $^1$H NMR (400 MHz, Acetone-d$_6$) δ 7.88-7.77 (m, 2H), 7.51 (d, J=24.4 Hz, 1H), 7.43-7.32 (m, 2H), 7.30-6.88 (m, 1H), 6.49 (d, J=5.2 Hz, 1H), 6.45 (dd, J=5.0, 2.1 Hz, 1H), 6.18 (q, J=2.1 Hz, 1H), 5.32-5.15 (m, 2H), 5.13 (d, J=2.3 Hz, 2H), 4.82-4.48 (m, 3H), 4.43 (d, J=13.0 Hz, 1H), 3.70 (d, J=3.3 Hz, 3H), 3.43 (d, J=2.5 Hz, 3H), 3.40 (s, 3H). LC/MS (m/z): 505.269 [M+H$^+$]; UPLC $t_R$ 1.34 min.

The MOM-protected intermediate (41.6 mg, 82 µmol) was deprotected using General Procedure F to afford 24.5 mg of 93 (71% yield) after purification using mass-guided preparative HPLC. $^1$H NMR (400 MHz, CD$_3$OD) δ 7.67-7.61 (m, 2H), 7.38 (s, 1H), 7.36-7.28 (m, 2H), 7.28-7.22 (m, 1H), 6.37 (s, 1H), 5.94 (d, J=2.1 Hz, 1H), 5.77 (d, J=2.1 Hz, 1H), 4.78-4.44 (m, 4H), 3.71 (s, 3H). LC/MS (m/z): 417.233 [M+H$^+$]; UPLC $t_R$ 1.01 min.

5-((1-tert-Butyl-3-phenyl-1H-pyrazol-5-yl)amino)-4-(5H,6H,7H-pyrrolo[3,4-b]pyridine-6-carbonyl)benzene-1,3-diol (94)

Acid 19t (41.5 mg, 91.1 µmmol) was coupled with 6,7-dihydro-5H-pyrrolo[3,4-b]pyridine dihydrochloride (26.4 mg, 140 µmol), and triethylamine (100 µL, 680 µmol) using General Procedure G to give 39.9 mg of MOM-protected intermediate (79% yield) after purification via an automated flash system (0% to 3% methanol in CH$_2$Cl$_2$) and manual chromatography (70:30:1 CH$_2$Cl$_2$:ethyl acetate: saturated NH$_4$OH (aq.)). $^1$H NMR (400 MHz, CDCl$_3$) δ 8.52 (dd, J=18.4, 4.9 Hz, 1H), 7.84-7.74 (m, 2H), 7.60 (dd, J=59.2, 7.8 Hz, 1H), 7.36 (t, J=7.7 Hz, 2H), 7.27-7.17 (m, 2H), 6.75 (d, J=7.3 Hz, 1H), 6.51-6.36 (m, 2H), 6.30 (dd, J=9.4, 2.1 Hz, 1H), 5.32-5.01 (m, 6H), 4.94 (d, J=16.5 Hz, 1H), 4.68 (d, J=14.7 Hz, 1H), 3.47 (s, 3H), 3.44 (d, J=1.9 Hz, 3H), 2.80 (s, 3H), 1.64 (s, 9H). $^{13}$C NMR (101 MHz, CDCl$_3$) δ 167.7, 167.6, 160.1, 160.1, 157.7, 157.2, 155.7, 155.6, 149.4, 149.3, 147.7, 147.7, 145.2, 145.2, 139.5, 139.4, 134.0, 131.1, 130.6, 129.9, 128.5, 127.2, 125.2, 122.5, 122.4, 106.5, 106.4, 99.3, 99.1, 96.5, 96.3, 95.5, 95.4, 94.6, 94.5, 94.3, 94.2, 59.7, 59.7, 56.7, 56.6, 56.3, 56.2, 53.5, 52.7, 51.5, 50.8, 38.6, 29.7. LC/MS (m/z): 558.328 [M+H$^+$]; UPLC $t_R$ 1.84 min.

The MOM-protected intermediate (39.9 mg, 72 µmol) was deprotected using General Procedure F to afford 24.3 mg of 94 (72% yield) after purification using mass-guided preparative HPLC. $^1$H NMR (400 MHz, CD$_3$OD) δ 8.42 (dd, J=5.1, 1.5 Hz, 1H), 7.78 (d, J=7.7 Hz, 1H), 7.74-7.65 (m, 2H), 7.41-7.26 (m, 3H), 7.26-7.18 (m, 1H), 6.45 (s, 1H), 5.89 (d, J=2.1 Hz, 1H), 5.80 (d, J=2.0 Hz, 1H), 5.08-4.70 (m, 4H), 1.63 (s, 9H). $^{13}$C NMR (101 MHz, CD$_3$OD) δ 170.7, 161.8, 158.3, 157.4, 149.7, 149.5, 147.3, 142.2, 135.5, 133.4, 132.6, 129.6, 128.5, 126.3, 124.3, 103.8, 101.9, 95.1, 94.5, 61.2, 40.6, 30.4. LC/MS (m/z): 470.337 [M+H$^+$]; UPLC $t_R$ 1.51 min.

5-((1-tert-Butyl-3-phenyl-1H-pyrazol-5-yl)amino)-4-(1H,4H,5H,6H-pyrrolo[3,4-c]pyrazole-5-carbonyl)benzene-1,3-diol (95)

Acid 19t (62.2 mg, 137 µmmol) was coupled with 1H,4H,5H,6H-pyrrolo[3,4-c]pyrazole (22.3 mg, 205 µmol), and triethylamine (38 µL, 270 µmol) using General Procedure G to give 44.4 mg of MOM-protected intermediate (59% yield) as a solid after purification via automated flash system (10% to 30% acetone in CH$_2$Cl$_2$). $^1$H NMR (400 MHz, (CD$_3$)$_2$SO) δ 12.70 (s, 1H), 7.80-7.71 (m, 3H), 7.71-7.62 (m, 1H), 7.53 (d, J=31.5 Hz, 1H), 7.45-7.30 (m, 3H), 7.28-7.20 (m, 1H), 7.04 (d, J=2.7 Hz, 1H), 6.60 (d, J=9.9 Hz, 1H), 6.27 (t, J=2.5 Hz, 1H), 5.85 (dd, J=10.4, 2.1 Hz, 1H), 5.24-5.11 (m, 3H), 5.10-4.99 (m, 3H), 4.66 (dd, J=14.4, 6.5 Hz, 1H), 4.56-4.39 (m, 3H), 4.34 (d, J=12.9 Hz, 1H), 3.28 (s, 6H), 2.87 (s, 3H), 1.54 (d, J=1.1 Hz, 9H). LC/MS (m/z): 547.346 [M+H$^+$]; UPLC $t_R$ 1.60 min.

The MOM-protected intermediate (43.4 mg, 79 µmol) was deprotected using General Procedure F to afford 15.5 mg of 95 (43% yield) after purification using mass-guided preparative HPLC. $^1$H NMR (400 MHz, CD$_3$OD) δ 7.78-7.70 (m, 2H), 7.45 (s, 1H), 7.39-7.29 (m, 2H), 7.27-7.21 (m, 1H), 6.46 (s, 1H), 5.87 (d, J=2.1 Hz, 1H), 5.77 (t, J=1.9 Hz, 1H), 4.84-4.44 (m, 4H), 1.63 (s, 9H). LC/MS (m/z): 459.266 [M+H$^+$]; UPLC $t_R$ 1.40 min.

5-((1-Cyclohexyl-3-phenyl-1H-pyrazol-5-yl)amino)-4-(5H,6H,7H-pyrrolo[3,4-b]pyridine-6-carbonyl)benzene-1,3-diol (96)

Acid 19u (51.9 mg, 108 µmmol) was coupled with 6,7-dihydro-5H-pyrrolo[3,4-b]pyridine dihydrochloride (31.2 mg, 162 µmol), and triethylamine (110 µL, 810 µmol) using General Procedure G to give 39.5 mg of MOM-protected intermediate (63% yield) after purification via an automated flash system (0% to 3% methanol in CH$_2$Cl$_2$) and manual chromatography (65:35:1 CH$_2$Cl$_2$:ethyl acetate: saturated NH$_4$OH (aq.)). $^1$H NMR (400 MHz, CDCl$_3$) δ 8.58-8.44 (m, 1H), 7.83-7.74 (m, 2H), 7.61 (dd, J=59.5, 7.7 Hz, 1H), 7.42-7.30 (m, 2H), 7.31-7.17 (m, 3H), 6.62 (d, J=3.9 Hz, 1H), 6.43 (dd, J=8.5, 2.1 Hz, 1H), 6.32 (d, J=3.0 Hz, 1H), 6.22 (dd, J=7.2, 2.1 Hz, 1H), 5.19 (d, J=5.7 Hz, 3H), 5.08 (s, 3H), 4.96 (d, J=14.1 Hz, 1H), 4.69 (d, J=14.1 Hz, 1H), 4.03 (td, J=11.2, 4.1 Hz, 1H), 3.47 (d, J=1.0 Hz, 3H), 3.43 (d, J=1.3 Hz, 3H), 2.80 (s, 3H), 2.09-1.75 (m, 6H), 1.75-1.57 (m, 1H), 1.25 (s, 3H). $^{13}$C NMR (101 MHz, CDCl$_3$) δ 167.6, 167.5, 160.0, 157.6, 155.6, 155.5, 149.6, 149.5, 149.3, 145.1, 145.0, 138.9, 138.8, 134.0, 131.1, 130.6, 128.5, 127.3, 127.3, 125.3, 122.5, 106.9, 106.8, 96.8, 96.7, 96.5, 96.4, 95.5, 95.4, 95.1, 95.0, 94.2, 94.2, 56.8, 56.8, 56.6, 56.6, 56.2, 56.2, 53.6, 52.7, 51.6, 50.7, 38.6, 32.8, 32.4, 25.6, 25.2. LC/MS (m/z): 584.351 [M+H$^+$]; UPLC $t_R$ 1.88 min.

The MOM-protected intermediate (43.4 mg, 79 µmol) was deprotected using General Procedure F to afford 15.5 mg of 96 (43% yield) after purification using mass-guided preparative HPLC. $^1$H NMR (400 MHz, CD$_3$OD) δ 8.36 (dd, J=5.1, 1.5 Hz, 1H), 7.71 (d, J=7.7 Hz, 1H), 7.67-7.55 (m, 2H), 7.39-7.05 (m, 4H), 6.33 (s, 1H), 5.93 (d, J=2.1 Hz, 1H), 5.79 (d, J=2.1 Hz, 1H), 5.21-4.68 (m, 4H), 4.19 (p, J=7.9 Hz, 1H), 2.08-1.76 (m, 6H), 1.72-1.59 (m, 1H), 1.49-1.20 (m, 3H). LC/MS (m/z): 496.271 [M+H$^+$]; UPLC $t_R$ 1.54 min.

5-((1-Cyclohexyl-3-phenyl-1H-pyrazol-5-yl)amino)-4-(1H,4H,5H,6H-pyrrolo[3,4-c]pyrazole-5-carbonyl)benzene-1,3-diol (97)

Acid 19u (54.8 mg, 114 µmmol) was coupled with 1H,4H,5H,6H-pyrrolo[3,4-c]pyrazole (18.6 mg, 172 µmol), and triethylamine (32 µL, 230 µmol) using General Procedure G1. The resulting suspension was diluted with CH$_2$Cl$_2$ and saturated NaHCO$_3$ (aq.). The layers were separated and the organic layer was washed with brine. The organic layer was dried with anhydrous sodium sulfate. The desired amide was collected along with sodium sulfate following vacuum filtration through Celite®. The desired product and residual Celite® was separated from sodium sulfate and used without purification.

To a mixture of the intermediate amide and residual Celite® in methanol (8.3 mL) was add HCl (2 M, 0.37 µL, 740 µmol). The resulting mixture was stirred at 50° C. three nights. Additional HCl (2 M, 0.37 µL, 740 µmol) was added to the mixture and stirred at 50° C. overnight. The mixture was cooled to room temperature and volatile material were condensed in vacuo. The residue was dissolved in DMSO and the residual Celite® was removed via filtration. The crude mixture was purified using mass-guided preparative HPLC to afford 13.7 mg of 97 (25% yield over 2 steps). $^1$H NMR (400 MHz, CD$_3$OD) δ 7.73-7.61 (m, 2H), 7.41 (s, 1H), 7.33 (dd, J=8.3, 6.7 Hz, 2H), 7.28-7.12 (m, 1H), 6.36 (s, 1H), 5.91 (d, J=2.1 Hz, 1H), 5.73 (d, J=2.1 Hz, 1H), 4.81-4.45 (m, 4H), 4.16 (p, J=9.3, 8.7 Hz, 1H), 2.04-1.78 (m, 6H), 1.67 (d, J=10.9 Hz, 1H), 1.48-1.10 (m, 3H). LC/MS (m/z): 485.245 [M+H$^+$]; UPLC $t_R$ 1.41 min.

5-((1-(2-Methylpropyl)-3-phenyl-1H-pyrazol-5-yl)amino)-4-(5H,6H,7H-pyrrolo[3,4-b]pyridine-6-carbonyl)benzene-1,3-diol (98)

Acid 19v (52.5 mg, 115 µmmol) was coupled with 6,7-dihydro-5H-pyrrolo[3,4-b]pyridine dihydrochloride (33.4 mg, 173 µmol), and triethylamine (120 µL, 860 µmol) using General Procedure G to give 46.6 mg of MOM-protected intermediate (73% yield) after purification via an automated flash system (1% to 4% methanol in CH$_2$Cl$_2$) and manual chromatography (20:80:1 CH$_2$Cl$_2$:ethyl acetate:saturated NH$_{40}$H (aq.)). $^1$H NMR (400 MHz, CDCl$_3$) δ 8.51 (dd, J=21.5, 4.8 Hz, 1H), 7.80-7.71 (m, 2H), 7.71-7.45 (m, 1H), 7.37 (td, J=7.4, 1.3 Hz, 2H), 7.33-7.15 (m, 2H), 6.79 (d, J=7.2 Hz, 1H), 6.45 (dd, J=8.4, 2.1 Hz, 1H), 6.38-6.30 (m, 2H), 5.14 (d, J=32.1 Hz, 6H), 4.94 (d, J=15.8 Hz, 1H), 4.67 (d, J=14.2 Hz, 1H), 3.82 (dd, J=7.5, 2.4 Hz, 2H), 3.47 (d, J=0.9 Hz, 3H), 3.45 (d, J=1.0 Hz, 3H), 2.80 (s, 3H), 2.32-2.17 (m, 1H), 0.88 (d, J=6.4 Hz, 6H). $^{13}$C NMR (101 MHz, CDCl$_3$) δ 167.6, 167.4, 160.1, 157.6, 157.2, 155.7, 155.6, 149.9, 149.5, 149.3, 144.4, 144.3, 140.3, 140.2, 133.8, 131.1, 130.6, 130.3, 129.8, 128.5, 127.5, 127.5, 125.3, 122.5, 122.5, 107.0, 106.9, 96.7, 96.6, 95.8, 95.7, 95.5, 95.4, 95.2, 95.1, 94.3, 94.3, 56.6, 56.6, 56.3, 56.2, 55.3, 55.2, 53.5, 52.7, 51.6, 50.8, 38.6, 29.4, 20.0. LC/MS (m/z): 558.372 [M+H$^+$]; UPLC $t_R$ 1.72 min.

The MOM-protected intermediate (46.6 mg, 79 µmol) was deprotected using General Procedure F to afford 26.0 mg of 98 (66% yield) after purification using mass-guided preparative HPLC. $^1$H NMR (400 MHz, CD$_3$OD) δ 8.37 (dd, J=5.0, 1.5 Hz, 1H), 7.71 (d, J=7.7 Hz, 1H), 7.66-7.56 (m, 2H), 7.38-7.19 (m, 4H), 6.39 (s, 1H), 5.94 (dd, J=12.6, 2.1 Hz, 2H), 5.16-4.61 (m, 4H), 3.83 (d, J=7.5 Hz, 2H), 2.19 (hept, J=6.9 Hz, 1H), 0.86 (d, J=6.7 Hz, 6H). $^{13}$C NMR (101 MHz, CD$_3$OD) δ 170.5, 161.8, 158.2, 157.6, 151.5, 149.7, 146.1, 143.6, 134.8, 133.4, 132.5, 129.7, 128.8, 126.5, 124.3, 104.8, 98.1, 96.0, 95.4, 56.3, 40.6, 30.7, 20.4. LC/MS (m/z): 470.293 [M+H$^+$]; UPLC $t_R$ 1.38 min.

5-((1-(2-Methylpropyl)-3-phenyl-1H-pyrazol-5-yl)amino)-4-(1H,4H,5H,6H-pyrrolo[3,4-c]pyrazole-5-carbonyl)benzene-1,3-diol (99)

Acid 19v (59.0 mg, 130 µmmol) was coupled with 1H,4H,5H,6H-pyrrolo[3,4-c]pyrazole (21.2 mg, 195 µmol), and triethylamine (36 µL, 260 µmol) using General Procedure G1. The reaction mixture was diluted with CH$_2$Cl$_2$ and saturated NaHCO$_3$ (aq.). The layers were separated and brine was added to the organic layer. The combined mixture was filtered through a Celite® plug and the plug was washed with water, methanol and CH$_2$Cl$_2$. The organic layer from the combined filtrate evaporated to leave a fine powder. The remaining water layer was decanted from the solid. The solid was dried to afford 33.9 mg of impure MOM-protected amide which was used without further purification.

The impure MOM-protected amide from above was deprotected using General Procedure F to afford 15.3 mg of 99 (59% overall yield) after purification using mass-guided preparative HPLC. $^1$H NMR (400 MHz, CD$_3$OD) δ 7.73-7.64 (m, 2H), 7.41 (s, 1H), 7.38-7.31 (m, 2H), 7.30-7.17 (m, 1H), 5.93 (d, J=2.1 Hz, 1H), 5.88 (d, J=2.1 Hz, 1H), 4.67 (s, 4H), 3.82 (d, J=7.5 Hz, 2H), 2.19 (hept, J=6.9 Hz, 1H), 0.87 (d, J=6.7 Hz, 6H). LC/MS (m/z): 459.31 [M+H$^+$]; UPLC $t_R$ 1.27 min.

4-(2,3-Dihydro-1H-isoindole-2-carbonyl)-5-((1-methyl-3-(propan-2-yl)-1H-pyrazol-5-yl)amino)benzene-1,3-diol (100)

Acid 19w (45 mg, 120 µmol) was subjected to General Procedure H$_1$ to afford 15.3 mg of 100 (33% yield) after purification using mass-guided preparative HPLC $^1$H NMR (400 MHz, CD$_3$OD) δ 7.28 (s, 4H), 5.93 (dd, J=12.6, 2.0 Hz, 1H), 5.84 (s, 1H), 5.67 (d, J=2.1 Hz, 1H), 5.06-4.67 (m, 4H), 3.58 (s, 4H), 2.76 (p, J=7.0 Hz, 1H), 1.15 (d, J=7.0 Hz, 6H). LC/MS (m/z): 393.106 [M+H$^+$]; UPLC $t_R$ 1.30 min.

5-((1-Methyl-3-(propan-2-yl)-1H-pyrazol-5-yl)amino)-4-(5H,6H,7H-pyrrolo[3,4-b]pyridine-6-carbonyl)benzene-1,3-diol (101)

Acid 19w (45 mg, 120 µmol) was subjected to General Procedure H$_2$ to afford 9.9 mg of 101 (21% yield) after purification using mass-guided preparative HPLC. $^1$H NMR (400 MHz, CD$_3$OD) δ 8.44 (dd, J=5.0, 1.5 Hz, 1H), 7.80 (d, J=7.7 Hz, 1H), 7.35 (dd, J=7.8, 5.0 Hz, 1H), 5.92 (d, J=2.1 Hz, 1H), 5.85 (s, 1H), 5.68 (d, J=2.1 Hz, 1H), 5.09-4.72 (m, 4H), 3.59 (s, 3H), 2.76 (hept, J=6.6 Hz, 1H), 1.14 (d, J=6.9 Hz, 6H). LC/MS (m/z): 394.253 [M+H$^+$]; UPLC $t_R$ 1.29 min.

5-((1-Methyl-3-(propan-2-yl)-1H-pyrazol-5-yl)amino)-4-(1H,4H,5H,6H-pyrrolo[3,4-c]pyrazole-5-carbonyl)benzene-1,3-diol (102)

Acid 19w (45 mg, 120 µmol) was subjected to General Procedure H$_3$ to afford 12.5 mg of 102 (28% yield) after purification using mass-guided preparative HPLC. $^1$H NMR (400 MHz, CD$_3$OD) δ 7.45 (s, 1H), 5.91 (d, J=2.1 Hz, 1H), 5.85 (s, 1H), 5.66 (d, J=2.1 Hz, 1H), 4.85-4.44 (m, 4H), 3.59 (s, 3H), 2.78 (dq, J=13.9, 6.9 Hz, 1H), 1.17 (d, J=6.9 Hz, 6H). LC/MS (m/z): 383.314 [M+H$^+$]; UPLC $t_R$ 0.92 min.

5-((3-Cyclohexyl-1-methyl-1H-pyrazol-5-yl)amino)-4-(2,3-dihydro-1H-isoindole-2-carbonyl)benzene-1,3-diol (103)

Acid 19x (38.9 mg, 92.7 µmol) was subjected to General Procedure H$_1$ to afford 16.1 mg of 103 (40% yield) after purification using mass-guided preparative HPLC. $^1$H NMR (400 MHz, CD$_3$OD) δ 7.28 (s, 4H), 5.92 (d, J=2.1 Hz, 1H), 5.80 (s, 1H), 5.69 (d, J=2.1 Hz, 1H), 5.09-4.64 (m, 4H), 3.58 (s, 3H), 2.44-2.21 (m, 1H), 1.99-1.62 (m, 5H), 1.48-1.09 (m, 5H). LC/MS (m/z): 433.376 [M+H$^+$]; UPLC $t_R$ 1.51 min.

5-((3-Cyclohexyl-1-methyl-1H-pyrazol-5-yl)amino)-4-(5H,6H,7H-pyrrolo[3,4-b]pyridine-6-carbonyl)benzene-1,3-diol (104)

Acid 19x (39.9 mg, 95.1 µmol) was subjected to General Procedure H$_2$ to afford 3.3 mg of 104 (8.0% yield) after purification using mass-guided preparative HPLC. $^1$H NMR (400 MHz, CD$_3$OD) δ 8.54 (s, 1H), 8.44 (dd, J=5.1, 1.5 Hz, 1H), 7.79 (d, J=7.7 Hz, 1H), 7.35 (dd, J=7.8, 5.0 Hz, 1H), 5.92 (d, J=2.1 Hz, 1H), 5.81 (s, 1H), 5.71 (d, J=2.1 Hz, 1H), 5.04-4.38 (m, 4H), 3.59 (s, 4H), 2.39 (d, J=10.8 Hz, 1H), 1.73 (dq, J=23.1, 11.6, 8.8 Hz, 6H), 1.27 (hept, J=11.6 Hz, 4H). LC/MS (m/z): 434.346 [M+H$^+$]; UPLC $t_R$ 1.32 min.

5-((3-Cyclohexyl-1-methyl-1H-pyrazol-5-yl)amino)-4-(1H,4H,5H,6H-pyrrolo[3,4-c]pyrazole-5-carbonyl)benzene-1,3-diol (105)

Acid 19x (44 mg, 100 µmol) was subjected to General Procedure H$_3$ to afford 12.5 mg of 105 (28% yield) after purification using mass-guided preparative HPLC. H NMR (400 MHz, CD$_3$OD) δ 7.44 (s, 1H), 5.91 (d, J=2.1 Hz, 1H), 5.81 (s, 1H), 5.68 (d, J=2.1 Hz, 1H), 4.78-4.36 (m, 4H), 3.59 (s, 3H), 2.51-2.27 (m, 1H), 1.89-1.61 (m, 5H), 1.43-1.09 (m, 5H). LC/MS (m/z): 423.363 [M+H$^+$]; UPLC $t_R$ 1.15 min.

4-(2,3-Dihydro-1H-isoindole-2-carbonyl)-5-((1-methyl-3-(2-methylphenyl)-1H-pyrazol-5-yl)amino)benzene-1,3-diol (106)

Acid 19y (50.3 mg, 118 µmol) was subjected to General Procedure H$_2$ to afford 18.8 mg of 106 (36% yield) after purification using mass-guided preparative HPLC. $^1$H NMR (400 MHz, CD$_3$OD) δ 7.34 (dd, J=7.1, 1.3 Hz, 1H), 7.27 (s, 4H), 7.22-7.17 (m, 2H), 7.17-7.09 (m, 1H), 6.17 (s, 1H), 5.94 (d, J=2.1 Hz, 1H), 5.75 (d, J=2.1 Hz, 1H), 5.01-4.72 (m, 4H), 3.70 (s, 3H), 2.37 (s, 3H). $^{13}$C NMR (101 MHz, CD$_3$OD) δ 170.2, 161.6, 157.5, 151.9, 145.9, 142.8, 137.7, 137.2, 134.7, 131.7, 130.3, 129.0, 128.8, 126.9, 123.9, 105.3, 101.6, 95.9, 94.9, 40.6, 35.3, 21.3. LC/MS (m/z): 441.315 [M+H$^+$]; UPLC $t_R$ 1.65 min.

5-((1-Methyl-3-(2-methylphenyl)-1H-pyrazol-5-yl)amino)-4-(5H,6H,7H-pyrrolo[3,4-b]pyridine-6-carbonyl)benzene-1,3-diol (107)

Acid 19y (50.4 mg, 118 µmol) was subjected to General Procedure H$_1$ to afford 14.6 mg of 107 (28% yield) after purification using mass-guided preparative HPLC. $^1$H NMR (400 MHz, CD$_3$OD) δ 8.40 (dd, J=5.0, 1.5 Hz, 1H), 7.75 (d, J=7.7 Hz, 1H), 7.44-7.27 (m, 2H), 7.27-7.16 (m, 2H), 7.16-7.08 (m, 1H), 6.17 (s, 1H), 5.94 (d, J=2.1 Hz, 1H), 5.77 (d, J=2.1 Hz, 1H), 5.02-4.65 (m, 4H), 3.72 (s, 3H), 2.37 (s, 3H). LC/MS (m/z): 442.329 [M+H$^+$]; UPLC $t_R$ 1.40 min.

5-((1-Methyl-3-(2-methylphenyl)-1H-pyrazol-5-yl)amino)-4-(1H,4H,5H,6H-pyrrolo[3,4-c]pyrazole-5-carbonyl)benzene-1,3-diol (108)

Acid 19y (50.4 mg, 118 µmol) was subjected to General Procedure H$_3$ to afford 14.6 mg of 108 (28% yield) after purification using mass-guided preparative HPLC. $^1$H NMR (400 MHz, CD$_3$OD) δ 7.42 (s, 1H), 7.36 (dd, J=7.0, 1.6 Hz, 1H), 7.25-7.11 (m, 3H), 6.18 (s, 1H), 5.93 (d, J=2.1 Hz, 1H), 5.74 (d, J=2.1 Hz, 1H), 4.80-4.47 (m, 4H), 3.71 (s, 3H), 2.39 (s, 3H). $^{13}$C NMR (101 MHz, CD$_3$OD) δ 170.7, 161.6, 157.4, 152.0, 145.9, 142.9, 137.2, 134.7, 131.7, 130.3, 129.0, 126.9, 105.2, 101.7, 95.9, 95.0, 40.6, 35.3, 21.3. LC/MS (m/z): 431.347 [M+H$^+$]; UPLC $t_R$ 1.31 min.

4-(2,3-Dihydro-1H-isoindole-2-carbonyl)-5-((1-methyl-3-(3-methylphenyl)-1H-pyrazol-5-yl)amino)benzene-1,3-diol (109)

Acid 19z (54.1 mg, 127 µmol) was subjected to General Procedure H$_1$ to afford 20.2 mg of 109 (36% yield) after purification using mass-guided preparative HPLC. $^1$H NMR (400 MHz, CD$_3$OD) δ 7.49-7.36 (m, 2H), 7.24 (s, 4H), 7.18 (t, J=7.6 Hz, 1H), 7.06 (d, J=7.6 Hz, 1H), 6.34 (s, 1H), 5.94 (d, J=2.1 Hz, 1H), 5.78 (d, J=2.1 Hz, 1H), 4.96-4.70 (m, 4H), 3.69 (s, 3H), 2.31 (s, 3H). LC/MS (m/z): 441.094 [M+H$^+$]; UPLC $t_R$ 1.57 min.

5-((1-Methyl-3-(3-methylphenyl)-1H-pyrazol-5-yl)amino)-4-(5H,6H,7H-pyrrolo[3,4-b]pyridine-6-carbonyl)benzene-1,3-diol (110)

Acid 19z (56.7 mg, 133 µmol) was subjected to General Procedure H$_2$ to afford 16.2 mg of 110 (28% yield) after purification using mass-guided preparative HPLC. $^1$H NMR (400 MHz, CD$_3$OD) δ 8.34 (dd, J=4.9, 1.4 Hz, 1H), 7.73-7.62 (m, 1H), 7.46-7.29 (m, 2H), 7.24 (dd, J=7.7, 5.0 Hz, 1H), 7.15 (t, J=7.6 Hz, 1H), 7.04 (d, J=7.6 Hz, 1H), 6.33 (s, 1H), 5.95 (d, J=2.1 Hz, 1H), 5.83 (d, J=2.1 Hz, 1H), 5.02-4.65 (m, 4H), 3.72 (s, 3H), 2.31 (s, 3H). LC/MS (m/z): 442.329 [M+H$^+$]; UPLC $t_R$ 1.29 min.

5-((1-Methyl-3-(3-methylphenyl)-1H-pyrazol-5-yl)amino)-4-(1H,4H,5H,6H-pyrrolo[3,4-c]pyrazole-5-carbonyl)benzene-1,3-diol (111)

Acid 19z (57.6 mg, 135 µmol) was subjected to General Procedure H$_3$ to afford 20.3 mg of 111 (35% yield) after purification using mass-guided preparative HPLC. $^1$H NMR (400 MHz, CD$_3$OD) δ 7.51-7.40 (m, 2H), 7.38 (s, 1H), 7.20 (t, J=7.6 Hz, 1H), 7.13-7.05 (m, 1H), 6.34 (s, 1H), 5.94 (d, J=2.1 Hz, 1H), 5.78 (d, J=2.1 Hz, 1H), 4.79-4.45 (m, 4H), 3.70 (s, 3H), 2.33 (s, 3H). $^{13}$C NMR (101 MHz, CD$_3$OD) δ 170.6, 161.6, 157.4, 151.7, 145.8, 143.7, 139.4, 134.6, 129.6, 127.0, 123.6, 105.2, 98.4, 95.9, 95.3, 40.6, 35.3, 21.7. LC/MS (m/z): 431.347 [M+H$^+$]; UPLC $t_R$ 1.22 min

4-(2,3-Dihydro-1H-isoindole-2-carbonyl)-5-((3-(3-methoxyphenyl)-1-methyl-1H-pyrazol-5-yl)amino)benzene-1,3-diol (112)

Acid 19aa (48.6 mg, 110 µmol) was subjected to General Procedure H$_1$ to afford 18.2 mg of 112 (36% yield) after purification using mass-guided preparative HPLC. $^1$H NMR (400 MHz, CD$_3$OD) δ 8.54 (s, 1H), 7.34-7.09 (m, 7H), 6.82 (s, 1H), 6.36 (s, 1H), 5.94 (s, 1H), 5.77 (s, 1H), 5.17-4.70 (m, 4H), 3.80 (s, 3H), 3.70 (s, 3H). $^{13}$C NMR (101 MHz, (CD$_3$)$_2$SO) δ 166.4, 159.5, 159.3, 155.5, 148.1, 143.9, 143.8, 141.5, 141.4, 135.0, 129.6, 127.2, 122.9, 117.1, 113.1, 109.6, 104.0, 96.9, 94.3, 92.7, 55.0, 40.4, 35.0. LC/MS (m/z): 457.061 [M+H$^+$]; UPLC $t_R$ 1.58 min.

5-((3-(3-Methoxyphenyl)-1-methyl-1H-pyrazol-5-yl)amino)-4-(5H,6H,7H-pyrrolo[3,4-b]pyridine-6-carbonyl)benzene-1,3-diol (113)

Acid 19aa (52.6 mg, 119 µmol) was subjected to General Procedure H$_2$ to afford 6.7 mg of 113 (12% yield) after purification using mass-guided preparative HPLC. $^1$H NMR (400 MHz, CD$_3$OD) δ 8.34 (dd, J=5.0, 1.5 Hz, 1H), 7.67 (dd, J=7.8, 1.4 Hz, 1H), 7.23 (dd, J=7.8, 5.0 Hz, 1H), 7.21-7.07 (m, 3H), 6.78 (ddd, J=7.9, 2.6, 1.3 Hz, 1H), 6.34 (s, 1H), 5.95 (d, J=2.1 Hz, 1H), 5.83 (d, J=2.1 Hz, 1H), 4.98-4.63 (m, 4H), 3.79 (s, 3H), 3.72 (s, 3H). $^{13}$C NMR (101 MHz, CD$_3$OD) δ 170.4, 161.8, 161.5, 158.1, 157.6, 151.2, 149.6, 146.2, 144.0, 135.9, 133.3, 132.5, 130.7, 124.2, 118.8, 114.6, 111.4, 104.9, 98.3, 96.0, 95.9, 55.8, 40.6, 35.4. LC/MS (m/z): 458.296 [M+H$^+$]; UPLC $t_R$ 1.30 min.

5-((3-(3-Methoxyphenyl)-1-methyl-1H-pyrazol-5-yl)amino)-4-(1H,4H,5H,6H-pyrrolo[3,4-c]pyrazole-5-carbonyl)benzene-1,3-diol (114)

Acid 19aa (55.5 mg, 125 μmol) was subjected to General Procedure H$_3$ to afford 21.6 mg of 114 (37% yield) after purification using mass-guided preparative HPLC. $^1$H NMR (400 MHz, CD$_3$OD) δ 7.38 (s, 1H), 7.30-7.15 (m, 3H), 6.82 (ddd, J=7.6, 2.6, 1.7 Hz, 1H), 6.37 (s, 1H), 5.94 (d, J=2.1 Hz, 1H), 5.77 (d, J=2.1 Hz, 1H), 4.80-4.47 (m, 4H), 3.80 (s, 3H), 3.71 (s, 3H). $^{13}$C NMR (101 MHz, CD$_3$OD) δ 170.7, 161.6, 161.5, 157.4, 151.4, 145.8, 143.7, 136.0, 130.8, 119.0, 114.7, 111.5, 98.6, 95.9, 95.3, 55.8, 40.6, 35.3. LC/MS (m/z): 447.313 [M+H$^+$]; UPLC $t_R$ 1.25 min.

4-(2,3-Dihydro-1H-isoindole-2-carbonyl)-5-((1-methyl-3-(3-(trifluoromethyl)phenyl)-1H-pyrazol-5-yl)amino)benzene-1,3-diol (115)

Acid 19ab (50.5 mg, 105 μmol) was subjected to General Procedure H$_1$ to afford 22 mg of 115 (42% yield) after purification using mass-guided preparative HPLC. $^1$H NMR (400 MHz, CD$_3$OD) δ 7.94 (s, 1H), 7.81 (d, J=7.6 Hz, 1H), 7.49 (dt, J=15.4, 7.8 Hz, 2H), 7.20 (s, 4H), 6.44 (s, 1H), 5.96 (d, J=2.1 Hz, 1H), 5.81 (d, J=2.1 Hz, 1H), 4.98-4.65 (m, 4H), 3.72 (s, 3H). 13C NMR (126 MHz, CD$_3$OD) δ 170.1, 161.6, 157.6, 149.7, 145.73, 145.66, 144.2, 137.6, 135.8, 132.0 (q, $^2J_{C-F}$=32.5 Hz), 130.6, 129.9, 128.8, 125.8 (q, $^1J_{C-F}$=270.0 Hz), 125.1 (q, $^3J_{C-F}$=3.8 Hz), 123.8, 122.6 (q, $^3J_{C-F}$=3.7 Hz), 105.5, 98.5, 96.1, 95.6, 40.6, 35.5. $^{19}$F NMR (376 MHz, CD$_3$OD) δ −64.2. LC/MS (m/z): 495.301 [M+H$^+$]; UPLC $t_R$ 1.78 min.

5-((1-Methyl-3-(3-(trifluoromethyl)phenyl)-1H-pyrazol-5-yl)amino)-4-(5H,6H,7H-pyrrolo[3,4-b]pyridine-6-carbonyl)benzene-1,3-diol (116)

Acid 19ab (56.4 mg, 117 μmol) was subjected to General Procedure H$_2$ to afford 18.7 mg of 116 (32% yield) after purification using mass-guided preparative HPLC. $^1$H NMR (400 MHz, CD$_3$OD) δ 8.30 (dd, J=5.0, 1.4 Hz, 1H), 7.89 (d, J=2.2 Hz, 1H), 7.79 (d, J=7.5 Hz, 1H), 7.66 (dd, J=7.8, 1.5 Hz, 1H), 7.54-7.40 (m, 2H), 7.20 (dd, J=7.8, 5.0 Hz, 1H), 6.45 (s, 1H), 5.97 (d, J=2.1 Hz, 1H), 5.85 (d, J=2.1 Hz, 1H), 4.98-4.63 (m, 4H), 3.75 (s, 3H). $^{13}$C NMR (126 MHz, CD$_3$OD) δ 170.4, 161.8, 158.2, 157.7, 149.62, 149.59, 146.1, 144.5, 135.7, 133.3, 132.0 (q, $^2J_{C-F}$=31.5 Hz), 130.6, 129.8, 125.8 (q, $^1J_{C-F}$=267.0 Hz), 125.1 (q, $^3J_{C-F}$=3.8 Hz), 124.2, 122.5 (q, $^3J_{C-F}$=4.8 Hz), 105.1, 98.3, 96.2, 96.1, 40.6, 35.6. $^{19}$F NMR (376 MHz, CD$_3$OD) δ −64.2. LC/MS (m/z): 496.316 [M+H$^+$]; UPLC $t_R$ 1.52 min.

5-((1-Methyl-3-(3-(trifluoromethyl)phenyl)-1H-pyrazol-5-yl)amino)-4-(1H,4H,5H,6H-pyrrolo[3,4-c]pyrazole-5-carbonyl)benzene-1,3-diol (117)

Acid 19ab (57.2 mg, 119 μmol) was subjected to General Procedure H$_3$ to afford 18.9 mg of 117 (33% yield) after purification using mass-guided preparative HPLC. $^1$H NMR (400 MHz, CD$_3$OD) δ 7.97 (s, 1H), 7.86 (d, J=7.3 Hz, 1H), 7.60-7.47 (m, 2H), 7.36 (s, 1H), 6.47 (s, 1H), 5.95 (d, J=2.1 Hz, 1H), 5.80 (d, J=2.1 Hz, 1H), 4.82-4.45 (m, 4H), 3.73 (s, 3H). $^{13}$C NMR (126 MHz, CD$_3$OD) δ 170.6, 161.6, 157.4, 149.8, 145.7, 144.2, 135.9, 132.1 (q, $^2J_{C-F}$=31.5 Hz), 130.6, 129.9, 125.8 (q, $^1J_{C-F}$=270.8 Hz), 125.2 (q, $^3J_{C-F}$=4.8 Hz), 122.7 (q, $^3J_{C-F}$=3.8 Hz), 105.4, 98.5, 96.1, 95.6, 40.6, 35.6. $^{19}$F NMR (376 MHz, CD$_3$OD) δ −64.2. LC/MS (m/z): 485.289 [M+H$^+$]; UPLC $t_R$ 1.45 min.

4-(2,3-Dihydro-1H-isoindole-2-carbonyl)-5-((1-methyl-3-(4-methylphenyl)-1H-pyrazol-5-yl)amino)benzene-1,3-diol (118)

Acid 19ac (44.5 mg, 104 μmol) was subjected to General Procedure H$_1$ to afford 18.2 mg of 118 (40% yield) after purification using mass-guided preparative HPLC. $^1$H NMR (400 MHz, CD$_3$OD) δ 7.58-7.43 (m, 2H), 7.24 (s, 4H), 7.12 (d, J=8.0 Hz, 2H), 6.31 (s, 1H), 5.94 (d, J=2.1 Hz, 1H), 5.76 (d, J=2.1 Hz, 1H), 4.96-4.69 (m, 4H), 3.68 (s, 3H), 2.31 (s, 3H). $^{13}$C NMR (101 MHz, CD$_3$OD) δ 170.2, 161.6, 157.5, 151.7, 145.8, 143.6, 138.8, 137.7, 131.9, 130.3, 128.8, 126.4, 123.9, 105.2, 98.1, 95.9, 95.1, 40.6, 35.3, 21.4. LC/MS (m/z): 441.094 [M+H$^+$]; UPLC $t_R$ 1.66 min.

5-((1-Methyl-3-(4-methylphenyl)-1H-pyrazol-5-yl)amino)-4-(5H,6H,7H-pyrrolo[3,4-b]pyridine-6-carbonyl)benzene-1,3-diol (119)

Acid 19ac (46.6 mg, 109 μmol) was subjected to General Procedure H$_2$ to afford 14.2 mg of 119 (30% yield) after purification using mass-guided preparative HPLC. $^1$H NMR (400 MHz, CD$_3$OD) δ 8.35 (dd, J=5.0, 1.5 Hz, 1H), 7.69 (dd, J=7.9, 1.5 Hz, 1H), 7.52-7.42 (m, 2H), 7.25 (dd, J=7.8, 5.0 Hz, 1H), 7.09 (d, J=7.9 Hz, 2H), 6.30 (s, 1H), 5.95 (d, J=2.1 Hz, 1H), 5.81 (d, J=2.1 Hz, 1H), 4.99-4.64 (m, 4H), 3.70 (s, 3H), 2.31 (s, 3H). LC/MS (m/z): 442.329 [M+H$^+$]; UPLC $t_R$ 1.40 min.

5-((1-Methyl-3-(4-methylphenyl)-1H-pyrazol-5-yl)amino)-4-(1H,4H,5H,6H-pyrrolo[3,4-c]pyrazole-5-carbonyl)benzene-1,3-diol (120)

Acid 19ac (50.8 mg, 119 μmol) was subjected to General Procedure H$_3$ to afford 16.5 mg of 120 (32% yield) after purification using mass-guided preparative HPLC. $^1$H NMR (400 MHz, CD$_3$OD) δ 7.58-7.46 (m, 2H), 7.38 (s, 1H), 7.14 (d, J=7.9 Hz, 2H), 6.32 (s, 1H), 5.93 (d, J=2.1 Hz, 1H), 5.76 (d, J=2.1 Hz, 1H), 4.79-4.45 (m, 4H), 3.69 (s, 3H), 2.32 (s, 3H). LC/MS (m/z): 431.303 [M+H$^+$]; UPLC $t_R$ 1.32 min.

4-(2,3-Dihydro-1H-isoindole-2-carbonyl)-5-((3-(4-methoxyphenyl)-1-methyl-1H-pyrazol-5-yl)amino)benzene-1,3-diol (121)

Acid 19ad (54.2 mg, 122 μmol) was subjected to General Procedure H$_1$ to afford 21.4 mg of 121 (38% yield) after purification using mass-guided preparative HPLC. $^1$H NMR (400 MHz, CD$_3$OD) δ 7.58-7.47 (m, 2H), 7.24 (s, 4H), 6.93-6.81 (m, 2H), 6.27 (s, 1H), 5.94 (d, J=2.1 Hz, 1H), 5.77 (d, J=2.1 Hz, 1H), 4.99-4.72 (m, 4H), 3.78 (s, 3H), 3.67 (s, 3H). $^{13}$C NMR (101 MHz, CD$_3$OD) δ 170.2, 161.6, 161.0, 157.5, 151.5, 145.9, 143.6, 137.7, 128.8, 128.1, 127.7, 127.4, 123.9, 115.1, 105.3, 97.8, 95.9, 95.2, 55.8, 40.6, 35.2. LC/MS (m/z): 457.105 [M+H$^+$]; UPLC $t_R$ 1.47 min.

5-((3-(4-Methoxyphenyl)-1-methyl-1H-pyrazol-5-yl)amino)-4-(5H,6H,7H-pyrrolo[3,4-b]pyridine-6-carbonyl)benzene-1,3-diol (122)

Acid 19ad (55.4 mg, 125 μmol) was subjected to General Procedure H$_2$ to afford 14.4 mg of 122 (25% yield) after purification using mass-guided preparative HPLC. ¹H NMR (400 MHz, CD₃OD) δ 8.36 (dd, J=5.1, 1.5 Hz, 1H), 7.69 (dd, J=7.8, 1.5 Hz, 1H), 7.58-7.42 (m, 2H), 7.26 (dd, J=7.8, 5.0 Hz, 1H), 6.88-6.74 (m, 2H), 6.26 (s, 1H), 5.95 (d, J=2.1 Hz, 1H), 5.82 (d, J=2.1 Hz, 1H), 5.09-4.66 (m, 4H), 3.79 (s, 3H), 3.70 (s, 3H). ¹³C NMR (101 MHz, CD₃OD) δ 170.4, 161.8, 161.0, 158.2, 157.6, 151.4, 149.6, 146.2, 143.9, 133.4, 127.6, 127.3, 124.3, 115.1, 104.9, 97.7, 96.0, 95.7, 55.9, 40.6, 35.2. LC/MS (m/z): 458.241 [M+H⁺]; UPLC $t_R$ 1.04 min.

5-((3-(4-Methoxyphenyl)-1-methyl-1H-pyrazol-5-yl)amino)-4-(1H,4H,5H,6H-pyrrolo[3,4-c]pyrazole-5-carbonyl)benzene-1,3-diol (123)

Acid 19ad (55.6 mg, 125 μmol) was subjected to General Procedure H₃ to afford 12.9 mg of 123 (23% yield) after purification using mass-guided preparative HPLC. ¹H NMR (400 MHz, CD₃OD) δ 7.61-7.51 (m, 2H), 7.39 (s, 1H), 6.93-6.82 (m, 2H), 6.28 (s, 1H), 5.93 (d, J=2.1 Hz, 1H), 5.76 (d, J=2.1 Hz, 1H), 4.85-4.41 (m, 4H), 3.79 (s, 3H), 3.68 (s, 3H). ¹³C NMR (126 MHz, CD₃OD) δ 170.7, 161.6, 161.1, 157.4, 151.6, 145.9, 143.7, 127.7, 127.4, 115.1, 105.3, 97.9, 95.9, 95.3, 55.9, 40.6, 35.2. LC/MS (m/z): 447.216 [M+H⁺]; UPLC $t_R$ 0.98 min.

4-(2,3-Dihydro-1H-isoindole-2-carbonyl)-5-((1-methyl-3-(4-(trifluoromethyl)phenyl)-1H-pyrazol-5-yl)amino)benzene-1,3-diol (124)

Acid 19ae (61.4 mg, 128 μmol) was subjected to General Procedure H₁ to afford 20.5 mg of 124 (32% yield) after purification using mass-guided preparative HPLC. ¹H NMR (400 MHz, CD₃OD) δ 7.81-7.71 (m, 2H), 7.56 (d, J=8.2 Hz, 2H), 7.21 (s, 4H), 6.45 (s, 1H), 5.96 (d, J=2.1 Hz, 1H), 5.81 (d, J=2.1 Hz, 1H), 4.98-4.68 (m, 4H), 3.73 (s, 3H). ¹⁹F NMR (376 MHz, CD₃OD) δ -64.1. LC/MS (m/z): 495.301 [M+H⁺]; UPLC $t_R$ 1.78 min.

5-((1-Methyl-3-(4-(trifluoromethyl)phenyl)-1H-pyrazol-5-yl)amino)-4-(5H,6H,7H-pyrrolo[3,4-b]pyridine-6-carbonyl)benzene-1,3-diol (125)

Acid 19ae (61.5 mg, 128 μmol) was subjected to General Procedure H₂ to afford 15.2 mg of 125 (24% yield) after purification using mass-guided preparative HPLC. ¹H NMR (400 MHz, CD₃OD) δ 8.30 (d, J=5.0 Hz, 1H), 7.76-7.69 (m, 2H), 7.65 (dd, J=7.9, 1.4 Hz, 1H), 7.54 (d, J=8.2 Hz, 2H), 7.20 (dd, J=7.8, 5.0 Hz, 1H), 6.45 (s, 1H), 5.97 (d, J=2.1 Hz, 1H), 5.85 (d, J=2.1 Hz, 1H), 4.96-4.59 (m, 4H), 3.75 (s, 3H). ¹⁹F NMR (376 MHz, CD₃OD) δ -64.0. LC/MS (m/z): 496.271 [M+H⁺]; UPLC $t_R$ 1.53 min.

5-((1-Methyl-3-(4-(trifluoromethyl)phenyl)-1H-pyrazol-5-yl)amino)-4-(1H,4H,5H,6H-pyrrolo[3,4-c]pyrazole-5-carbonyl)benzene-1,3-diol (126)

Acid 19ae (62.2 mg, 129 μmol) was subjected to General Procedure H₃ to afford 15 mg of 126 (24% yield) after purification using mass-guided preparative HPLC. ¹H NMR (400 MHz, CD₃OD) δ 7.81 (d, J=8.1 Hz, 2H), 7.61 (d, J=8.1 Hz, 2H), 7.37 (s, 1H), 6.47 (s, 1H), 5.95 (d, J=2.1 Hz, 1H), 5.79 (d, J=2.1 Hz, 1H), 4.79-4.41 (m, 4H), 3.74 (s, 3H). ¹⁹F NMR (376 MHz, CD₃OD) δ -64.0. LC/MS (m/z): 485.289 [M+H⁺]; UPLC $t_R$ 1.47 min.

5-((3-(4-tert-Butylphenyl)-1-methyl-1H-pyrazol-5-yl)amino)-4-(2,3-dihydro-1H-isoindole-2-carbonyl)benzene-1,3-diol (127)

Acid 19af (59 mg, 130 μmol) was subjected to General Procedure H₁ to afford 18.4 mg of 127 (30% yield) after purification using mass-guided preparative HPLC ¹H NMR (400 MHz, CD₃OD) δ 7.62-7.47 (m, 2H), 7.38-7.30 (m, 2H), 7.23 (s, 4H), 6.32 (s, 1H), 5.94 (d, J=2.1 Hz, 1H), 5.78 (d, J=2.1 Hz, 1H), 5.05-4.68 (m, 4H), 3.69 (s, 3H), 1.31 (s, 9H). LC/MS (m/z): 483.392 [M+H⁺]; UPLC $t_R$ 1.90 min.

5-((3-(4-tert-Butylphenyl)-1-methyl-1H-pyrazol-5-yl)amino)-4-(5H,6H,7H-pyrrolo[3,4-b]pyridine-6-carbonyl)benzene-1,3-diol (128)

Acid 19af (59.8 mg, 127 μmol) was subjected to General Procedure H₂ to afford 18.1 mg of 128 (29% yield) after purification using mass-guided preparative HPLC. ¹H NMR (400 MHz, CD₃OD) δ 8.33 (dd, J=5.0, 1.5 Hz, 1H), 7.68 (dd, J=7.9, 1.5 Hz, 1H), 7.54-7.42 (m, 2H), 7.36-7.28 (m, 2H), 7.23 (dd, J=7.8, 5.0 Hz, 1H), 6.32 (s, 1H), 5.95 (d, J=2.1 Hz, 1H), 5.83 (d, J=2.1 Hz, 1H), 4.93-4.66 (m, 4H), 3.72 (s, 3H), 1.31 (s, 9H). LC/MS (m/z): 484.363 [M+H⁺]; UPLC $t_R$ 1.64 min.

5-((3-(4-tert-Butylphenyl)-1-methyl-1H-pyrazol-5-yl)amino)-4-(1H,4H,5H,6H-pyrrolo[3,4-c]pyrazole-5-carbonyl)benzene-1,3-diol (129)

Acid 19af (61.7 mg, 131 μmol) was subjected to General Procedure H₃ to afford 18.1 mg of 129 (29% yield) after purification using mass-guided preparative HPLC. ¹H NMR (400 MHz, CD₃OD) δ 7.57 (d, J=8.5 Hz, 2H), 7.42-7.31 (m, 3H), 6.34 (s, 1H), 5.93 (d, J=2.1 Hz, 1H), 5.76 (d, J=2.1 Hz, 1H), 4.81-4.47 (m, 4H), 3.70 (s, 3H), 1.32 (s, 9H). LC/MS (m/z): 473.336 [M+H⁺]; UPLC $t_R$ 1.57 min.

4-(2,3-Dihydro-1H-isoindole-2-carbonyl)-5-((1-methyl-3-(4-(trifluoromethoxy)phenyl)-1H-pyrazol-5-yl)amino)benzene-1,3-diol (130)

Acid 19ag (51.3 mg, 103 μmol) was subjected to General Procedure H₁ to afford 21.3 mg of 130 (40% yield) after purification using mass-guided preparative HPLC. ¹H NMR (400 MHz, CD₃OD) δ 7.72-7.55 (m, 2H), 7.21 (s, 4H), 7.20-7.12 (m, 2H), 6.36 (s, 1H), 5.96 (d, J=2.1 Hz, 1H), 5.80 (d, J=2.1 Hz, 1H), 4.99-4.66 (m, 4H), 3.71 (s, 3H). ¹³C NMR (126 MHz, CD₃OD) δ 170.2, 161.6, 157.5, 150.0, 149.9, 145.8, 144.1, 137.7, 134.0, 128.8, 127.9, 123.9, 122.3, 122.1 (q, $^1J_{C-F}$=253.8 Hz), 105.5, 98.3, 96.1, 95.7, 40.6, 35.4. ¹⁹F NMR (376 MHz, CD₃OD) δ -59.5. LC/MS (m/z): 511.162 [M+H⁺]; UPLC $t_R$ 1.61 min.

5-((1-Methyl-3-(4-(trifluoromethoxy)phenyl)-1H-pyrazol-5-yl)amino)-4-(5H,6H,7H-pyrrolo[3,4-b]pyridine-6-carbonyl)benzene-1,3-diol (131)

Acid 19ag (53.1 mg, 107 μmol) was subjected to General Procedure H₂ to afford 18.6 mg of 131 (34% yield) after purification using mass-guided preparative HPLC. ¹H NMR (400 MHz, CD₃OD) δ 8.31 (dd, J=5.0, 1.5 Hz, 1H), 7.69-7.59 (m, 3H), 7.21 (dd, J=7.8, 5.0 Hz, 1H), 7.19-7.11 (m, 2H), 6.37 (s, 1H), 5.96 (d, J=2.1 Hz, 1H), 5.85 (d, J=2.1 Hz, 1H), 4.97-4.64 (m, 4H), 3.73 (s, 3H). ¹³C NMR (126 MHz, CD₃OD) δ 170.4, 161.7, 158.1, 157.6, 149.9, 149.4, 133.8, 133.5, 132.6, 127.7, 124.7, 122.1 (q, $^1J_{C-F}$=253.8

Hz), 105.1, 98.2, 96.24, 96.17, 40.6, 35.4. $^{19}$F NMR (376 MHz, CD$_3$OD) δ −59.4. LC/MS (m/z): 512.326 [M+H$^+$]; UPLC t$_R$ 1.48 min.

5-((1-Methyl-3-(4-(trifluoromethoxy)phenyl)-1H-pyrazol-5-yl)amino)-4-(1H,4H,5H,6H-pyrrolo[3,4-c]pyrazole-5-carbonyl)benzene-1,3-diol (132)

Acid 19ag (54.4 mg, 109 µmol) was subjected to General Procedure H$_3$ to afford 17 mg of 132 (31% yield) after purification using mass-guided preparative HPLC. $^1$H NMR (400 MHz, CD$_3$OD) δ 7.77-7.67 (m, 2H), 7.37 (s, 1H), 7.28-7.17 (m, 2H), 6.39 (s, 1H), 5.94 (d, J=2.1 Hz, 1H), 5.78 (d, J=2.1 Hz, 1H), 4.79-4.45 (m, 4H), 3.72 (s, 3H). $^{13}$C NMR (126 MHz, CD$_3$OD) δ 170.6, 161.5, 157.4, 150.0, 149.9, 145.6, 144.1, 134.0, 127.9, 124.1, 122.3, 122.1 (q, $^1J_{C-F}$=255.0 Hz), 105.4, 98.2, 96.1, 95.6, 40.6, 35.4. $^{19}$F NMR (376 MHz, CD$_3$OD) δ −59.5. LC/MS (m/z): 501.151 [M+H$^+$]; UPLC t$_R$ 1.28 min.

4-Amino Pyrazole RAP Experimental Procedures

2-Bromo-4,6-dimethoxybenzaldehyde

To a 250 mL round-bottom flask equipped with a magnetic stir-bar was added 3,5-dimethoxybromobenzene (10.0g, 46.1 mmol) and DMF (23 mL, 2 M). The mixture was cooled to 0° C. and POCl$_3$ (12.8 mL, 138 mmol, 3 equiv) was added dropwise over 5 minutes. The reaction was warmed to room temperature then heated to 90° C. for 6 hours. The reaction was cooled to room temperature and poured into ice water (200 mL). The reaction was quenched with a slow addition of KOH (55 g) to reach pH 14. The slurry was warmed to room temperature and stirred for 16 hours. The aqueous phase was extracted with Et$_2$O (3×200 mL), the combined organic extracts were washed with water (3×100 mL) and brine (150 mL), dried with Na$_2$SO$_4$ and concentrated under reduced pressure. No further purification was required affording 2-bromo-4,6-dimethoxybenzaldehyde as a brown solid (10.4g, 92% yield).

$^1$H NMR (400 MHz, CDCl$_3$) δ 10.31 (s, 1H), 6.78 (d, J=2.2 Hz, 1H), 6.44 (d, J=2.2 Hz, 1H), 3.95-3.80 (m, 6H).

UPLC/MS [M+H]=245.359, T$_R$=1.41 min.

2-Bromo-4,6-dihydroxybenzaldehyde

To a flamed-dried 250 mL round-bottom flask equipped with a magnetic stir-bar was added 2-bromo-4,6-dimethoxybenzaldehyde (10 g, 40.8 mmol). The flask was fitted with a rubber septum, evacuated and backfilled with N$_2$. Anhydrous CH$_2$Cl$_2$ (150 mL, 0.27 M) was added and the mixture was cooled to 0° C. In a separate round-bottom flask, a solution of BBr$_3$ (11.6 mL, 122 mmol, 3 equiv.) in anhydrous CH$_2$Cl$_2$ (30 mL, 4 M) was prepared. The BBr$_3$ solution was added dropwise via cannula over 15 minutes. The reaction was slowly warmed to room temperature as the ice bath melted and stirred for 18 hours. The reaction was poured on to ice water (300 mL), extracted with EtOAc (3×200 mL), washed with brine (300 mL), dried with Na$_2$SO$_4$ and concentrated under reduced pressure. The crude product was purified by silica flash chromatography (5-50% acetone in hexanes) affording 2-bromo-4,6-dihydroxybenzaldehyde (6.61g, 75% yield) as a light purple solid.

$^1$H NMR (400 MHz, DMSO-d$_6$) δ 12.19 (s, 1H), 9.97 (s, 1H), 6.71 (d, J=2.1 Hz, 1H), 6.30 (d, J=2.0 Hz, 1H).

UPLC/MS [M+H]=216.956, T$_R$=1.29 min.

2,4-Bis(benzyloxy)-6-bromobenzaldehyde

To a 200 mL round-bottom flask equipped with a magnetic stir-bar was added 2-bromo-4,6-dihydroxybenzaldehyde (3.33 g, 15.3 mmol), K$_2$CO$_3$ (5.3 g, 38.3 mmol, 2.5 equiv), benzyl bromide (4.6 mL, 38.3 mmol, 2.5 equiv) and MeCN (45 mL, 0.33 M). The flask was fitted with a reflux condenser and the reaction was heated at reflux in a 90° C. oil bath for 16 hours. The reaction was cooled to room temperature and the salts were removed by vacuum filtration washing with EtOAc (100 mL). The filtrate was concentrated under reduced pressure and purified by silica flash chromatography (2-40% EtOAc in hexanes) affording 2,4-bis(benzyloxy)-6-bromobenzaldehyde (5.0 g, 82% yield) as a colorless solid.

$^1$H NMR (400 MHz, CDCl$_3$) δ 10.39 (s, 1H), 7.49-7.29 (m, 10H), 6.89 (d, J=2.1 Hz, 1H), 6.57 (d, J=2.2 Hz, 1H), 5.13 (s, 2H), 5.07 (s, 2H).

$^{13}$C NMR (101 MHz, CDCl$_3$) δ 188.86, 163.47, 162.92, 135.66, 135.43, 128.94, 128.87, 128.71, 128.40, 127.76, 127.18, 126.64, 117.63, 113.07, 100.33, 70.96, 70.76.

UPLC/MS [M+H]=397.337, T$_R$=2.30 min.

(2,4-Bis(benzyloxy)-6-bromophenyl)(isoindolin-2-yl)methanone

To a 100 mL round-bottom flask equipped with a magnetic stir-bar was added 2,4-bis(benzyloxy)-6-bromobenzaldehyde (1.59 g, 4 mmol), tBuOH (12 mL) and THF (10 mL). In a separate flask sodium chlorite (1.09 g, 12 mmol, 3 equiv) and sodium monobasic phosphate monohydrate (4.14 g, 30 mmol, 7.5 equiv) were dissolved in H$_2$O (10 mL). The aqueous solution was added to the reaction portion-wise over 2 minutes turning the reaction bright yellow. 2-Methy-2-butene (5.1 mL, 48 mmol, 12 equiv) was added and the reaction was stirred for 30 minutes until the yellow color dissipated and the reaction returned to colorless. The reaction was quenched with 3 M HCl (30 mL) and extracted with EtOAc (3×50 mL). The combined organic extracts were washed with saturated NH$_4$Cl solution (2×50 mL), washed with brine (50 mL), dried with Na$_2$SO$_4$ and concentrate under reduced pressure. The resulting benzoic acid was immediately used without purification.

In a 100 mL round-bottom flask equipped with a magnetic stir-bar, the crude benzoic acid was dissolved in CH$_2$Cl$_2$ (12 mL) and THF (12 mL). Isoindoline hydrochloride (685 mg, 4.40 mmol, 1.1 equiv), DIPEA (1.74 mL, 10 mmol, 2.5 equiv) and HATU (1.83 g, 4.80 mmol, 1.2 equiv) were added. The reaction was stirred at room temperature for 3 hours. The reaction was quenched with saturated NaHCO$_3$ solution (30 mL), extracted with CH$_2$Cl$_2$ (3×50 mL), washed with brine (75 mL), dried with Na$_2$SO$_4$ and concentrate under reduced pressure. The crude product was purified by silica flash chromatography (5-60% EtOAc in hexane) to afford (2,4-bis(benzyloxy)-6-bromophenyl)(isoindolin-2-yl)methanone (1.67 g, 81% yield) as a colorless solid.

$^1$H NMR (400 MHz, CDCl$_3$) δ 7.48-7.22 (m, 13H), 7.15 (d, J=7.3 Hz, 1H), 6.85 (d, J=2.1 Hz, 1H), 6.59 (d, J=2.1 Hz, 1H), 5.16-5.05 (m, 2H), 5.02 (d, J=7.1 Hz, 4H), 4.68-4.45 (m, 2H).

$^{13}$C NMR (101 MHz, CDCl$_3$) δ 165.90, 160.46, 156.51, 136.54, 136.47, 136.16, 136.03, 128.86, 128.70, 128.48, 128.12, 127.86, 127.71, 127.62, 127.04, 123.27, 122.74, 122.19, 120.39, 110.63, 100.80, 70.75, 70.63, 53.32, 51.89 UPLC/MS [M+H]=514.231, $T_R$=2.10 min.

Synthesis of N-aryl-4-nitropyrazoles

General Procedure I

To a 20 mL scintillation vial equipped with a magnetic stir-bar was added 4-nitro-1H-pyrazole (565 mg, 5 mmol, 1 equiv), CuI (95 mg, 0.5 mmol, 0.1 equiv) and $K_2CO_3$ (1.38 g, 10 mmol, 2 equiv). The vial was fitted with a rubber septum, evacuated and backfilled with $N_2$. Anhydrous DMF (10 mL, 0.5 M) and Aryl-I (10 mmol, 2 equiv) were added. The vial was capped and sealed with PTFE tape and heated at 110° C. for 16 hours. The reaction was cooled to room temperature, diluted with $H_2O$ (50 mL) and extracted with EtOAc (3×50 mL). The combined organic extracts were washed with brine (4×50 mL), dried with $Na_2SO_4$ and concentrated under reduced pressure. The crude residue was purified by silica flash chromatography (2-50% EtOAc in hexanes) to afford the desired N-aryl-4-nitropyrazole.

4-Nitro-1-phenyl-1H-pyrazole was prepared according to General Procedure I using iodobenzene (1.11 mL, 10 mmol). 4-Nitro-1-phenyl-1H-pyrazole (622 mg, 3.29 mmol, 65% yield) as an off-white solid.

$^1$H NMR (400 MHz, $CDCl_3$) δ 8.63 (s, 1H), 8.27 (s, 1H), 7.76-7.68 (m, 2H), 7.59-7.49 (m, 2H), 7.44 (t, J=7.4 Hz, 1H).

4-Nitro-1-(o-tolyl)-1H-pyrazole was prepared according to General Procedure I using 2-iodotoluene (1.28 mL, 10 mmol). 4-Nitro-1-(o-tolyl)-1H-pyrazole (292 mg, 1.23 mmol, 24% yield) as an off-white solid.

$^1$H NMR (400 MHz, $CDCl_3$) δ 8.33 (s, 1H), 8.28 (s, 1H), 7.30-7.21 (m, 2H), 7.09 (t, J=7.1 Hz, 1H), 7.03-6.94 (m, 1H), 2.28 (s, 3H).

1-(2-Methoxyphenyl)-4-nitro-1H-pyrazole was prepared according to General Procedure I using 2-iodoanisole (1.30 mL, 10 mmol). 1-(2-Methoxyphenyl)-4-nitro-1H-pyrazole (182 mg, 0.83 mmol, 16% yield) as an off-white solid.

$^1$H NMR (400 MHz, $CDCl_3$) δ 8.80 (s, 1H), 8.23 (s, 1H), 7.83-7.74 (m, 1H), 7.42-7.34 (m, 1H), 7.17-7.01 (m, 2H), 3.94 (s, 3H).

4-Nitro-1-(2-(trifluoromethyl)phenyl)-1H-pyrazole was prepared according to General Procedure I using 1-iodo-2-(trifluoromethyl)benzene (1.40 mL, 10 mmol). 4-Nitro-1-(2-(trifluoromethyl)phenyl)-1H-pyrazole (157 mg, 0.61 mmol, 12% yield) as an off-white solid.

$^1$H NMR (400 MHz, $CDCl_3$) δ 8.40 (s, 1H), 8.28 (s, 1H), 7.89-7.84 (m, 1H), 7.79-7.65 (m, 2H), 7.62-7.53 (m, 1H).

4-Nitro-1-(m-tolyl)-1H-pyrazole was prepared according to General Procedure I using 3-iodotoluene (1.28 mL, 10 mmol). 4-Nitro-1-(m-tolyl)-1H-pyrazole (738 mg, 3.63 mmol, 72% yield) as an off-white solid.

$^1$H NMR (400 MHz, $CDCl_3$) δ 8.61 (s, 1H), 8.26 (s, 1H), 7.57-7.51 (m, 1H), 7.48 (d, J=8.3 Hz, 1H), 7.45-7.35 (m, 1H), 7.29-7.20 (m, 1H), 2.45 (s, 3H).

4-Nitro-1-(3-(trifluoromethyl)phenyl)-1H-pyrazole was prepared according to General Procedure I using 1-iodo-3-(trifluoromethyl)benzene (1.45 mL, 10 mmol). 4-Nitro-1-(3-(trifluoromethyl)phenyl)-1H-pyrazole (679 mg, 2.64 mmol, 52% yield) as an off-white solid.

$^1$H NMR (400 MHz, $CDCl_3$) δ 8.71 (s, 1H), 8.30 (s, 1H), 8.05-7.99 (m, 1H), 7.96-7.87 (m, 1H), 7.74-7.63 (m, 2H).

Synthesis of N-aryl-3,5-dimethyl-4-nitropyrazoles

General Procedure J

To a 20 mL scintillation equipped with a magnetic stir-bar vial was added 3,5-dimethyl-4-nitro-1H-pyrazole (282 mg, 2 mmol, 1 equiv), CuI (38 mg, 0.2 mmol, 0.1 equiv), 8-hydroxyquinoline (87 mg, 0.6 mmol, 0.3 equiv) and $K_2CO_3$ (829 mg, 6 mmol, 2 equiv). The vial was fitted with a rubber septum, evacuated and backfilled with $N_2$. DMSO (5 mL, 0.4 M) and Aryl-I (4 mmol, 2 equiv) were added. The vial was capped and sealed with PTFE tape and heated at 130° C. for 16 hours. The reaction was cooled to room temperature, diluted with $H_2O$ (50 mL) and extracted with EtOAc (3×50 mL). The combined organic extracts were washed with brine (4×50 mL), dried with $Na_2SO_4$ and concentrated under reduced pressure. The crude residue was purified by silica flash chromatography (2-40% EtOAc in hexanes) to afford the desired N-aryl-3,5-dimethyl-4-nitropyrazole.

3,5-Dimethyl-4-nitro-1-(m-tolyl)-1H-pyrazole was prepared according to General Procedure J using 3-iodotoluene (1.28 mL, 10 mmol). 3,5-Dimethyl-4-nitro-1-(m-tolyl)-1H-pyrazole (180 mg, 0.78 mmol, 15% yield) as an off-white solid.

$^1$H NMR (400 MHz, $CDCl_3$) δ 7.40 (t, J=7.7 Hz, 1H), 7.33-7.27 (m, 1H), 7.24-7.20 (m, 1H), 7.21-7.13 (m, 1H), 2.62 (s, 3H), 2.60 (s, 3H), 2.43 (s, 3H).

3,5-Dimethyl-4-nitro-1-(3-(trifluoromethyl)phenyl)-1H-pyrazole was prepared according to General Procedure J using 1-iodo-3-(trifluoromethyl)benzene (0.58 mL, 4 mmol). 3,5-Dimethyl-4-nitro-1-(3-(trifluoromethyl)phenyl)-1H-pyrazole (253 mg, 0.89 mmol, 44% yield) as an off-white solid.

$^1$H NMR (400 MHz, $CDCl_3$) δ 7.80-7.74 (m, 1H), 7.74-7.70 (m, 1H), 7.68 (d, J=7.8 Hz, 1H), 7.65-7.60 (m, 1H), 2.67 (s, 3H), 2.61 (s, 3H).

1-(2-Methoxyphenyl)-3,5-dimethyl-4-nitro-1H-pyrazole was prepared according to General Procedure J using 2-iodoanisole (0.52 mL, 4 mmol). 1-(2-Methoxyphenyl)-3,5-dimethyl-4-nitro-1H-pyrazole (43 mg, 0.17 mmol, 9% yield) as an off-white solid.

$^1$H NMR (400 MHz, $CDCl_3$) δ 7.55-7.45 (m, 1H), 7.35-7.30 (m, 1H), 7.13-7.01 (m, 2H), 3.82 (s, 3H), 2.60 (s, 3H), 2.44 (s, 3H).

Reduction of N-aryl-4-nitropyrazoles

General Procedure K

To a 20 mL scintillation vial equipped with a magnetic stir-bar was added N-aryl-4-nitropyrazole (1 mmol, 1 equiv), palladium on carbon (20 mg, 10% w.t.), EtOH (1 mL) and hydrazine hydrate (0.5 mL). The vial was capped with a septa line cap and sealed with PTFE tape. The vial was heated at 80° C. for 30 minutes. The reaction was cooled to room temperature and filtered through a celite plug, eluting with EtOAc (6 mL) and MeOH (6 mL). The filtrate was concentrated under reduced pressure and purified by flash column chromatography (0-10% MeOH in $CH_2Cl_2$) affording the desired N-aryl-4-aminopyrazole.

1-Phenyl-1H-pyrazol-4-amine: 4-Nitro-1-phenyl-1H-pyrazole (189 mg, 1 mmol) was treated according to General Procedure K. 1-Phenyl-1H-pyrazol-4-amine (128 mg, 80% yield) was isolated as a yellow oil.

$^1$H NMR (400 MHz, $CDCl_3$)
UPLC/MS [M+H]=161.049, $T_R$=0.58 min.

1-(o-Tolyl)-1H-pyrazol-4-amine: 4-Nitro-1-(o-tolyl)-1H-pyrazole (249 mg, 1.23 mmol) was treated according to General Procedure K. 1-(o-Tolyl)-1H-pyrazol-4-amine (115 mg, 54% yield) was isolated as a yellow oil.
$^1$H NMR (400 MHz, CDCl$_3$) δ 7.42-7.34 (m, 1H), 7.32-7.23 (m, 4H), 7.23-7.20 (m, 1H), 3.02 (s, 2H), 2.27 (s, 3H).
UPLC/MS [M+2H]=175.105, T$_R$=0.60 min.

1-(2-Methoxyphenyl)-1H-pyrazol-4-amine: 1-(2-Methoxyphenyl)-4-nitro-1H-pyrazole (182 mg, 0.83 mmol) was treated according to General Procedure K. 1-(2-Methoxyphenyl)-1H-pyrazol-4-amine (141 mg, 89% yield) was isolated as a yellow oil.
$^1$H NMR (400 MHz, CDCl$_3$) δ 7.70-7.64 (m, 2H), 7.40-7.36 (m, 1H), 7.28-7.20 (m, 1H), 7.07-6.94 (m, 2H), 3.87 (s, 3H), 3.05 (s, 2H).

1-(2-(Trifluoromethyl)phenyl)-1H-pyrazol-4-amine: 4-Nitro-1-(2-(trifluoromethyl)phenyl)-1H-pyrazole (157 mg, 0.61 mmol) was treated according to General Procedure K. 1-(2-(Trifluoromethyl)phenyl)-1H-pyrazol-4-amine (110 mg, 79% yield) was isolated as a yellow oil.
$^1$H NMR (400 MHz, CDCl$_3$) δ 7.77 (d, J=8.0 Hz, 1H), 7.63 (t, J=7.7 Hz, 1H), 7.56-7.47 (m, 2H), 7.47-7.42 (m, 1H), 7.31 (s, 1H), 3.07 (s, 2H).

1-(m-Tolyl)-1H-pyrazol-4-amine: 4-Nitro-1-(m-tolyl)-1H-pyrazole (305 mg, 1.5 mmol) was treated according to General Procedure K. 1-(m-Tolyl)-1H-pyrazol-4-amine (234 mg, 90% yield) was isolated as a yellow oil.
$^1$H NMR (400 MHz, CDCl$_3$) δ 7.51-7.45 (m, 2H), 7.39-7.33 (m, 2H), 7.31-7.24 (m, 1H), 7.06-7.00 (m, 1H), 3.06 (s, 2H), 2.41-2.37 (m, 3H).

1-(3-(Trifluoromethyl)phenyl)-1H-pyrazol-4-amine: 4-Nitro-1-(3-(trifluoromethyl)phenyl)-1H-pyrazole (385 mg, 1.5 mmol) was treated according to General Procedure K. 1-(3-(Trifluoromethyl)phenyl)-1H-pyrazol-4-amine (296 mg, 86% yield) was isolated as a yellow oil.
$^1$H NMR (400 MHz, CDCl$_3$) δ 7.89 (s, 1H), 7.78 (d, J=7.9 Hz, 1H), 7.57-7.50 (m, 2H), 7.50-7.39 (m, 2H), 3.11 (s, 2H).

3,5-Dimethyl-1-(m-tolyl)-1H-pyrazol-4-amine: 3,5-Dimethyl-4-nitro-1-(m-tolyl)-1H-pyrazole (180 mg, 0.78 mmol) was treated according to General Procedure K. 3,5-Dimethyl-1-(m-tolyl)-1H-pyrazol-4-amine (58 mg, 37% yield) was isolated as a yellow oil.
$^1$H NMR (400 MHz, CDCl$_3$) δ 7.33-7.22 (m, 2H), 7.18-7.08 (m, 2H), 2.76 (s, 2H), 2.38 (s, 3H), 2.25 (s, 3H), 2.23 (s, 3H).

3,5-Dimethyl-1-(3-(trifluoromethyl)phenyl)-1H-pyrazol-4-amine: 3,5-Dimethyl-4-nitro-1-(m-tolyl)-1H-pyrazole (253 mg, 0.89 mmol) was treated according to General Procedure K. 3,5-Dimethyl-1-(3-(trifluoromethyl)phenyl)-1H-pyrazol-4-amine (194 mg, 85% yield) was isolated as a yellow oil.
$^1$H NMR (400 MHz, CDCl$_3$) δ 7.73-7.69 (m, 1H), 7.64-7.57 (m, 2H), 7.57-7.52 (m, 2H), 2.79 (s, 2H), 2.28-2.27 (m, 3H), 2.27-2.25 (m, 3H).

1-(2-Methoxyphenyl)-3,5-dimethyl-1H-pyrazol-4-amine: 1-(2-Methoxyphenyl)-3,5-dimethyl-4-nitro-1H-pyrazole (43 mg, 0.17 mmol) was treated according to General Procedure K. 1-(2-Methoxyphenyl)-3,5-dimethyl-1H-pyrazol-4-amine (34 mg, 90% yield) was isolated as a yellow oil.
$^1$H NMR (400 MHz, Chloroform-d) δ 7.40-7.32 (m, 1H), 7.32-7.27 (m, 1H), 7.05-6.96 (m, 2H), 3.79 (s, 3H), 2.52 (s, 2H), 2.25 (s, 3H), 2.02 (s, 3H).

General Procedure L

L1a: To a flame-dried 2D vial equipped with a magnetic stir-bar was added (2,4-bis(benzyloxy)-6-bromophenyl)(isoindolin-2-yl)methanone (77 mg, 0.15 mmol, 1 equiv) N-aryl-4-aminopyrazole (0.165 mmol, 1.1 equiv), Pd(OAc)$_2$ (3.4 mg, 15 µmol, 0.1 equiv), xantphos (17.4 mg, 30 µmol, 0.2 equiv) and Cs$_2$CO$_3$ (98 mg, 0.3 mmol, 2 equiv). The vial was fitted with a rubber septum, evacuated, backfilled with N$_2$ and anhydrous toluene (0.6 mL, 0.25 M) was added. The septum was replaced with a cap and the vial was sealed with PTFE tape. The reaction was heated at 130° C. for 16 hours in a heating block. The reaction was cooled to room temperature and a filtered through a silica plug eluting with EtOAc (12 mL). The filtrate was concentrated and purified by silica flash chromatography.

L1b: To a flame-dried microwave vial equipped with a magnetic stir-bar was added (2,4-bis(benzyloxy)-6-bromophenyl)(isoindolin-2-yl)methanone (77 mg, 0.15 mmol, 1 equiv) N-aryl-4-aminopyrazole (0.165 mmol, 1.1 equiv), Pd$_2$(dba)$_3$ (8.7 mg, 6 µmol, 0.04 equiv), xanthphos (5.5 mg, 15 µmol, 0.1 equiv), and sodium phenoxide (26 mg, 0.225 mmol, 1.5 equiv). The vial was fitted with a rubber septum, evacuated, backfilled with N$_2$ and anhydrous 1,4-dioxane (1.5 mL, 0.1 M) was added. The septum was replaced with a microwave cap and the reaction was heated in a microwave holding at 170° C. for 2 hours. The reaction was cooled to room temperature and a filtered through a silica plug eluting with EtOAc (12 mL). The filtrate was concentrated and purified by silica flash chromatography.

L2: In a 2D vial equipped with a magnetic stir-bar was added benzyl protected RAP (1 equiv), MeOH (2 mL) and Pd/C (20% w.t.). The vial was fitted with a rubber septum and a hydrogen balloon. Hydrogen was bubbled through the solution for 10 minutes then the reaction was stirred under hydrogen atmosphere for 16 hours or until full conversion was observed by UPLC/MS. The reaction was filtered through a celite plug eluting with MeOH (6 mL) and EtOAc (6 mL) and concentrated. The crude material was purified by mass-guided preparative HPLC.

(2,4-Dihydroxy-6-((1,3,5-trimethyl-1H-pyrazol-4-yl)amino)phenyl)(isoindolin-2-yl)methanone: (2,4-Bis(benzyloxy)-6-bromophenyl)(isoindolin-2-yl)methanone (77 mg, 0.15 mmol, 1 equiv) was coupled to 1,3,5-trimethylpyrazol-4-amine (20.7 mg, 0.165 mmol, 1.1 equiv) according to general procedure L1a. The resulting product was deprotected using procedure L2. (2,4-Dihydroxy-6-((1,3,5-trimethyl-1H-pyrazol-4-yl)amino)phenyl)(isoindolin-2-yl)methanone (25.0 mg, 66 µmol) was obtained in 44% yield over 2 steps.
$^1$H NMR (400 MHz, DMSO-d$_6$) δ 9.35 (s, 1H), 9.00 (s, 1H), 7.36-7.19 (m, 4H), 6.15 (s, 1H), 5.68 (d, J=2.5 Hz, 1H), 5.20 (t, J=2.0 Hz, 1H), 4.72 (s, 4H), 3.58 (s, 4H), 1.96 (s, 3H), 1.86 (s, 3H).
$^{13}$C NMR (101 MHz, DMSO-d$_6$) δ 167.10, 159.22, 155.33, 147.11, 143.05, 136.84, 135.14, 127.29, 122.92, 118.43, 102.46, 92.31, 90.78, 51.85, 36.08, 10.99, 8.79.
UPLC/MS [M+H]=379.282, T$_R$=1.05 min.

(2,4-Dihydroxy-6-((1-isopropyl-1H-pyrazol-4-yl)amino)phenyl)(isoindolin-2-yl)methanone: (2,4-Bis(benzyloxy)-6-bromophenyl)(isoindolin-2-yl)methanone (64 mg, 0.125 mmol, 1 equiv) was coupled to 1-isopropylpyrazol-4-amine hydrochloride (22.2 mg, 0.137 mmol, 1.1 equiv) according to general procedure L1a. The resulting product was deprotected using procedure L2. (2,4-Dihydroxy-6-((1-isopropyl-1H-pyrazol-4-yl)amino)phenyl)(isoindolin-2-yl)methanone (21.6 mg, 57 µmol) was obtained in 46% yield over 2 steps.
$^1$H NMR (400 MHz, DMSO-d$_6$) δ 9.40 (s, 1H), 9.12 (s, 1H), 7.58 (s, 1H), 7.33-7.19 (m, 4H), 6.51 (s, 1H), 5.73 (dd, J=14.1, 2.1 Hz, 2H), 4.69 (s, 4H), 4.36 (p, J=6.6 Hz, 1H), 1.33 (d, J=6.7 Hz, 6H).

¹³C NMR (101 MHz, DMSO-d₆) δ 166.95, 159.23, 155.38, 146.05, 133.80, 127.27, 123.52, 122.90, 121.72, 102.75, 92.74, 91.19, 53.06, 51.85, 22.63.

UPLC/MS [M+H]=379.282, T$_R$=1.18 min.

(2,4-Dihydroxy-6-((1-phenyl-1H-pyrazol-4-yl)amino) phenyl)(isoindolin-2-yl)methanone: (2,4-Bis(benzyloxy)-6-bromophenyl)(isoindolin-2-yl)methanone (102 mg, 0.2 mmol, 1 equiv) was coupled to 1-Phenyl-H-pyrazol-4-amine (31.8 mg, 0.2 mmol, 1 equiv) according to general procedure L1b. The resulting product was deprotected using procedure L2. (2,4-Dihydroxy-6-((1-phenyl-1H-pyrazol-4-yl)amino) phenyl)(isoindolin-2-yl)methanone (28.8 mg, 70 mol) was obtained in 37% yield over 2 steps.

¹H NMR (400 MHz, DMSO-d₆) δ 9.51 (s, 1H), 9.20 (s, 1H), 8.32 (s, 1H), 7.81-7.66 (m, 2H), 7.61 (s, 1H), 7.47-7.36 (m, 2H), 7.35-7.17 (m, 5H), 6.83 (s, 1H), 5.96-5.89 (m, 1H), 5.82-5.71 (m, 1H), 4.72 (s, 4H).

UPLC/MS [M+H]=413.222, T$_R$=1.33 min.

(2,4-Dihydroxy-6-((1-(o-tolyl)-1H-pyrazol-4-yl)amino) phenyl)(isoindolin-2-yl)methanone: (2,4-Bis(benzyloxy)-6-bromophenyl)(isoindolin-2-yl)methanone (77 mg, 0.15 mmol, 1 equiv) was coupled to 1-(o-Tolyl)-1H-pyrazol-4-amine (28.6 mg, 0.165 mmol, 1.1 equiv) according to general procedure L1b. The resulting product was deprotected using procedure L2. 2,4-Dihydroxy-6-((1-(o-tolyl)-1H-pyrazol-4-yl)amino)phenyl)(isoindolin-2-yl)methanone (19.6 mg, 46 μmol) was obtained in 31% yield over 2 steps.

¹H NMR (400 MHz, DMSO-d₆) δ 9.51 (s, 1H), 9.22 (s, 1H), 7.89 (s, 1H), 7.66-7.56 (m, 1H), 7.41-7.23 (m, 8H), 6.79 (s, 1H), 5.94 (d, J=2.1 Hz, 1H), 5.80 (d, J=2.1 Hz, 1H), 4.76 (s, 4H), 2.25 (s, 3H).

¹³C NMR (101 MHz, DMSO-d₆) δ 166.90, 159.31, 155.48, 145.44, 139.80, 135.95, 132.45, 131.36, 128.81, 127.91, 127.31, 126.71, 125.48, 125.30, 124.50, 122.94, 103.15, 93.14, 91.47, 51.94, 18.11.

UPLC/MS [M+H]=427.236, T$_R$=1.31 min.

(2,4-Dihydroxy-6-((1-(2-methoxyphenyl)-1H-pyrazol-4-yl)amino)phenyl)(isoindolin-2-yl)methanone: (2,4-Bis(benzyloxy)-6-bromophenyl)(isoindolin-2-yl)methanone (77 mg, 0.15 mmol, 1 equiv) was coupled to 1-(2-Methoxyphenyl)-1H-pyrazol-4-amine (28.4 mg, 0.15 mmol, 1 equiv) according to general procedure L1b. The resulting product was deprotected using procedure L2. (2,4-Dihydroxy-6-((1-(2-methoxyphenyl)-1H-pyrazol-4-yl)amino)phenyl)(isoindolin-2-yl)methanone (20.4 mg, 46 mol) was obtained in 31% yield over 2 steps.

¹H NMR (400 MHz, DMSO-d₆) δ 9.51 (s, 1H), 9.22 (s, 1H), 8.04 (s, 1H), 7.69-7.53 (m, 2H), 7.38-7.25 (m, 5H), 7.22 (dd, J=8.5, 1.3 Hz, 1H), 7.06 (td, J=7.8, 1.3 Hz, 1H), 6.80 (s, 1H), 5.92 (d, J=2.1 Hz, 1H), 5.80 (d, J=2.1 Hz, 1H), 4.75 (s, 4H), 3.86 (s, 3H).

¹³C NMR (101 MHz, DMSO-d₆) δ 166.85, 159.29, 155.49, 150.56, 145.36, 135.79, 129.21, 127.91, 127.31, 125.25, 124.87, 124.08, 122.94, 120.93, 112.95, 103.25, 93.16, 91.45, 60.34, 56.02.

UPLC/MS [M+H]=443.477, T$_R$=1.34 min.

(2,4-Dihydroxy-6-((1-(2-(trifluoromethyl)phenyl)-1H-pyrazol-4-yl)amino)phenyl)(isoindolin-2-yl)methanone: (2,4-Bis(benzyloxy)-6-bromophenyl)(isoindolin-2-yl) methanone (77 mg, 0.15 mmol, 1 equiv) was coupled to 1-(2-(Trifluoromethyl)phenyl)-1H-pyrazol-4-amine (34.1 mg, 0.165 mmol, 1.1 equiv) according to general procedure L1b. The resulting product was deprotected using procedure L2. (2,4-Dihydroxy-6-((1-(2-(trifluoromethyl)phenyl)-1H-pyrazol-4-yl)amino)phenyl)(isoindolin-2-yl)methanone (34.4 mg, 72 μmol) was obtained in 48% yield over 2 steps.

¹H NMR (400 MHz, DMSO-d₆) δ 9.53 (s, 1H), 9.26 (s, 1H), 7.96-7.88 (m, 2H), 7.88-7.77 (m, 1H), 7.74-7.64 (m, 2H), 7.59 (d, J=7.9 Hz, 1H), 7.37-7.20 (m, 4H), 6.86 (s, 1H), 5.98-5.93 (m, 1H), 5.87-5.81 (m, 1H), 5.07-4.40 (m, 4H).

UPLC/MS [M+H]=481.446, T$_R$=1.42 min.

(2,4-Dihydroxy-6-((1-(m-tolyl)-1H-pyrazol-4-yl)amino) phenyl)(isoindolin-2-yl)methanone: (2,4-Bis(benzyloxy)-6-bromophenyl)(isoindolin-2-yl)methanone (77 mg, 0.15 mmol, 1 equiv) was coupled to 1-(m-Tolyl)-1H-pyrazol-4-amine (28.6 mg, 0.165 mmol, 1.1 equiv) according to general procedure L1b. The resulting product was deprotected using procedure L2. (2,4-Dihydroxy-6-((1-(m-tolyl)-1H-pyrazol-4-yl)amino)phenyl)(isoindolin-2-yl)methanone (19 mg, 44.6 μmol) was obtained in 30% yield over 2 steps.

¹H NMR (400 MHz, DMSO-d₆) δ 9.54 (s, 1H), 9.24 (s, 1H), 8.34 (s, 1H), 7.63 (s, 2H), 7.57 (d, J=8.1 Hz, 1H), 7.38-7.24 (m, 5H), 7.08 (d, J=7.5 Hz, 1H), 6.86 (s, 1H), 5.96 (d, J=2.0 Hz, 1H), 5.82 (d, J=2.1 Hz, 1H), 4.97-4.55 (m, 4H), 2.36 (s, 3H).

¹³C NMR (101 MHz, DMSO-d₆) δ 166.83, 159.33, 155.49, 145.07, 139.75, 139.04, 136.69, 129.31, 127.31, 127.08, 126.70, 126.43, 122.93, 120.25, 118.25, 114.86, 103.33, 93.32, 91.67, 51.96, 21.11.

UPLC/MS [M+H]=427.195, T$_R$=1.40 min.

(2,4-Dihydroxy-6-((1-(3-(trifluoromethyl)phenyl)-1H-pyrazol-4-yl)amino)phenyl)(isoindolin-2-yl)methanone: (2,4-Bis(benzyloxy)-6-bromophenyl)(isoindolin-2-yl) methanone (77 mg, 0.15 mmol, 1 equiv) was coupled to 1-(3-(Trifluoromethyl)phenyl)-1H-pyrazol-4-amine (37.5 mg, 0.165 mmol, 1.1 equiv) according to general procedure L1b. The resulting product was deprotected using procedure L2. (2,4-Dihydroxy-6-((1-(3-(trifluoromethyl)phenyl)-1H-pyrazol-4-yl)amino)phenyl)(isoindolin-2-yl)methanone (27.9 mg, 58 μmol) was obtained in 37% yield over 2 steps.

¹H NMR (400 MHz, DMSO-d₆) δ 9.56 (s, 1H), 9.27 (s, 1H), 8.56 (s, 1H), 8.18-8.06 (m, 2H), 7.77-7.65 (m, 2H), 7.61 (d, J=7.9 Hz, 1H), 7.39-7.21 (m, 4H), 6.94 (s, 1H), 5.99 (d, J=2.1 Hz, 1H), 5.84 (d, J=2.2 Hz, 1H), 4.76 (s, 4H).

UPLC/MS [M+H]=481.183, T$_R$=1.59 min.

(2-((3,5-Dimethyl-1-(m-tolyl)-1H-pyrazol-4-yl)amino)-4,6-dihydroxyphenyl)(isoindolin-2-yl)methanone: (2,4-Bis(benzyloxy)-6-bromophenyl)(isoindolin-2-yl)methanone (77 mg, 0.15 mmol, 1 equiv) was coupled to 3,5-Dimethyl-1-(m-tolyl)-1H-pyrazol-4-amine (33.2 mg, 0.165 mmol, 1.1 equiv) according to general procedure L1b. The resulting product was deprotected using procedure L2. (2-((3,5-Dimethyl-1-(m-tolyl)-1H-pyrazol-4-yl)amino)-4,6-dihydroxyphenyl)(isoindolin-2-yl)methanone (30.7 mg, 68 mol) was obtained in 45% yield over 2 steps.

¹H NMR (400 MHz, DMSO-d₆) δ 9.43 (s, 1H), 9.10 (s, 1H), 7.50-7.22 (m, 7H), 7.17 (d, J=7.5 Hz, 1H), 6.39 (s, 1H), 5.75 (d, J=2.1 Hz, 1H), 5.35 (d, J=2.1 Hz, 1H), 4.77 (s, 4H), 2.37 (s, 3H), 2.13 (s, 3H), 2.02 (s, 3H).

¹³C NMR (101 MHz, DMSO-d₆) δ 166.99, 159.24, 155.40, 146.61, 145.87, 139.85, 138.79, 136.85, 135.33, 128.89, 127.46, 127.30, 124.06, 122.94, 120.92, 120.48, 102.73, 92.58, 91.00, 51.90, 20.94, 11.23, 10.64.

UPLC/MS [M+H]=455.262, T$_R$=1.44 min.

(2-((3,5-Dimethyl-1-(3-(trifluoromethyl)phenyl)-1H-pyrazol-4-yl)amino)-4,6-dihydroxyphenyl)(isoindolin-2-yl) methanone: (2,4-Bis(benzyloxy)-6-bromophenyl)(isoindolin-2-yl)methanone (77 mg, 0.15 mmol, 1 equiv) was coupled to 3,5-Dimethyl-1-(3-(trifluoromethyl)phenyl)-1H-pyrazol-4-amine (42.1 mg, 0.165 mmol, 1.1 equiv) according to general procedure L1b. The resulting product was deprotected using procedure L2. (2-((3,5-Dimethyl-1-(3-(trifluoromethyl)phenyl)-1H-pyrazol-4-yl)amino)-4,6-dihydroxyphenyl)(isoindolin-2-yl)methanone (33.1 mg, 65 μmol) was obtained in 43% yield over 2 steps.

$^1$H NMR (400 MHz, DMSO-d$_6$) δ 9.45 (s, 1H), 9.10 (s, 1H), 7.90-7.79 (m, 2H), 7.79-7.64 (m, 2H), 7.43-7.22 (m, 4H), 6.45 (s, 1H), 5.84-5.70 (m, 1H), 5.49-5.31 (m, 1H), 4.77 (s, 4H), 2.21 (s, 3H), 2.08-1.98 (m, 3H).

UPLC/MS [M+H]=509.533, T$_R$=1.58 min.

(2,4-Dihydroxy-6-((1-(2-methoxyphenyl)-3,5-dimethyl-1H-pyrazol-4-yl)amino)phenyl)(isoindolin-2-yl)methanone: (2,4-Bis(benzyloxy)-6-bromophenyl)(isoindolin-2-yl) methanone (51 mg, 0.1 mmol, 1 equiv) was coupled to 1-(2-Methoxyphenyl)-3,5-dimethyl-1H-pyrazol-4-amine (23.9 mg, 0.11 mmol, 1.1 equiv) according to general procedure L1b. The resulting product was deprotected using procedure L2. (2,4-Dihydroxy-6-((1-(2-methoxyphenyl)-3,5-dimethyl-1H-pyrazol-4-yl)amino)phenyl)(isoindolin-2-yl)methanone (8.6 mg, 18 μmol) was obtained in 18% yield over 2 steps.

UPLC/MS [M+2H]=472.273, T$_R$=1.33 min.

$^1$H NMR (400 MHz, DMSO-d$_6$) δ 9.39 (s, 1H), 9.11 (s, 1H), 7.49-7.40 (m, 1H), 7.39-7.22 (m, 5H), 7.20 (d, J=8.2 Hz, 1H), 7.10-7.01 (m, 1H), 6.34 (s, 1H), 5.73 (d, J=2.1 Hz, 1H), 5.34 (d, J=2.1 Hz, 1H), 4.76 (s, 4H), 3.76 (s, 3H), 1.99 (s, 3H), 1.83 (s, 3H).

Macrocycle Preparations

Pent-4-en-1-ylhydrazine hydrochloride To a 20 mL scintillation vial was added 5-bromo-1-pentene (300 μL, 2 mmol, 1 equiv), tert-butyl carbazate (529 mg, 4 mmol, 2 equiv), triethylamine (558 μL, 4 mmol, 2 equiv) and absolute ethanol (4 mL, 0.5 M). The flask was capped, sealed with PTFE tape and stirred at 95° C. for 16 hours. The reaction was cooled to room temperature and concentrated under reduced pressure. The crude residue was taken up in 35% NaOH containing 3 g NaCl (25 mL) and this solution was extracted with EtOAc (3×75 mL). The combined organic extracts were dried over Na$_2$SO$_4$ and concentrated. Purification by silica flash chromatography (10-100% EtOAc/Hex) afforded tert-butyl 2-(pent-4-en-1-yl)hydrazine-1-carboxylate (240 mg, 1.2 mmol, 59% yield).

$^1$H NMR (400 MHz, Chloroform-d) δ 5.87-5.68 (m, 1H), 5.07-4.85 (m, 2H), 2.84 (t, J=7.3 Hz, 2H), 2.15-2.05 (m, 2H), 1.62-1.47 (m, 2H), 1.45 (s, 9H).

In a 20 mL scintillation vial the purified residue (240 mg, 1.2 mmol, 1 equiv) was dissolved in MeOH (3 mL) and 4M HCl solution in dioxane (1.5 mL, 6 mmol, 5 equiv) was added. The solution was stirred at room temperature for 16 hours. The reaction was concentrated under reduced pressure and pent-4-en-1-ylhydrazine hydrochloride used without further purification.

$^1$H NMR (400 MHz, DMSO-d$_6$) δ 5.89-5.67 (m, 1H), 5.20-4.89 (m, 2H), 4.54-3.66 (br m, 4H) 2.87 (t, J=7.8 Hz, 2H), 2.06 (q, J=7.9 Hz, 2H), 1.62 (q, J=7.7 Hz, 2H).

General Procedure M

To a microwave vial equipped with a magnetic stir bar was added α-cyanoketone (1 equiv), N-alkyl-hydrazine hydrochloride (1.1 equiv), triethylamine (1.5 equiv) and absolute ethanol (1 M). The vial was capped and heated in a microwave reactor maintaining 120° C. for 90 minutes. The vial was cooled to room temperature and then reaction was concentrated under reduced pressure. The crude residue was purified by silica flash chromatography (5-50% EtOAc in hexanes) to afford the desired 5-aminopyrazole.

Ethyl 2-(5-amino-3-phenyl-1H-pyrazol-1-yl)acetate was prepared benzoylacetonitrile (290 mg, 2 mmol, 1 equiv) and ethyl 2-hydrazinoacetate hydrochloride (340 mg, 2.2 mmol, 1.1 equiv) according to General Procedure M. (302 mg, 1.23 mmol, 61% yield).

$^1$H NMR (400 MHz, Chloroform-d) δ 7.78-7.66 (m, 2H), 7.40-7.32 (m, 2H), 7.33-7.25 (m, 1H), 5.96 (d, J=0.8 Hz, 1H), 4.88 (d, J=1.9 Hz, 2H), 4.33-4.14 (m, 2H), 1.45-1.15 (m, 3H).

UPLC/MS [M+H]=246.555, R$^F$=1.16 min.

1-(Pent-4-en-1-yl)-3-phenyl-1H-pyrazol-5-amine was prepared benzoylacetonitrile (159 mg, 1.1 mmol, 1 equiv) and pent-4-en-1-ylhydrazine hydrochloride (165 mg, 1.2 mmol, 1.1 equiv) according to General Procedure M. (106 mg, 0.46 mmol, 42% yield).

$^1$H NMR (400 MHz, Chloroform-d) δ 7.79-7.69 (m, 2H), 7.45-7.31 (m, 2H), 7.31-7.19 (m, 1H), 5.94-5.76 (m, 2H), 5.13-4.93 (m, 2H), 4.00 (t, J=7.3 Hz, 2H), 3.53 (s, 2H), 2.14 (q, J=7.1 Hz, 2H), 2.06-1.85 (m, 2H).

General Procedure N

To a flame-dried microwave vial equipped with a magnetic stir-bar was added methyl 2,4-bis(benzyloxy)-6-bromobenzoate (1 equiv) 5-aminopyrazole (1.1 equiv), Pd$_2$(dba)$_3$ (0.04 equiv), xanthphos (0.1 equiv), and sodium phenoxide (1.5 equiv). The vial was fitted with a rubber septum, evacuated, backfilled with N$_2$ and anhydrous 1,4-dioxane (1.5 mL, 0.1 M) was added. The septum was replaced with a microwave cap and the reaction was heated in a microwave holding at 170° C. for 2 hours. The reaction was cooled to room temperature and a filtered through a silica plug eluting with EtOAc (12 mL). The filtrate was concentrated and purified by silica flash chromatography.

Methyl 2,4-bis(benzyloxy)-6-((1-(2-ethoxy-2-oxoethyl)-3-phenyl-1H-pyrazol-5-yl)amino)benzoate Methyl 2,4-bis(benzyloxy)-6-bromobenzoate (1 equiv) is coupled to ethyl 2-(5-amino-3-phenyl-1H-pyrazol-1-yl)acetate (1.1 equiv) according to General Procedure N.

Methyl 2,4-bis(benzyloxy)-6-((1-(pent-4-en-1-yl)-3-phenyl-1H-pyrazol-5-yl)amino)benzoate Methyl 2,4-bis(benzyloxy)-6-bromobenzoate (1 equiv) is coupled to 1-(pent-4-en-1-yl)-3-phenyl-1H-pyrazol-5-amine (1.1 equiv) according to General Procedure N.

General Procedure O

To a solution of ester (1 equiv) in EtOH/water (1:1 ratio, 0.06 M) was added potassium hydroxide (9.2 equiv), and then the mixture was heated to 95° C. for 1 h. After cooling to room temperature, volatile materials were condensed in vacuo. The residue was suspended in saturated NH$_4$Cl$_2$ (aq) and CH$_2$Cl$_2$. The layers were separated, and the aqueous layer was extracted three times with CH$_2$Cl$_2$. The combined organic layers were washed twice with water, brine and then dried with anhydrous Na$_2$SO$_4$. The salts were removed via gravity filtration, and volatile materials were condensed in vacuo.

The crude acid and (1 equiv) and 5-bromoisoindoline (1.5 equiv) in THF/CH$_2$Cl$_2$ (1:1 ratio, 77 mM) was added trimethylamine (4 equiv) followed by HOBt hydrate (1.2 equiv) and PS-carbodiimide (1.18 mmol/g loading, 1.2 equiv). The suspension was stirred overnight at room temperature. The resin was removed via filtration materials were condensed in vacuo. The resulting residue was purified by silica flash chromatography.

Ethyl 2-(5-((3,5-bis(benzyloxy)-2-(5-bromoisoindoline-2-carbonyl)phenyl)amino)-3-phenyl-1H-pyrazol-1-yl)acetate is prepared from methyl 2,4-bis(benzyloxy)-6-((1-(2-ethoxy-2-oxoethyl)-3-phenyl-1H-pyrazol-5-yl)amino) benzoate according to General Procedure 0.

(2,4-Bis(benzyloxy)-6-((1-(pent-4-en-1-yl)-3-phenyl-1H-pyrazol-5-yl)amino)phenyl)(5-bromoisoindolin-2-yl)methanone is prepared from methyl 2,4-bis(benzyloxy)-6-((1-(pent-4-en-1-yl)-3-phenyl-1H-pyrazol-5-yl)amino)benzoate according to General Procedure 0.

Ethyl 2-(5-((3,5-bis(benzyloxy)-2-(5-((4-((tert-butoxycarbonyl)amino)butyl)amino)isoindoline-2-carbonyl)phenyl)amino)-3-phenyl-1H-pyrazol-1-yl)acetate is prepared from ethyl 2-(5-((3,5-bis(benzyloxy)-2-(5-bromoisoindoline-2-carbonyl)phenyl)amino)-3-phenyl-1H-pyrazol-1-yl)acetate (1 equiv) and N-Boc-1,4-butanediamine (1.1 equiv) according to General Procedure 0.

Macrocycle M1 Ethyl 2-(5-((3,5-bis(benzyloxy)-2-(5-((4-((tert-butoxycarbonyl)amino)butyl)amino)isoindoline-2-carbonyl)phenyl)amino)-3-phenyl-1H-pyrazol-1-yl)acetate (1 equiv) is dissolved in MeOH (0.5 M) and HCl 4M in dioxane (5 equiv) is added. The reaction is stirred at room temperature. The reaction is monitored by UPC/MS. Upon full conversion to boc-deprotected product the reaction is suspended in saturated $NH_4Cl$ (aq) and $CH_2Cl_2$. The layers are separated, and the aqueous layer is extracted three times with $CH_2Cl_2$. The combined organic layers are washed twice with water, brine and then dried with anhydrous $Na_2SO_4$. The salts are removed via gravity filtration, and volatile materials are condensed in vacuo.

The crude residue is dissolved in $THF/CH_2Cl_2$ (0.05 M), DIPEA (2.5 equiv) and HATU (1.2 equiv) is added. The reaction is stirred at room temperature. Upon completion the reaction is quenched with $NaHCO_3$, extracted with $CH_2Cl_2$ (3×), washed with brine, dried with $Na_2SO_4$ and concentrated under reduced pressure.

The crude macrocycle M1 is dissolved in MeOH (0.1) and Pd/C (20% w.t.). The vial is fitted with a rubber septum and a hydrogen balloon. Hydrogen is bubbled through the solution for 10 minutes then the reaction is stirred under hydrogen atmosphere for 16 hours or until full conversion is observed by UPLC/MS. The reaction is filtered through a celite plug eluting with MeOH and EtOAc and concentrated. The crude material is purified by mass-guided preparative HPLC.

(5-(Allylamino)isoindolin-2-yl)(2,4-bis(benzyloxy)-6-((1-(pent-4-en-1-yl)-3-phenyl-1H-pyrazol-5-yl)amino)phenyl)methanone can be prepared from (2,4-bis(benzyloxy)-6-((1-(pent-4-en-1-yl)-3-phenyl-1H-pyrazol-5-yl)amino)phenyl)(5-bromoisoindolin-2-yl)methanone (1 equiv) and allylamine (1.1 equiv) according to General Procedure L1b.

Macrocycle M2 To a flame-dried vial is added (5-(Allylamino)isoindolin-2-yl)(2,4-bis(benzyloxy)-6-((1-(pent-4-en-1-yl)-3-phenyl-1H-pyrazol-5-yl)amino)phenyl)methanone (1 equiv) and Hoveyda-Grubbs catalyst $2^{nd}$ generation (5 mol %). The vial is fitted with a rubber septum and was evacuated and backfilled with $N_2$. Anhydrous 1,2-DCE (0.05 M) is added and the reaction is stirred at 60° C. until full conversion is observed by UPC/MS. The reaction is filtered through a celite plug, eluting with $CH_2Cl_2$ and concentrated under reduced pressure.

The crude macrocycle M2 is dissolved in MeOH (0.1) and Pd/C (20% w.t.). The vial is fitted with a rubber septum and a hydrogen balloon. Hydrogen is bubbled through the solution for 10 minutes then the reaction is stirred under hydrogen atmosphere for 16 hours or until full conversion is observed by UPLC/MS. The reaction is filtered through a celite plug eluting with MeOH and EtOAc and concentrated. The crude material is purified by mass-guided preparative HPLC.

Additional Screening Data

Table 13 shows compounds that are C. neoformans active (biochemical not whole cell), and selective to C. neoformans

| Comp. | C. alb Active (bio-chemical) | C. alb Selective | C. neo MIC90 (uM) | C. neo MIC80 (uM) | C. neo EC50 (uM) | C. neo Selectivity (FS) | C. neo FS calculated using | C. alb EC50 (uM) | C. alb Selectivity (FS) |
|---|---|---|---|---|---|---|---|---|---|
| ACSM01348 | Yes | Yes | >25 | >25 | 0.62 | 107.7 | Ki | 2.249 | >5 |
| ACSM01375 | No | No | >25 | >25 | 1.238 | 9.6 | EC50 | >10 | — |
| ACSM01280 | No | No | >25 | >25 | 1.998 | 6 | EC50 | >10 | — |
| ACSM01301 | No | No | >25 | >25 | 2.399 | 5 | EC50 | >10 | — |
| 30 | No | No | >25 | >25 | 1.33 | 5.8 | EC50 | >9 | — |
| BUCMD00433 | Yes | Yes | >25 | >25 | 0.075 | 13 | EC50 | 0.011 | 31 |
| ACSM01349 | Yes | Yes | >25 | >25 | 0.246 | 159.7 | Ki | 1.207 | 9.5 |
| ACSM01350 | Yes | Yes | >25 | >25 | 0.106 | 259.7 | Ki | 0.233 | 9.2 |
| 117 | Yes | No | >25 | >25 | 0.434 | 10.1 | Ki | 0.294 | 4.6 |
| ACSM01351 | Yes | No | >25 | >25 | 0.244 | 98 | Ki | 0.628 | 4.6 |
| 116 | Yes | No | >25 | >25 | 1.523 | 6.4 | Ki | 0.594 | 4.4 |
| 95 | Yes | No | >25 | >25 | 0.379 | 6.7 | EC50 | 0.182 | 4.1 |
| 119 | Yes | No | >25 | >25 | 1.781 | 11.3 | Ki | 1.779 | 4 |
| 94 | Yes | No | >25 | >25 | 0.517 | 9.7 | EC50 | 0.379 | 3.9 |
| ACSM01491 | Yes | No | >25 | >25 | 0.047 | 62.2 | EC50 | 0.724 | 3.9 |
| ACSM01279 | Yes | No | >25 | >25 | 0.449 | 18.3 | EC50 | 2.148 | 3.7 |
| ACSM01371 | Yes | No | >25 | >25 | 0.417 | 190 | Ki | 3.184 | 3.5 |
| 123 | Yes | No | >25 | >25 | 0.489 | 6.8 | EC50 | 0.376 | 3.4 |
| 120 | Yes | No | >25 | >25 | 0.424 | 19.1 | Ki | 0.636 | 3.4 |
| 122 | Yes | No | >25 | >25 | 1.289 | 6.9 | EC50 | 1.139 | 3.1 |
| 109 | Yes | No | >25 | >25 | 0.267 | 16.3 | EC50 | 0.573 | 3 |
| 118 | Yes | No | >25 | >25 | 1.318 | 18.9 | Ki | 1.067 | 2.6 |
| 111 | Yes | No | >25 | >25 | 0.176 | 73 | Ki | 0.396 | 2.5 |
| 110 | Yes | No | >25 | >25 | 0.421 | 15.1 | EC50 | 1.03 | 2.4 |

| Comp. | C. alb Active (bio-chemical) | C. alb Selective | C. neo MIC90 (uM) | C. neo MIC80 (uM) | C. neo EC50 (uM) | C. neo Selectivity (FS) | C. neo FS calculated using | C. alb EC50 (uM) | C. alb Selectivity (FS) |
|---|---|---|---|---|---|---|---|---|---|
| ACSM01487 | Yes | No | >25 | >25 | 0.055 | 50.1 | EC50 | 1.161 | 2.3 |
| ACSM01271 | Yes | No | >25 | >25 | 1.25 | 87.8 | Ki | 5.339 | 2.2 |
| 115 | Yes | No | >25 | >25 | 4.601 | 11.7 | Ki | 2.236 | 2.1 |
| 112 | Yes | No | >25 | >25 | 0.281 | 27.9 | Ki | 1.642 | 2 |
| 113 | Yes | No | >25 | >25 | 0.852 | 16.8 | Ki | 5 | 1.7 |
| ACSM01476 | Yes | No | >25 | >25 | 0.537 | 5.8 | EC50 | 2.116 | 1.4 |
| 114 | Yes | No | >25 | >25 | 0.244 | 36.3 | Ki | 1.881 | 1.3 |
| 83 | Yes | No | >25 | >25 | 0.044 | 12.8 | EC50 | 0.366 | 1.1 |
| ACSM01272 | Yes | No | >25 | >25 | 0.227 | >720.1 | Ki | 6.199 | 1.1 |
| ACSM01492 | Yes | No | >25 | >25 | 0.258 | 46.2 | EC50 | 10.62 | 1.1 |
| 108 | Yes | No | >25 | >25 | 0.084 | 12.4 | EC50 | 0.398 | 0.9 |
| ACSM01130 | Yes | No | >50 | >50 | 1.155 | 14.9 | EC50 | 5.817 | 0.9 |
| 92 | Yes | No | >25 | >25 | 0.127 | 8.2 | EC50 | 0.395 | 0.8 |
| 107 | Yes | No | >25 | >25 | 0.139 | 12.9 | EC50 | 0.795 | 0.8 |
| 58 | Yes | No | >25 | >25 | 0.142 | 5.1 | EC50 | 0.377 | 0.7 |
| 93 | Yes | No | >25 | >25 | 0.066 | 6.7 | EC50 | 0.213 | 0.6 |
| 91 | Yes | No | >25 | >25 | 0.078 | 9.2 | EC50 | 0.328 | 0.4 |
| 104 | Yes | No | >25 | >25 | 0.114 | 6.5 | EC50 | 0.672 | 0.4 |
| BUCMD00467 | Yes | No | >25 | >25 | 0.151 | 57.3 | Ki | 1.035 | 0.4 |
| ACSM01494 | Yes | No | >25 | >25 | 0.03 | 97.7 | EC50 | 1.593 | 1.8 |
| ACSM01493 | Yes | No | >25 | >25 | 0.191 | 7.2 | EC50 | 1.062 | 1.2 |
| ACSM01486 | Yes | No | >25 | >25 | 0.034 | 43.4 | EC50 | 2.062 | 0.7 |

Table 14 shows compounds that are *C. neoformans* active (biochemical and whole cell) and selective to *C. neoformans*.

| Comp. | C. alb Active (biochemical) | C. alb Selective | C. neo MIC90 (uM) | C. neo MIC80 (uM) | C. neo EC50 (uM) | C. neo Selectivity (FS) | C. neo FS calculated using | C. alb EC50 (uM) | C. alb Selectivity (FS) |
|---|---|---|---|---|---|---|---|---|---|
| ACSM01362 | Yes | No | >25 | 25 | 0.867 | 612.5 | Ki | 4.169 | 2 |
| ACSM01273 | Yes | No | 12.5 | 12.5 | 0.108 | >141.3 | Ki | 1.843 | 1.7 |
| ACSM01268 | Yes | No | 25 | 25 | 0.202 | >69.8 | Ki | 1.678 | 1.2 |
| ACSM01473 | Yes | No | 25 | 6.25 | 0.034 | 38.8 | EC50 | 1.25 | 1 |
| ACSM01305 | Yes | No | 3 | 6.25 | 0.577 | 8.1 | EC50 | 1.891 | 0.9 |
| ACSM01269 | Yes | No | 25 | 25 | 0.19 | >26.5 | Ki | 2.214 | 0.8 |
| 106 | Yes | No | 25 | <25 | 0.065 | 14.1 | EC50 | 0.599 | 0.7 |
| ACSM01345 | Yes | No | >25 | 25 | 0.076 | >34 | Ki | 1.252 | 0.7 |
| ACSM01135 | Yes | No | 25 | <25 | 0.199 | 5 | EC50 | 0.904 | 0.6 |
| ACSM01270 | Yes | No | 25 | 12.5 | 0.115 | >19.4 | Ki | 1.121 | 0.6 |

Table 15 shows test results for compounds that are active to *C. albicans* (biochemical) and selective to *C. albicans*.

| Comp. | C. neo Active (bio-chemical) | C. neo Active (cells) | C. neo selective | C. neo MIC90 (uM) | C. neo MIC80 (uM) | C. neo EC50 (uM) | C. neo Selectivity (FS) | C. neo FS calculated using | C. alb EC50 (uM) | C. alb Select. (FS) |
|---|---|---|---|---|---|---|---|---|---|---|
| ACSM01348 | Yes | No | Yes | >25 | >25 | 0.62 | 107.7 | Ki | 2.249 | >5 |
| BUCMD00433 | Yes | No | Yes | >25 | >25 | 0.075 | 13 | EC50 | 0.011 | 31 |
| 131 | Yes | No | No | >25 | >25 | 1.262 | 1.9 | EC50 | 0.05 | 18.2 |
| 132 | Yes | No | No | >25 | >25 | 0.514 | 1.3 | EC50 | 0.016 | 15.9 |
| 130 | Yes | No | No | >25 (sol. Issues) | >25 | 5.402 | 1 | EC50 | 0.134 | 15.3 |
| ACSM01349 | Yes | No | Yes | >25 | >25 | 0.246 | 159.7 | Ki | 1.207 | 9.5 |
| ACSM01350 | Yes | No | Yes | >25 | >25 | 0.106 | 259.7 | Ki | 0.233 | 9.2 |
| 23 | Yes | No | No | >25 | >25 | 0.142 | 4 | EC50 | 0.068 | 6.2 |
| 121 | Yes | No | No | >25 | >25 | 0.63 | 4.4 | EC50 | 0.186 | 5.8 |
| 129 | Yes | No | No | >25 | >25 | 2.262 | 0.5 | EC50 | 0.071 | 5 |

REFERENCES

1. Brown, G. D.; Denning, D. W.; Gow, N. A.; Levitz, S. M.; Netea, M. G.; White, T. C., Hidden killers: human fungal infections. *Sci. Trans. Med.* 2012, 4(165), 165rv113.
2. Robbins, N.; Wright, G. D.; Cowen, L. E., Antifungal drugs: the current armamentarium and development of new agents. In *The Fungal Kingdom*, Heitman, J.; Howlett, B.; Crous, P.; Stukenbrock, E.; James, T.; Gow, N., Eds. ASM Press: Washington D.C., 2017; Vol. 4, pp 903-922.
3. McKenzie, C. G.; Koser, U.; Lewis, L. E.; Bain, J. M.; Mora-Montes, H. M.; Barker, R. N.; Gow, N. A.; Erwig, L. P., Contribution of *Candida albicans* cell wall components to recognition by and escape from murine macrophages. *Infect. Immun.* 2010, 78 (4), 1650-1658.
4. Cowen, L. E.; Singh, S. D.; Kohler, J. R.; Collins, C.; Zaas, A. K.; Schell, W. A.; Aziz, H.; Mylonakis, E.; Perfect, J. R.; Whitesell, L.; Lindquist, S., Harnessing Hsp90 function as a powerful, broadly effective therapeutic strategy for fungal infectious disease. *Proc. Nat. Acad. Sci. USA* 2009, 106 (8), 2818-2823.
5. Cowen, L. E.; Lindquist, S., Hsp90 potentiates the rapid evolution of new traits: drug resistance in diverse fungi. *Science* 2005, 309 (5744), 2185-2189.
6. Singh, S. D.; Robbins, N.; Zaas, A. K.; Schell, W. A.; Perfect, J. R.; Cowen, L. E., Hsp90 governs echinocandin resistance in the pathogenic yeast *Candida albicans* via calcineurin. *PLoS Pathog.* 2009, 5 (7), e1000532.
7. Chatterjee, S.; Tatu, U., Heat shock protein 90 localizes to the surface and augments virulence factors of *Cryptococcus neoformans*. *PLoS Negl. Trop. Dis.* 2017, 11 (8), e0005836.
8. Cordeiro Rde, A.; Evangelista, A. J.; Serpa, R.; Marques, F. J.; de Melo, C. V.; de Oliveira, J. S.; Franco Jda, S.; de Alencar, L. P.; Bandeira Tde, J.; Brilhante, R. S.; Sidrim, J. J.; Rocha, M. F., Inhibition of heat-shock protein 90 enhances the susceptibility to antifungals and reduces the virulence of *Cryptococcus neoformans/Cryptococcus gattii* species complex. *Microbiology* (Reading, England) 2016, 162 (2), 309-317.
9. Ferraro, M.; D'Annessa, I.; Moroni, E.; Morra, G.; Paladino, A.; Rinaldi, S.; Compostella, F.; Colombo, G., Allosteric modulators of HSP90 and HSP70: dynamics meets function through structure-based drug design. *J. Med. Chem.* 2019, 62 (1), 60-87.
10. Taipale, M.; Jarosz, D. F.; Lindquist, S., HSP90 at the hub of protein homeostasis: emerging mechanistic insights. *Nat. Rev. Mol. Cell Biol.* 2010, 11, 515-528.
11. Whitesell, L.; Robbins, N.; Huang, D. S.; McLellan, C. A.; Shekhar-Guturja, T.; LeBlanc, E. V.; Nation, C. S.; Hui, R.; Hutchinson, A.; Collins, C.; Chatterjee, S.; Trilles, R.; Xie, J. L.; Krysan, D. J.; Lindquist, S.; Porco, J. A.; Tatu, U.; Brown, L. E.; Pizarro, J.; Cowen, L. E., Structural basis for species-selective targeting of Hsp90 in a pathogenic fungus. *Nat. Commun.* 2019, 10 (1), 402.
12. Rehn, A.; Moroni, E.; Zierer, B. K.; Tippel, F.; Morra, G.; John, C.; Richter, K.; Colombo, G.; Buchner, J., Allosteric regulation points control the conformational dynamics of the molecular chaperone Hsp90. *J. Mol. Biol.* 2016, 428 (22), 4559-4571.
13. Gewirth, D. T., Paralog specific Hsp90 inhibitors—a brief history and a bright future. *Curr. Top. Med. Chem.* 2016, 16 (25), 2779-2791.
14. Lee, C.; Park, H. K.; Jeong, H.; Lim, J.; Lee, A. J.; Cheon, K. Y.; Kim, C. S.; Thomas, A. P.; Bae, B.; Kim, N. D.; Kim, S. H.; Suh, P. G.; Ryu, J. H.; Kang, B. H., Development of a mitochondria-targeted Hsp90 inhibitor based on the crystal structures of human TRAP. *J. Am. Chem. Soc.* 2015, 137 (13), 4358-4367.
15. Crowley, V. M.; Khandelwal, A.; Mishra, S.; Stothert, A. R.; Huard, D. J. E.; Zhao, J.; Muth, A.; Duerfeldt, A. S.; Kizziah, J. L.; Lieberman, R. L.; Dickey, C. A.; Blagg, B. S. J., Development of glucose regulated protein 94-selective inhibitors based on the BnIm and radamide scaffold. *J. Med. Chem.* 2016, 59 (7), 3471-3488.
16. Patel, P. D.; Yan, P.; Seidler, P. M.; Patel, H. J.; Sun, W.; Yang, C.; Que, N. S.; Taldone, T.; Finotti, P.; Stephani, R. A.; Gewirth, D. T.; Chiosis, G., Paralog-selective Hsp90 inhibitors define tumor-specific regulation of HER2. *Nat. Chem. Biol.* 2013, 9, 677-684.
17. Duerfeldt, A. S.; Peterson, L. B.; Maynard, J. C.; Ng, C. L.; Eletto, D.; Ostrovsky, O.; Shinogle, H. E.; Moore, D. S.; Argon, Y.; Nicchitta, C. V.; Blagg, B. S., Development of a Grp94 inhibitor. *J. Am. Chem. Soc.* 2012, 134, 9796-9804.
18. Stothert, A. R.; Suntharalingam, A.; Tang, X.; Crowley, V. M.; Mishra, S. J.; Webster, J. M.; Nordhues, B. A.; Huard, D. J. E.; Passaglia, C. L.; Lieberman, R. L.; Blagg, B. S. J.; Blair, L. J.; Koren, J.; Dickey, C. A., Isoform-selective Hsp90 inhibition rescues model of hereditary open-angle glaucoma. *Sci. Rep.* 2017, 7 (1), 17951.
19. Muth, A.; Crowley, V.; Khandelwal, A.; Mishra, S.; Zhao, J.; Hall, J.; Blagg, B. S. J., Development of radamide analogs as Grp94 inhibitors. *Bioorg. Med. Chem.* 2014, 22 (15), 4083-4098.
20. Khandelwal, A.; Kent, C. N.; Balch, M.; Peng, S.; Mishra, S. J.; Deng, J.; Day, V. W.; Liu, W.; Subramanian, C.; Cohen, M.; Holzbeierlein, J. M.; Matts, R.; Blagg, B. S. J., Structure-guided design of an Hsp90β N-terminal isoform-selective inhibitor. *Nat. Commun.* 2018, 9 (1), 425.
21. Ohkubo, S.; Kodama, Y.; Muraoka, H.; Hitotsumachi, H.; Yoshimura, C.; Kitade, M.; Hashimoto, A.; Ito, K.; Gomori, A.; Takahashi, K.; Shibata, Y.; Kanoh, A.; Yonekura, K., TAS—116, a highly selective inhibitor of heat shock protein 90α and β, demonstrates potent antitumor activity and minimal ocular toxicity in preclinical models. *Mol. Cancer Ther.* 2015, 14 (1), 14-22.
22. Ernst, J. T.; Neubert, T.; Liu, M.; Sperry, S.; Zuccola, H.; Turnbull, A.; Fleck, B.; Kargo, W.; Woody, L.; Chiang, P.; Tran, D.; Chen, W.; Snyder, P.; Alcacio, T.; Nezami, A.; Reynolds, J.; Alvi, K.; Goulet, L.; Stamos, D., Identification of novel HSP90α/β isoform selective inhibitors using structure-based drug design. Demonstration of potential utility in treating CNS disorders such as Huntington's Disease. *J. Med Chem.* 2014, 57 (8), 3382-3400.
23. Ernst, J. T.; Liu, M.; Zuccola, H.; Neubert, T.; Beaumont, K.; Turnbull, A.; Kallel, A.; Vought, B.; Stamos, D., Correlation between chemotype-dependent binding conformations of HSP90α/P and isoform selectivity Implications for the structure-based design of HSP90α/P selective inhibitors for treating neurodegenerative diseases. *Bioorg. Med. Chem. Lett.* 2014, 24 (1), 204-208.
24. Woodhead, A. J.; Angove, H.; Carr, M. G.; Chessari, G.; Congreve, M.; Coyle, J. E.; Cosme, J.; Graham, B.; Day, P. J.; Downham, R.; Fazal, L.; Feltell, R.; Figueroa, E.; Frederickson, M.; Lewis, J.; McMenamin, R.; Murray, C. W.; O'Brien, M. A.; Parra, L.; Patel, S.; Phillips, T.; Rees, D. C.; Rich, S.; Smith, D. M.; Trewartha, G.; Vinkovic, M.; Williams, B.; Woolford, A. J., Discovery of (2,4-dihydroxy-5-isopropylphenyl)-[5-(4-methylpiperazin-1-ylmethyl)-1,3-dihydrois oindol-2-yl]methanone (AT13387), a novel inhibitor of the molecular chaperone Hsp90 by fragment based drug design. *J. Med. Chem.* 2010, 53, 5956-5969.

25. Do, K.; Speranza, G.; Chang, L.-C.; Polley, E. C.; Bishop, R.; Zhu, W.; Trepel, J. B.; Lee, S.; Lee, M.-J.; Kinders, R. J.; Phillips, L.; Collins, J.; Lyons, J.; Jeong, W.; Antony, R.; Chen, A. P.; Neckers, L.; Doroshow, J. H.; Kummar, S., Phase I study of the heat shock protein 90 (Hsp90) inhibitor onalespib (AT13387) administered on a daily for 2 consecutive days per week dosing schedule in patients with advanced solid tumors. *Invest. New Drug.* 2015, 33 (4), 921-930.

26. Wagner, A. J.; Agulnik, M.; Heinrich, M. C.; Mahadevan, D.; Riedel, R. F.; von Mehren, M.; Trent, J.; Demetri, G. D.; Corless, C. L.; Yule, M.; Lyons, J. F.; Oganesian, A.; Keer, H., Dose-escalation study of a second-generation non-ansamycin HSP90 inhibitor, onalespib (AT13387), in combination with imatinib in patients with metastatic gastrointestinal stromal tumour. *Eur. J. Cancer* 2016, 61, 94-101.

27. Canella, A.; Welker, A. M.; Yoo, J. Y.; Xu, J.; Abas, F. S.; Kesanakurti, D.; Nagarajan, P.; Beattie, C. E.; Sulman, E. P.; Liu, J.; Gumin, J.; Lang, F. F.; Gurcan, M. N.; Kaur, B.; Sampath, D.; Puduvalli, V. K., Efficacy of onalespib, a long-acting second-generation HSP90 inhibitor, as a single agent and in combination with temozolomide against malignant gliomas. *Clin. Cancer Res.* 2017, 23 (20), 6215-6226.

28. Stuhmer, T.; Zollinger, A.; Siegmund, D.; Chatterjee, M.; Grella, E.; Knop, S.; Kortum, M.; Unzicker, C.; Jensen, M. R.; Quadt, C.; Chene, P.; Schoepfer, J.; Garcia-Echeverria, C.; Einsele, H.; Wajant, H.; Bargou, R. C., Signalling profile and antitumour activity of the novel Hsp90 inhibitor NVP-AUY922 in multiple myeloma. *Leukemia* 2008, 22, 1604-1612.

29. Jensen, M. R.; Schoepfer, J.; Radimerski, T.; Massey, A.; Guy, C. T.; Brueggen, J.; Quadt, C.; Buckler, A.; Cozens, R.; Drysdale, M. J.; Garcia-Echeverria, C.; Chene, P., NVP-AUY922: a small molecule HSP90 inhibitor with potent antitumor activity in preclinical breast cancer models. *Breast Cancer Res.* 2008, 10 (2), R33.

30. Doi, T.; Onozawa, Y.; Fuse, N.; Yoshino, T.; Yamazaki, K.; Watanabe, J.; Akimov, M.; Robson, M.; Boku, N.; Ohtsu, A., Phase I dose-escalation study of the HSP90 inhibitor AUY922 in Japanese patients with advanced solid tumors. *Cancer Chemother. Pharmacol.* 2014, 74 (3), 629-636.

31. Seggewiss-Bernhardt, R.; Bargou, R. C.; Goh, Y. T.; Stewart, A. K.; Spencer, A.; Alegre, A.; Blade, J.; Ottmann, O. G.; Fernandez-Ibarra, C.; Lu, H.; Pain, S.; Akimov, M.; Iyer, S. P., Phase 1/1B trial of the heat shock protein 90 inhibitor NVP-AUY922 as monotherapy or in combination with bortezomib in patients with relapsed or refractory multiple myeloma. *Cancer* 2015, 121 (13), 2185-2192.

32. Renouf, D. J.; Hedley, D.; Krzyzanowska, M. K.; Schmuck, M.; Wang, L.; Moore, M. J., A phase II study of the HSP90 inhibitor AUY922 in chemotherapy refractory advanced pancreatic cancer. *Cancer Chemother. Pharmacol.* 2016, 78 (3), 541-545.

33. Bendell, J. C.; Bauer, T. M.; Lamar, R.; Joseph, M.; Penley, W.; Thompson, D. S.; Spigel, D. R.; Owera, R.; Lane, C. M.; Earwood, C.; Burris, H. A., A phase 2 study of the Hsp90 inhibitor AUY922 as treatment for patients with refractory gastrointestinal stromal tumors. *Cancer Invest.* 2016, 34 (6), 265-270.

34. Lin, T.-Y.; Bear, M.; Du, Z.; Foley, K. P.; Ying, W.; Barsoum, J.; London, C., The novel HSP90 inhibitor STA-9090 exhibits activity against Kit-dependent and -independent malignant mast cell tumors. *Exp. Hematol.* 2008, 36 (10), 1266-1277.

35. Ying, W. W.; Du, Z. J.; Sun, L. J.; Foley, K. P.; Proia, D. A.; Blackman, R. K.; Zhou, D.; Inoue, T.; Tatsuta, N.; Sang, J.; Ye, S. X.; Acquaviva, J.; Ogawa, L. S.; Wada, Y.; Barsoum, J.; Koya, K., Ganetespib, a unique triazolone-containing Hsp90 inhibitor, exhibits potent antitumor activity and a superior safety profile for cancer therapy. *Mol. Cancer Ther.* 2012, 11 (2), 475-484.

36. Lock, R. B.; Carol, H.; Maris, J. M.; Kang, M. H.; Reynolds, C. P.; Kolb, E. A.; Gorlick, R.; Keir, S. T.; Billups, C. A.; Kurmasheva, R. T.; Houghton, P. J.; Smith, M. A., Initial testing (stage 1) of ganetespib, an Hsp90 inhibitor, by the pediatric preclinical testing program. *Pediatr. Blood Cancer* 2013, 60 (7), E42-E45.

37. Jhaveri, K.; Wang, R.; Teplinsky, E.; Chandarlapaty, S.; Solit, D.; Cadoo, K.; Speyer, J.; D'Andrea, G.; Adams, S.; Patil, S.; Haque, S.; O'Neill, T.; Friedman, K.; Esteva, F. J.; Hudis, C.; Modi, S., A phase I trial of ganetespib in combination with paclitaxel and trastuzumab in patients with human epidermal growth factor receptor-2 (HER2)-positive metastatic breast cancer. *Breast Cancer Res.* 2017, 19 (1), 89.

38. Thakur, M. K.; Heilbrun, L. K.; Sheng, S.; Stein, M.; Liu, G.; Antonarakis, E. S.; Vaishampayan, U.; Dzinic, S. H.; Li, X.; Freeman, S.; Smith, D.; Heath, E. I., A phase II trial of ganetespib, a heat shock protein 90 Hsp90) inhibitor, in patients with docetaxel-pretreated metastatic castrate-resistant prostate cancer (CRPC)-a prostate cancer clinical trials consortium (PCCTC) study. *Invest. New Drug.* 2016, 34 (1), 112-118.

39. Goyal, L.; Wadlow, R. C.; Blaszkowsky, L. S.; Wolpin, B. M.; Abrams, T. A.; McCleary, N. J.; Sheehan, S.; Sundaram, E.; Karol, M. D.; Chen, J.; Zhu, A. X., A phase I and pharmacokinetic study of ganetespib (STA-9090) in advanced hepatocellular carcinoma. *Invest. New Drug.* 2015, 33 (1), 128-137.

40. Socinski, M. A.; Goldman, J.; El-Hariry, I.; Koczywas, M.; Vukovic, V.; Horn, L.; Paschold, E.; Salgia, R.; West, H.; Sequist, L. V.; Bonomi, P.; Brahmer, J.; Chen, L.-C.; Sandler, A.; Belani, C. P.; Webb, T.; Harper, H.; Huberman, M.; Ramalingam, S.; Wong, K.-K.; Teofilovici, F.; Guo, W.; Shapiro, G. I., A multicenter phase II study of ganetespib monotherapy in patients with genotypically defined advanced non-small cell lung cancer. *Clin. Cancer Res.* 2013, 19 (11), 3068-3077.

41. Jhaveri, K.; Chandarlapaty, S.; Lake, D.; Gilewski, T.; Robson, M.; Goldfarb, S.; Drullinsky, P.; Sugarman, S.; Wasserheit-Leiblich, C.; Fasano, J.; Moynahan, M. E.; D'Andrea, G.; Lim, K.; Reddington, L.; Haque, S.; Patil, S.; Bauman, L.; Vukovic, V.; El-Hariry, I.; Hudis, C.; Modi, S., A phase II open-label study of ganetespib, a novel heat shock protein 90 inhibitor for patients with metastatic breast cancer. *Clin. Breast Cancer* 2014, 14 (3), 154-160.

42. Goldman, J. W.; Raju, R. N.; Gordon, G. A.; El-Hariry, I.; Teofilivici, F.; Vukovic, V. M.; Bradley, R.; Karol, M. D.; Chen, Y.; Guo, W.; Inoue, T.; Rosen, L. S., A first in human, safety, pharmacokinetics, and clinical activity phase I study of once weekly administration of the Hsp90 inhibitor ganetespib (STA-9090) in patients with solid malignancies. *BMC Cancer* 2013, 13 (1), 152.

43. Nakashima, T.; Ishii, T.; Tagaya, H.; Seike, T.; Nakagawa, H.; Kanda, Y.; Akinaga, S.; Soga, S.; Shiotsu, Y., New molecular and biological mechanism of antitumor activities of KW-2478, a novel nonansamycin heat shock protein 90 inhibitor, in multiple myeloma cells. *Clin. Cancer Res.* 2010, 16 (10), 2792-2802.

44. Ishii, T.; Seike, T.; Nakashima, T.; Juliger, S.; Maharaj, L.; Soga, S.; Akinaga, S.; Cavenagh, J.; Joel, S.; Shiotsu, Y., Anti-tumor activity against multiple myeloma by combination of KW-2478, an Hsp90 inhibitor, with bortezomib. *Blood Cancer J* 2012, 2, e68.

45. Yong, K.; Cavet, J.; Johnson, P.; Morgan, G.; Williams, C.; Nakashima, D.; Akinaga, S.; Oakervee, H.; Cavenagh, J., Phase I study of KW-2478, a novel Hsp90 inhibitor, in patients with B-cell malignancies. *Br. J. Cancer* 2015, 114, 7-13.

46. Cavenagh, J.; Oakervee, H.; Baetiong-Caguioa, P.; Davies, F.; Gharibo, M.; Rabin, N.; Kurman, M.; Novak, B.; Shiraishi, N.; Nakashima, D.; Akinaga, S.; Yong, K., A phase I/II study of KW-2478, an Hsp90 inhibitor, in combination with bortezomib in patients with relapsed/refractory multiple myeloma. *Br. J. Cancer* 2017, 117, 1295-1302.

47. Ritchie, T. J.; Macdonald, S. J. F.; Peace, S.; Pickett, S. D.; Luscombe, C. N., The developability of heteroaromatic and heteroaliphatic rings—do some have a better pedigree as potential drug molecules than others? *MedChemComm* 2012, 3 (9), 1062-1069.

48. Khandelwal, A.; Crowley, V. M.; Blagg, B. S. J., Resorcinol-based Grp94-selective inhibitors. *ACS Med. Chem. Lett* 2017, 8 (10), 1013-1018.

49. Kung, P.-P.; Funk, L.; Meng, J.; Collins, M.; Zhou, J. Z.; Catherine Johnson, M.; Ekker, A.; Wang, J.; Mehta, P.; Yin, M.-J.; Rodgers, C.; Davies, J. F.; Bayman, E.; Smeal, T.; Maegley, K. A.; Gehring, M. R., Dihydroxylphenyl amides as inhibitors of the Hsp90 molecular chaperone. *Bioorg. Med Chem. Lett.* 2008, 18 (23), 6273-6278.

50. Kung, P.-P.; Huang, B.; Zhang, G.; Zhou, J. Z.; Wang, J.; Digits, J. A.; Skaptason, J.; Yamazaki, S.; Neul, D.; Zientek, M.; Elleraas, J.; Mehta, P.; Yin, M.-J.; Hickey, M. J.; Gajiwala, K. S.; Rodgers, C.; Davies, J. F.; Gehring, M. R., Dihydroxyphenylisoindoline amides as orally bioavailable inhibitors of the heat shock protein 90 (Hsp90) molecular chaperone. *J. Med Chem.* 2010, 53 (1), 499-503.

51. Murray, C. W.; Carr, M. G.; Callaghan, O.; Chessari, G.; Congreve, M.; Cowan, S.; Coyle, J. E.; Downham, R.; Figueroa, E.; Frederickson, M.; Graham, B.; McMenamin, R.; O'Brien, M. A.; Patel, S.; Phillips, T. R.; Williams, G.; Woodhead, A. J.; Woolford, A. J., Fragment-based drug discovery applied to Hsp90. Discovery of two lead series with high ligand efficiency. *J. Med Chem.* 2010, 53, 5942-5955.

52. Patel, B. H.; Barrett, A. G. M., Total synthesis of resorcinol amide Hsp90 inhibitor AT13387. *J. Org. Chem.* 2012, 77 (24), 11296-11301.

53. Ren, J.; Li, J.; Wang, Y.; Chen, W.; Shen, A.; Liu, H.; Chen, D.; Cao, D.; Li, Y.; Zhang, N.; Xu, Y.; Geng, M.; He, J.; Xiong, B.; Shen, J., Identification of a new series of potent diphenol HSP90 inhibitors by fragment merging and structure-based optimization. *Bioorg. Med Chem. Lett.* 2014, 24 (11), 2525-2529.

54. Moss, T. A.; Addie, M. S.; Nowak, T.; Waring, M. J., Room-temperature palladium-catalyzed coupling of heteroaryl amines with aryl or heteroaryl bromides. *Synlett* 2012, 2012 (02), 285-289.

55. Schulte II, J. P.; Tweedie, S. R., Palladium-catalyzed couplings of heteroaryl amines with aryl halides using sodium phenolate as the stoichiometric base. *Synlett* 2007, 2007(15),2331-2336.

56. Park, S. Y.; Oh, Y. J.; Lho, Y.; Jeong, J. H.; Liu, K.-H.; Song, J.; Kim, S.-H.; Ha, E.; Seo, Y. H., Design, synthesis, and biological evaluation of a series of resorcinol-based N-benzyl benzamide derivatives as potent Hsp90 inhibitors. *Eur. J. Med. Chem.* 2018, 143, 390-401.

57. Ritchie, T. J.; Macdonald, S. J., The impact of aromatic ring count on compound developability—are too many aromatic rings a liability in drug design? *Drug Discov. Today* 2009, 14 (21-22), 1011-1020.

58. White, T. C., Increased mRNA levels of ERG16, CDR, and MDR1 correlate with increases in azole resistance in *Candida albicans* isolates from a patient infected with human immunodeficiency virus. *Antimicrob. Agents Chemother.* 1997, 41 (7), 1482-1487.

59. Odds, F. C.; Brown, A. J.; Gow, N. A., *Candida albicans* genome sequence: a platform for genomics in the absence of genetics. Genome Biol. 2004, 5 (7), 230.

60. Granger, D. L.; Perfect, J. R.; Durack, D. T., Virulence of *Cryptococcus neoformans*. Regulation of capsule synthesis by carbon dioxide. *J. Cin. Invest.* 1985, 76 (2), 508-516.

61. LaFayette, S. L.; Collins, C.; Zaas, A. K.; Schell, W. A.; Betancourt-Quiroz, M.; Gunatilaka, A. A.; Perfect, J. R.; Cowen, L. E., PKC signaling regulates drug resistance of the fungal pathogen *Candida albicans* via circuitry comprised of Mkc1, calcineurin, and Hsp90. *PLoS Pathog.* 2010, 6 (8), e1001069.

62. Rossi, A. M.; Taylor, C. W., Analysis of protein-ligand interactions by fluorescence polarization. *Nat. Protoc.* 2011, 6 (3), 365-387.

63. Houston, J. B., Utility of in vitro drug metabolism data in predicting in vivo metabolic clearance. *Biochem. Pharmacol.* 1994, 47 (9), 1469-1479.

64. Jung, F. H.; Morgentin, R. R.; Ple, P. Quinoline derivatives. WO2007099323, 2007.

65. Nikolovska-Coleska, Z.; Abulwerdi, F.; Showalter, H.; Miao, L.; Stuckey, J.; Mady, A. Small molecule inhibitors of MCL-1 and uses thereof. WO2015153959, 2015.

66. Jefson, M. R.; Lowe, J. A.; Dey, F.; Bergmann, A.; Schoop, A.; Fuller, N. O. Hetero-halo inhibitors of histone deacetylase. WO2017007756, 2017.

67. D. Weiniger "SMILES, a Chemical Language and Information System. 1. Introduction to Methodology and Encoding Rules" *J. Chem. Inf Comput. Sci., Vol.* 28, No. 1, 1988, pages 31-36.

As used herein the term "comprising" or "comprises" is used in reference to compositions, methods, and respective component(s) thereof, that are essential to the claimed invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the claimed invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A compound having the structure of Formula (I) or (II):

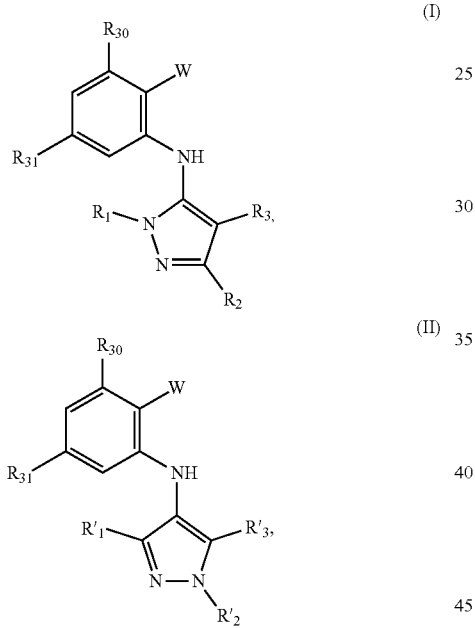

or stereoisomers, tautomers, or a pharmaceutically acceptable salt or ester thereof, wherein:
$R_{30}$ and $R_{31}$ are independently selected from OH, halide, alkyl, alkenyl, alkynyl, alkoxy, acyl, cycloalkyl, heterocycle, aryl, protected hydroxyl, or benzyl;

$R_1$, $R_2$, $R_3$, $R'_1$, $R'_2$ and $R'_3$ are independently selected from the H, OH, protected hydroxyl, —$CO_2H$, amide, alkyl, alkenyl, alkynyl, alkoxy, acyl, cycloalkyl, heterocycle, aryl, or benzyl;

W is —C(O)$NR_4R_5$ or —C(O)Z wherein Z is an aryl, heteroaryl, cycloalkyl or heterocyclyoxazol; and W and any one of $R_1$, $R_2$, $R_3$, $R'_1$, $R'_2$ or $R'_3$ can be connected;

$R_4$ is H, alkyl, alkenyl, alkynyl, acyl, cycloalkyl, heterocycle, aryl, benzyl;

$R_5$ is alkyl, alkenyl, alkynyl, acyl, cycloalkyl, heterocycle, aryl, benzyl, or $R_4$ and $R_5$ together with the nitrogen to which they are attached form a heterocyclic ring;

wherein any alkyl, alkenyl, alkynyl, alkoxy, acyl, amide, cycloalkyl, and heterocycle is optionally substituted with one or more substituents independently selected from the group consisting of halogen, —OH, alkyl, O-alkyl, —$NR^AR^B$, —S-alkyl, —SO-alkyl, —$SO_2$-alkyl, alkenyl, alkynyl, aryl, heteroaryl, cycloalkyl or heterocycle; and the alkenyl, alkynyl, or acyl group optionally includes —O—, —S—, —$SO_2$—, —N($R^E$)— substituting one or more carbons in the carbon chain, wherein any aryl, benzyl or heteroaryl, whether alone or as part of a sub stituent group, is optionally substituted with one or more substituents independently selected from the group consisting of halogen, OH, alkyl, O-alkyl, —COOH, —C(O)—$C_{1-4}$ alkyl, —C(O)O—$C_{1-4}$ alkyl, —$NR^CR^D$, —S-alkyl, —SO-alkyl and —$SO_2$-alkyl;

wherein $R^A$, $R^B$, $R^C$, $R^D$, and $R^E$ are each independently selected from hydrogen and $C_{1-4}$ alkyl.

2. The compound according to claim 1 having structure (I), wherein $R_1$, $R_2$, and $R_3$ are independently selected from H, methyl, ethyl, butyl, phenyl, isopropyl, t-butyl, cyclopropyl, cyclopentyl, cyclohexyl, phenyl-2,3-disubstituted, phenyl-2,5-disubstituted, phenyl-2,4-disubstituted, phenyl-3,4-disubstituted, phenyl-2-methyl, phenyl-4-methyl, phenyl-4-methoxy, phenyl-3-methoxy, phenyl-2-methoxy, phenyl-2-$CF_3$, phenyl-3-methyl, phenyl-2-fluro, phenyl-3-chloro, phenyl-2-$OCF_3$, phenyl-4-fluoro, phenyl-2,6-disubstituted, phenyl-3-fluoro, phenyl-4-t-butyl, phenyl-3-$OCF_3$, phenyl-4-$CF_3$, 2-pyridine, 3-pyridine, 3-furan, phenyl-4-$OCF_3$,—$CH_2CO_2H$, —$CH_2$-cyclohexyl, benzyl, benzyl-2-chloro, benzyl-4-$CF_3$, benzyl-4-isopropyl, benzyl-4-methyl, benzyl-2-methyl, benzyl-4-isopropyl, —$CH_2$-2-furan, $CH_2C(O)NHMe$, or benzyl-4-methoxy.

3. The compound according to claim 2, wherein:

$R_1$ is selected from phenyl, methyl, —$CH_2CO_2H$, phenyl-4-methoxy, —CH2-cyclohexyl, t-butyl, isopropyl, isobutyl, cyclohexyl, benzyl, benzyl-2-chloro, benzyl-4-$CF_3$, benzyl-4-isopropyl, benzyl-4-methyl, benzyl-2-methyl, benzyl-4-isopropyl, —$CH_2$-2-furan, $CH_2C(O)NHMe$, benzyl-4-methoxy, or cyclopentyl;

$R_2$ is selected from H, methyl, ethyl, t-butyl, phenyl, isopropyl, cyclopropyl, cyclopentyl, cyclohexyl, phenyl-2,3-disubstituted, phenyl-2,5-disubstituted, phenyl-2-methyl, phenyl-3-methyl, phenyl-4-methyl, phenyl-2-methoxy, phenyl-3-methoxy, phenyl-2-$CF_3$, phenyl-4-$CF_3$, phenyl-2-fluro, phenyl-3-chloro, phenyl-2-$OCF_3$, phenyl-3-fluoro, phenyl-4-fluoro, phenyl-2,6-disubstituted, phenyl-4-t-butyl, phenyl-3-$OCF_3$, phenyl-4-$OCF_3$, 2-pyridine, 3-pyridine, or 3-furan;

$R_3$ is selected form H, methyl, isopropyl, phenyl, benzyl.

4. The compound according to claim 1 having structure (II), wherein $R'_1$, $R'_2$, and $R'_3$ are independently selected from H, methyl, ethyl, isopropyl, phenyl, phenyl-2,4-disubstituted, phenyl-2,3-disubstituted, phenyl-3,5-disubstituted, phenyl-3,4-disubstituted, phenyl-2-$CF_3$, phenyl-3-$CF_3$, phenyl-2-methoxy, phenyl-3-methyl, phenyl-2-methyl, and —$CH_2CH_2NMe_2$.

5. The compound according to claim 1, wherein the compound has structure (I) or (II), and W is —C(O)$NR_4R_5$.

6. A compound having the structure of Formula (I) or (II):

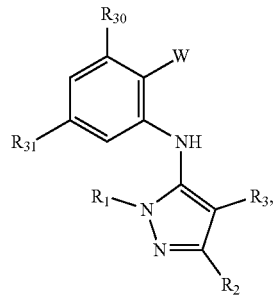
(I)

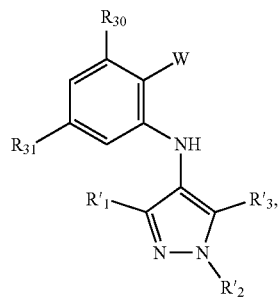
(II)

or stereoisomers, tautomers, or a pharmaceutically acceptable salt or ester thereof, wherein:

$R_{30}$ and $R_{31}$ are independently selected from H, OH, halide, alkyl, alkenyl, alkynyl, alkoxy, acyl, cycloalkyl, heterocycle, aryl, protected hydroxyl, or benzyl;

$R_1$, $R_2$, $R_3$, $R'_1$, $R'_2$ and $R'_3$ are independently selected from the H, OH, protected hydroxyl, —CO$_2$H, amide, alkyl, alkenyl, alkynyl, alkoxy, acyl, cycloalkyl, heterocycle, aryl, or benzyl;

W is —C(O)NR$_4$R$_5$, where:

(i) R$_4$ and R$_5$ together with the nitrogen to which they are attached form a heterocyclic ring of structure (III):

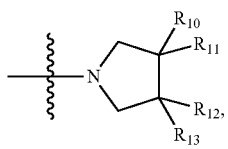
(III)

wherein $R_{10}$, $R_{11}$, $R_{12}$, and $R_{13}$, are independently selected from the group consisting of H, OH, protected hydroxyl, —CO$_2$H, amide, halide, alkyl, alkenyl, alkynyl, alkoxy, acyl, cycloalkyl, heterocycle, aryl, or benzyl; any $R_{10}$, $R_{11}$, $R_{12}$, and $R_{13}$ and carbons to which they are attached can form a spiro or fused ring structure; or (ii) R$_4$ and R$_5$ together with the nitrogen to which they are attached form a heterocyclic ring of structure (IV):

(IV)

wherein $B_1$, $B_2$ and $B_3$ are independently CR$_{15}$, CR$_{16}$, NR$_{17}$ or N;

where $R_{15}$, $R_{16}$, $R_{17}$ are independently selected from the group consisting of H, OH, protected hydroxyl, —CO$_2$H, amide, halide, alkyl, alkenyl, alkynyl, alkoxy, acyl, cycloalkyl, heterocycle, aryl, or benzyl; or (iii) R$_4$ and R$_5$ together with the nitrogen to which they are attached form heterocyclic ring of structure (V):

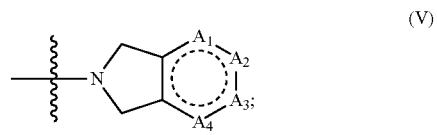
(V)

wherein $A_1$ is N, C(O), NR$_{24}$ or CR$_{20}$; $A_2$ is N, C(O), NR$_{24}$ or CR$_{21}$; $A_3$ is N, C(O), NH or CR$_{22}$; $A_4$ is N, C(O), NR$_{24}$ or CR$_{23}$;

$R_{20}$, $R_{21}$, $R_{22}$ and $R_{23}$ are independently selected from the group consisting of H, OH, protected hydroxyl, —CO$_2$H, amide, halide, alkyl, alkenyl, alkynyl, alkoxy, acyl, cycloalkyl, heterocycle, aryl, or benzyl; and each $R_{24}$ is H, OH, protected hydroxyl, —CO$_2$H, amide, halide, alkyl, alkenyl, alkynyl, alkoxy, acyl, cycloalkyl, heterocycle, aryl, or benzyl, or W is oxazole amide (A30) having structure,

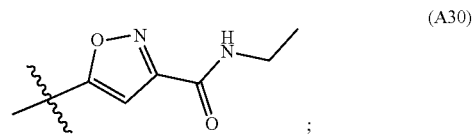 [SMILES: *c1cc(C(=O)NCC)no1]
(A30)

wherein any alkyl, alkenyl, alkynyl, alkoxy, acyl, amide, cycloalkyl, and heterocycle is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or acyl group optionally includes —O—, —S—, —SO$_2$—, —N(R$^E$)— substituting one or more carbons in the carbon chain, wherein any aryl, benzyl or heteroaryl, whether alone or as part of a substituent group, is optionally substituted with one or more substituents independently selected from the group consisting of halogen, OH, alkyl, O-alkyl, —COOH, —C(O)—C$_{1-4}$ alkyl, —C(O)O—C$_{1-4}$ alkyl, —NR$^C$R$^D$, —S-alkyl, —SO-alkyl and —SO$_2$-alkyl;

wherein R$^A$, R$^B$, R$^C$, and R$^E$ are each independently selected from hydrogen and C$_{1-4}$ alkyl.

7. The compound according to claim 6, wherein the compound has structure (I) or (II), and where W is —C(O)

NR$_4$R$_5$, where R$_4$ and R$_5$ together with the nitrogen to which they are attached form a heterocyclic ring of structure (III):

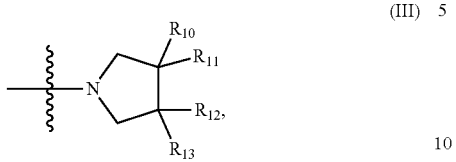
(III)

wherein R$_{10}$, R$_{11}$, R$_{12}$, and R$_{13}$, are independently selected from the group consisting of H, OH, protected hydroxyl, —CO$_2$H, amide, halide, alkyl, alkenyl, alkynyl, alkoxy, acyl, cycloalkyl, heterocycle, aryl, or benzyl; any R$_{10}$, R$_{11}$, R$_{12}$, and R$_{13}$ and carbons to which they are attached can form a spiro or fused ring structure.

8. The compound according to claim 6, wherein the compound has structure (I) or (II), and W is —C(O)NR$_4$R$_5$, where R$_4$ and R$_5$ together with the nitrogen to which they are attached form a heterocyclic ring of structure (IV):

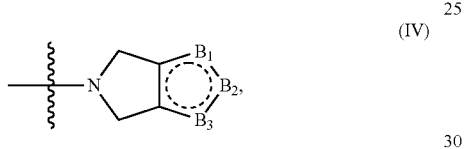
(IV)

wherein B$_1$, B$_2$ and B$_3$ are independently CR$_{15}$, CR$_{16}$, NR$_{17}$ or N;
where R$_{15}$, R$_{16}$, R$_{17}$ are independently selected from the group consisting of H, OH, protected hydroxyl, —CO$_2$H, amide, halide, alkyl, alkenyl, alkynyl, alkoxy, acyl, cycloalkyl, heterocycle, aryl, or benzyl.

9. The compound according to claim 8, wherein two of B$_1$, B$_2$ and B$_3$ are CR$_{15}$ and CR$_{16}$, and the remaining B$_1$, B$_2$ or B$_3$ is NR$_{17}$.

10. The compound according to claim 8, wherein one of B$_1$, B$_2$ and B$_3$ is CR$_{15}$, one of B$_1$, B$_2$ and B$_3$ is N, and one of B$_1$, B$_2$ and B$_3$ is NR$_{17}$.

11. The compound according to claim 6, wherein the compound has structure (I) or (II), and W is —C(O)NR$_4$R$_5$, where R$_4$ and R$_5$ together with the nitrogen to which they are attached form heterocyclic ring of structure (V):

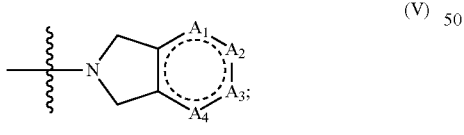
(V)

wherein A$_1$ is N, C(O), NR$_{24}$ or CR$_{20}$; A$_2$ is N, C(O), NR$_{24}$ or CR$_{21}$; A$_3$ is N, C(O), NH or CR$_{22}$; A$_4$ is N, C(O), NR$_{24}$ or CR$_{23}$;
R$_{20}$, R$_{21}$, R$_{22}$ and R$_{23}$ are independently selected from the group consisting of H, OH, protected hydroxyl, —CO$_2$H, amide, halide, alkyl, alkenyl, alkynyl, alkoxy, acyl, cycloalkyl, heterocycle, aryl, or benzyl; and
each R$_{24}$ is H, OH, protected hydroxyl, —CO$_2$H, amide, halide, alkyl, alkenyl, alkynyl, alkoxy, acyl, cycloalkyl, heterocycle, aryl, or benzyl.

12. The compound according to claim 6, wherein the compound has structure (I) or (II) and W is oxazole amide (A30) having structure, or

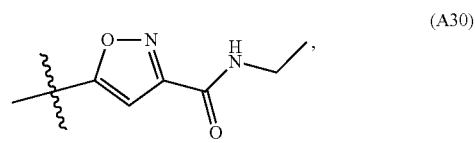 [SMILES: *c1cc(C(=O)NCC)no1]
(A30)

or
W is —C(O)NR$_4$R$_5$, where R$_4$ and R$_5$ together with the nitrogen to which they are attached form a heterocyclic ring selected from:

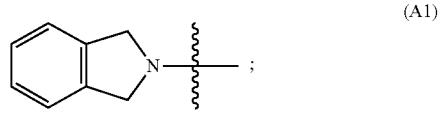
(A1)

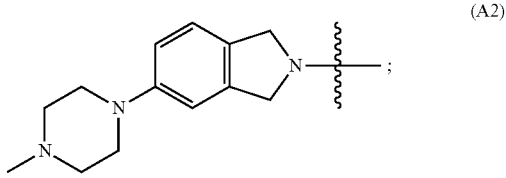
(A2)

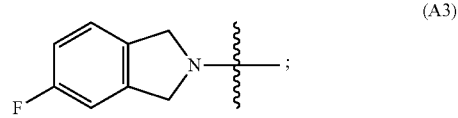
(A3)

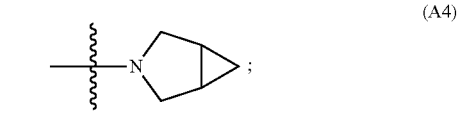
(A4)

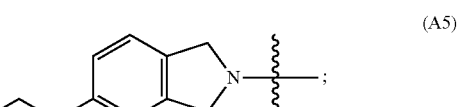
(A5)

(A6)

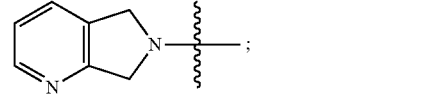
(A7)

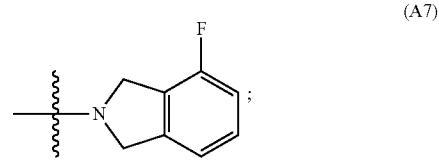
(A8)

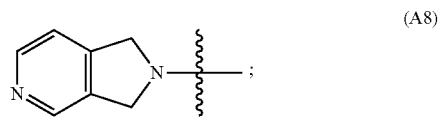
(A9)

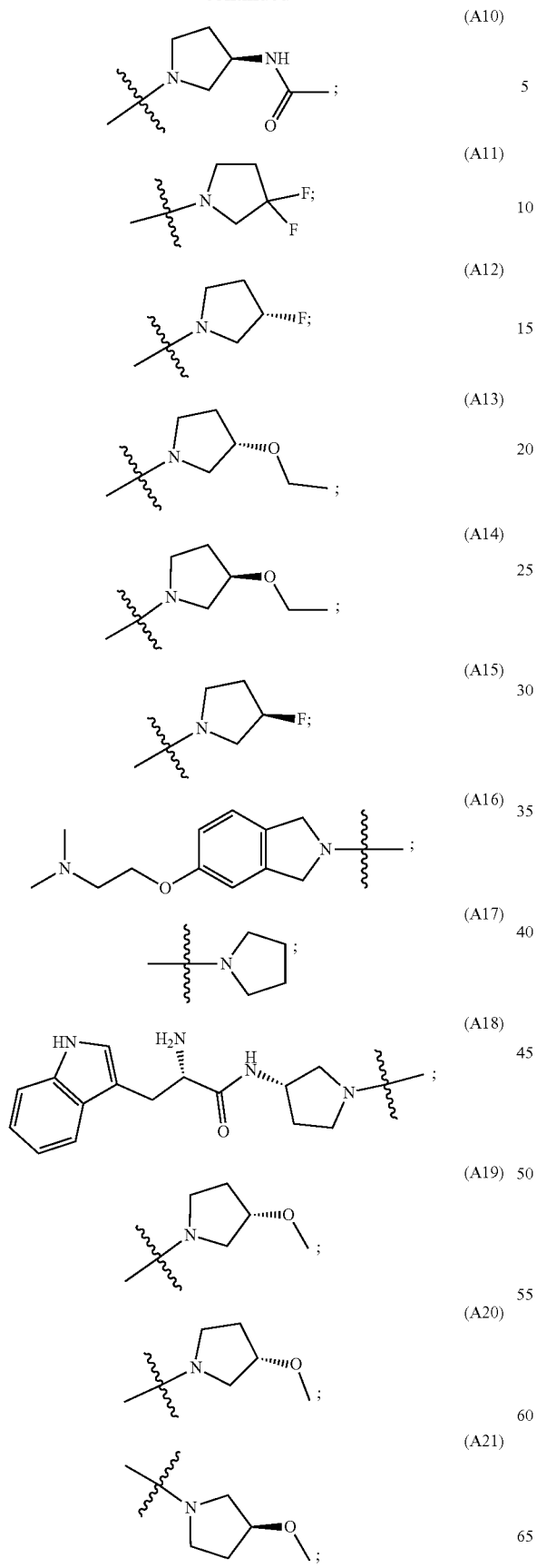
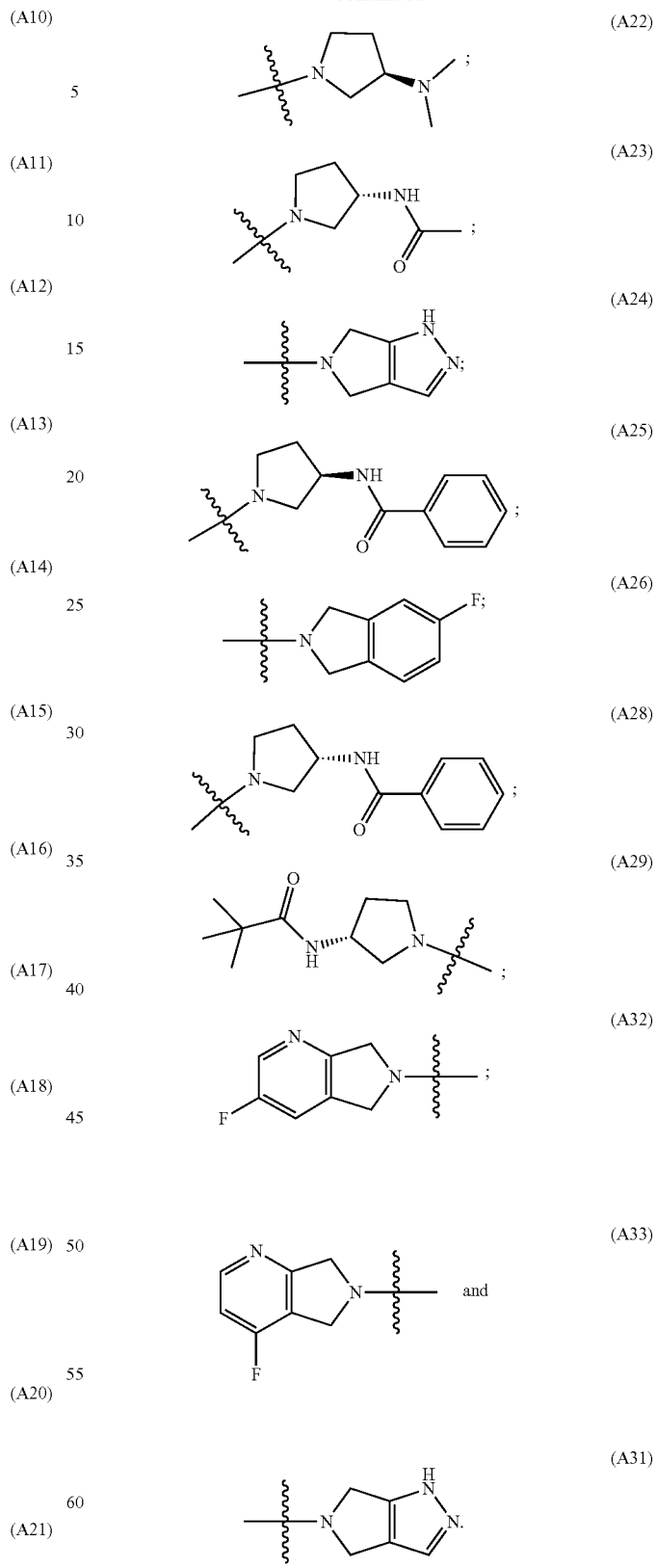
13. The compound according to claim 6, wherein the compound has structure (I) and is further defined as structure (X):

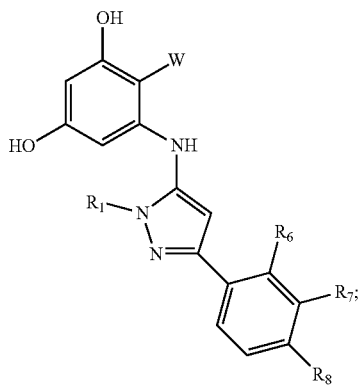

(X)

W is —C(O)NR₄R₅, where R₄ and R₅ together with the nitrogen to which they are attached form a heterocyclic ring selected from the group consisting of

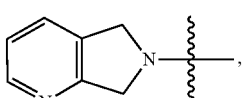

(A1)

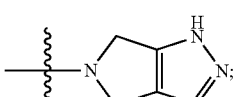

(A6)

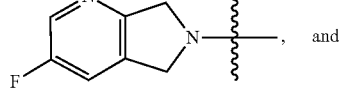

(A24)

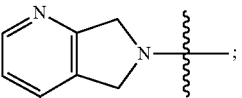

(A32)

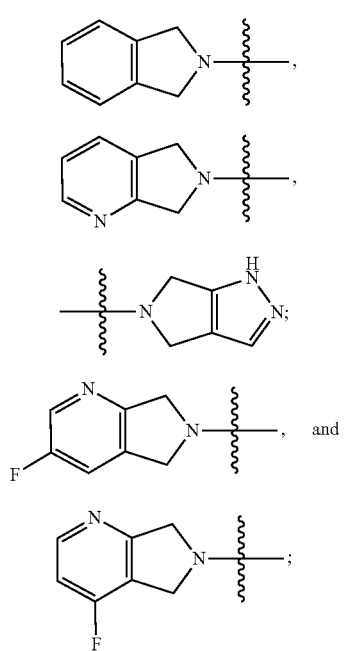

, and (A33)

$R_1$, $R_6$, $R_7$, $R_8$ are independently selected from H, alkyl, and alkoxy;

wherein any alkyl or alkoxy is optionally substituted with one or more substituents independently selected from the group consisting of halogen, —OH, alkyl, O-alkyl, —NR$^F$R$^G$, —S-alkyl, —SO-alkyl, —SO₂-alkyl, alkenyl, alkynyl, aryl, heteroaryl, cycloalkyl or heterocycle; and the alkenyl, alkynyl, or acyl group optionally includes —O—, —S—, —SO₂—, —N(R$^H$)— substituting one or more carbons in the carbon chain, wherein R$^F$, R$^G$, and R$^H$ are each independently selected from hydrogen and C$_{1-4}$ alkyl.

14. The compound according to claim 6, wherein the compound has structure (II) and is further defined as structure (XI):

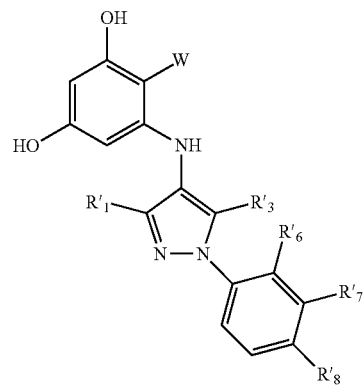

(XI)

W is —C(O)NR₄R₅, where R₄ and R₅ together with the nitrogen to which they are attached form (A1),

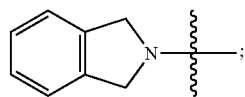

(A1)

R'$_1$, R'$_3$, R'$_6$, R'$_7$, R'$_8$ are independently selected from H, alkyl, and alkoxy;

wherein any alkyl or alkoxy is optionally substituted with one or more substituents independently selected from the group consisting of halogen, —OH, alkyl, O-alkyl, —NR$^L$R$^M$, —S-alkyl, —SO-alkyl, —SO₂-alkyl, alkenyl, alkynyl, aryl, heteroaryl, cycloalkyl or heterocycle; and the alkenyl, alkynyl, or acyl group optionally includes —O—, —S—, —SO₂—, —N(R$^N$)— substituting one or more carbons in the carbon chain, wherein R$^L$, R$^M$, and R$^N$ are each independently selected from hydrogen and C$_{1-4}$ alkyl.

15. A compound selected from the group consisting of:

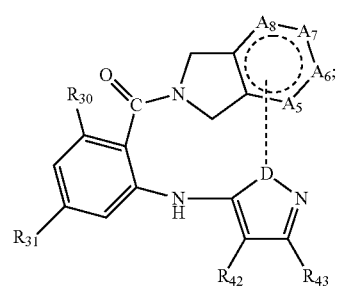

(XV)

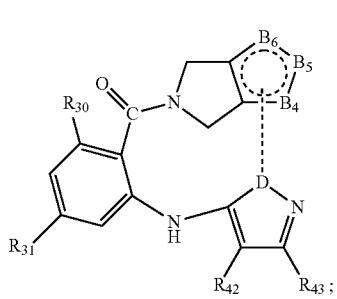

(XVI)

-continued (XVII)

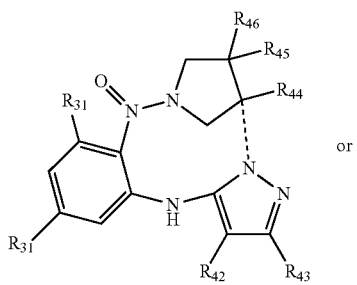

or (XVIII)

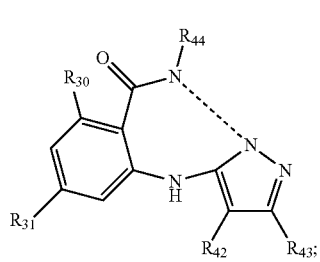

where in (XV) D is N, and 3 of the $A_5$, $A_6$, $A_7$ and $A_8$ are independently N or CH, and the remaining $A_5$, $A_6$, $A_7$ and $A_8$ is C and is bonded to D by a linker (—);

wherein in (XVI) D is N, and 2 of the $B_4$, $B_5$, and $B_6$ are independently N, or CH, and the remaining $B_4$, $B_5$, and $B_6$ is C or N and is bonded to D by a linker (-----);

Wherein the linker (-----) is a chain of 2 to 12 carbons wherein one or more carbons in the chain is substituted with —O—, —S—, —N($R^R$)—, —N($R^S$)C(O)—, —SO$_2$—, —C≡C—, —C=C—, and wherein any carbon is optionally substituted with one or more substituents;

$R_{30}$ and $R_{31}$ are independently selected from OH, halide, alkyl, alkenyl, alkynyl, alkoxy, acyl, cycloalkyl, heterocycle, aryl, protected hydroxyl, or benzyl;

$R^R$ and $R^S$ independently are H or alkyl;

$R_{42}$, $R_{43}$, are independently H, —CO$_2$H, amide, halide, alkyl, alkenyl, alkynyl, alkoxy, acyl, cycloalkyl, heterocycle, aryl, or benzyl;

$R_{44}$, $R_{45}$, and $R_{46}$ are independently H, —CO$_2$H, amide, halide, alkyl, alkenyl, alkynyl, alkoxy, acyl, cycloalkyl, heterocycle, aryl, or benzyl; any $R_{44}$, $R_{45}$, and $R_{46}$ and carbons to which they are attached can form a spiro or fused ring structure;

wherein any alkyl or alkoxy is optionally substituted with one or more substituents independently selected from the group consisting of halogen, —OH, alkyl, O-alkyl, —NR$^O$R$^P$, —S-alkyl, —SO-alkyl, —SO$_2$-alkyl, alkenyl, alkynyl, aryl, heteroaryl, cycloalkyl or heterocycle; and the alkenyl, alkynyl, or acyl group optionally includes —O—, —S—, —SO$_2$—, —N(R$^Q$)— substituting one or more carbons in the carbon chain;

wherein R$^O$, R$^P$, and R$^Q$ are each independently selected from hydrogen and $C_{1-4}$ alkyl.

16. The compound according to claim 15, wherein the linker is

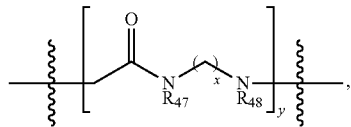

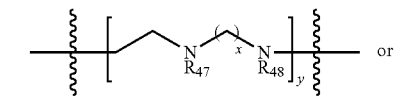  or

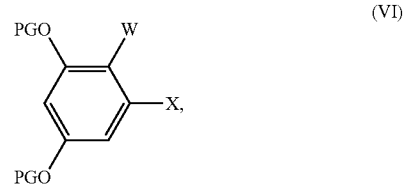

wherein $R_{47}$ and $R_{48}$ are independently H or alkyl, x is 1 to 10, and y is 1 to 5.

17. A method for preparing a compound having formula (I-H$_2$), the method comprising:

providing a solution of a compound having formula (VI) and (VII) in the presence of a catalyst to provide protected product (I'), and de-protecting (I') to afford (I-H$_2$), wherein the structures are as follows:

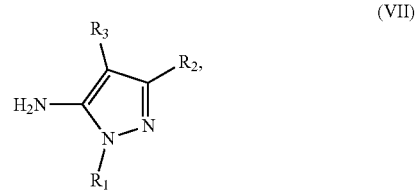

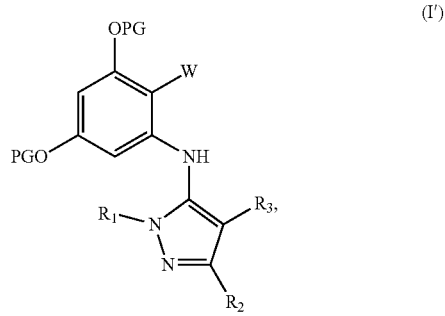

-continued

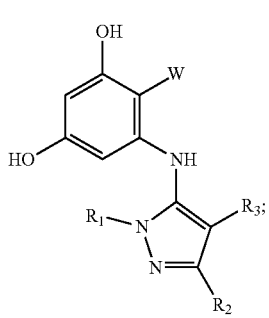

(I-H₂)

wherein:
PG is a protecting group;
X is a halide selected from chlorine, bromine or iodine;
$R_1$, $R_2$ and $R_3$ are independently selected from the group consisting of H, OH, protected hydroxyl, —CO₂H, amide, alkyl, alkenyl, alkynyl, alkoxy, acyl, cycloalkyl, heterocycle, aryl, or benzyl;
W is —C(O)NR₄R₅;
$R_4$ is H, alkyl, alkenyl, alkynyl, acyl, cycloalkyl, heterocycle, aryl, or benzyl;
$R_5$ is alkyl, alkenyl, alkynyl, acyl, cycloalkyl, heterocycle, aryl, or benzyl, or $R_4$ and $R_5$ together with the nitrogen to which they are attached form a heterocyclic ring;
wherein any alkyl, alkenyl, alkynyl, alkoxy, acyl, cycloalkyl, is optionally substituted with one or more substituents independently selected from the group consisting of halogen, —OH, alkyl, O-alkyl, —NR$^A$R$^B$, —S-alkyl, —SO-alkyl, —SO₂-alkyl, alkenyl, alkynyl, aryl, heteroaryl, cycloalkyl or heterocycle; and the alkenyl, alkynyl, or acyl group optionally includes —O—, —S—, —SO₂—, —N(R$^E$)— substituting one or more carbons in the carbon chain,
wherein any aryl, benzyl or heteroaryl, whether alone or as part of a substituent group, is optionally substituted with one or more substituents independently selected from the group consisting of halogen, OH, alkyl, O-alkyl, —COOH, —C(O)—C₁₋₄ alkyl, —C(O)O—C₁₋₄ alkyl, —NR$^C$R$^D$, —S-alkyl, —SO-alkyl and —SO₂-alkyl;
wherein R$^A$, R$^B$, R$^C$, R$^D$, and R$^E$ are each independently selected from hydrogen and C₁₋₄ alkyl.

18. A method of inhibiting Hsp90 function, the method comprising contacting a Hsp90 with at least one compound of claim 1.

19. The method of claim 18, wherein the Hsp90 is comprised in a cell and the method further comprises administering the compound to the cell.

20. The method of claim 19, wherein the cell is a fungal cell.

21. The method of claim 18, wherein the Hsp90 is a fungal Hsp90 isoform.

22. A method of treating a Hsp90 related disease or disorder in a subject, the method comprising:
administering to the subject a therapeutically effective amount of a compound of claim 1 to a subject in need thereof.

23. The method according to claim 22, wherein the Hsp90 related disease or disorder is selected from the group consisting of cancers, autoimmune diseases, neurodegenerative diseases, infectious diseases and any combinations thereof.

24. The method of claim 22, wherein the Hsp90 related disease or disorder is a fungal infection.

25. The method of claim 24, wherein the fungal infection is a mucosal or an invasive systemic infection by a human fungal pathogen.

26. The method of claim 24, wherein the fungal infection is caused by a *Candida*, an *Aspergillus* or a *Cryptococcus* species.

27. The method of claim 26, wherein the fungal infection is caused by *Candida albicans, Candida auris, Aspergillus fumigatus, Cryptococcus neoformans, Cyrptococus gatti* or *Candida glabrata*.

28. The method of claim 22, wherein the subject has a compromised immune function, cardiovascular disease, decompensated liver cirrhosis, is undergoing treatment for a burn injury, is undergoing treatment from a surgery, has a GI tract perforation, has pancreatitis, is being ventilated, is undergoing dialysis, has renal failure, is being administered broad-spectrum antibiotics, is receiving parenteral nutrition or is in close contact with vectors for infection.

29. The method of claim 28, wherein the subject is immunocompromised as a consequence of a pre-existing medical condition.

30. The method of claim 22, wherein the subject is receiving a treatment for rheumatoid arthritis, psoriatic arthritis, myeloproliferative disorders, chronic myeloid leukemia, chronic lymphocytic leukemia, steroid-refractory graft-versus host disease, follicular lymphoma, polycythaemia rubra vera, or Waldenström macroglobulinaemia.

31. The compound of claim 1, wherein $R_4$ and $R_5$ are independently selected from H and ethyl; or methyl and —CH₂-3-pyridine; or H and benzyl; or methyl and benzyl; or methyl and CH₂-oxazole; or methyl and —CH₂-pyran; or methyl and —CH₂-4-pyridine; or methyl and —CH₂-cyclopropyl.

* * * * *